United States Patent
Huang et al.

(10) Patent No.: US 10,786,817 B2
(45) Date of Patent: Sep. 29, 2020

(54) DEVICES AND METHOD FOR ENRICHMENT AND ALTERATION OF CELLS AND OTHER PARTICLES

(71) Applicants: The General Hospital Corporation, Boston, MA (US); GPB Scientific, LLC, Richmond, VA (US)

(72) Inventors: Lotien Richard Huang, Chestnut Hill, MA (US); Thomas A. Barber, Sudbury, MA (US); Bruce L. Carvalho, Watertown, MA (US); Ravi Kapur, Sharon, MA (US); Paul Vernucci, Billerica, MA (US); Mehmet Toner, Charlestown, MA (US); Zihua Wang, Newton, MA (US)

(73) Assignees: The General Hospital Corporation, Boston, MA (US); GPB Scientific, LLC, Richmond, VA (US)

(*) Notice: Subject to any disclaimer, the term of this patent is extended or adjusted under 35 U.S.C. 154(b) by 0 days.

(21) Appl. No.: 15/965,128

(22) Filed: Apr. 27, 2018

(65) Prior Publication Data

US 2019/0001344 A1    Jan. 3, 2019

Related U.S. Application Data

(60) Continuation of application No. 14/930,313, filed on Nov. 2, 2015, now Pat. No. 9,956,562, which is a
(Continued)

(51) Int. Cl.
*B03C 1/30* (2006.01)
*B01L 3/00* (2006.01)
(Continued)

(52) U.S. Cl.
CPC .......... *B03C 1/30* (2013.01); *B01L 3/502746* (2013.01); *B01L 3/502753* (2013.01);
(Continued)

(58) Field of Classification Search
CPC .......... B03C 1/30; B03C 1/32; G01N 1/4077; G01N 33/5044; B01L 3/502746;
(Continued)

(56) References Cited

U.S. PATENT DOCUMENTS 3,906,929 A   9/1975   Augspurger
3,924,947 A   12/1975  Hogg
(Continued)

FOREIGN PATENT DOCUMENTS

CA   2466896    3/2003
DE   19712309   5/1998
(Continued)

OTHER PUBLICATIONS

"Cancer Genetics" Am. J. Hum. Genet., (1988) 43 (3):A35.
(Continued)

*Primary Examiner* — Melanie Brown
(74) *Attorney, Agent, or Firm* — Fish & Richardson P.C.

(57) ABSTRACT

The invention features devices and methods for the deterministic separation of particles. Exemplary methods include the enrichment of a sample in a desired particle or the alteration of a desired particle in the device. The devices and methods are advantageously employed to enrich for rare cells, e.g., fetal cells, present in a sample, e.g., maternal blood and rare cell components, e.g., fetal cell nuclei. The invention further provides a method for preferentially lysing cells of interest in a sample, e.g., to extract clinical information from a cellular component, e.g., a nucleus, of the cells of interest. In general, the method employs differential
(Continued)

lysis between the cells of interest and other cells (e.g., other nucleated cells) in the sample.

20 Claims, 73 Drawing Sheets

Related U.S. Application Data division of application No. 13/232,781, filed on Sep. 14, 2011, now Pat. No. 9,174,222, which is a continuation of application No. 11/449,149, filed on Jun. 8, 2006, now Pat. No. 8,021,614, which is a continuation of application No. PCT/US2006/012820, filed on Apr. 5, 2006, which is a continuation of application No. 60/704,067, filed on Jul. 29, 2005.

(60) Provisional application No. 60/668,415, filed on Apr. 5, 2005.

(51) Int. Cl.
  *B03C 1/32* (2006.01)
  *C12M 1/00* (2006.01)
  *G01N 33/50* (2006.01)
  *G01N 1/40* (2006.01)
  *B33Y 80/00* (2015.01)
  *G01N 35/00* (2006.01)

(52) U.S. Cl.
  CPC .......... *B01L 3/502761* (2013.01); *B03C 1/32* (2013.01); *C12M 47/04* (2013.01); *C12M 47/06* (2013.01); *G01N 1/4077* (2013.01); *G01N 33/5044* (2013.01); *B01L 2200/0647* (2013.01); *B01L 2300/0816* (2013.01); *B01L 2300/0864* (2013.01); *B01L 2400/043* (2013.01); *B01L 2400/0406* (2013.01); *B01L 2400/0409* (2013.01); *B01L 2400/0415* (2013.01); *B01L 2400/0472* (2013.01); *B01L 2400/0487* (2013.01); *B01L 2400/086* (2013.01); *B03C 2201/18* (2013.01); *B33Y 80/00* (2014.12); *G01N 1/40* (2013.01); *G01N 2035/00237* (2013.01); *Y10T 137/0318* (2015.04); *Y10T 137/8593* (2015.04); *Y10T 436/25* (2015.01); *Y10T 436/25375* (2015.01)

(58) Field of Classification Search
  CPC ........ B01L 3/502753; B01L 3/502761; C12M 47/04; C12M 47/06
  See application file for complete search history.

(56) References Cited

U.S. PATENT DOCUMENTS

| | | |
|---|---|---|
| 4,009,435 A | 2/1977 | Hogg |
| 4,055,799 A | 10/1977 | Coster et al. |
| 4,115,534 A | 9/1978 | Ithakissios |
| 4,190,535 A | 2/1980 | Luderer et al. |
| 4,415,405 A | 11/1983 | Ruddle et al. |
| 4,434,156 A | 2/1984 | Trowbridge |
| 4,508,625 A | 4/1985 | Graham |
| 4,584,268 A | 4/1986 | Ceriani et al. |
| 4,664,796 A | 5/1987 | Graham et al. |
| 4,675,286 A | 6/1987 | Calenoff |
| 4,729,949 A | 3/1988 | Weinreb et al. |
| 4,789,628 A | 12/1988 | Nayak |
| 4,790,640 A | 12/1988 | Nason |
| 4,800,159 A | 1/1989 | Mullis et al. |
| 4,814,098 A | 3/1989 | Inada et al. |
| 4,886,761 A | 12/1989 | Gustafson et al. |
| 4,894,343 A | 1/1990 | Tanaka et al. |
| 4,895,805 A | 1/1990 | Sato et al. |
| 4,906,439 A | 3/1990 | Grenner |
| 4,925,788 A | 5/1990 | Liberti |
| 4,963,498 A | 10/1990 | Hillman et al. |
| 4,968,600 A | 11/1990 | Haraguchi et al. |
| 4,971,904 A | 11/1990 | Luddy |
| 4,977,078 A | 12/1990 | Niimura et al. |
| 4,984,574 A | 1/1991 | Goldberg et al. |
| 4,999,283 A | 3/1991 | Zavos et al. |
| 5,039,426 A | 8/1991 | Giddings |
| 5,101,825 A | 4/1992 | Gravenstein et al. |
| 5,135,627 A | 8/1992 | Soane |
| 5,147,606 A | 9/1992 | Charlton et al. |
| 5,153,117 A | 10/1992 | Simons |
| 5,173,158 A | 12/1992 | Schmukler |
| 5,183,744 A | 2/1993 | Kawamura et al. |
| 5,186,827 A | 2/1993 | Liberti et al. |
| 5,215,926 A | 6/1993 | Etchells, III et al. |
| 5,240,856 A | 8/1993 | Goffe et al. |
| 5,275,933 A | 1/1994 | Teng et al. |
| 5,296,375 A | 3/1994 | Kricka et al. |
| 5,300,779 A | 4/1994 | Hillman et al. |
| 5,304,487 A | 4/1994 | Wilding et al. |
| 5,306,420 A | 4/1994 | Bisconte |
| 5,310,674 A | 5/1994 | Weinreb et al. |
| 5,328,843 A | 7/1994 | Fukuda et al. |
| 5,427,663 A | 6/1995 | Austin et al. |
| 5,427,946 A | 6/1995 | Kricka et al. |
| 5,432,054 A | 7/1995 | Saunders et al. |
| 5,437,987 A | 8/1995 | Teng et al. |
| 5,447,842 A | 9/1995 | Simons |
| 5,457,024 A | 10/1995 | Goldbard |
| 5,466,574 A | 11/1995 | Liberti et al. |
| 5,472,842 A | 12/1995 | Stokke et al. |
| 5,486,335 A | 1/1996 | Wilding et al. |
| 5,489,506 A | 2/1996 | Crane |
| 5,498,392 A | 3/1996 | Wilding et al. |
| 5,506,141 A | 4/1996 | Weinreb et al. |
| 5,541,072 A | 7/1996 | Wang et al. |
| 5,587,070 A | 12/1996 | Pall et al. |
| 5,622,831 A | 4/1997 | Liberti et al. |
| 5,629,147 A | 5/1997 | Asgari et al. |
| 5,635,358 A | 6/1997 | Wilding et al. |
| 5,637,458 A | 6/1997 | Frankel et al. |
| 5,637,469 A | 6/1997 | Wilding et al. |
| 5,639,669 A | 6/1997 | Ledley |
| 5,641,628 A | 6/1997 | Bianchi |
| 5,646,001 A | 7/1997 | Terstappen et al. |
| 5,648,220 A | 7/1997 | Bianchi et al. |
| 5,662,813 A | 9/1997 | Sammons et al. |
| 5,665,540 A | 9/1997 | Lebo |
| 5,672,481 A | 9/1997 | Minshall et al. |
| 5,676,849 A | 10/1997 | Sammons et al. |
| 5,707,799 A | 1/1998 | Hansmann et al. |
| 5,707,801 A | 1/1998 | Bresser et al. |
| 5,709,943 A | 1/1998 | Coleman et al. |
| 5,714,325 A | 2/1998 | Bianchi |
| 5,715,946 A | 2/1998 | Reichenbach |
| 5,726,026 A | 3/1998 | Wilding et al. |
| 5,731,156 A | 3/1998 | Golbus |
| 5,750,015 A | 5/1998 | Soane et al. |
| 5,750,339 A | 5/1998 | Smith |
| 5,753,014 A | 5/1998 | Van Rijn |
| 5,766,843 A | 6/1998 | Asgari et al. |
| 5,770,029 A | 6/1998 | Nelson et al. |
| 5,830,679 A | 11/1998 | Bianchi et al. |
| 5,837,115 A | 11/1998 | Austin et al. |
| 5,837,200 A | 11/1998 | Diessel et al. |
| 5,840,502 A | 11/1998 | Van Vlasselaer |
| 5,842,787 A | 12/1998 | Kopf-Sill et al. |
| 5,843,767 A | 12/1998 | Beattie |
| 5,846,708 A | 12/1998 | Hollis et al. |
| 5,856,174 A | 1/1999 | Lipshutz et al. |
| 5,858,187 A | 1/1999 | Ramsey et al. |
| 5,858,188 A | 1/1999 | Soane et al. |
| 5,858,195 A | 1/1999 | Ramsey |
| 5,858,649 A | 1/1999 | Asgari et al. |
| 5,861,253 A | 1/1999 | Asgari et al. |
| 5,863,502 A | 1/1999 | Southgate et al. |
| 5,866,345 A | 2/1999 | Wilding et al. |

(56) References Cited

U.S. PATENT DOCUMENTS

| | | |
|---|---|---|
| 5,869,004 A | 2/1999 | Parce et al. |
| 5,879,624 A | 3/1999 | Boehringer et al. |
| 5,882,465 A | 3/1999 | McReynolds |
| 5,891,651 A | 4/1999 | Roche et al. |
| 5,906,724 A | 5/1999 | Sammons et al. |
| 5,928,880 A | 7/1999 | Wilding et al. |
| 5,948,278 A | 9/1999 | Sammons et al. |
| 5,952,173 A | 9/1999 | Hansmann et al. |
| 5,957,579 A | 9/1999 | Kopf et al. |
| 5,962,234 A | 10/1999 | Golbus |
| 5,972,721 A | 10/1999 | Bruno et al. |
| 5,993,665 A | 11/1999 | Terstappen et al. |
| 6,001,229 A | 12/1999 | Ramsey |
| 6,004,762 A | 12/1999 | Tse et al. |
| 6,007,690 A | 12/1999 | Nelson et al. |
| 6,008,007 A | 12/1999 | Fruehauf et al. |
| 6,008,010 A | 12/1999 | Greenberger et al. |
| 6,013,188 A | 1/2000 | Terstappen et al. |
| 6,027,623 A | 2/2000 | Ohkawa |
| 6,030,581 A | 2/2000 | Virtanen |
| 6,033,546 A | 3/2000 | Ramsey |
| 6,036,857 A | 3/2000 | Chen et al. |
| 6,043,027 A | 3/2000 | Selick et al. |
| 6,045,990 A | 4/2000 | Baust et al. |
| 6,048,498 A | 4/2000 | Kennedy |
| 6,054,034 A | 4/2000 | Soane et al. |
| 6,056,859 A | 5/2000 | Ramsey et al. |
| 6,062,261 A | 5/2000 | Jacobson et al. |
| 6,066,449 A | 5/2000 | Ditkoff et al. |
| 6,068,818 A | 5/2000 | Ackley et al. |
| 6,071,394 A | 6/2000 | Cheng et al. |
| 6,074,827 A | 6/2000 | Nelson et al. |
| 6,083,761 A | 7/2000 | Kedar et al. |
| 6,086,740 A | 7/2000 | Kennedy |
| 6,087,134 A | 7/2000 | Saunders |
| 6,100,029 A | 8/2000 | Lapidus et al. |
| 6,100,033 A | 8/2000 | Smith et al. |
| 6,110,343 A | 8/2000 | Ramsey et al. |
| 6,120,666 A | 9/2000 | Jacobson et al. |
| 6,120,856 A | 9/2000 | Liberti et al. |
| 6,129,848 A | 10/2000 | Chen et al. |
| 6,130,098 A | 10/2000 | Handique et al. |
| 6,132,607 A | 10/2000 | Chen et al. |
| 6,143,247 A | 11/2000 | Sheppard, Jr. et al. |
| 6,143,576 A | 11/2000 | Buechler |
| 6,150,119 A | 11/2000 | Kopf et al. |
| 6,153,073 A | 11/2000 | Dubrow et al. |
| 6,156,270 A | 12/2000 | Buechler |
| 6,165,270 A | 12/2000 | Konishi et al. |
| 6,169,816 B1 | 1/2001 | Ravkin |
| 6,174,683 B1 | 1/2001 | Hahn et al. |
| 6,176,962 B1 | 1/2001 | Soane et al. |
| 6,184,029 B1 | 2/2001 | Wilding et al. |
| 6,184,043 B1 | 2/2001 | Fodstad et al. |
| 6,186,660 B1 | 2/2001 | Kopf-Sill |
| 6,197,523 B1 | 3/2001 | Rimm et al. |
| 6,200,765 B1 | 3/2001 | Murphy et al. |
| 6,210,574 B1 | 4/2001 | Sammons et al. |
| 6,210,889 B1 | 4/2001 | Drouin et al. |
| 6,210,910 B1 | 4/2001 | Walt et al. |
| 6,213,151 B1 | 4/2001 | Jacobson et al. |
| 6,214,558 B1 | 4/2001 | Shuber et al. |
| 6,235,474 B1 | 5/2001 | Feinberg et al. |
| 6,241,894 B1 | 6/2001 | Briggs et al. |
| 6,242,209 B1 | 6/2001 | Ransom et al. |
| 6,245,227 B1 | 6/2001 | Moon et al. |
| 6,251,343 B1 | 6/2001 | Dubrow et al. |
| 6,251,691 B1 | 6/2001 | Seul |
| 6,258,540 B1 | 7/2001 | Lo et al. |
| 6,265,229 B1 | 7/2001 | Fodstad et al. |
| 6,274,337 B1 | 8/2001 | Parce et al. |
| 6,274,339 B1 | 8/2001 | Moore et al. |
| 6,277,489 B1 | 8/2001 | Abbott et al. |
| 6,277,569 B1 | 8/2001 | Bittner et al. |
| 6,280,967 B1 | 8/2001 | Ransom et al. |
| 6,291,249 B1 | 9/2001 | Mahant et al. |
| 6,296,752 B1 | 10/2001 | McBride et al. |
| 6,306,578 B1 | 10/2001 | Schellenberger et al. |
| 6,309,889 B1 | 10/2001 | Cutler et al. |
| 6,315,940 B1 | 11/2001 | Nisch et al. |
| 6,315,953 B1 | 11/2001 | Ackley et al. |
| 6,319,468 B1 | 11/2001 | Sheppard, Jr. et al. |
| 6,331,274 B1 | 12/2001 | Ackley et al. |
| 6,344,326 B1 | 2/2002 | Nelson et al. |
| 6,355,491 B1 | 3/2002 | Zhou et al. |
| 6,361,958 B1 | 3/2002 | Shieh et al. |
| 6,365,362 B1 | 4/2002 | Terstappen et al. |
| 6,365,562 B1 | 4/2002 | Fischer et al. |
| 6,368,871 B1 | 4/2002 | Christel et al. |
| 6,372,432 B1 | 4/2002 | Tocque et al. |
| 6,376,181 B2 | 4/2002 | Ramsey et al. |
| 6,377,721 B1 | 4/2002 | Walt et al. |
| 6,379,884 B2 | 4/2002 | Wada et al. |
| 6,383,759 B1 | 5/2002 | Murphy et al. |
| 6,387,290 B1 | 5/2002 | Brody et al. |
| 6,387,707 B1 | 5/2002 | Seul et al. |
| 6,394,942 B2 | 5/2002 | Moon et al. |
| 6,395,232 B1 | 5/2002 | McBride |
| 6,399,023 B1 | 6/2002 | Chow |
| 6,432,630 B1 | 8/2002 | Blankenstein |
| 6,432,720 B2 | 8/2002 | Chow |
| 6,444,461 B1 | 9/2002 | Knapp et al. |
| 6,453,928 B1 | 9/2002 | Kaplan et al. |
| 6,454,938 B2 | 9/2002 | Moon et al. |
| 6,454,945 B1 | 9/2002 | Weigl et al. |
| 6,455,260 B1 | 9/2002 | Muller et al. |
| 6,465,225 B1 | 10/2002 | Fuhr et al. |
| 6,479,299 B1 | 11/2002 | Parce et al. |
| 6,488,895 B1 | 12/2002 | Kennedy |
| 6,495,340 B2 | 12/2002 | Huberman et al. |
| 6,500,612 B1 | 12/2002 | Gray et al. |
| 6,511,967 B1 | 1/2003 | Weissleder et al. |
| 6,517,234 B1 | 2/2003 | Kopf-Sill et al. |
| 6,521,188 B1 | 2/2003 | Webster |
| 6,524,456 B1 | 2/2003 | Ramsey et al. |
| 6,529,835 B1 | 3/2003 | Wada et al. |
| 6,537,505 B1 | 3/2003 | LaBudde et al. |
| 6,540,895 B1 | 4/2003 | Spence et al. |
| 6,551,841 B1 | 4/2003 | Wilding et al. |
| 6,569,626 B2 | 5/2003 | Bittner et al. |
| 6,576,478 B1 | 6/2003 | Wagner et al. |
| 6,582,904 B2 | 6/2003 | Dahm |
| 6,582,969 B1 | 6/2003 | Wagner et al. |
| 6,589,791 B1 | 7/2003 | LaBudde |
| 6,596,144 B1 | 7/2003 | Regnier et al. |
| 6,596,545 B1 | 7/2003 | Wagner et al. |
| 6,605,453 B2 | 8/2003 | Ozkan et al. |
| 6,605,454 B2 | 8/2003 | Barenburg et al. |
| 6,613,525 B2 | 9/2003 | Nelson et al. |
| 6,632,619 B1 | 10/2003 | Harrison et al. |
| 6,632,652 B1 | 10/2003 | Austin et al. |
| 6,632,655 B1 | 10/2003 | Mehta et al. |
| 6,635,163 B1 | 10/2003 | Han et al. |
| 6,637,463 B1 | 10/2003 | Lei et al. |
| 6,645,731 B2 | 11/2003 | Terstappen et al. |
| 6,664,104 B2 | 12/2003 | Pourahmadi et al. |
| 6,673,541 B1 | 1/2004 | Klein et al. |
| 6,674,525 B2 | 1/2004 | Bardell et al. |
| 6,685,841 B2 | 2/2004 | Lopez et al. |
| 6,689,615 B1 | 2/2004 | Murto et al. |
| 6,692,952 B1 | 2/2004 | Braff et al. |
| 6,743,636 B2 | 6/2004 | Chung et al. |
| 6,746,503 B1 | 6/2004 | Benett et al. |
| 6,762,059 B2 | 7/2004 | Chan et al. |
| 6,770,434 B2 | 8/2004 | Shvets et al. |
| 6,783,647 B2 | 8/2004 | Culbertson et al. |
| 6,805,841 B2 | 10/2004 | Shvets et al. |
| 6,815,664 B2 | 11/2004 | Wang et al. |
| 6,818,184 B2 | 11/2004 | Fulwyler et al. |
| 6,830,936 B2 | 12/2004 | Anderson et al. |
| 6,849,423 B2 | 2/2005 | Mutz et al. |
| 6,858,439 B1 | 2/2005 | Xu et al. |
| 6,875,619 B2 | 4/2005 | Blackburn |
| 6,878,271 B2 | 4/2005 | Gilbert et al. |

(56) References Cited

U.S. PATENT DOCUMENTS

| | | |
|---|---|---|
| 6,881,315 B2 | 4/2005 | Iida et al. |
| 6,893,836 B2 | 5/2005 | Mutz et al. |
| 6,893,881 B1 | 5/2005 | Fodstad et al. |
| 6,911,345 B2 | 6/2005 | Quake et al. |
| 6,913,605 B2 | 7/2005 | Fletcher et al. |
| 6,913,697 B2 | 7/2005 | Lopez et al. |
| 6,942,978 B1 | 9/2005 | O'Brien |
| 6,953,668 B1 | 10/2005 | Israeli et al. |
| 6,958,245 B2 | 10/2005 | Seul et al. |
| 6,960,449 B2 | 11/2005 | Wang et al. |
| 6,991,917 B2 | 1/2006 | Mutz et al. |
| 7,150,812 B2 | 12/2006 | Huang et al. |
| 8,304,230 B2 | 11/2012 | Toner et al. |
| 8,722,423 B2 | 5/2014 | Bergman et al. |
| 2001/0007749 A1 | 7/2001 | Feinberg |
| 2001/0018192 A1 | 8/2001 | Terstappen et al. |
| 2001/0036672 A1 | 11/2001 | Anderson et al. |
| 2002/0005354 A1 | 1/2002 | Spence et al. |
| 2002/0006621 A1 | 1/2002 | Bianchi et al. |
| 2002/0009738 A1 | 1/2002 | Houghton et al. |
| 2002/0012931 A1 | 1/2002 | Waldman et al. |
| 2002/0019001 A1 | 2/2002 | Light |
| 2002/0028431 A1 | 3/2002 | Julien |
| 2002/0058332 A1 | 5/2002 | Quake et al. |
| 2002/0076825 A1 | 6/2002 | Cheng et al. |
| 2002/0086329 A1 | 7/2002 | Shvets et al. |
| 2002/0090741 A1 | 7/2002 | Jurgensen et al. |
| 2002/0098535 A1 | 7/2002 | Wang et al. |
| 2002/0106715 A1 | 8/2002 | Huberman et al. |
| 2002/0108859 A1 | 8/2002 | Wang et al. |
| 2002/0110835 A1 | 8/2002 | Kumar |
| 2002/0115163 A1 | 8/2002 | Wang et al. |
| 2002/0115164 A1 | 8/2002 | Wang et al. |
| 2002/0115201 A1 | 8/2002 | Barenburg et al. |
| 2002/0119482 A1 | 8/2002 | Nelson et al. |
| 2002/0123078 A1 | 9/2002 | Seul et al. |
| 2002/0123112 A1 | 9/2002 | Wang et al. |
| 2002/0127616 A1 | 9/2002 | Burchell et al. |
| 2002/0132315 A1 | 9/2002 | Wang et al. |
| 2002/0132316 A1 | 9/2002 | Wang et al. |
| 2002/0137088 A1 | 9/2002 | Bianchi |
| 2002/0142471 A1 | 10/2002 | Handique et al. |
| 2002/0160363 A1 | 10/2002 | Mc Devitt et al. |
| 2002/0164825 A1 | 11/2002 | Chen |
| 2002/0166760 A1 | 11/2002 | Prentiss et al. |
| 2002/0172987 A1 | 11/2002 | Terstappen et al. |
| 2002/0173043 A1 | 11/2002 | Merabet et al. |
| 2003/0017514 A1 | 1/2003 | Pachmann |
| 2003/0036054 A1 | 2/2003 | Ladisch |
| 2003/0036100 A1 | 2/2003 | Fisk et al. |
| 2003/0040119 A1 | 2/2003 | Takayama et al. |
| 2003/0049563 A1 | 3/2003 | Iida et al. |
| 2003/0072682 A1 | 4/2003 | Kikinis |
| 2003/0077292 A1 | 4/2003 | Hanash et al. |
| 2003/0082148 A1 | 5/2003 | Ludwig |
| 2003/0091476 A1 | 5/2003 | Zhou et al. |
| 2003/0003528 A1 | 6/2003 | Brxostwoicz et al. |
| 2003/0113528 A1 | 6/2003 | Moya |
| 2003/0119077 A1 | 6/2003 | Ts'o et al. |
| 2003/0129676 A1 | 7/2003 | Terstappen et al. |
| 2003/0134416 A1 | 7/2003 | Yamanishi et al. |
| 2003/0153085 A1 | 8/2003 | Leary et al. |
| 2003/0159999 A1 | 8/2003 | Oakey et al. |
| 2003/0165852 A1 | 9/2003 | Schueler et al. |
| 2003/0165927 A1 | 9/2003 | Hulten et al. |
| 2003/0170631 A1 | 9/2003 | Houghton et al. |
| 2003/0170703 A1 | 9/2003 | Piper et al. |
| 2003/0175990 A1 | 9/2003 | Hayenga et al. |
| 2003/0180762 A1 | 9/2003 | Tuma et al. |
| 2003/0186889 A1 | 10/2003 | Forssmann et al. |
| 2003/0190602 A1 | 10/2003 | Pressman et al. |
| 2003/0199685 A1 | 10/2003 | Pressman et al. |
| 2003/0206901 A1 | 11/2003 | Chen |
| 2003/0232350 A1 | 12/2003 | Afar et al. |
| 2004/0005582 A1 | 1/2004 | Shipwash |
| 2004/0009471 A1 | 1/2004 | Cao |
| 2004/0018116 A1 | 1/2004 | Desmond et al. |
| 2004/0018509 A1 | 1/2004 | Bianchi |
| 2004/0018611 A1 | 1/2004 | Ward et al. |
| 2004/0019300 A1 | 1/2004 | Leonard |
| 2004/0023222 A1 | 2/2004 | Russell et al. |
| 2004/0043506 A1 | 3/2004 | Haussecker et al. |
| 2004/0048360 A1 | 3/2004 | Wada et al. |
| 2004/0053352 A1 | 3/2004 | Ouyang et al. |
| 2004/0063162 A1 | 4/2004 | Dunlay et al. |
| 2004/0063163 A1 | 4/2004 | Buffiere et al. |
| 2004/0072278 A1 | 4/2004 | Chou et al. |
| 2004/0077105 A1 | 4/2004 | Wu et al. |
| 2004/0101444 A1 | 5/2004 | Sommers et al. |
| 2004/0121343 A1 | 6/2004 | Beuchler et al. |
| 2004/0142463 A1 | 7/2004 | Walker et al. |
| 2004/0144651 A1 | 7/2004 | Huang et al. |
| 2004/0166555 A1 | 8/2004 | Braff et al. |
| 2004/0214240 A1 | 10/2004 | Cao |
| 2004/0232074 A1 | 11/2004 | Peters et al. |
| 2004/0241653 A1 | 12/2004 | Feinstein et al. |
| 2004/0241707 A1 | 12/2004 | Gao et al. |
| 2004/0245102 A1 | 12/2004 | Gilbert et al. |
| 2004/0251171 A1 | 12/2004 | Iida et al. |
| 2005/0003351 A1 | 1/2005 | Fejgin et al. |
| 2005/0014208 A1 | 1/2005 | Krehan et al. |
| 2005/0042685 A1 | 2/2005 | Albert et al. |
| 2005/0042766 A1 | 2/2005 | Ohman et al. |
| 2005/0049793 A1 | 3/2005 | Paterlini-Brechot et al. |
| 2005/0069886 A1 | 3/2005 | Sun et al. |
| 2005/0092662 A1 | 5/2005 | Gilbert et al. |
| 2005/0100951 A1 | 5/2005 | Pircher |
| 2005/0118591 A1 | 6/2005 | Tamak et al. |
| 2005/0121604 A1 | 6/2005 | Mueth et al. |
| 2005/0123454 A1 | 6/2005 | Cox |
| 2005/0124009 A1 | 6/2005 | van Weeghel et al. |
| 2005/0129582 A1 | 6/2005 | Breiclford et al. |
| 2005/0136551 A1 | 6/2005 | Mpock |
| 2005/0142663 A1 | 6/2005 | Pathasarathy et al. |
| 2005/0145497 A1 | 7/2005 | Gilbert et al. |
| 2005/0147977 A1 | 7/2005 | Koo et al. |
| 2005/0153329 A1 | 7/2005 | Hakansson et al. |
| 2005/0153342 A1 | 7/2005 | Chen |
| 2005/0164158 A1 | 7/2005 | Wang et al. |
| 2005/0170373 A1 | 8/2005 | Monforte et al. |
| 2005/0170418 A1 | 8/2005 | Moreland et al. |
| 2005/0175505 A1 | 8/2005 | Cantor et al. |
| 2005/0175981 A1 | 8/2005 | Voldman et al. |
| 2005/0175996 A1 | 8/2005 | Chen |
| 2005/0181353 A1 | 8/2005 | Rao et al. |
| 2005/0181463 A1 | 8/2005 | Rao et al. |
| 2005/0191636 A1 | 9/2005 | Hahn |
| 2005/0207940 A1 | 9/2005 | Butler et al. |
| 2005/0211556 A1 | 9/2005 | Childers et al. |
| 2005/0214855 A1 | 9/2005 | Wagner et al. |
| 2005/0236314 A1 | 10/2005 | Neyer et al. |
| 2005/0239101 A1 | 10/2005 | Sukumar et al. |
| 2005/0244843 A1 | 11/2005 | Chen et al. |
| 2005/0249635 A1 | 11/2005 | Okun et al. |
| 2005/0250111 A1 | 11/2005 | Xie et al. |
| 2005/0250199 A1 | 11/2005 | Anderson et al. |
| 2005/0252840 A1 | 11/2005 | Arnold et al. |
| 2005/0255001 A1 | 11/2005 | Padmanabhan et al. |
| 2005/0262577 A1 | 11/2005 | Guelly et al. |
| 2005/0266433 A1 | 12/2005 | Kapur et al. |
| 2005/0272049 A1 | 12/2005 | Banerjee et al. |
| 2005/0272103 A1 | 12/2005 | Chen |
| 2005/0282196 A1 | 12/2005 | Costa |
| 2005/0282220 A1 | 12/2005 | Prober et al. |
| 2005/0282293 A1 | 12/2005 | Cosman et al. |
| 2006/0000772 A1 | 1/2006 | Sano et al. |
| 2006/0008807 A1 | 1/2006 | O'Hara et al. |
| 2006/0008824 A1 | 1/2006 | Ronaghi et al. |
| 2006/0019235 A1 | 1/2006 | Soen et al. |
| 2006/0035386 A1 | 2/2006 | Hattori et al. |
| 2006/0051265 A1 | 3/2006 | Mohamed et al. |
| 2006/0051775 A1 | 3/2006 | Bianchi |
| 2006/0060767 A1 | 3/2006 | Wang et al. |
| 2006/0121624 A1 | 6/2006 | Huang et al. |

(56) References Cited

U.S. PATENT DOCUMENTS

| | | | |
|---|---|---|---|
| 2006/0128006 A1 | 6/2006 | Gerhardt et al. | |
| 2006/0134599 A1 | 6/2006 | Toner et al. | |
| 2006/0160243 A1 | 7/2006 | Tang et al. | |
| 2006/0223178 A1 | 10/2006 | Barber et al. | |
| 2006/0252054 A1 | 11/2006 | Lin et al. | |
| 2006/0252087 A1 | 11/2006 | Tang et al. | |
| 2007/0026381 A1 | 2/2007 | Huang et al. | |
| 2007/0026413 A1 | 2/2007 | Toner et al. | |
| 2007/0026414 A1 | 2/2007 | Fuchs et al. | |
| 2007/0026415 A1 | 2/2007 | Fuchs et al. | |
| 2007/0026416 A1 | 2/2007 | Fuchs et al. | |
| 2007/0026417 A1 | 2/2007 | Fuchs et al. | |
| 2007/0026418 A1 | 2/2007 | Fuchs et al. | |
| 2007/0026419 A1 | 2/2007 | Fuchs et al. | |
| 2007/0026469 A1 | 2/2007 | Fuchs et al. | |
| 2007/0059680 A1 | 3/2007 | Kapur et al. | |
| 2007/0059683 A1 | 3/2007 | Barber et al. | |
| 2007/0059716 A1 | 3/2007 | Balis et al. | |
| 2007/0059718 A1 | 3/2007 | Toner et al. | |
| 2007/0059719 A1 | 3/2007 | Grisham et al. | |
| 2007/0059774 A1 | 3/2007 | Grisham et al. | |
| 2007/0059781 A1 | 3/2007 | Kapur et al. | |
| 2007/0099207 A1 | 5/2007 | Fuchs et al. | |
| 2007/0160503 A1 | 7/2007 | Sethu et al. | |
| 2007/0196820 A1 | 8/2007 | Kapur et al. | |
| 2007/0202525 A1 | 8/2007 | Quake et al. | |
| 2008/0023399 A1 | 1/2008 | Inglis et al. | |
| 2008/0038733 A1 | 2/2008 | Bischoff et al. | |
| 2009/0305236 A1* | 12/2009 | Boehmer | G01N 33/5002 435/6.11 |
| 2010/0035246 A1* | 2/2010 | Lushi | C12Q 1/6879 435/6.11 |

FOREIGN PATENT DOCUMENTS

| | | |
|---|---|---|
| EP | 0094193 | 11/1983 |
| EP | 0057907 | 12/1986 |
| EP | 0405972 | 1/1991 |
| EP | 0430402 | 6/1991 |
| EP | 0444115 | 9/1991 |
| EP | 0637996 | 2/1995 |
| EP | 0689051 | 12/1995 |
| EP | 0739240 | 10/1996 |
| EP | 0549709 | 1/1997 |
| EP | 0791659 | 8/1997 |
| EP | 0500727 | 1/1998 |
| EP | 0919812 | 6/1999 |
| EP | 0920627 | 6/1999 |
| EP | 0970365 | 1/2000 |
| EP | 1198595 | 4/2002 |
| EP | 1221342 | 7/2002 |
| EP | 1262776 | 12/2002 |
| EP | 1328803 | 7/2003 |
| EP | 1338894 | 8/2003 |
| EP | 1409727 | 4/2004 |
| EP | 1413346 | 4/2004 |
| EP | 1418003 | 5/2004 |
| EP | 1462800 | 9/2004 |
| EP | 1483052 | 12/2004 |
| EP | 1485713 | 12/2004 |
| EP | 1539350 | 6/2005 |
| EP | 1561507 | 8/2005 |
| FR | 2659347 | 9/1991 |
| GB | 2238619 | 6/1991 |
| GB | 2239311 | 6/1991 |
| JP | 200537346 | 2/2005 |
| WO | WO1985002201 | 5/1985 |
| WO | WO1986006170 | 10/1986 |
| WO | WO1990006509 | 6/1990 |
| WO | WO1991007660 | 5/1991 |
| WO | WO1991007661 | 5/1991 |
| WO | WO1991008304 | 6/1991 |
| WO | WO1991013338 | 9/1991 |
| WO | WO1991016452 | 10/1991 |
| WO | WO1992005185 | 4/1992 |
| WO | WO1993022053 | 11/1993 |
| WO | WO1993022055 | 11/1993 |
| WO | WO1994029707 | 12/1994 |
| WO | WO1996032467 | 10/1996 |
| WO | WO1997046882 | 12/1997 |
| WO | WO1998002528 | 1/1998 |
| WO | WO1998008931 | 3/1998 |
| WO | WO1998010267 | 3/1998 |
| WO | WO1998012539 | 3/1998 |
| WO | WO1998022819 | 5/1998 |
| WO | 98/26284 * | 6/1998 |
| WO | WO1998031839 | 7/1998 |
| WO | WO1998040746 | 9/1998 |
| WO | WO1998057159 | 12/1998 |
| WO | WO1999009042 | 2/1999 |
| WO | WO1999031503 | 6/1999 |
| WO | WO1999044064 | 9/1999 |
| WO | WO1999061888 | 12/1999 |
| WO | WO2000000816 | 1/2000 |
| WO | WO2000037163 | 6/2000 |
| WO | WO2000062931 | 10/2000 |
| WO | WO2001035071 | 5/2001 |
| WO | WO2001037958 | 5/2001 |
| WO | WO2001051668 | 7/2001 |
| WO | WO2001071026 | 9/2001 |
| WO | WO2001081621 | 11/2001 |
| WO | WO2002007302 | 1/2002 |
| WO | WO2002008751 | 1/2002 |
| WO | WO2002012896 | 2/2002 |
| WO | WO2002028523 | 4/2002 |
| WO | WO2002030562 | 4/2002 |
| WO | WO2002031506 | 4/2002 |
| WO | WO2002043866 | 6/2002 |
| WO | WO2002044318 | 6/2002 |
| WO | WO2002044319 | 6/2002 |
| WO | WO2002044689 | 6/2002 |
| WO | WO2002073204 | 9/2002 |
| WO | WO2003000418 | 1/2003 |
| WO | WO2003018198 | 3/2003 |
| WO | WO2003018757 | 3/2003 |
| WO | WO2003019141 | 3/2003 |
| WO | WO2003023057 | 3/2003 |
| WO | WO2003031938 | 4/2003 |
| WO | WO2003035894 | 5/2003 |
| WO | WO2003035895 | 5/2003 |
| WO | WO2003044224 | 5/2003 |
| WO | WO2003069421 | 8/2003 |
| WO | WO2003071277 | 8/2003 |
| WO | WO2003071278 | 8/2003 |
| WO | WO2003079006 | 9/2003 |
| WO | WO2003085379 | 10/2003 |
| WO | WO2003093795 | 11/2003 |
| WO | WO2004004906 | 1/2004 |
| WO | WO2004015411 | 2/2004 |
| WO | WO2004024327 | 3/2004 |
| WO | WO2004025251 | 3/2004 |
| WO | WO2004029221 | 4/2004 |
| WO | WO2004037374 | 5/2004 |
| WO | WO2004044236 | 5/2004 |
| WO | WO2004051230 | 6/2004 |
| WO | WO2004056978 | 7/2004 |
| WO | WO2004076643 | 9/2004 |
| WO | WO2004101762 | 11/2004 |
| WO | WO2004113877 | 12/2004 |
| WO | WO2005028663 | 3/2005 |
| WO | WO2005042713 | 5/2005 |
| WO | WO2005043121 | 5/2005 |
| WO | WO2005047529 | 5/2005 |
| WO | WO2005049168 | 6/2005 |
| WO | WO2005058937 | 6/2005 |
| WO | WO2005061075 | 7/2005 |
| WO | WO2005068503 | 7/2005 |
| WO | WO2005084374 | 9/2005 |
| WO | WO2005084380 | 9/2005 |
| WO | WO2005085861 | 9/2005 |
| WO | WO2005089253 | 9/2005 |
| WO | WO2005091756 | 10/2005 |
| WO | WO2005098046 | 10/2005 |

(56) References Cited

FOREIGN PATENT DOCUMENTS

| WO | WO2005108621 | 11/2005 |
|---|---|---|
| WO | WO2005108963 | 11/2005 |
| WO | WO2005109238 | 11/2005 |
| WO | WO2005116264 | 12/2005 |
| WO | WO2005121362 | 12/2005 |
| WO | WO2006012820 | 2/2006 |
| WO | WO2006035846 | 4/2006 |
| WO | WO2006037561 | 4/2006 |
| WO | WO2006076567 | 7/2006 |
| WO | WO2006078470 | 7/2006 |
| WO | WO2006108087 | 10/2006 |
| WO | WO2006108101 | 10/2006 |
| WO | WO2006133208 | 12/2006 |
| WO | WO2007035414 | 3/2007 |
| WO | WO2007035498 | 3/2007 |
| WO | WO2007035585 | 3/2007 |

OTHER PUBLICATIONS

"Micromechanics Imitate Blood Vessels," Design News 15 (Mar. 22, 1993).
Adinolfi et al., "Gene Amplification to Detect Fetal Nucleated Cells in Pregnant Women," Lancet 2(8658):328-329 (1989).
Adinolfi, "On a Non-Invasive Approach to Prenatal Diagnosis Based on the Detection of Fetal Nucleated Cells in Maternal Blood Samples," Prenat Diagn. 11:799-804 (1991).
Ahn, et al. A fully integrated micromachined magnetic particle separator. Journal of Microelectromechanical Systems. 1996; 5(3):151-158.
Al Saadi, "Cystic Hygroma Cells as Source for Prenatal Diagnosis," Am J Hum Genet. Supplemental to 45(4):A252-(0990); (1989).
Al-Mufti et al., "Distribution of fetal and embryonic hemoglobins in fetal erythroblasts enriched from maternal blood," Haematologica 86(4):357-362 (2001).
Alvarez, "Morphology and Physiopathology of the Human Placenta," Obstet Gynecol. 23:813-817;819-825 (1964).
Anderson et al., "Simultaneous Fluorescence-Activated Cell Sorter Analysis of Two Distinct Transcriptional Elements within a Single Cell Using Engineered Green Fluorescent Proteins," Proc Natl Acad Sci USA 93:8508-8511 (1996).
Archer et al., "Cell Reactions to Dielectrophoretic Manipulation," Biochem Biophys Res Comm. 257:687-698 (1999).
Armani et al., "Re-configurable Fluid Circuits by PDMS Elastomer Micromachining," Proc 12th International Conference on MEMS 17-21:222-227 (1999).
Associate Press "Blood Test May Erase Risk of Amniocentesis," The Worcester Telegram & Gazette A7 (Oct. 9, 1991).
Authorized Officer L. Smith-Hewitt. Extended European Search Report in European Application No. 12169261.0, dated Jul. 23, 2012, 6 pages.
Bartley et al., "Adrenal Hypoplasia, Mental Retardation, Microcephaly, Short Stature, and Small Testes in a Male with a Xp21 Deletion of LOCI DXS28 (C7), DXS68 (L1.4) and DXS67 (B24)," Pediatr Res. 139A (1989). (Abstract).
Basch et al., "Cell Separation Using Positive Immunoselective Techniques," J Immunol Methods 56:269-280 (1983).
Bauer, "Advances in Cell Separation: Recent Developments in Counterflow Centrifugal Elutriation and Continuous Flow Cell Separation," J Chromatogr B 722:55-69 (1999).
Becker et al., "Fabrication of Microstructures with High Aspect Ratios and Great Structural Heights by Synchrotron Radiation Lithography, Galvanoforming, and Plastic Moulding (LIGA Process)," Microelectronic Eng. 4:35-56 (1986).
Becker et al., "Planar Quartz Chips with Submicron Channels for Two-Dimensional Capillary Electrophoresis Applications," J Micromech Microeng. 8:24-28 (1998).
Beebe et al., "Functional Hydrogel Structures for Autonomous Flow Control Inside Microfluidic Channels," Nature 404:588-590 (2000).

Benincasa et al., "Cell Sorting by One Gravity SPLITT Fractionation," Anal Chem. 77:5294-5301 (2005).
Ben-Yoseph et al., "Diagnosis and Carrier Detection of Father Disease (Ceramidase Deficiency) in Plasma and Leukocytes," Pediatr Res. 139A-(817); (1989).
Berenson et al., "Antigen CD34.sup.+ Marrow Cells Engraft Lethally Irradiated Baboons," J Clin Invest. 81:951-955 (1988).
Berenson et al., "Cellular Immunoabsorption Using Monoclonal Antibodies," Transplantation 38:136-143 (1984).
Berenson et al., "Positive Selection of Viable Cell Populations Using Avidin-Biotin Immunoadsorption," J Immunol Methods 91:11-19 (1986).
Berg H.C., Random Walks in Biology, Princeton University Press: Princeton, NJ. Ch. 4, pp. 48-64 (1993).
Berger et al., "Design of a microfabricated magnetic cell separator," Electrophoresis 22:3883-3892 (2001).
Beroud et al., "Prenatal diagnosis of spinal muscular atrophy by genetic analysis of circulating fetal cells," Lancet 361:1013-1014 (2003).
Bertero et al., "Circulating 'Trophoblast' Cells in Pregnancy Have Maternal Genetic Markers," Prenat Diagn. 8:585-590 (1988).
Bianchi et al., "Demonstration of Fetal Gene Sequences in Nucleated Erythrocytes Isolated from Maternal Blood," Am. J. Hum. Genet. Supplement to 45(4):A252 (0991) (1989).
Bianchi et al., "Direct Hybridization to DNA from Small Numbers of Flow-Sorted Nucleated Newborn Cells," Cytometry 8:197-202 (1987).
Bianchi et al., "Fetal Nucleated Erythrocytes (FNRBC) in Maternal Blood: Erythroid-Specific Antibodies Improve Detection," Am J Hum Genet. Supplemental to 51:996 (1992). (Abstract).
Bianchi et al., "Isolation of Fetal DNA from Nucleated Erythrocytes in Maternal Blood," Proc Natl Acad Sci USA 87:3279-3283 (1990).
Bianchi et al., "Isolation of Male Fetal DNA from Nucleated Erythrocytes (NRNC) in Maternal Blood," Pediatr Res. 139A-(818); (1989). (Abstract).
Bianchi et al., "PCR Quantitation of Fetal Cells in Maternal Blood in Normal and Aneuploid Pregnancies" Am. J. Hum. Genet. 61:822-829, 1997.
Bianchi et al., "Possible Effect of Gestational Age on the Detection of Fetal Nucleated Erythrocytes in Maternal Blood," Prenat Diagn. 11:523-528 (1991).
Bick et al., "Prenatal Diagnosis and Investigation of a Fetus with Chondrodysplasia Punctata, Ichthyosis and Kallmann Syndrome due to an Xp Deletion," Prenat Diagn. 12:19-29 (1992).
Bickers et al., "Fetomaternal Transfusion Following Trauma," Obstet Gynecol. 61:258-259 (1983).
Bigbee et al., "Monoclonal Antibodies Specific for the M- and N-Forms of Human Glycophorin A," Mol Immunol. 20:1353-1362 (1983).
Black et al., "Complex Mosaicism on Chorionic Sampling Confirmed Postnatally," Am J Hum Genet. Supplemental to 45(4):A252-(0993); (1989). (Abstract).
Bodurtha et al., "Genetic Analysis of Fat Deposition in 11-Year Old Twins." Pediatr Res. 139A-(819); (1989). (Abstract).
Boehm et al., "Analysis of Defective Dystrophin Genes with cDNA Probes: Rearrangement Polymorphism, Detection of Deletions in Carrier Females, and Lower Than Expected Frequency of Carrier Mothers in Isolated Cases of Deletions," Pediatr Res. 139A-(820); (1989). (Abstract).
Bohmer et al., "Differential Development of Fetal and Adult Haemoglobin Profiles in Colony Culture: Isolation of Fetal Nucleated Red Cells by Two-Colour Fluorescence Labelling," Br J Haematol. 103:351-360 (1998).
Bousse et al., "Micromachined Multichannel Systems for the Measurement of Cellular Metabolism," Sens Actuators B Chem. 20:145-150 (1994).
Boyer et al., "Enrichment of Erythrocytes of Fetal Origin from Adult-Fetal Blood Mixtures via Selective Hemolysis of Adult Blood Cells: An Aid to Antenatal Diagnosis of Hemoglobinopathies," Blood 47:883-897 (1976).
Brison et al., "General Method for Cloning Amplified DNA by Differential Screening with Genomic Probes," Mol Cell Biol. 2:578-587 (1982).

(56) References Cited

OTHER PUBLICATIONS

Brizot et al. "Maternal serum hCG and fetal nuchal translucency thickness for the prediction of fetal trisomies in the first trimester of pregnancy," British J. Obstetrics and Gynaecology 102:127-132 (1995).
Brizot et al., "Maternal Serum Pregnancy-Associated Plasma Protein A and Fetal Nuchal Translucency Thickness for the Prediction of Fetal Trisomies in Early Pregnancy," Obstet Gynecol. 84(6):918-922 (1994).
Brody et al., "Biotechnology at Low Reynolds Numbers," Biophys J. 71:3430-3441 (1996).
Brody et al., "Deformation and Flow of Red Blood Cells in a Synthetic Lattice: Evidence for an Active Cytoskeleton." Biophys J. 68:2224-2232 (1995).
Bulmer and Johnson, "Antigen Expression by Trophoblast Populations in the Human Placenta and Their Possible Immunobiological Relevance," Placenta 6:127-140 (1985).
Butterworth et al., "Human Cytotrophoblast Populations Studied by Monoclonal Antibodies Using Single and Double Biotin-Avidin-Peroxidase Immunocytochemistry," J Histochem Cytochem. 33:977-983 (1985).
Caggana, M. Microfabricated deviCes for sparse cell isolation. CNF Project #905-00. Cornell NanoScale Facility. 2003; pp. 38-39.
Caggana, M. Microfabricated devices for sparse cell isolation. CNF Project #905-00. Cornell NanoScale Facility. 2004-2005; pp. 32-33.
Cai et al., "A New TATA Box Mutation Detected at Prenatal Diagnosis for .beta.-Thalassemia," Am J Hum Genet. 45:112-114 (1989).
Cai et al., "Rapid Prenatal Diagnosis of .beta. Thalassemia Using DNA Amplification and Nonradioactive Probes," Blood 73:372-374 (1989).
Calin et al., "A microRNA signature Associated with prognosis and progression in chronic lymphocytic leukemia," N Engl J Med. 353:1793-1801 (2005).
Carlson et al., "Self-Sorting of White Blood Cells in a Lattice," Phys Rev Lett. 79:2149-2152 (1997).
Chamberlain et al., "Deletion Screening of the Duchenne Muscular Dystrophy Locus via Multiplex DNA Amplification," Nucleic Acids Res. 16:11141-11156 (1988).
Chang et al., "Biomimetic technique for adhesion-based collection and separation of cells in a microfluidic channel," Lab Chip. 5:64-73 (2005).
Charnas et al., "Prader Willi Syndrome in a Patient with Septo-Optic Dysplasia," Pediatr Res. 139A (821); (1989). (Abstract).
Charnas, et al. Prader Willi Syndrome in a Patient with Septo-Optic Dysplasia. Pediatric Research Apr. 1989: 139A-821.
Cheung et al., "Prenatal Diagnosis of Sickle Cell Anaemia and Thalassaemia by Analysis of Fetal Cells in Maternal Blood," Nat Genet. 14(3):264-8 (1996).
Chinn et al., "Reactive Ion Etching for Submicron Structures," J Vac Sci Technol. 19:1418-1422 (1981).
Chiu et al., "Patterned Deposition of Cells and Proteins onto Surfaces by Using Three-Dimensional Microfluidic Systems," Proc Natl Acad Sci USA 2408-2413 (2000).
Choolani et al., "Characterization of First Trimester Fetal Erythroblasts for Non-Invasive Prenatal Diagnosis," Mol Hum Reprod. 9:227-235 (2003).
Chou et al., "Sorting by Diffusion: An Asymmetric Obstacle Course for Continuous Molecular Separation," Proc Natl Acad Sci USA 96:13762-13765 (1999).
Chou et al., A Microfabricated Device for Sizing and Sorting DNA Molecules. Proc Natl Acad Sci USA 96:11-13 (1999).
Christel et al. "High Aspect Ratio Silicon Microstructures for Nucleic Acid Extraction. Solid-State Sensor and Actuator Workshop," Hilton Head, SC, Jun. 8-11, 1998, 363-366.
Christensen et al., "Fetal Cells in Maternal Blood: A Comparison of Methods for Cell Isolation and Identification," Fetal Diagn Ther. 20:106-112 (2005).
Christensen, et al. Sensitivity and specificity of the identification of fetal cells in maternal blood by combined staining with antibodies against beta-, gamma- and epsilon-globin chains. Fetal Diagn Ther. 2003;18(6):479-84. (Abstract only).
Chueh and Golbus, "Prenatal Diagnosis Using Fetal Cells from the Maternal Circulation," West J Med. 159:308-311 (1993).
Chueh and Golbus, "Prenatal Diagnosis Using Fetal Cells in the Maternal Circulation," Semin Perinatol Med. 14:471-482 (1990).
Chueh and Golbus, "The Search for Fetal Cells in the Maternal Circulation," J Perinatol 19:411-420 (1991).
Clayton et al., "Fetal Erythrocytes in the Maternal Circulation of Pregnant Women," Obstetr Gynecol. 23:915-919 (1964).
Cohen and Zuelzer, "Mechanisms of Isoimmunization II. Transplacental Passage and Postnatal Survival of Fetal Erythrocytes in Heterospecific Pregnancies," Blood 30:796-804 (1967).
Covone et al., "Analysis of Peripheral Maternal Blood Samples for the Presence of Placenta-Derived Cells Using Y-Specific Probes and McAb H315," Prenat Diagn. 8:591-607 (1988).
Covone et al., "Trophoblast Cells in Peripheral Blood from Pregnant Women," Lancet 2(8407):841-843 (1984).
Cremer et al., "Detection of Chromosome Aberrations in Metaphase and Interphase Tumor Cells by In Situ Hybridization Using Chromosome-Specific Library Probes," Hum Genet. 80:235-246 (1988).
Cremer et al., "Detection of Chromosome Aberrations in the Human Interphase Nucleus by Visualization of Specific Target DNAs with Radioactive and Non-Radioactive In Situ Hybridization Techniques: Diagnosis of Trisomy 18 with Probe L1.84," Hum Genet. 74:346-352 (1986).
Das et al., "Dielectrophoretic Segregation of Different Human Cell Types on Microscope Slides," Anal Chem. 77:2708-2719 (2005).
de Kretser et al., "The Separation of Cell Populations Using Monoclonal Antibodies Attached to Sepharose," Tissue Antigens 16:317-324 (1980).
Delamarche et al., "Microfluidic Networks for Chemical Patterning of Substrates: Design and Application to Bioassays," J Am Chem Soc. 120:500-508 (1998).
Delamarche et al., "Patterned Delivery of Immunoglobulins to Surfaces Using Microfluidic Networks," Science 276:779-781 (1997).
Deng et al., "Manipulation of Magnetic Microbeads in Suspension Using Micromagnetic Systems Fabricated with Soft Lithography," Appl Phys Lett. 78(12):1775-1777 (2001).
Deshmukh et al., "Continuous Micromixer with Pulsatile Micropumps," Solid-State Sensor and Actuator Workshop, Hilton Head Island, South Carolina; Jun. 4-8, 2000.
DiLella et al., "Screening for Phenylketonuria Mutations by DNA Amplification with the Polymerase Chain Reaction," Lancet 1(8584):497-499 (1988).
Douglas et al., "Trophoblast in the Circulating Blood During Pregnancy," Am J Obstet Gynecol. 78:960-973 (1959).
Doyle et al., "Self-Assembled Magnetic Matrices for DNA Separation Chips," Science 295:2237 (2002).
Duke et al., "Microfabricated sieve for the continuous sorting of macromolecules" Phys Rev Lett. 80:1552-1555 (1998).
Duna et al., "Electroosmotic Flow Control in Complex Microgeometries," J Microelectromech Syst. 11:36-44 (2002).
Eigen et al., "Sorting Single Molecules: Application to Diagnostics and Evolutionary Biotechnology," Proc Nat Acad Sci USA 91:5740-5747 (1994).
Elias, "Prenatal Blood Test Can Signal Genetic Disorders," The Boston Globe. Oct. 8, 1991.
Evans et al., "The Bubble Spring and Channel (BSAC) Valve: An Actuated, Bi-Stable Mechanical Valve for In-Plane Fluid Control," Transducers '99, 1122-1125; Sendai, Japan; Jun. 7-10, 1999.
Farber et al., "Demonstration of Spontaneous XX/XY Chimerism by DNA Fingerprinting," Hum Genet. 82:197-198 (1989).
Farooqui and Evans, "Microfabrication of Submicron Nozzles in Silicon Nitride," J Microelectromech Syst. 1(2):86-88 (1992).
Fibach et al., "Proliferation and Maturation of Human Erythroid Progenitors in Liquid Culture," Blood 73:100-103 (1989).
Fiedler et al., "Dielectrophoretic Sorting of Particles and Cells in a Microsystem," Anal Chem. 70:1909-1915 (1998).
Forestier et al., "Hematological Values of 163 Normal Fetuses between 18 and 30 Weeks of Gestation," Pediatr Res. 20(4):342-346 (1986).

(56) References Cited

OTHER PUBLICATIONS

Freemantle, "Downsizing Chemistry: Chemical Analysis and Synthesis on Microchips Promise a Variety of Potential Benefits," Chem Eng News 27-36 (1999).
Fu et al., "A Microfabricated Fluorescence-Activated Cell Sorter," Nat Biotechnol. 17:1109-1111 (1999).
Fu et al., "An Integrated Microfabricated Cell Sorter," Anal Chem. 74:2451-2457 (2002).
Fuhr et al., "Biological Application of Microstructures," Top Cuff Chem. 194:83-116 (1997).
Galbraith et al., "Demonstration of Transferrin Receptors on Human Placental Trophoblast," Blood 55:240-242 (1980).
Ganshirt-Ahlert et al., "Magnetic Cell Sorting and the Transferrin Receptor as Potential Means of Prenatal Diagnosis from Maternal Blood," Am J Obstet Gynecol. 166:1350-1355 (1992).
Ganshirt-Ahlert et al., "Noninvasive Prenatal Diagnosis: Triple Density Gradient, Magnetic Activated Cell Sorting and FISH prove to Be an Efficient and Reproducible Method for Detection of Fetal Aneuploidies from Maternal Blood," 182 Amer Soc Hum Gene; 1992.
Gasparini et al., "First-Trimester Prenatal Diagnosis of Cystic Fibrosis Using the Polymerase Chain Reaction: Report of Eight Cases," Prenat Diagn. 9:349-355 (1989).
GB Office Action for Application No. GB0612649.4 dated Aug. 12, 2010 (7 pages).
Giddings, "Chemistry: 'Eddy' Diffusion in Chromatography," Nature 184(4683):357-358 (1959).
Giddings, "Field-Flow Fractionation: Analysis of Macromolecular, Colloidal, and Particulate Materials," Science 260:1456-1465 (1993).
Giddings, Unified Separation Science, New York:John Wiley & Sons, Inc., Cover Page & Table of Contents only (1991).
Goldberg, "Test reveals gender early in pregnancy ethicists fear use in sex selection" The Boston Globe, Jun. 27, 2005.
Graham, "Efficiency comparison of two preparative mechanisms for magnetic separation of erythrocytes from whole blood", J Appl Phys. 52:2578-2580 (1981).
Greaves et al., "Expression of the OKT Monoclonal Antibody Defined Antigenic Determinants in Malignancy," Int J Immunopharmacol. 3(3):283-299 (1981).
Guerin et al., "A New TaqI BO Variant Detected with the p49 Probe on the Human Y Chromosome," Nucleic Acids Res. 16:7759 (1988).
Hall et al., "Isolation and Purification of CD34+ Fetal Cells from Maternal Blood," Am J Hum Genet. Supplemental to 51(4):1013 (1992). (Abstract).
Hames et al., Nucleic Acid Hybridisation: A Practical Approach, Oxford: IRL Press Limited, 190-193 (1985).
Han et al., "Separation of Long DNA Molecules in a Microfabricated Entropic Trap Array," Science 288:1026-1029 (2000).
Handyside et al., "Biopsy of Human Preimplantation Embryos and Sexing by DNA Amplification," Lancet. 1(8634):347-349 (1989).
Hartmann et al., "Gene expression profiling of single cells on large-scale oligonucleotide arrays," Nucleic Acids Research. 2006; 34(21): e143. (11 pages).
Hatch et al., "A rapid diffusion immunoassay in a T-sensor" Nat Biotechnol. 19:461-465 (2001).
Hennerbichler et al., "Detection and relocation of cord blood nucleated red blood cells by laser scanning cytometry," Cytometry 48:87-92 (2002).
Henning, "Microfluidic MEMS," Proc. IEEE Aerospace Conference 1:471-486 (1998).
Herzenberg et al., "Fetal Cells in the Blood of Pregnant Women: Detection and Enrichment by Fluorescence-Activated Cell Sorting," Proc Nat Acad Sci USA 76(3):1453-1455 (1979).
Holzgreve et al., "Fetal Cells in the Maternal Circulation," J Reprod Med. 37:410-418 (1992).
Huang et al., "A DNA Prism for High-Speed Continuous Fractionation of Large DNA Molecules," Nat. Biotechnol. 20:1048-1051 (2002).
Huang et al., "Continuous Particle Separation Through Deterministic Lateral Displacement," Science 304:987-990 (2004).
Huang et al., "Electric Manipulation of Bioparticles and Macromolecules on Microfabricated Electrodes," Anal Chem. 73(7):1549-1559 (2001).
Huang et al., "Role of Molecular Size in Ratchet Fractionation," Phys Rev Lett. 89:178301-1-4 (2002).
Huh et al., "Gravity-Driven Microhydrodynamics-Based Cell Sorter (microHYCS) for Rapid, Inexpensive, and Efficient Cell Separation and Size-Profiling," 2nd Annual International IEEE-EMBS Special Topic Conference on Microtechnologies in Medicine and Biology Poster 180:466-469 (2002).
Huie et al., "Antibodies to human fetal erythroid cells from a nonimmune phage antibody library," Proc Nat Acad Sci USA 2001; 98(5): 2682-7.
Hviid, "In-Cell PCR Method for Specific Genotyping of Genomic DNA from One Individual in a Mixture of Cells from Two Individuals: A Model Study with Specific Relevance to Prenatal Diagnosis Based on Fetal Cells in Maternal Blood." Clin Chem. 48(12):2115-2123 (2002).
International Preliminary Report on Patentability of International Application No. PCT/US2006/036061 (dated Mar. 27, 2008).
International Search Report (PCT/US05/07058) unofficial copy.
Iverson et al., "Detection and Isolation of Fetal Cells from Maternal Blood Using the Fluorescence-Activated Cell Sorter (FACS)," Prenat Diagn. 1:61-73 (1981).
Ivker, "Direct Observation of Reptation in Artificial Gel Environments," Bachelor of Arts thesis, Princeton University. Spring 1991.
Jan and Herzenberg, "Fetal Erythrocytes Detected and Separated from Maternal Blood by Electronic Fluorescent Cell Sorter," Texas Rep Biol Med. 31:575 (1973). (Abstract).
Jansen et al., "The Effect of Chorionic Villus Sampling on the Number of Fetal Cells Isolated From Maternal Blood and on Maternal Serum Alpha-fetoprotein Levels" Prenat Diagn. 17:953-959 (1997).
Jayasena et al., "Aptamers: An emerging class of molecules that rival antibodies in diagnostics," Clinical Chemistry, 1999, vol. 45, pp. 1628-1650.
Jeon et al., "Generation of Solution and surface Gradients Using Microfluidic Systems," Langmuir 16:8311-8316 (2000).
Kamholz et al., "Quantitative Analysis of Molecular Interaction in a Microfluidic Channel: the T-Sensor," Anal Chem. 71:5340-5347 (1999).
Kan et al., "Concentration of Fetal Red Blood Cells From a Mixture of Maternal and Fetal Blood by Anti-i Serum—An Aid to Prenatal Diagnosis of Hemoglobinopathies," Blood 43:411-415 (1974).
Kawata et al., "Transcriptional Control of HLA-A,B,C Antigen in Human Placental Cytotrophoblast Isolated Using Trophoblast- and HLA-Specific Monoclonal Antibodies and the Fluorescence-Activated Cell Sorter," J Exp Med. 160:633-651 (1984).
Kelly, "A Simpler, Safer Blood Test for Birth Defects," USA Today. (Nov. 14, 1989):1D.
Kenis et al., "Microfabrication Inside Capillaries Using Multiphase Laminar Flow Patterning," Science 285:83-85 (1999).
Kim et al., "Polymer Microstructures Formed by Moulding in Capillaries," Nature 376:581-584 (1995).
Klinger et al., "Rapid Detection of Chromosome Aneuploidies in Uncultured Amniocytes by Using Fluorescence in Situ Hybridization (FISH)," Am J Hum Genet. 51:55-65 (1992).
Kogan et al., "An Improved Method for Prenatal Diagnosis of Genetic Diseases by Analysis of Amplified DNA Sequences: Application to Hemophilia A," N Engl J Med. 317(16):985-990 (1987).
Kohn et al., "Elevated Maternal Serum Human Chorionic Gonadotropin Associated with a Chromosomal Deletion," Prenat Diagn. 12:853-854 (1992).
Krabchi et al., "Quantification of all fetal nucleated cells in maternal blood between the 18th and 22nd weeks of preganancy using molecular cytogenetic techniques," Clin. Genet. 2001, 60:145-150.
Krivacic et al., "A Rare-Cell Detector for Cancer." Proc Natl Acad Sci USA 101:10501-10504 (2004).
Kulch et al., "Racial Differences in Maternal Serum Human Chorionic Gonadotropin and Unconjugated Oestriol Levels," Prenat Diagn. 13:191-195 (1993).

(56) References Cited

OTHER PUBLICATIONS

Kulozik and Pawlowitzki, "Fetal Cell in the Maternal Circulation: Detection by Direct AFP-Immunofluorescence," Hum Genet. 62:221-224 (1982).
Kumar et al, "Cell Separation: A Review," Pathology 16:53-62 (1984).
Kwok and Higuchi, "Avoiding False Positives with PCR," Nature 339:237-238 (1989).
Lanier et al., "Subpopulations of Human Natural Killer Cells Defined by Expression of the Leu-7 (HNK-1) and Leu-11 (NK-15) Antigens," J Immunol. 131:1789-1796 (1983).
Latt, "Prenatal Genetic Diagnosis," eds. Avery and Taeusch. Philadelphia:W.B Saunders and Co., Cytogenetics 24-36 (1984).
Lau et al., "A Rapid Screening Test for Antenatal Sex Determination," Lancet 1(8367)14-16 (1984).
Li et al., "Amplification and Analysis of DNA Sequences in Single Human Sperm and Diploid Cells," Nature 335:414-417 (1988).
Li et al., "Transport, Manipulation, and Reaction of Biological Cells On-Chip Using Electrokinetic Effects," Anal Chem. 69:1564-1568 (1997).
Lichter et al., "Delineation of Individual Human Chromosomes in Metaphase and Interphase Cells by in Situ Suppression Hybridization Using Recombinant DNA Libraries," Hum Genet. 80:224-234 (1988).
Lin et al., "Microbubble Powered Actuator," Transducers '91, International Conference on Solid-State Sensors and Actuators. Digest of Technical Papers 1041-1044 (1991).
Lipinski et al., "Human Trophoblast Cell-Surface Antigens Defined by Monoclonal Antibodies," Proc Natl Acad Sci USA 78:5147-5150 (1981).
Lloyd et al., "Intrapartum Fetomaternal Bleeding in Rh-Negative Women," Obstet Gynecol. 56:285-287 (1980).
Lo et al., "False-Positive Results and the Polymerase Chain Reaction," Lancet 2(8612):679 (1988).
Lo et al., "Prenatal Sex Determination by DNA Amplification from Maternal Peripheral Blood," Lancet 2(8676):1363-1365 (1989).
Loken et al., "Flow Cytometric Analysis of Human Bone Marrow: I. Normal Erythroid Development," Blood 69:255-263 (1987).
MacAdam et al., "Standardization of Ultrasound Measurements in pregnancy dating for the purposes of triple marker screening," Am J Hum Genet. Supplemental to 51(4): 1620 (1992). (Abstract).
Mahr et al., "Fluorescence in Situ Hybridization of Fetal Nucleated Red Blood Cells," Am J Hum Genet. Supplement to 51(4):1621 (1992). (Abstract).
Maren et al., "Kinetics of Carbonic Anhydrase in Whole Red Cells as Measured by Transfer of Carbon Dioxide and Ammonia," Mol Pharmacol. 6:430-440 (1970).
Maxwell et al., "A Microbubble-Powered Bioparticle Actuator," J Microelectromech Syst. 12:630-640 (2003).
McCabe et al., "DNA Microextraction from Dried Blood Spots on Filter Paper Blotters: Potential Applications to Newborn Screening," Hum Genet. 75:213-216 (1987).
Mehrishi et al., "Electrophoresis of Cells and the Biological Relevance of Surface Charge," Electrophoresis 23:1984-1994 (2002).
Melville et al., "Direct Magnetic Separation of Red Cells from Whole Blood," Nature 255:706 (1975).
Millar et al., "Normal Blood Cell Values in the Early Mid-Trimester Fetus," Prenat Diagn. 5:367-373 (1985).
Mohamed et al., "Development of a rare cell fractionation device: application for cancer detection," IEEE Trans Nanobioscience 3(4):251-6 (2004).
Mohamed, et al. A Micromachined Sparse Cell Isolation Device: Application in Prenatal Diagnostics. Nanotech 2006 vol. 2; 641-644. (Abstract only).
Mohamed, et al. Biochip for separating fetal cells from maternal circulation. J Chromatogr A. Aug. 31, 2007;1162(2):187-92.
Moore et al., "Lymphocyte Fractionation Using Immunomagnetic Colloid and a Dipole Magnet Flow Cell Sorter," J Biochem Biophys Methods 37:11-33 (1998).
Mueller et al., "Identification of Extra-Villous Trophoblast Cells in Human Decidua Using an Apparently Unique Murine Monoclonal Antibody to Trophoblast," Histochem J. 19:288-296 (1987).
Mueller et al., "Isolation of Fetal Trophoblast Cells from Peripheral Blood of Pregnant Women," Lancet 336:197-200 (1990).
Muller et al., "Moderately Repeated DNA Sequences Specific for the Short Arm of the Human Y Chromosome are Present in XX Males and Reduced in Number in an XY Female," Nucleic Acids Res. 14(3):1325-1340 (1986).
Mullis et al., "Specific Enzymatic Amplification of DNA in Vitro: The Polymerase Chain Reaction," Cold Spring Harb. Symp. Quant. Biol. 51:263-273 (1986).
Nagrath, et al. Isolation of rare circulating tumour cells in cancer patients by microchip technology. Nature. 2007; 450: 1235-1241 (with Supplemental pp. 1-10).
Newman et al., "The Transferrin Receptor," Trends Biochem Sci. 7:397-400 (1982).
Oakey et al., "Laminar Flow-Based Separations at the Microscale," Biotechnol Prog. 18:1439-1442 (2002).
Oberle et al., "Genetic Screening for Hemophilia A (Classic Hemophilia) with a Polymorphic DNA Probe," N. Engl J Med. 312:682-686 (1985).
Ockenhouse et al., "Activation of Monocytes and Platelets by Monoclonal Antibodies or Malaria-Infected Erythrocytes Binding to the CD36 Surface Receptor In Vitro," J Clin Invest. 84:468-475 (1989).
Office Action (U.S. Appl. No. 10/529,453) dated Jul. 27, 2007.
Office Action (U.S. Appl. No. 11/228,462) dated Jun. 4, 2007.
Olson et al., "An In Situ Flow Cytometer for the Optical Analysis of Individual Particles in Seawater," Retrieved on the World Wide Web on Apr. 24, 2006 at: http://www.whoi.edu/science/B/Olsonlab/insitu2001.htm.
Owen, et al. High gradient magnetic separation of erythrocytes. Biophys. J. 1978; 22:171-178.
Pallavicini et al., "Analysis of Fetal Cells Sorted from Maternal Blood Using Fluorescence In Situ Hybridization," Am J Hum Genet. Supplement to 51(4):1031 (1992). (Abstract).
Papavasiliou et al., "Electrolysis-Bubble Actuated Gate Valve," Solid-State Sensor and Actuator Workshop, Hilton Head Island, SC. (Jun. 4-8, 2000).
Parano et al., "Noninvasive Prenatal Diagnosis of Chromosomal Aneuploidies by Isolation and Analysis of Fetal Cells from Maternal Blood," Am J Med Genet. 101:262-267 (2001).
Paterlini-Brechot et al., "Circulating tumor cells (CTC) detection: Clinical impact and future directions," Cancer Letter. 253(2):180-204 (2007).
Pawlik et al., "Prodrug Bioactivation and Oncolysis of Diffuse Liver Metastases by a Herpes Simplex Virus 1 Mutant That Expresses the CYP2B1 Transgene," Cancer 95:1171-1181 (2002).
Payne "The Development and Persistence of Leukoagglutinins in Parous Women," Blood 19:411-424 (1962).
Pembrey et al., "Maternal Synthesis of Haemoglobin F in Pregnancy," Lancet 1(7816):1350-1354 (1973).
Peng et al., "Real-time detection of gene expression in cancer cells using molecular beacon imaging: new strategies for cancer research," Cancer Res. 2005; 65(5):1909-17.
Petersen et al., "The Promise of Miniaturized Clinical Diagnostic Systems," IVD Technology (Jul. 1998).
Pinkel et al., "Cytogenetic Analysis Using Quantitative, High-Sensitivity, Fluorescence Hybridization," Proc Natl Acad Sci USA 83:2934-2938 (1986).
Pinkel et al., "Detection of Structural Chromosome Abberations in Metaphase Spreads and Interphase Nuclei by In Situ Hybridization High Complexity Probes Which Stain Entire Human Chromosomes," Am J Hum Genet. Supplemental to 43(3):0471 (1988). (Abstract).
Pinkel et al., "Fluorescence In Situ Hybridization with Human Chromosome-Specific Libraries: Detection of Trisomy 21 and Translocations of Chromosome 4," Proc Natl Aced Sci USA 85:9138-9142 (1988).
Pinzani et al., "Isolation by size of epithelial tumor cells in peripheral blood of patients with breast cancer: correlation with real-time

(56) References Cited

OTHER PUBLICATIONS reverse transcriptase-polymerase chain reaction results and feasibility of molecular analysis by laser microdissection," Hum Pathol. 37(6):711-8 (2006).

Price et al., "Prenatal diagnosis with fetal cells isolated from maternal blood by multiparameter flow cytometry," Am J Obstet Gynecol. 165:1731-1737 (1991).

Prieto, et al. Isolation of fetal nucleated red blood cells from maternal blood in normal and aneuploid pregnancies. Clin Chem Lab Med. Jul. 2002;40(7):667-72.

Product literature for GEM, a system for blood testing: GEM Premier 3000. Retrieved on the World Wide Web on Apr. 24, 2006 at: http://www.ilus.com/premier.sub.--gem3000.sub.--iqm.asp.

Purwosunu, et al. Clinical potential for noninvasive prenatal diagnosis through detection of fetal cells in maternal blood. Taiwan J Obstet Gynecol. Mar. 2006;45(1):10-20.

Raeburn, "Fetal Blood Cells Found in Pregnant Women's Blood" Associated Press (Jul. 28, 1989) [electronic version].

Raeburn, "Fetal Cells Isolated in Women's Blood ," Hickory (N.C.) Daily Record: B (Jul. 29, 1989).

Raymond et al., "Continuous Separation of High Molecular Weight Compounds Using a Microliter Volume Free-Flow Electrophoresis Microstructure," Anal Chem. 68:2515-2522 (1996).

Ried et al., "Multicolor Fluorescence In Situ Hybridization for the Simultaneous Detection of Probe Sets for Chromosomes 13, 18, 21, X and Y in Uncultured Amniotic Fluid Cells," Hum Mol Genet, 1:307-313 (1992).

Rolle et al., "Increase in Number of Circulating Disseminated Epithelial Cells After Surgery for Non-small Cell Lung Cancer Monitored by MAINTRAC is a Predictor for Relapse: A Preliminary Report," World J Surg Oncol. 3:18 (2005).

Ruan et al., "Identification of clinically significant tumor antigens by selecting phage antibody library on tumor cells in situ using laser capture microdissection," Molecular & Cellular Proteomics.5(12): 2364-73 (2006).

Saiki et al., "Diagnosis of Sickle Cell Anemia and .beta.-Thalassemia with Enzymatically Amplified DNA and Nonradioactive Allele-Specific Oligonucleotide Probes," N. Engl J Med. 319:537-541 (1988).

Saltus, "New Test Speeds Detection of Birth Defects," The Boston Globe 4. (Oct. 8, 1991).

Saltus, "Noninvasive Way is Cited to Detect Down Syndrome in Fetuses," The Boston Globe 8 (Nov. 12, 1992).

Sato et al., "Individual and Mass Operation of Biological Cells Using Micromechanical Silicon Devices," Sens Actuators A21-A23:948-953 (1990).

Schomburg et al., "Microfluidic Components in LIGA Technique," J Micromech Microeng. 4:186-191 (1994).

Schroder and de la Chapelle, "Fetal Lymphocytes in the Maternal Blood," Blood 39:153-162 (1972).

Schroder, "Transplacental Passage of Blood Cells," J Med Genet. 12:230-242 (1975).

Search report dated Oct. 2, 2009 from corresponding EP application 06740612.4.

Search report dated Oct. 5, 2009 from corresponding EP application 06749394.0.

Sethu et al., "Continuous Flow Microfluidic Device for Rapid Erythrocyte Lysis," Anal Chem. 76:6247-6253 (2004).

Shoji et al., "Microflow Devices and Systems," J Micromech Microeng. 4:157-171 (1994).

Simpson et al., "Elevated Second Trimester Maternal Serum Alpha Fetoprotein (MSAFP) is More Predictive of Certain Pregnancy Complications Than Elevated Third Trimester MSAFP: A Cohort Study," Am J Hum Genet. 51(4):A19-65 (1992). (Abstract).

Simpson et al., "Prenatal Genetic Diagnosis," Chapter 6, Genetics in Obstetrics and Gynecology, New York:Grune & Stratton, 101-120 (1982).

Sitar et al., "The use of non-physiological conditions to isolate fetal cells from maternal blood," Exp Cell Res. 302:153-161 (2005).

Snider, M., "Birth Defects Detected with Simple Blood Test," USA Today. (Oct. 9, 1991).

Sohda et al., "The Proportion of Fetal Nucleated Red Blood Cells in Maternal Blood: Estimation by FACS Analysis," Prenat Diagn. 17:743-752 (1997).Pinket.

Stipp, "IG Labs Licenses New Technology for Fetal Testing," The Wall Street Journal. B5 (Aug. 10, 1990).

Supplemental Search Report dated Oct. 22, 2009 from corresponding EP application 06749394.0.

Takayama et al., "Patterning Cells and Their Environments Using Multiple Laminar Fluid Flows in Capillary Networks," Proc Natl Acad Sci USA 96: 5545-5548 (1999).

Takayama et al., "Subcellular Position of Small Molecules," Nature 411:1016 (2001).

Takayasu et al., "Continuous Magnetic Separation of Blood Components from Whole Blood," IEEE Trans. on Applied Superconductivity. 10:927-930 (2000).

Teppetherg et al., "Prenatal Diagnosis Using Interphase Fluorescence in situ Hybridization (FISH): 2-year Multi-center Retrospective Study and Review of the Literature," Prenat Diagn. 21:293-301 (2001).

Theophilus et al., "Gaucher Disease: Molecular Heterogeneity and Phenotype-Genotype Correlations," Am J Hum Genet. 45:212-225 (1989).

Thomas et al., "Specific Binding and Release of Cells from Beads Using Cleavable Tetrameric Antibody Complexes," J Immunol Methods 120:221-231 (1989).

Tibbe et al., "Statistical considerations for enumeration of circulating tumor cells," Cytometry Part A 71(3):154-62 (2007).

Toner et al., "Blood-on-a-Chip," Annu Rev Biol Eng. 7: 77-103 (2005).

Tong et al., "Low Temperature Wafer Direct Bonding," J Microelectromech Systems. 3(1):29-35 (1994).

Trask et al., "Detection of DNA Sequences in Nuclei in Suspension by in Situ Hybridization and Dual Beam Flow Cytometry," Science 230:1401-1403 (1985).

Trowbridge et al., "Human Cell Surface Glycoprotein Related to Cell Proliferation is the Receptor for Transferrin," Proc Natl Acad Sci USA 78:3039-3043 (1981).

Turner et al., "Confinement-Induced Entropic Recoil of Single DNA Molecules in a Nanofluidic Structure," Phys Rev Lett. 88(12):128103-1-128103-4 (2002).

U.S. Final Office Action for U.S. Appl. No. 11/071,679 dated Nov. 5, 2007, 26 pages.

U.S. Final Office Action for U.S. Appl. No. 11/071,679 dated Oct. 12, 2006, 37 pages.

U.S. Non-Final Office Action for U.S. Appl. No. 11/071,679 dated Jan. 26, 2009, 23 pages.

U.S. Non-Final Office Action for U.S. Appl. No. 11/071,679 dated Jul. 2, 2007, 39 pages.

U.S. Non-Final Office Action for U.S. Appl. No. 11/071,679 dated Feb. 6, 2006, 24 pages.

U.S. Non-Final Office Action for U.S. Appl. No. 11/449,149 dated Nov. 9, 2010, 14 pages.

U.S. Notice of Allowance for U.S. Appl. No. 11/449,149 dated May 18, 2011, 10 pages.

UPI, "Researchers Find Safer Prenatal Tests," The Boston Herald. 25 (Nov. 14, 1989).

Vandelli et al., "Development of a MEMS Microvalve Array for Fluid Flow Control," J Microelectromech Syst. 7:395-403 (1998).

Voldman et al., "Holding Forces of Single-Particle Dielectrophoretic Traps," Biophys J. 80:531-541 (2001).

Volkmuth et al., "DNA Electrophoresis in Microlithographic Arrays," Nature 358:600-602 (1992).

Volkmuth et al., "Observation of Electrophoresis of Single DNA Molecules in Nanofabricated Arrays," Presentation at joint annual meeting of Biophysical Society and the American Society for Biochemistry and Molecular Biology. Feb. 9-13, 1992.

Vona et al., "Enrichment, Immunomorphological, and Genetic Characterization of Fetal Cells Circulating in Maternal Blood," Am J Pathol 160:51-58 (2002).

(56) References Cited

OTHER PUBLICATIONS

Vona et al., "Isolation by Size of Epithelial Tumor Cells: A New Method for the Immunomorphological and Molecular Characterization of Circulating Tumor Cells," Am J Pathol. 156:57-63 (2000).
Wachtel et al., "Fetal Cells in the Maternal Circulation: Isolation by Multiparameter Flow Cytometry and Confirmation by Polymerase Chain Reaction," Hum Reprod. 6(10):1466-1469 (1991).
Walknowska et al., "Practical and Theoretical Implications of Fetal/Maternal Lymphocyte Transfer," Lancet 1(7606):1119-1122 (1969).
Washizu et al., "Handling Biological Cells Utilizing a Fluid Integrated Circuit," IEEE Transactions of Industry Applications 26: 352-8 (1988).
Washizu et al., "Handling Biological Cells Utilizing a Fluid Integrated Circuit," Industry Applications Society Annual Meeting Presentations. Oct. 2-7, 1988: 1735-40.
Weigl et al., "Microfluidic Diffusion-Based Separation and Detection," Science 283:346-347 (1999).
Williams et al., "Comparison of Cell Separation Methods to Enrich the Proportion of Fetal Cells in Maternal Blood Samples," Am J Hum Genet. Supplemental to 51(4): A266 (1049) (1992). (Abstract).
Williams et al., "Prenatal Diagnosis of 46, XX Males: Confirmation of X-Y Interchange by Fluorescence In Situ Hybridization (FISH)," Am J Genet. Supplemental to 51(4):A266(1048) (1992). (Abstract).
Xu et al., "Dielectrophoresis of Human Red Cells in Microchips," Electrophoresis 20:1829-1831.
Yuan et al., "The Pumping Effect of Growing and Collapsing Bubbles in a Tube," J Micromech Microeng. 9:402-413 (1999).
Zborowski et al., "Red Blood Cell Magnetophoresis," Biophys J. 84:2638-2645 (2003).
Zhang and Manz, "High-Speed Free-Flow Electrophoresis on Chip," Anal Chem. 75:5759-5766 (2003).
Zhen et al., "Poly-Fish: A Technique of Repeated Hybridizations That Improves Cytogenic Analysis of Fetal Cells in Maternal Blood," Prenat Diagn. 18(11):1181-5 (1998).
Zheng et al., "Fetal cell identifiers: results of microscope slide-based immunocytochemical studies as a function of gestational age and abnormality," Am J Obstet Gynecol. 180(5):1234-9 (1999).
Zuska, "Microtechnology Opens Doors to the Universe of Small Space," MD&DI Jan. 1997.
Office Action in Indian Application No. 4390/CHENP/2007, dated Mar. 2, 2017, 6 pages.

\* cited by examiner

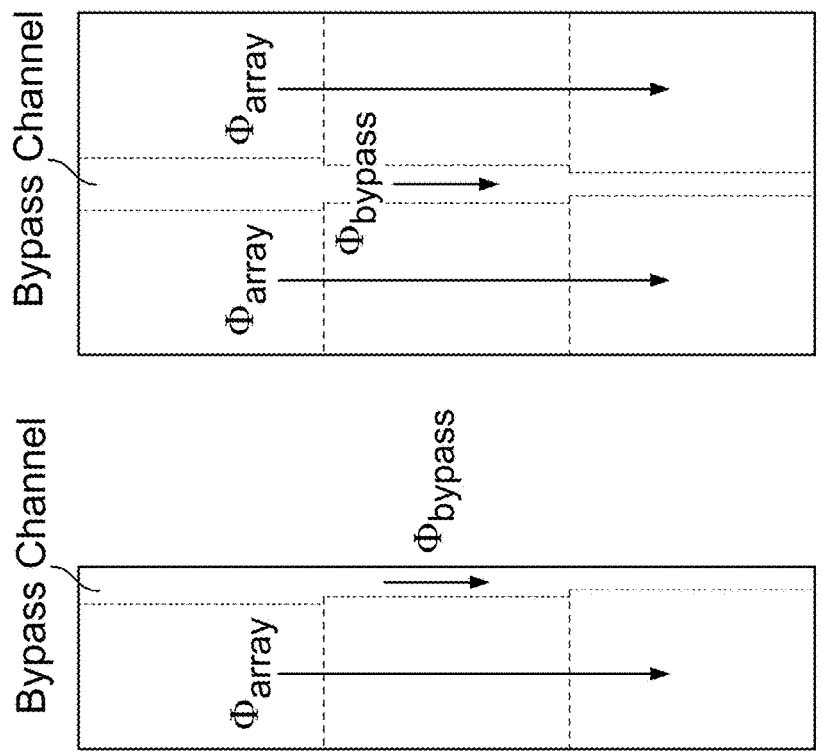
FIG. 14
FIG. 13
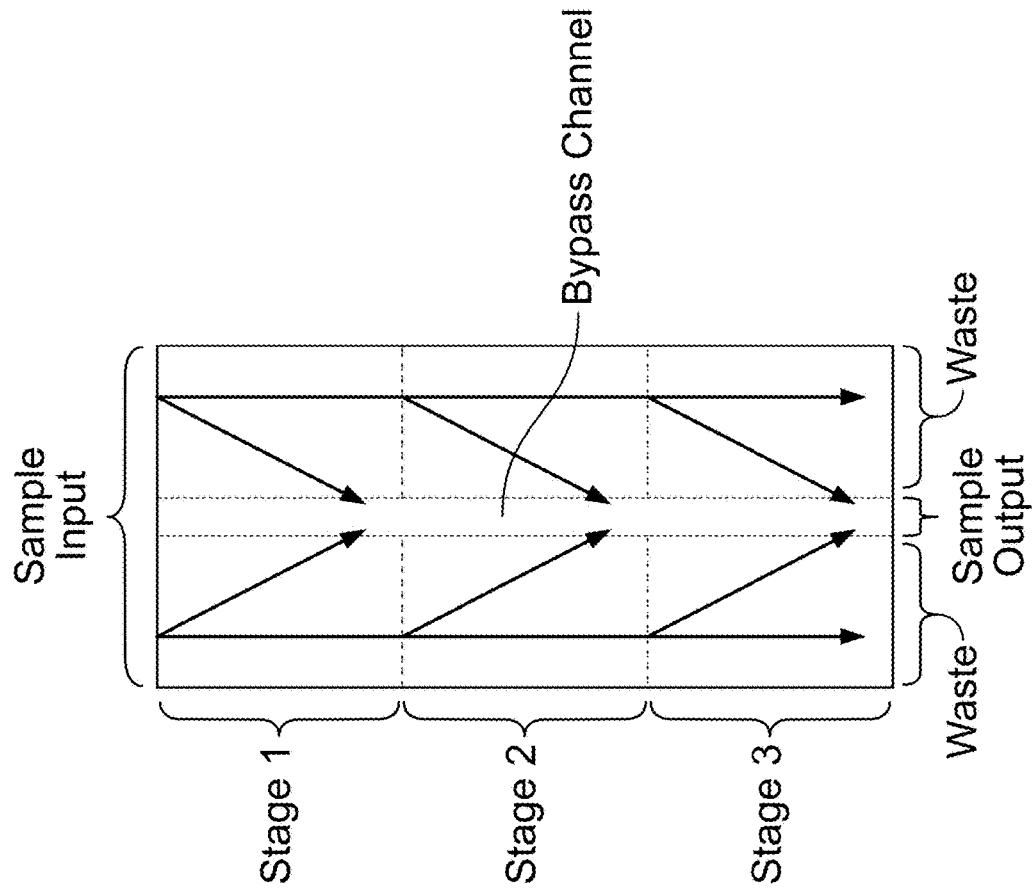
FIG. 12

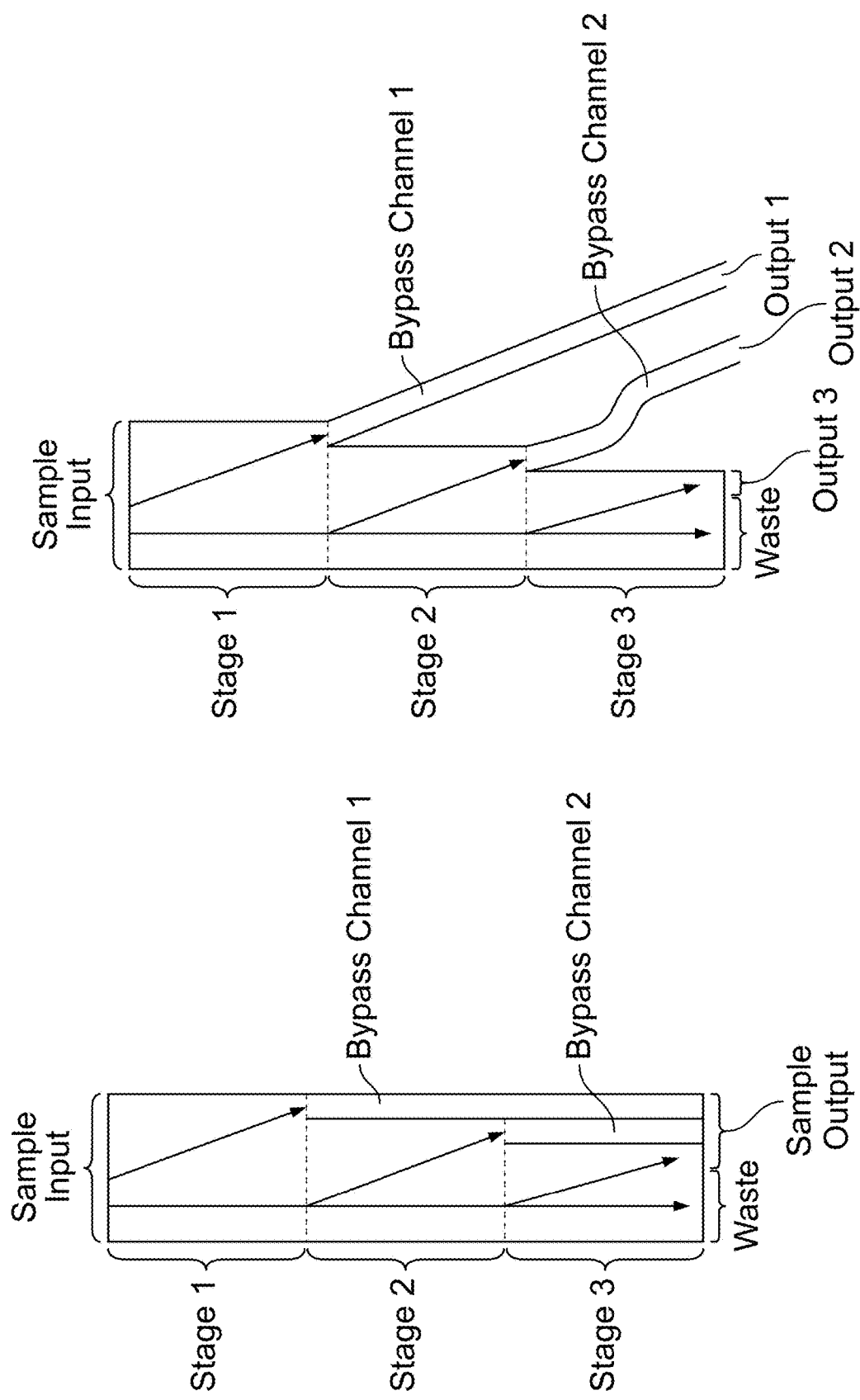

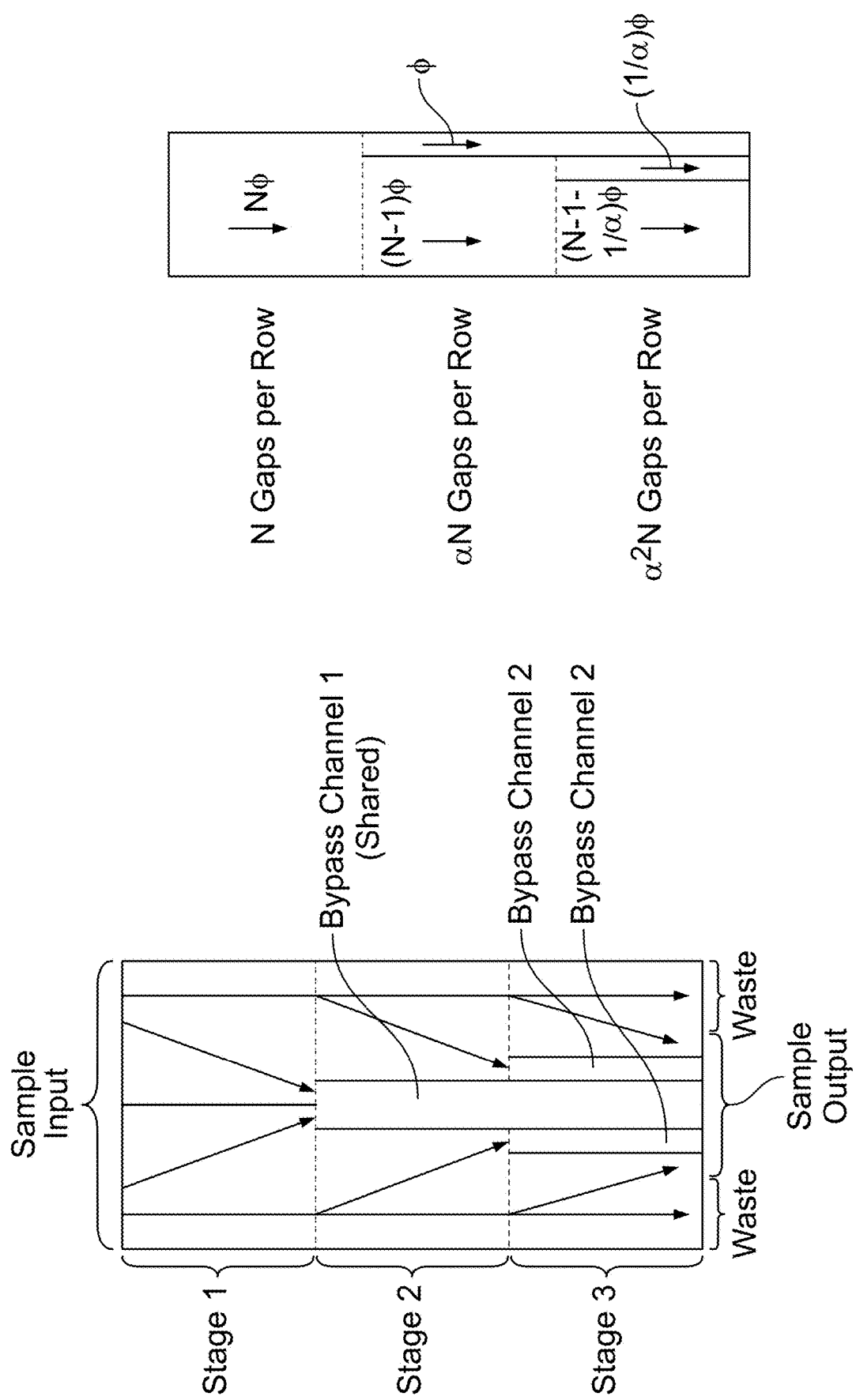

chip inlet array outlet

BLOOD

WBC HISTOGRAM

RBC HISTOGRAM

PRODUCT

WBC HISTOGRAM

RBC HISTOGRAM

WASTE

WBC HISTOGRAM

RBC HISTOGRAM chip inlet array outlet chip inlet array outlet

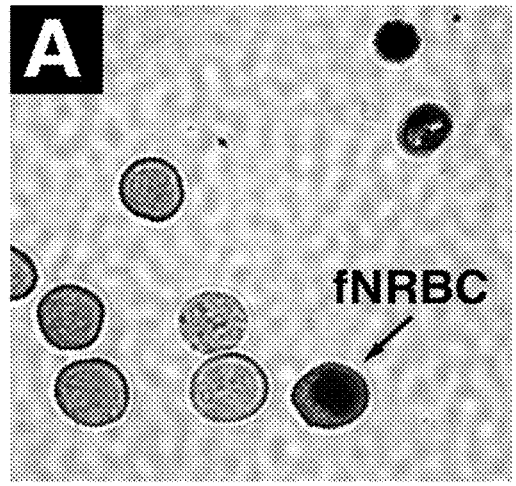
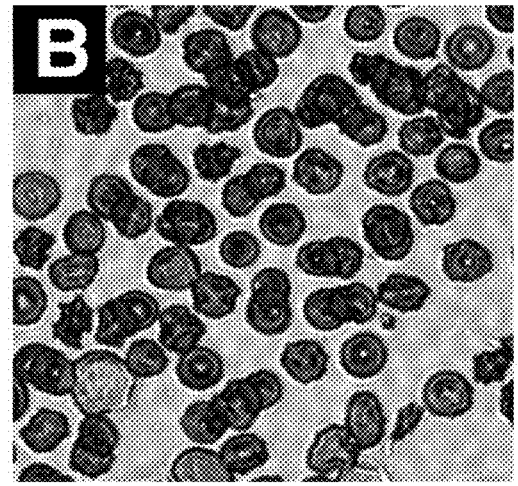
FIG. 46A  FIG. 46B
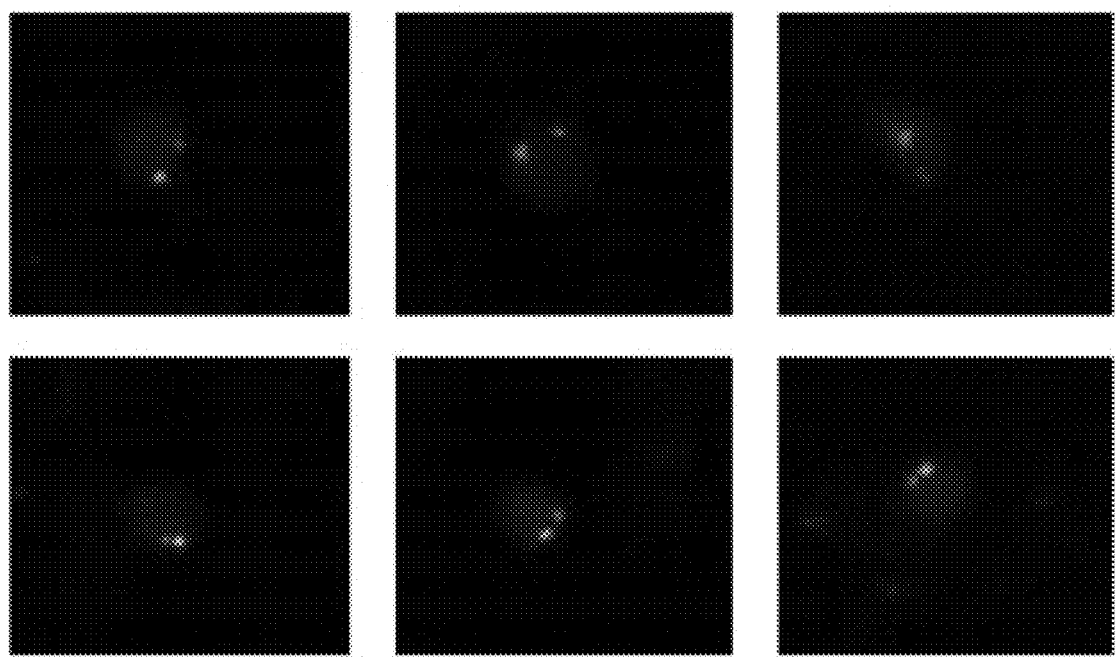
Figure 13A-F (Blue= nucleus, Red = X chromosome, Green = Y chromosome)
FIG. 47 chip inlet array outlet chip inlet array outlet

| Slide # | Nuclei input | Nuclei on Slide | Percentage of input (%) |
|---|---|---|---|
| LMS3972 | 10,000 | 9073 | 90.73% |
| LMS3973 | 10,000 | 9101 | 91.01% |
| LMS3974 | 10,000 | 9692 | 96.92% |
| A00356 | 6,900 | 6160 | 89.28% |
| A00357 | 6,900 | 6316 | 91.54% |
| A00358 | 6,900 | 6005 | 87.03% |

US 10,786,817 B2

DEVICES AND METHOD FOR ENRICHMENT AND ALTERATION OF CELLS AND OTHER PARTICLES

CROSS-REFERENCE TO RELATED APPLICATIONS

This application is a continuation of U.S. application Ser. No. 14/930,313, filed on Nov. 2, 2015, which is a divisional of U.S. application Ser. No. 13/232,781, filed on Sep. 14, 2011, which is a continuation of U.S. application Ser. No. 11/449,149, filed on Jun. 8, 2006 (now U.S. Pat. No. 8,021,614), which is a continuation of International Application No. PCT/US2006/012820, filed on Apr. 5, 2006, which further claims the benefit of U.S. Provisional Application No. 60/668,415, filed on Apr. 5, 2005, and 60/704,067, filed on Jul. 29, 2005. All of the aforementioned applications are incorporated herein by reference in their entireties.

BACKGROUND OF THE INVENTION

The invention relates to the fields of cell separation and fluidic devices.

Clinically or environmentally relevant information may often be present in a sample, but in quantities too low to detect. Thus, various enrichment or amplification methods are often employed in order to increase the detectability of such information.

For cells, different flow cytometry and cell sorting methods are available, but these techniques typically employ large and expensive pieces of equipment, which require large volumes of sample and skilled operators. These cytometers and sorters use methods like electrostatic deflection, centrifugation, fluorescence activated cell sorting (FACS), and magnetic activated cell sorting (MACS) to achieve cell separation. These methods often suffer from the inability to enrich a sample sufficiently to allow analysis of rare components of the sample. Furthermore, such techniques may result in unacceptable losses of such rare components, e.g., through inefficient separation or degradation of the components.

Thus, there is a need for new devices and methods for enriching samples.

SUMMARY OF THE INVENTION

In general, the invention features devices that contain one or more structures that deterministically deflect particles, in a fluid, having a hydrodynamic size above a critical size in a direction not parallel to the average direction of flow of the fluid in the structure. An exemplary structure includes an array of obstacles that form a network of gaps, wherein a fluid passing through the gaps is divided unequally into a major flux and a minor flux so that the average direction of the major flux is not parallel to the average direction of fluidic flow in the channel, and the major flux from the first outer region is directed either toward the second outer region or away from the second outer region, wherein the particles are directed into the major flux. The array of obstacles preferably includes first and second rows displaced laterally relative to one another so that fluid passing through a gap in the first row is divided unequally into two gaps in the second row. Such structures may be arranged in series in a single channel, in parallel in the same channel, e.g., a duplex configuration, in parallel in multiple channels in a device, or combinations thereof. Each channel will have at least one inlet and at least one outlet. A single inlet and outlet may be employed for two or more structures in parallel, in the same or different channels. Alternatively, each structure may have its own inlet and outlet or a single structure may contain multiple inlets and outlets, e.g., to introduce or collect two different fluids simultaneously.

The invention further features methods of enriching and altering samples employing a device of the invention.

In preferred embodiments, the devices of the invention include microfluidic channels. In other preferred embodiments, the devices of the invention are configured to separate blood components, e.g., red blood cells, white blood cells, or platelets from whole blood, rare cells such as nucleated red blood cells from maternal blood, and stem cells, pathogenic or parasitic organisms, or host or graft immune cells from blood. The methods may also be employed to separate all blood cells, or portions thereof, from plasma, or all particles in a sample such as cellular components or intracellular parasites, or subsets thereof, from the suspending fluid. Other particles that may be separated in devices of the invention are described herein.

The invention further provides methods for preferentially lysing cells of interest in a sample, e.g., to extract clinical information from a cellular component, e.g., a nucleus or nucleic acid, of the cells of interest, e.g., nucleated fetal red blood cells. In general, the method employs differential lysis between the cells of interest and other cells (e.g., other nucleated cells) in the sample. In certain embodiments, preferential lysis results in lysis of at least 10%, 20%, 30%, 40%, 50%, 60%, 70%, 80%, 90%, 95%, or 99% of cells of interest, e.g., red blood cells or fetal nucleated red blood cells, and lysis of less than 50%, 40%, 30%, 20%, 10%, 5%, or 1% of undesired cells, e.g. maternal white blood cells or maternal nucleated red blood cells.

By "gap" is meant an opening through which fluids and/or particles may flow. For example, a gap may be a capillary, a space between two obstacles wherein fluids may flow, or a hydrophilic pattern on an otherwise hydrophobic surface wherein aqueous fluids are confined. In a preferred embodiment of the invention, the network of gaps is defined by an array of obstacles. In this embodiment, the gaps are the spaces between adjacent obstacles. In a preferred embodiment, the network of gaps is constructed with an array of obstacles on the surface of a substrate.

By "obstacle" is meant an impediment to flow in a channel, e.g., a protrusion from one surface. For example, an obstacle may refer to a post outstanding on a base substrate or a hydrophobic barrier for aqueous fluids. In some embodiments, the obstacle may be partially permeable. For example, an obstacle may be a post made of porous material, wherein the pores allow penetration of an aqueous component but are too small for the particles being separated to enter.

By "hydrodynamic size" is meant the effective size of a particle when interacting with a flow, posts, and other particles. It is used as a general term for particle volume, shape, and deformability in the flow.

By "flow-extracting boundary" is meant a boundary designed to remove fluid from an array.

By "flow-feeding boundary" is meant a boundary designed to add fluid to an array.

By "swelling reagent" is meant a reagent that increases the hydrodynamic radius of a particle. Swelling reagents may act by increasing the volume, reducing the deformability, or changing the shape of a particle.

By "shrinking reagent" is meant a reagent that decreases the hydrodynamic radius of a particle. Shrinking reagents may act by decreasing the volume, increasing the deformability, or changing the shape of a particle.

By "labeling reagent" is meant a reagent that is capable of binding to or otherwise being localized with a particle and being detected, e.g., through shape, morphology, color, fluorescence, luminescence, phosphorescence, absorbance, magnetic properties, or radioactive emission.

By "channel" is meant a gap through which fluid may flow. A channel may be a capillary, a conduit, or a strip of hydrophilic pattern on an otherwise hydrophobic surface wherein aqueous fluids are confined.

By "microfluidic" is meant having at least one dimension of less than 1 mm. By "enriched sample" is meant a sample containing cells or other particles that has been processed to increase the relative population of cells or particles of interest relative to other components typically present in a sample. For example, samples may be enriched by increasing the relative population of particles of interest by at least 10%, 25%, 50%, 75%, 100% or by a factor of at least 1000, 10,000, 100,000, or 1,000,000.

By "intracellular activation" is meant activation of second messenger pathways, leading to transcription factor activation, or activation of kinases or other metabolic pathways. Intracellular activation through modulation of external cell membrane antigens can also lead to changes in receptor trafficking.

By "cellular sample" is meant a sample containing cells or components thereof. Such samples include naturally occurring fluids (e.g., blood, lymph, cerebrospinal fluid, urine, cervical lavage, and water samples) and fluids into which cells have been introduced (e.g., culture media, and liquefied tissue samples). The term also includes a lysate.

By "biological sample" is meant any same of biological origin or containing, or potentially containing, biological particles. Preferred biological samples are cellular samples.

By "biological particle" is meant any species of biological origin that is insoluble in aqueous media. Examples include cells, particulate cell components, viruses, and complexes including proteins, lipids, nucleic acids, and carbohydrates.

By "component" of a cell (or "cellular component") is meant any component of a cell that may be at least partially isolated upon lysis of the cell. Cellular components may be organelles (e.g., nuclei, peri-nuclear compartments, nuclear membranes, mitochondria, chloroplasts, or cell membranes), polymers or molecular complexes (e.g., lipids, polysaccharides, proteins (membrane, trans-membrane, or cytosolic), nucleic acids (native, therapeutic, or pathogenic), viral particles, or ribosomes), intracellular parasites or pathogens, or other molecules (e.g., hormones, ions, cofactors, or drugs).

By "blood component" is meant any component of whole blood, including host red blood cells, white blood cells, and platelets. Blood components also include the components of plasma, e.g., proteins, lipids, nucleic acids, and carbohydrates, and any other cells that may be present in blood, e.g., because of current or past pregnancy, organ transplant, or infection.

By "counterpart" is meant a cellular component, which although different at the detail level (e.g., sequence) is of the same class. Examples are nuclei, mitochondria, mRNA, and ribosomes from different cell types, e.g., fetal red blood cells and maternal white blood cells.

By "preferential lysis" is meant lysing a cell of interest to a greater extent than undesired cells on the time scale of the lysis. Undesired cells typically contain the same cellular component found in the cells of interest or a counterpart thereof or cellular components that damage the contents of cells of interest. Preferential lysis may result in lysis of at least 10%, 20%, 30%, 40%, 50%, 60%, 70%, 80%, 90%, 95%, or 99% of cells of interest, e.g., while lysing less than 50%, 40%, 30%, 20%, 10%, 5%, or 1% of undesired cells. Preferential lysis may also result in a ratio of lysis of cells of interest to undesired cells.

Other features and advantages will be apparent from the following description and the claims.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIG. 12 is a schematic depiction of a three-stage, duplex device having a common bypass channel.

FIG. 13 is a schematic depiction of a three-stage device having a common bypass channel, where the flow through the device is substantially constant.

FIG. 14 is a schematic depiction of a three-stage, duplex device having a common bypass channel, where the flow through the device is substantially constant.

FIG. 17 is a schematic depiction of a three-stage device having two, separate bypass channels.

FIG. 18 is a schematic depiction of a three-stage device having two, separate bypass channels, which are in arbitrary configuration.

FIG. 19 is a schematic depiction of a three-stage, duplex device having three, separate bypass channels.

FIG. 20 is a schematic depiction of a three-stage device having two, separate bypass channels, wherein the flow through each stage is substantially constant.

FIG. 46A is a micrograph of a sample enriched in fetal red blood cells. FIG. 46B is a micrograph of maternal red blood cell waste.

FIG. 47 is a series of micrographs showing the positive identification of male fetal cells (Blue=nucleus, Red=X chromosome, Green=Y chromosome).

FIG. 63$b$ is a photograph of a manifold of the invention.

DETAILED DESCRIPTION OF THE INVENTION

Device

In general, the devices include one or more arrays of obstacles that allow deterministic lateral displacement of components of fluids. Prior art devices that differ from those the present invention, but which, like those of the invention, employ obstacles for this purpose are described, e.g., in Huang et al. *Science* 304, 987-990 (2004) and U.S. Publication No. 20040144651. The devices of the invention for separating particles according to size employ an array of a network of gaps, wherein a fluid passing through a gap is divided unequally into subsequent gaps. The array includes a network of gaps arranged such that fluid passing through a gap is divided unequally, even though the gaps may be identical in dimensions.

The device uses a flow that carries cells to be separated through the array of gaps. The flow is aligned at a small angle (flow angle) with respect to a line-of-sight of the array. Cells having a hydrodynamic size larger than a critical size migrate along the line-of-sight in the array, whereas those having a hydrodynamic size smaller than the critical size follow the flow in a different direction. Flow in the device occurs under laminar flow conditions.

Figure 1A:
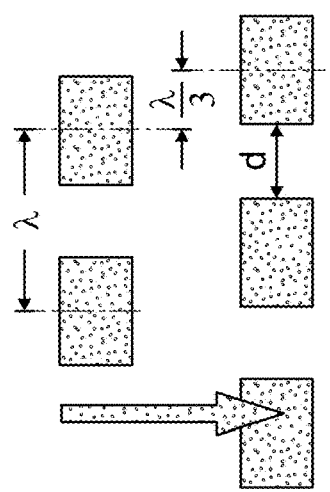
FIGS. 1A-1E are schematic depictions of an array that separated cells based on deterministic lateral displacement: (A) illustrates the lateral displacement of subsequent rows; (B) illustrates how fluid flowing through a gap is divide unequally around obstacles in subsequent rows; (C) illustrates how a particle with a hydrodynamic size above the critical size is displaced laterally in the device; (D) illustrates an array of cylindrical obstacles; and (E) illustrates an array of elliptical obstacles.
Figure 1B:
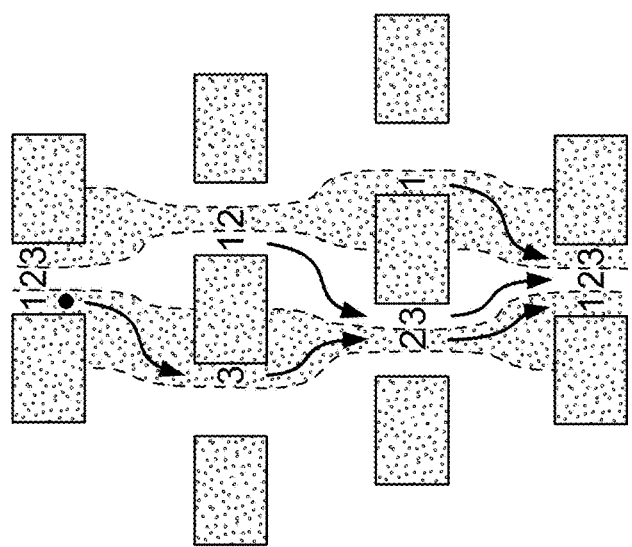
Figure 1C:
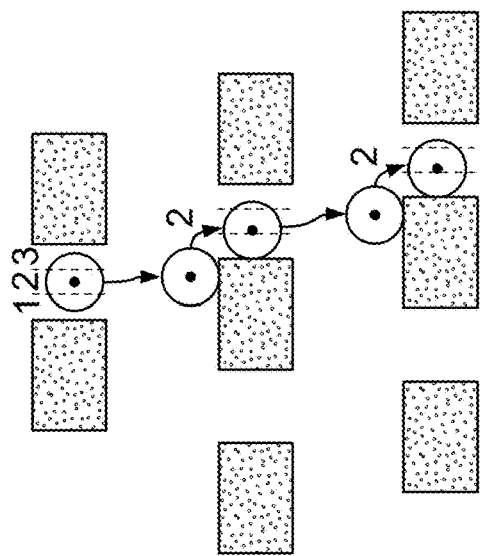
Figure 1D:
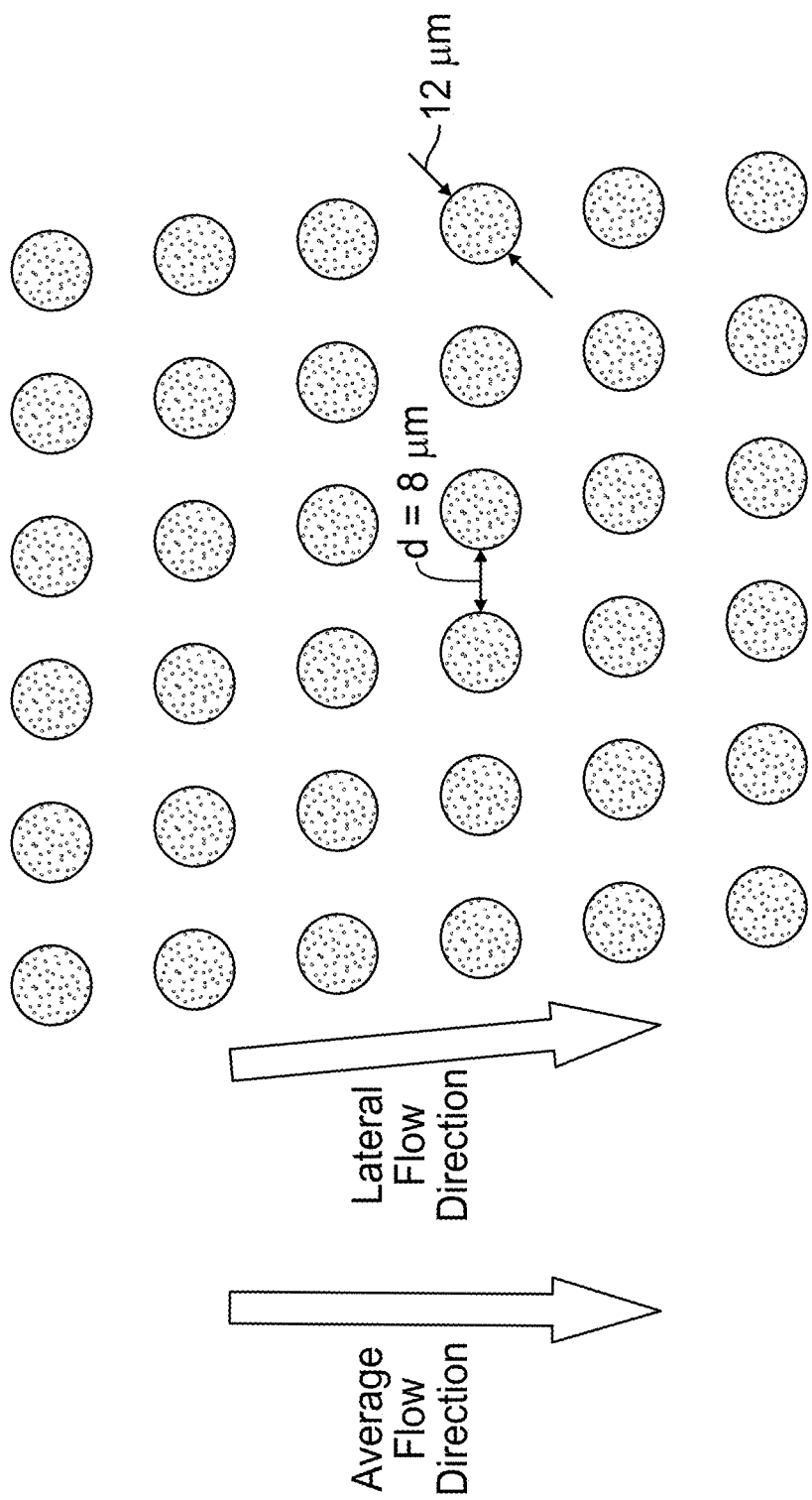
Figure 1E:
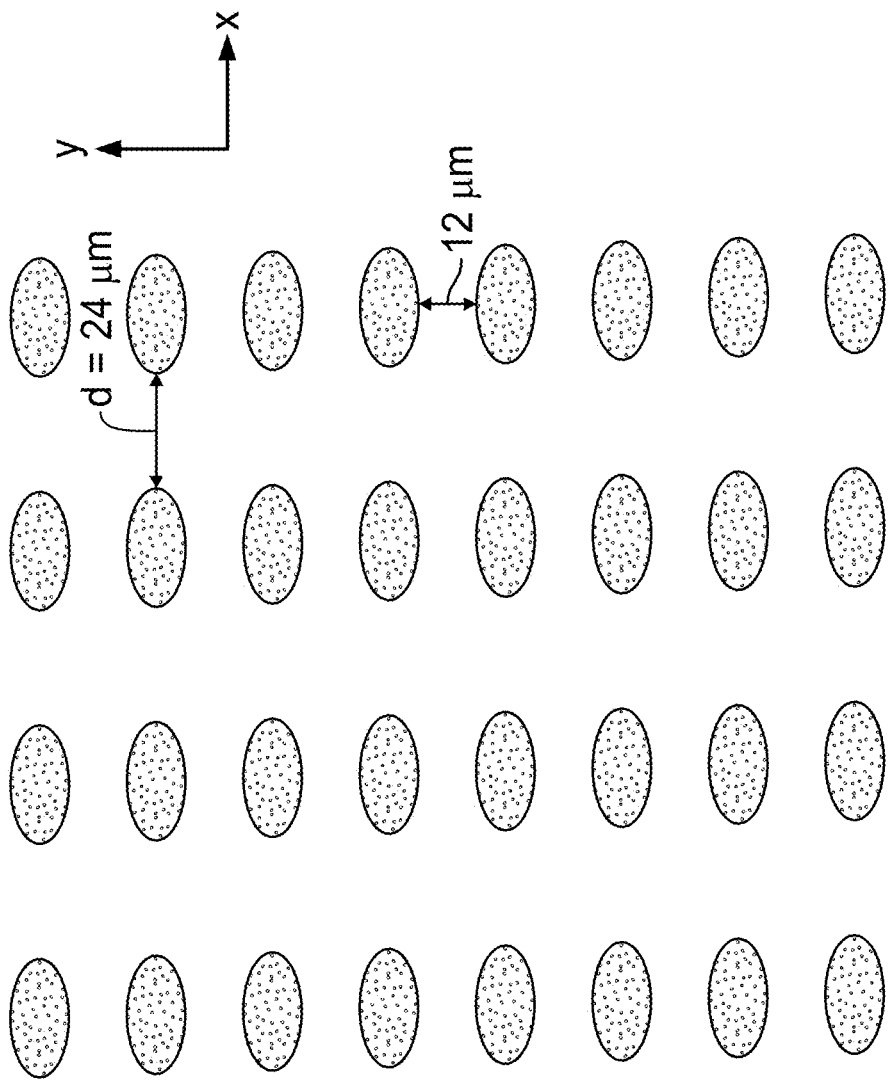
Figure 2:
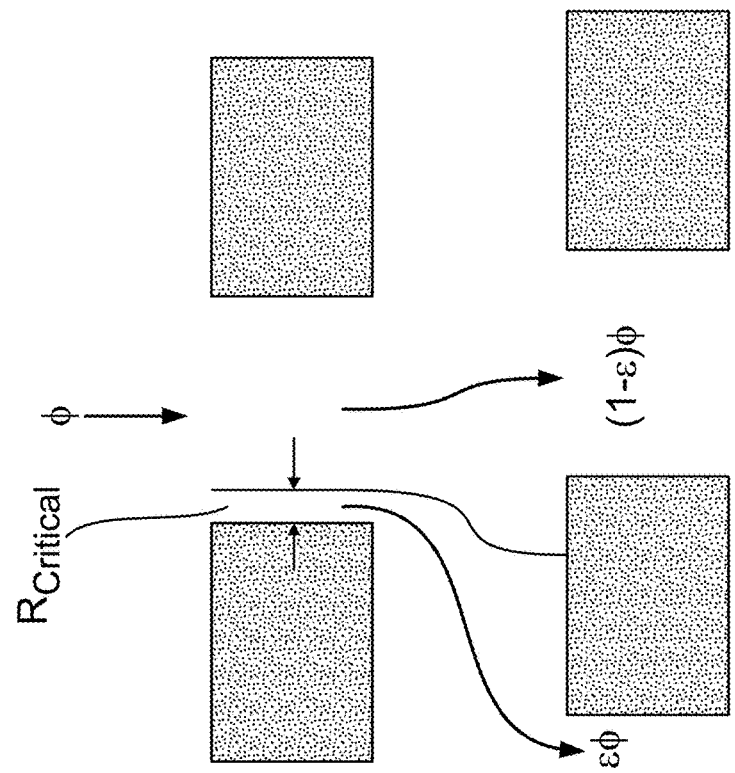
FIG. 2 is a schematic description illustrating the unequal division of the flux through a gap around obstacles in subsequent rows.

The critical size is a function of several design parameters. With reference to the obstacle array in FIG. 1, each row of posts is shifted horizontally with respect to the previous row by $\Delta\lambda$, where $\lambda$ is the center-to-center distance between the posts (FIG. 1A). The parameter $\Delta\lambda/\lambda$ (the "bifurcation ratio," $\varepsilon$) determines the ratio of flow bifurcated to the left of the next post. In FIG. 1, $\varepsilon$ is ⅓, for the convenience of illustration. In general, if the flux through a gap between two posts is $\phi$, the minor flux is $\varepsilon\phi$, and the major flux is $(1-\varepsilon\phi)$ (FIG. 2). In this example, the flux through a gap is divided essentially into thirds (FIG. 1B). While each of the three fluxes through a gap weaves around the array of posts, the average direction of each flux is in the overall direction of flow. FIG. 1C illustrates the movement of a particles sized above the critical size through the array. Such particles move with the major flux, being transferred sequentially to the major flux passing through each gap.

Figure 3:
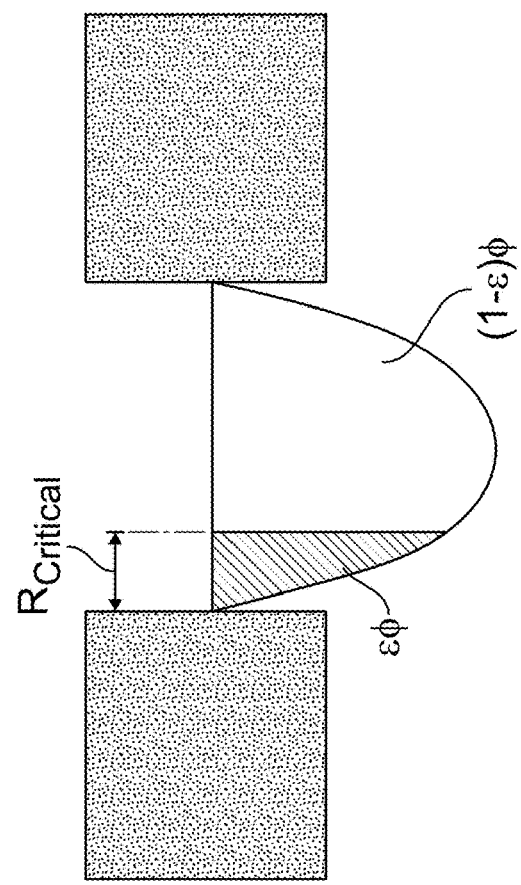
FIG. 3 is a schematic depiction of how the critical size depends on the flow profile, which is parabolic in this example.

Referring to FIG. 2, the critical size is approximately $2R_{critical}$, where $R_{critical}$ is the distance between the stagnant flow line and the post. If the center of mass of a particle, e.g., a cell, falls at least $R_{critical}$ away from the post, the particle would follow the major flux and move along the line-of-sight of the array. If the center of mass of a particle falls within $R_{critical}$ of the post, it follows the minor flux in a different direction. $R_{critical}$ can be determined if the flow profile across the gap is known (FIG. 3); it is the thickness of the layer of fluids that would make up the minor flux. For a given gap size, d, $R_{critical}$ can be tailored based on the bifurcation ratio, $\varepsilon$. In general, the smaller $\varepsilon$, the smaller $R_{critical}$.

Figure 5:
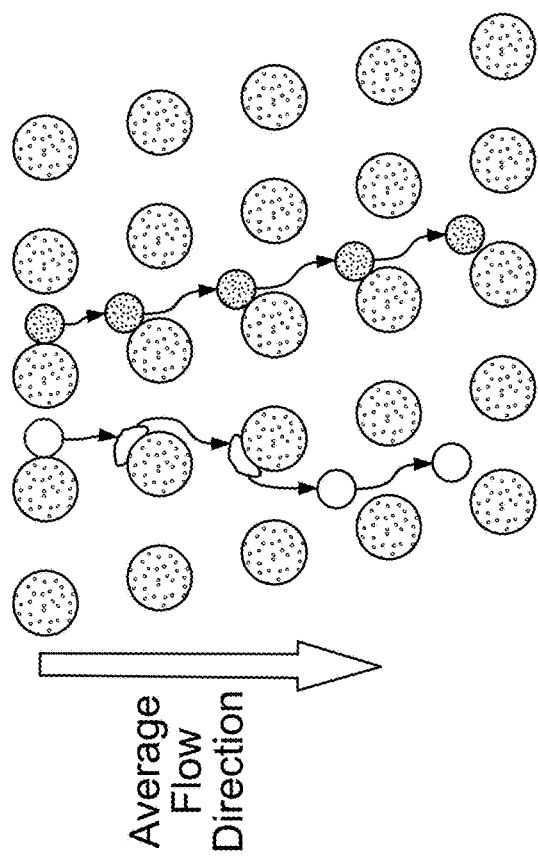
FIG. 5 is an illustration of how deformability affects the movement of particles through a device.
Figure 4:
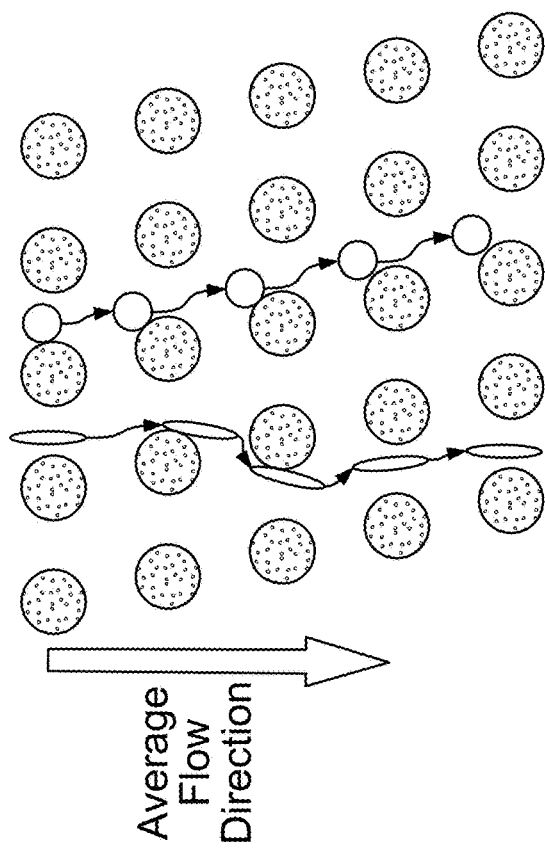
FIG. 4 is an illustration of how shape affects the movement of particles through a device.

In an array for deterministic lateral displacement, particles of different shapes behave as if they have different sizes (FIG. 4). For example, lymphocytes are spheres of ~5 µm diameter, and erythrocytes are biconcave disks of ~7 µm diameter, and ~1.5 µm thick. The long axis of erythrocytes (diameter) is larger than that of the lymphocytes, but the short axis (thickness) is smaller. If erythrocytes align their long axes to a flow when driven through an array of posts by the flow, their hydrodynamic size is effectively their thickness (~1.5 µm), which is smaller than lymphocytes. When an erythrocyte is driven through an array of posts by a hydrodynamic flow, it tends to align its long axis to the flow and behave like a ~1.5 µm-wide particle, which is effectively "smaller" than lymphocytes. The method and device may therefore separate cells according to their shapes, although the volumes of the cells could be the same. In addition, particles having different deformability behave as if they have different sizes (FIG. 5). For example, two particles having the undeformed shape may be separated by deterministic lateral displacement, as the cell with the greater deformability may deform when it comes into contact with an obstacle in the array and change shape. Thus, separation in the device may be achieved based on any parameter that affects hydrodynamic size including the physical dimensions, the shape, and the deformability of the particle.

Figure 7:
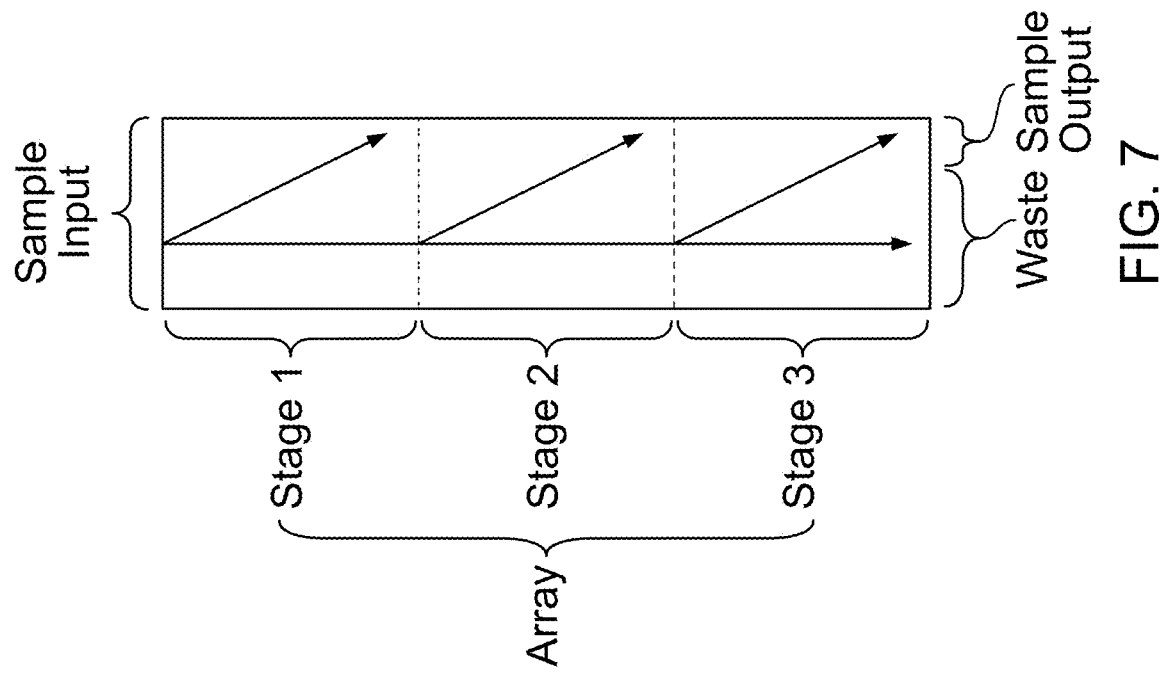
FIG. 7 is a schematic depiction of a three-stage device.
Figure 6:
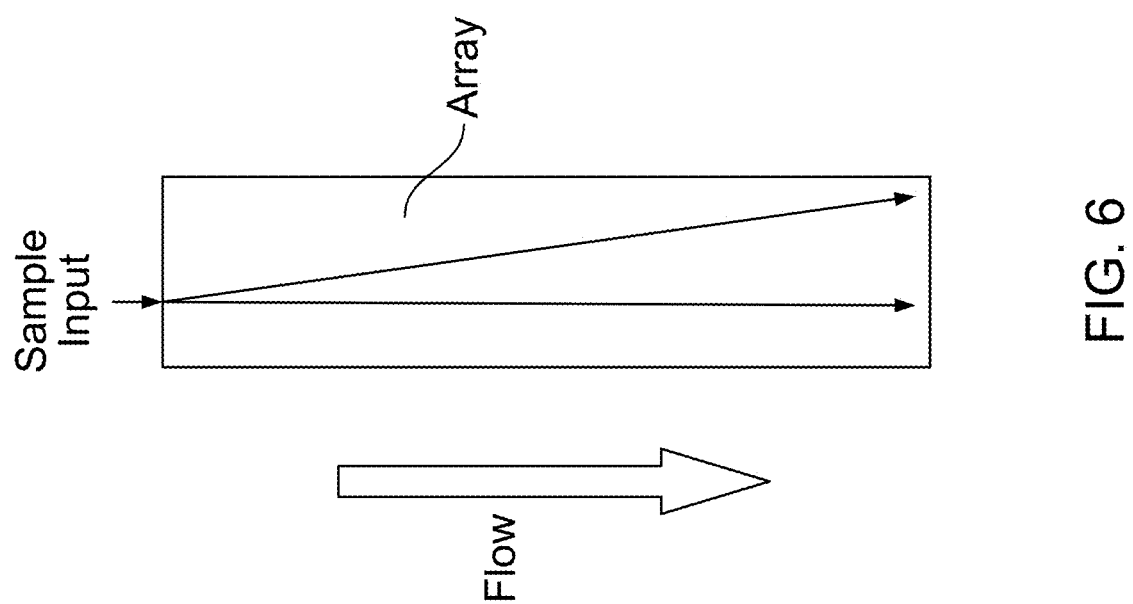
FIG. 6 is a schematic depiction of deterministic lateral displacement. Particles having a hydrodynamic size above the critical size move to the edge of the array, while particles having a hydrodynamic size below the critical size pass through the device without lateral displacement.

Referring to FIGS. 6 and 7, feeding a mixture of particles, e.g., cells, of different hydrodynamic sizes from the top of the array and collecting the particles at the bottom, as shown schematically, produces two products, the output containing cells larger than the critical size, $2R_{critical}$, and waste containing cells smaller than the critical size. Although labeled "waste" in FIG. 7, particles below the critical size may be collected while the particles above the critical size are discarded. Both types of outputs may also be desirably collected, e.g., when fractionating a sample into two or more sub-samples. Cells larger than the gap size will get trapped inside the array. Therefore, an array has a working size range. Cells have to be larger than a critical size ($2R_{critical}$) and smaller than a maximum pass-through size (array gap size) to be directed into the major flux.

Uses of Devices of the Invention

The invention features improved devices for the separation of particles, including bacteria, viruses, fungi, cells, cellular components, viruses, nucleic acids, proteins, and protein complexes, according to size. The devices may be used to effect various manipulations on particles in a sample. Such manipulations include enrichment or concentration of a particle, including size based fractionization, or alteration of the particle itself or the fluid carrying the particle. Preferably, the devices are employed to enrich rare particles from a heterogeneous mixture or to alter a rare particle, e.g., by exchanging the liquid in the suspension or by contacting a particle with a reagent. Such devices allow for a high degree of enrichment with limited stress on cells, e.g., reduced mechanical lysis or intracellular activation of cells.

Although primarily described in terms of cells, the devices of the invention may be employed with any other particles whose size allows for separation in a device of the invention.

Array Design

Single-stage array. In one embodiment, a single stage contains an array of obstacles, e.g., cylindrical posts (FIG. 1D). In certain embodiments, the array has a maximum pass-through size that is several times larger than the critical size, e.g., when separating white blood cells from red blood cells. This result may be achieved using a combination of a large gap size d and a small bifurcation ratio c. In preferred embodiments, the $\varepsilon$ is at most ½, e.g., at most ⅓, 1/10, 1/30, 1/100, 1/300, or 1/1000. In such embodiments, the obstacle shape may affect the flow profile in the gap; however, the obstacles can be compressed in the flow direction, in order to make the array short (FIG. 1E). Single stage arrays may include bypass channels as described herein.

Figure 8:
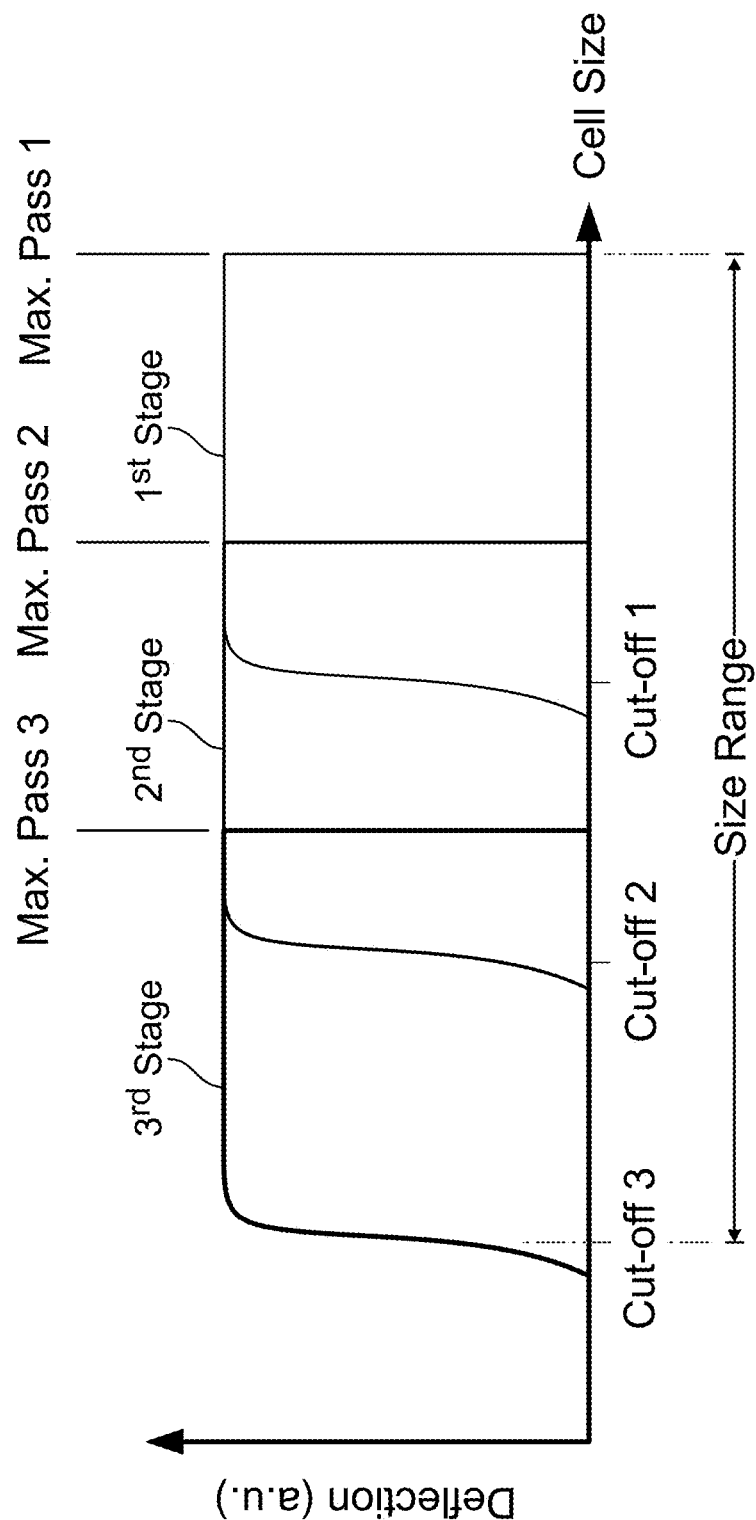
FIG. 8 is a schematic depiction of the maximum size and cut-off size (i.e., critical size) for the device of FIG. 7.

Multiple-stage arrays. In another embodiment, multiple stages are employed to separate particles over a wide range of sizes. An exemplary device is shown in FIG. 7. The device shown has three stages, but any number of stages may be employed. Typically, the cut-off size (i.e. critical size) in the first stage is larger than the cut-off in the second stage, and the first stage cut-off size is smaller than the maximum pass-through size of the second stage (FIG. 8). The same is true for the following stages. The first stage will deflect (and remove) particles, e.g., that would cause clogging in the second stage, before they reach the second stage. Similarly, the second stage will deflect (and remove) particles that would cause clogging in the third stage, before they reach the third stage. In general an array can have as many stages as desired.

As described, in a multiple-stage array, large particles, e.g., cells, that could cause clogging downstream are deflected first, and these deflected particles need to bypass the downstream stages to avoid clogging. Thus, devices of the invention may include bypass channels that remove output from an array. Although described here in terms of removing particles above the critical size, bypass channels may also be employed to remove output from any portion of the array.

Different designs for bypass channels are as follows.

Figure 9:
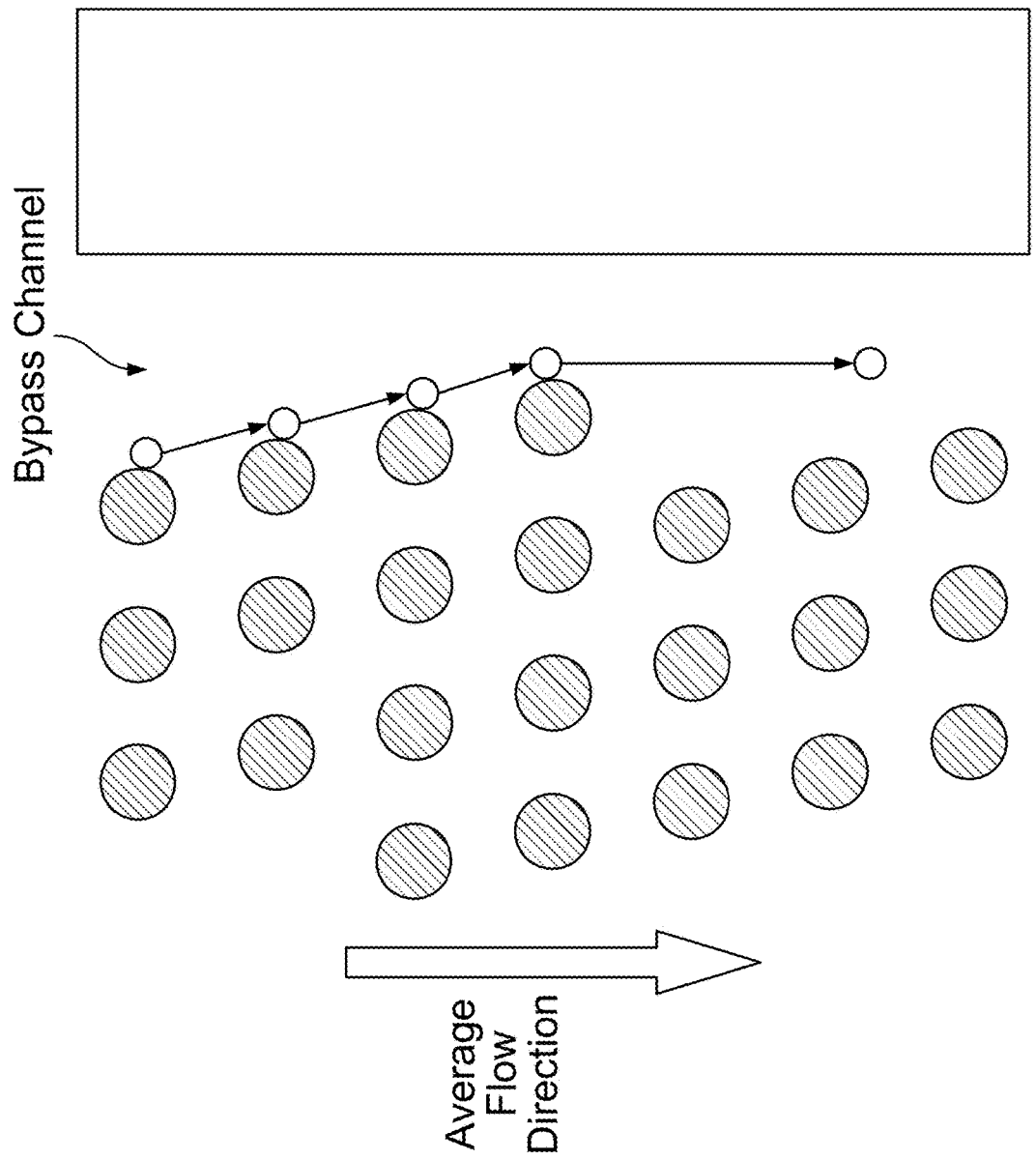
FIG. 9 is a schematic depiction of a bypass channel
Figure 11:
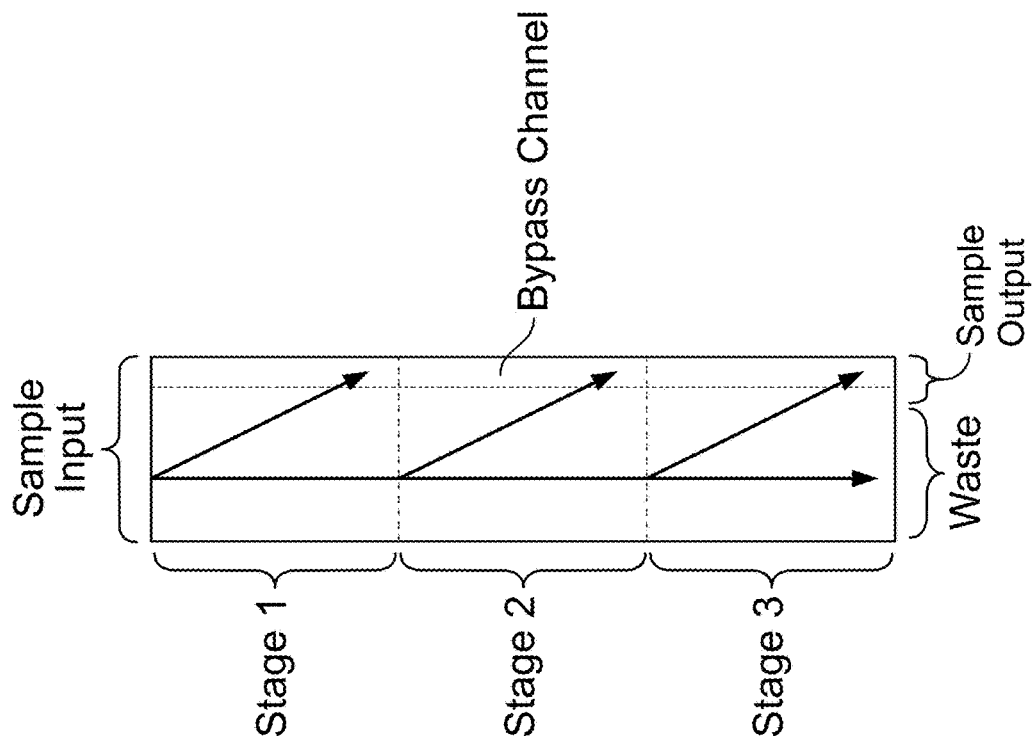
FIG. 11 is a schematic depiction of a three-stage device having a common bypass channel
Figure 10:
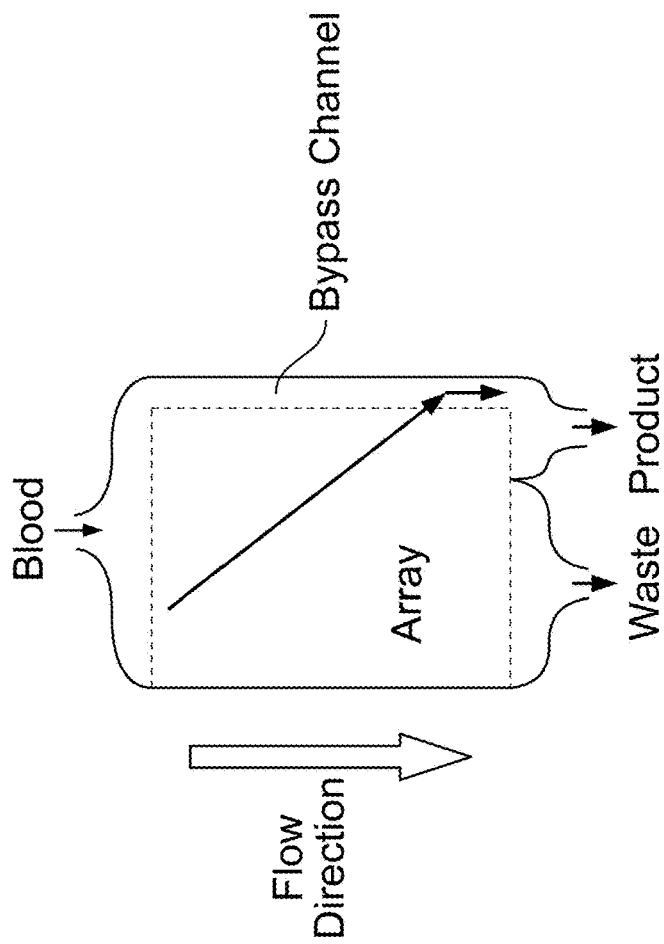
FIG. 10 is a schematic depiction of a bypass channel

Single bypass channels. In this design, all stages share one bypass channel, or there is only one stage. The physical boundary of the bypass channel may be defined by the array boundary on one side and a sidewall on the other side (FIGS. 9-11). Single bypass channels may also be employed with duplex arrays such that a central bypass channel separates the two arrays (i.e., two outer regions) (FIG. 12).

Figure 16:
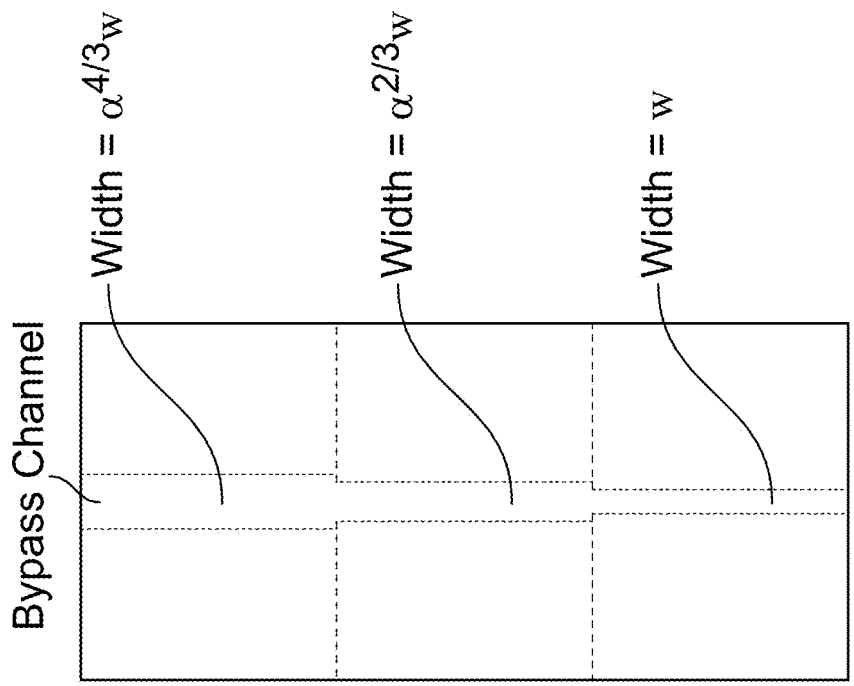
FIG. 16 is a schematic depiction of a three-stage, duplex device having a common bypass channel, where the fluidic resistance in the bypass channel and the adjacent stage are substantially constant.
Figure 15:
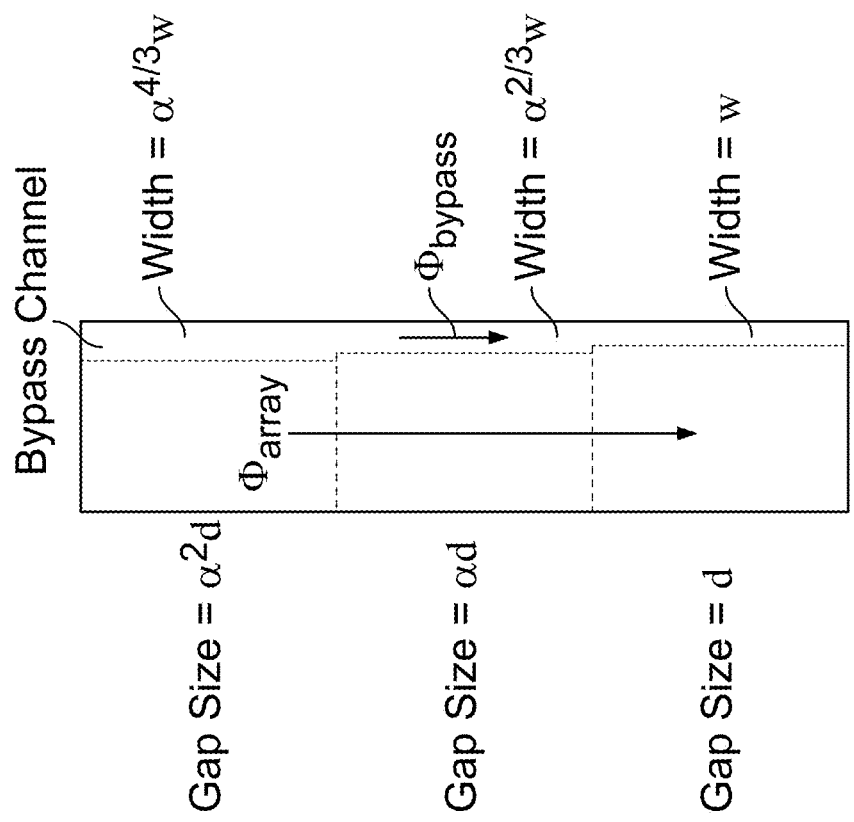
FIG. 15 is a schematic depiction of a three-stage device having a common bypass channel, where the fluidic resistance in the bypass channel and the adjacent stage are substantially constant.

Single bypass channels may also be designed, in conjunction with an array to maintain constant flux through a device (FIG. 13). The bypass channel has varying width designed to maintain constant flux through all the stages, so that the flow in the channel does not interfere with the flow in the arrays. Such a design may also be employed with an array duplex (FIG. 14). Single bypass channels may also be designed in conjunction with the array in order to maintain substantially constant fluidic resistance through all stages (FIG. 15). Such a design may also be employed with an array duplex (FIG. 16.)

Multiple bypass channels. In this design (FIG. 17), each stage has its own bypass channel, and the channels are separated from each other by sidewalls, e.g., to prevent the mixing of the contents of different channels. Large particles, e.g., cells are deflected into the major flux to the lower right corner of the first stage and then into in a bypass channel (bypass channel 1 in FIG. 17). Smaller cells that would not cause clogging in the second stage proceed to the second stage, and cells above the critical size of the second stage are deflected to the lower right corner of the second stage and into in another bypass channel (bypass channel 2 in FIG. 17). This design may be repeated for as many stages as desired. In this embodiment, the bypass channels are not fluidically connected, allowing for separate collection and other manipulations. The bypass channels do not need to be straight or be physically parallel to each other (FIG. 18). Multiple bypass channels may also be employed with duplex arrays (FIG. 19).

Figure 21:
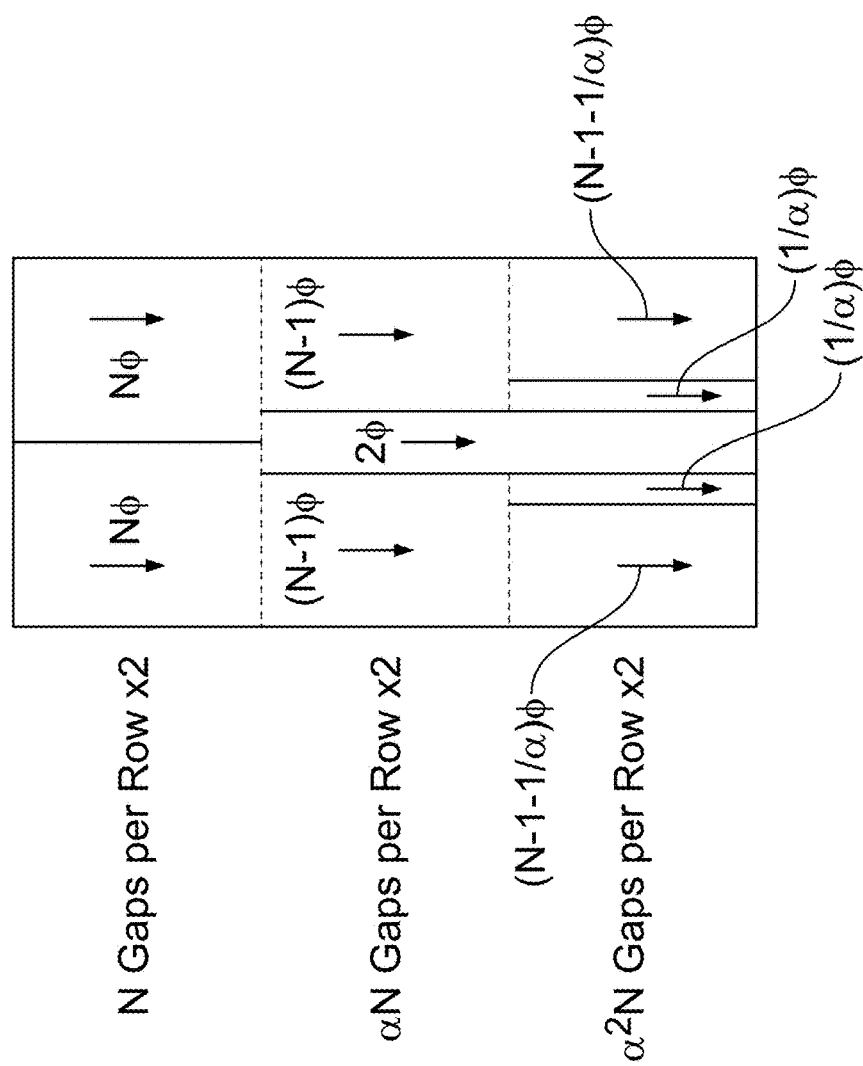
FIG. 21 is a schematic depiction of a three-stage, duplex device having three, separate bypass channels, wherein the flow through each stage is substantially constant.

Multiple bypass channels may be designed, in conjunction with an array to maintain constant flux through a device (FIG. 20). In this example, bypass channels are designed to remove an amount of flow so the flow in the array is not perturbed, i.e., substantially constant. Such a design may also be employed with an array duplex (FIG. 21). In this design, the center bypass channel may be shared between the two arrays in the duplex.

Optimal Boundary Design. If the array were infinitely large, the flow distribution would be the same at every gap. The flux $\phi$ going through a gap would be the same, and the minor flux would be $\varepsilon\phi$ for every gap. In practice, the boundaries of the array perturb this infinite flow pattern. Portions of the boundaries of arrays may be designed to generate the flow pattern of an infinite array. Boundaries may be flow-feeding, i.e., the boundary injects fluid into the array, or flow-extracting, i.e., the boundary extracts fluid from the array.

Figure 22:
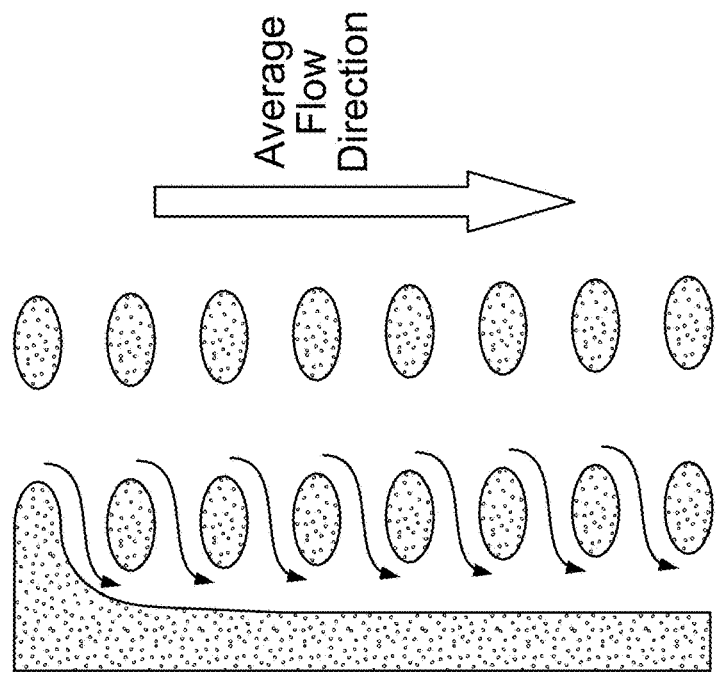
FIG. 22 is a schematic depiction of a flow-extracting boundary.

A preferred flow-extracting boundary widens gradually to extract $\varepsilon\phi$ (represented by arrows in FIG. 22) from each gap at the boundary (d=24 μm, $\varepsilon$=1/60). For example, the distance between the array and the sidewall gradually increases to allow for the addition of $\varepsilon0$ to the boundary from each gap along that boundary. The flow pattern inside this array is not affected by the bypass channel because of the boundary design.

Figure 23:
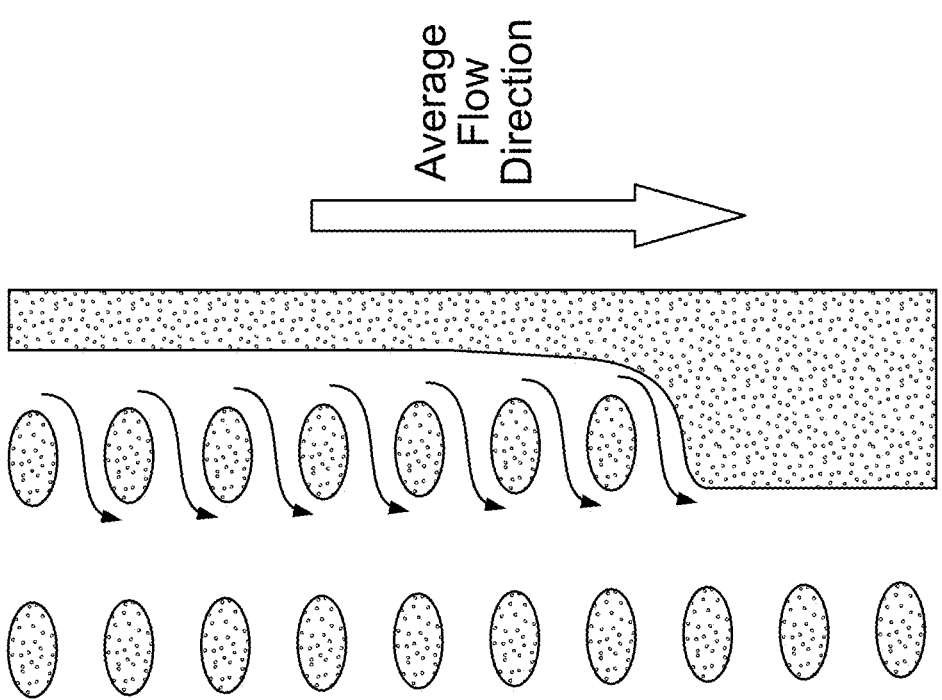
FIG. 23 is a schematic depiction of a flow-feeding boundary.

A preferred flow-feeding boundary narrows gradually to feed exactly $\varepsilon\phi$ (represented by arrows in FIG. 23) into each gap at the boundary (d=24 μm, $\varepsilon$=1/60). For example, the distance between the array and the sidewall gradually decreases to allow for the addition of $\varepsilon0$ to each gap along the boundary from that boundary. Again, the flow pattern inside this array is not affected by the bypass channel because of the boundary design.

Figure 24:
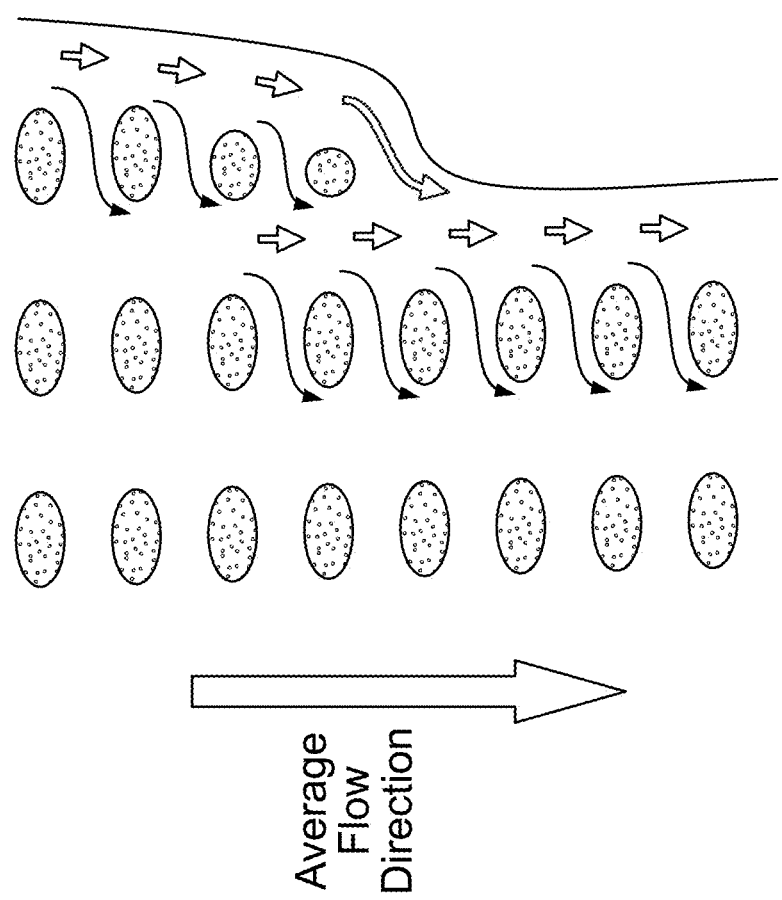
FIG. 24 is a schematic depiction of a flow-feeding boundary, including a bypass channel

A flow-feeding boundary may also be as wide as or wider than the gaps of an array (FIG. 24) (d=24 μm, $\varepsilon$=1/60). A wide boundary may be desired if the boundary serves as a bypass channel, e.g., to allow for collection of particles. A boundary may be employed that uses part of its entire flow to feed the array and feeds $\varepsilon\phi$ into each gap at the boundary (represented by arrows in FIG. 24).

Figure 25:
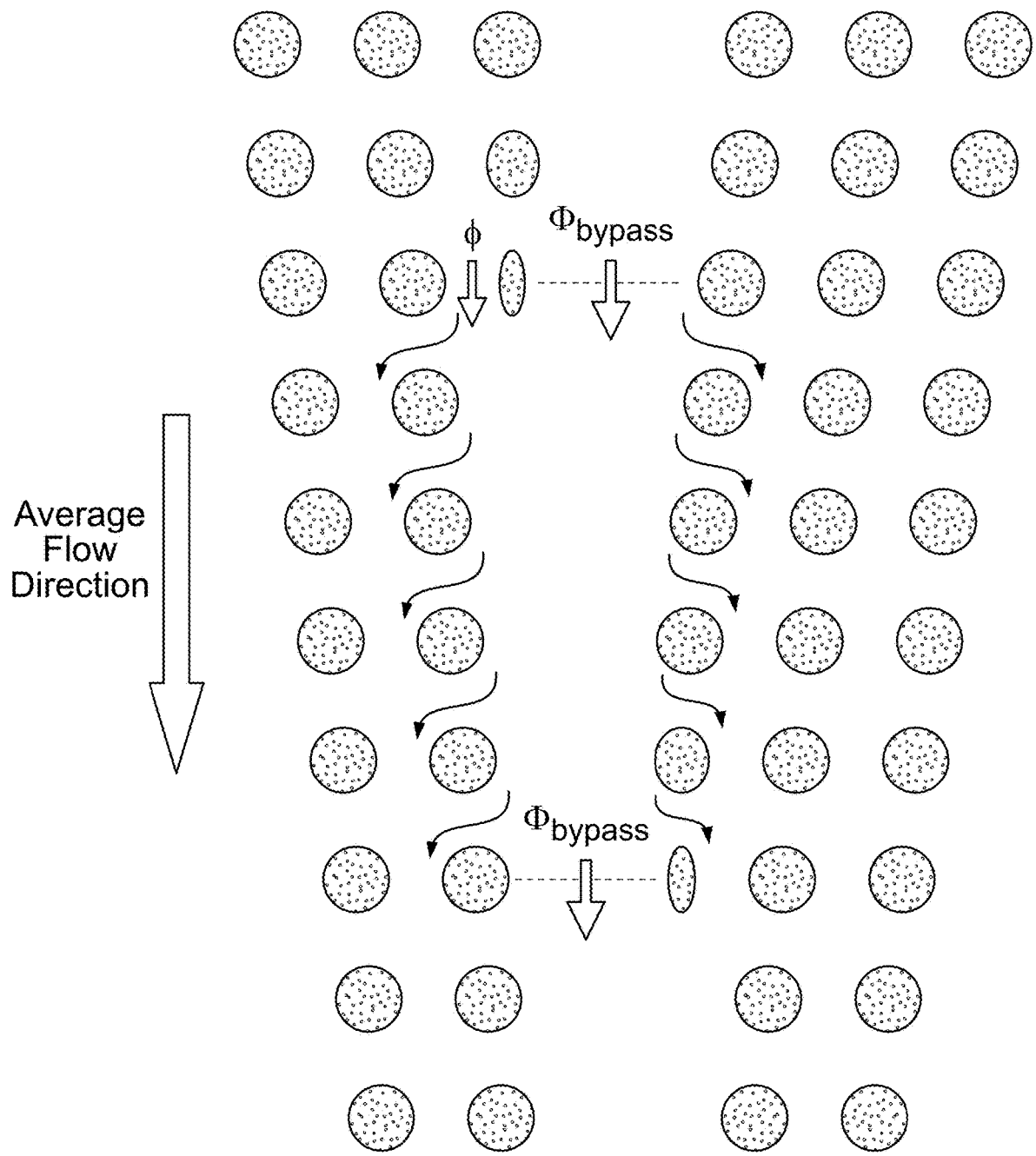
FIG. 25 is a schematic depiction of two flow-feeding boundaries flanking a central bypass channel.

FIG. 25 shows a single bypass channel in a duplex array (E=1/10, d=8 μm). The bypass channel includes two flow-feeding boundaries. The flux across the dashed line 1 in the bypass channel is $\Phi bypass$. A flow $\phi$ joins $\Phi bypass$ from a gap to the left of the dashed line. The shapes of the obstacles at the boundaries are adjusted so that the flows going into the arrays are $\varepsilon\phi$ at each gap at the boundaries. The flux at dashed line 2 is again $\Phi bypass$.

Device Design

On-chip Flow Resistor for Defining and Stabilizing Flow

Figures 26, 27:
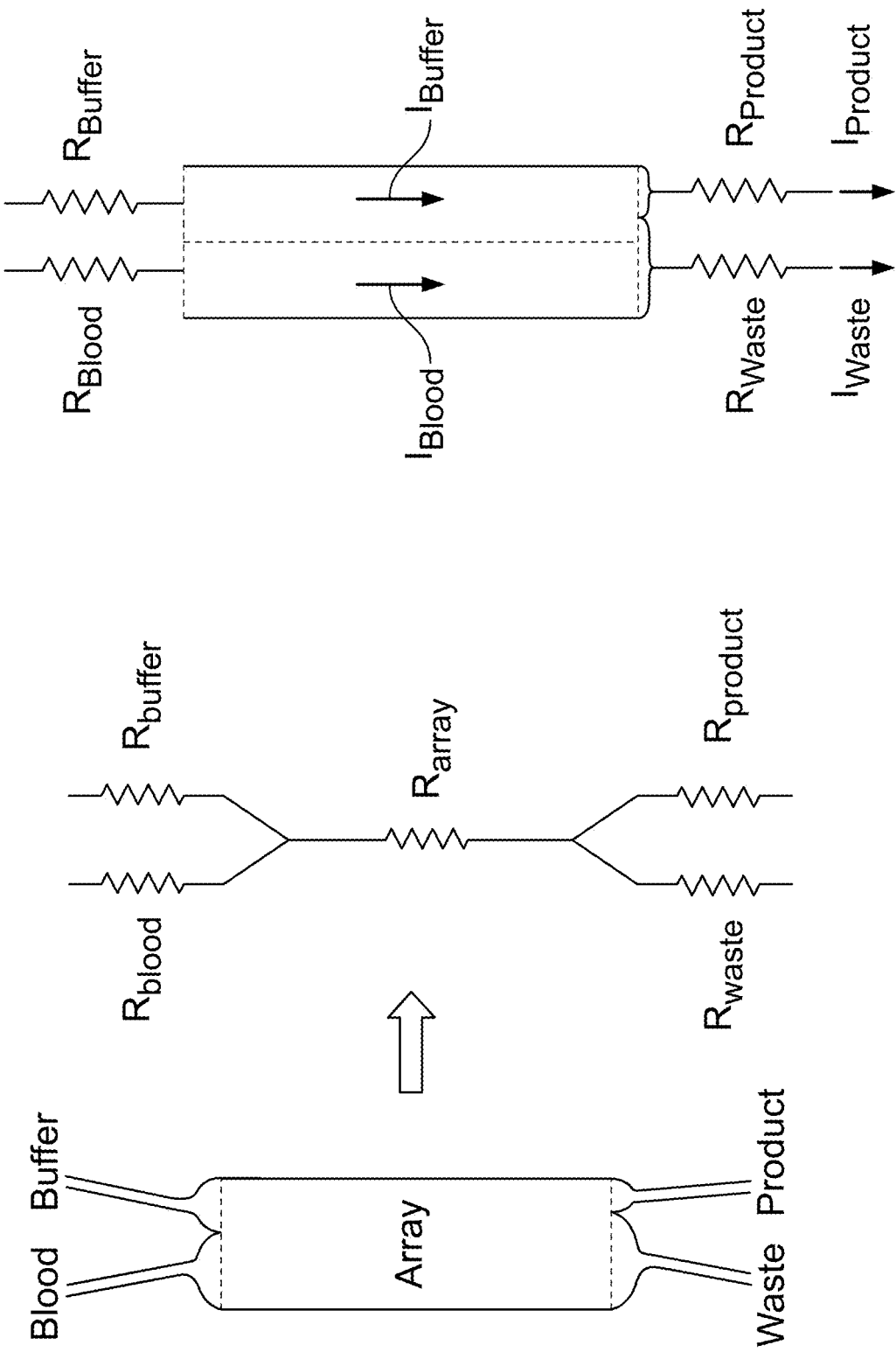
FIG. 26 is a schematic depiction of a device having four channels that act as on-chip flow resistors.
FIGS. 27 and 28 are schematic depictions of the effect of on-chip resistors on the relative width of two fluids flowing in a device.

Devices of the invention may also employ fluidic resistors to define and stabilize flows within an array and to also define the flows collected from the array. FIG. 26 shows a schematic of planar device; a sample, e.g., blood, inlet channel, a buffer inlet channel, a waste outlet channel, and a product outlet channel are each connected to an array. The inlets and outlets act as flow resistors. FIG. 26 also shows the corresponding fluidic resistances of these different device components.

Flow Definition within the Array

Figure 28:
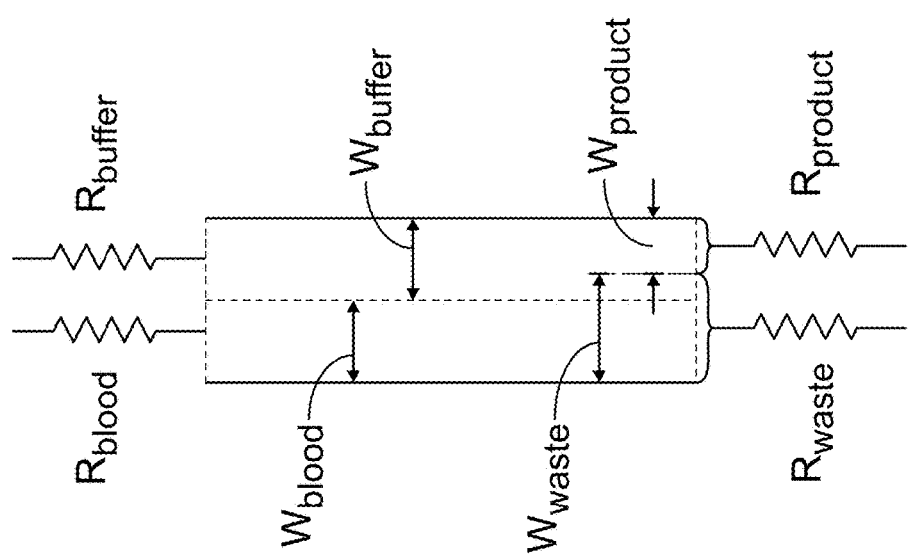

FIGS. 27 and 28 show the currents and corresponding widths of the sample and buffer flows within the array when the device has a constant depth and is operated with a given pressure drop. The flow is determined by the pressure drop divided by the resistance. In this particular device, $I_{blood}$ and $I_{buffer}$ are equivalent, and this determines equivalent widths of the blood and buffer streams in the array.

Definition of Collection Fraction

By controlling the relative resistance of the product and waste outlet channels, one can modulate the collection tolerance for each fraction. For example, in this particular set of schematics, when $R_{product}$ is greater than $R_{waste}$, a more concentrated product fraction will result at the expense of a potentially increased loss to and dilution of waste fraction. Conversely, when $R_{product}$ is less than $R_{waste}$, a more dilute and higher yield product fraction will be collected at the expense of potential contamination from the waste stream.

Flow Stabilization

Each of the inlet and outlet channels can be designed so that the pressure drops across the channels are appreciable to or greater than the fluctuations of the overall driving pressure. In typical cases, the inlet and outlet pressure drops are 0.001 to 0.99 times the driving pressure.

Multiplexed Arrays

The invention features multiplexed arrays. Putting multiple arrays on one device increases sample-processing throughput and allows for parallel processing of multiple samples or portions of the sample for different fractions or manipulations. Multiplexing is further desirable for preparative devices. The simplest multiplex device includes two devices attached in series, i.e., a cascade. For example, the output from the major flux of one device may be coupled to the input of a second device. Alternatively, the output from the minor flux of one device may be coupled to the input of the second device.

Figure 29:
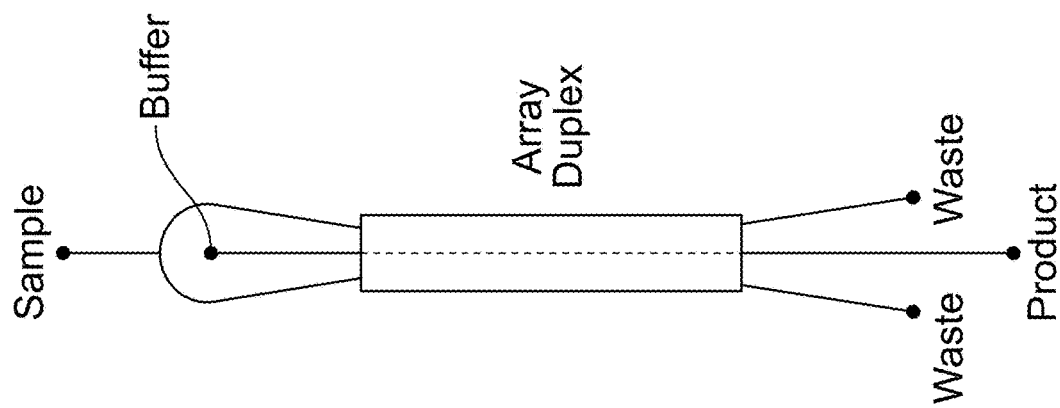
FIG. 29 is a schematic depiction of a duplex device having a common inlet for the two outer regions.

Duplexing. Two arrays can be disposed side-by-side, e.g., as mirror images (FIG. 29). In such an arrangement, the critical size of the two arrays may be the same or different. Moreover, the arrays may be arranged so that the major flux flows to the boundary of the two arrays, to the edge of each array, or a combination thereof. Such a duplexed array may also contain a central bypass channel disposed between the arrays, e.g., to collect particles above the critical size or to alter the sample, e.g., through buffer exchange, reaction, or labeling.

Multiplexing on a device. In addition to forming a duplex, two or more arrays that have separated inputs may be disposed on the same device (FIG. 30A). Such an arrangement could be employed for multiple samples, or the plurality of arrays may be connected to the same inlet for parallel processing of the same sample. In parallel processing of the same sample, the outlets may or may not be fluidically connected. For example, when the plurality of arrays has the same critical size, the outlets may be connected for high throughput sample processing. In another example, the arrays may not all have the same critical size or the particles in the arrays may not all be treated in the same manner, and the outlets may not be fluidically connected.

Figure 30B:
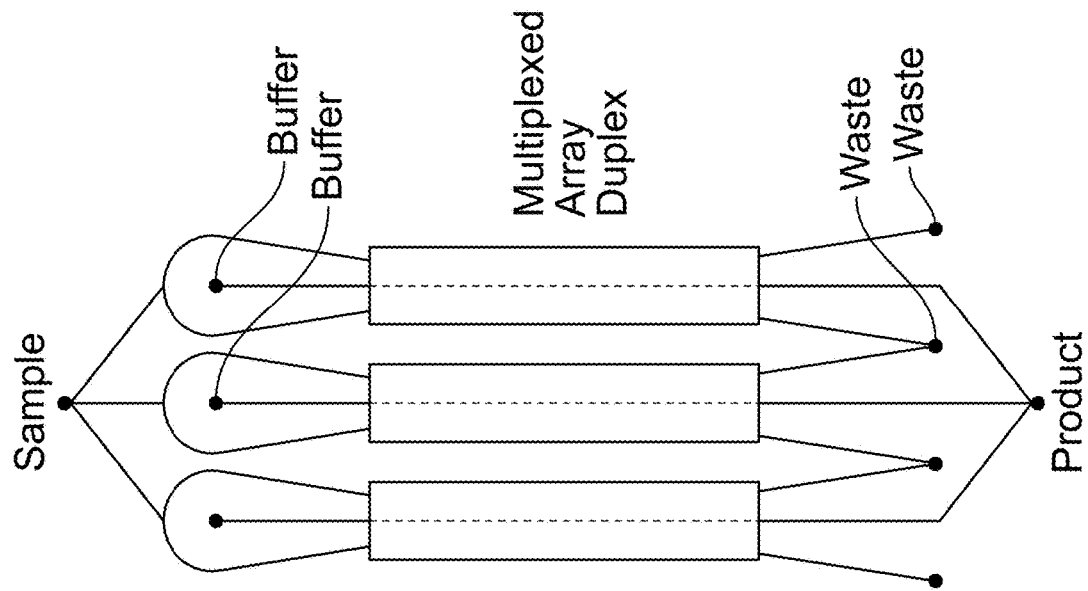
FIG. 30B is a schematic depiction of multiple arrays with common inlets and product outlets on a device.
Figure 30A:
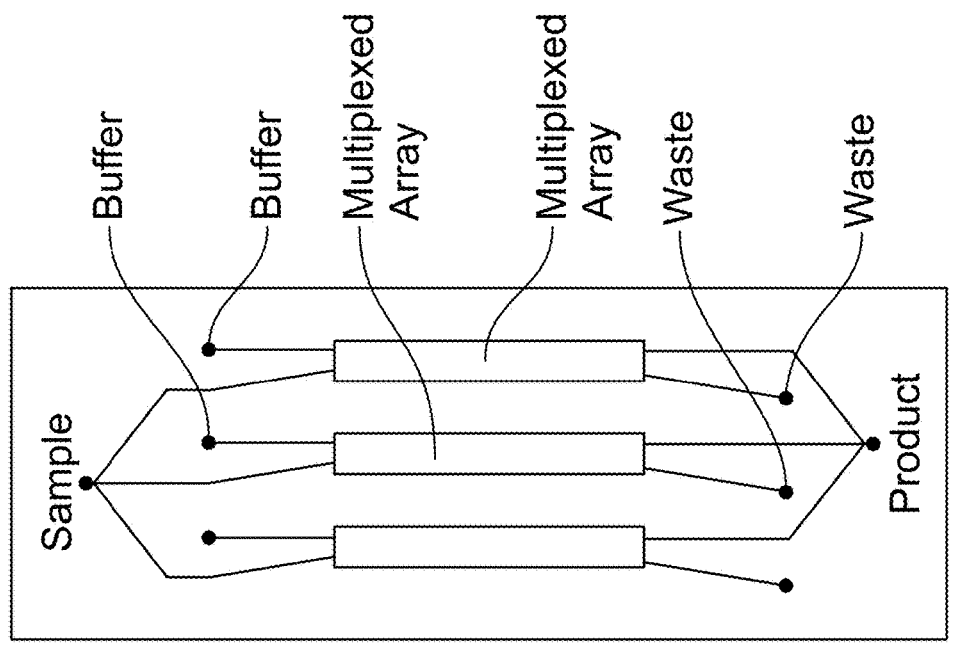
FIG. 30A is a schematic depiction of a multiple arrays on a device.

Multiplexing may also be achieved by placing a plurality of duplex arrays on a single device (FIG. 30B). A plurality of arrays, duplex or single, may be placed in any possible three-dimensional relationship to one another.

Figure 31:
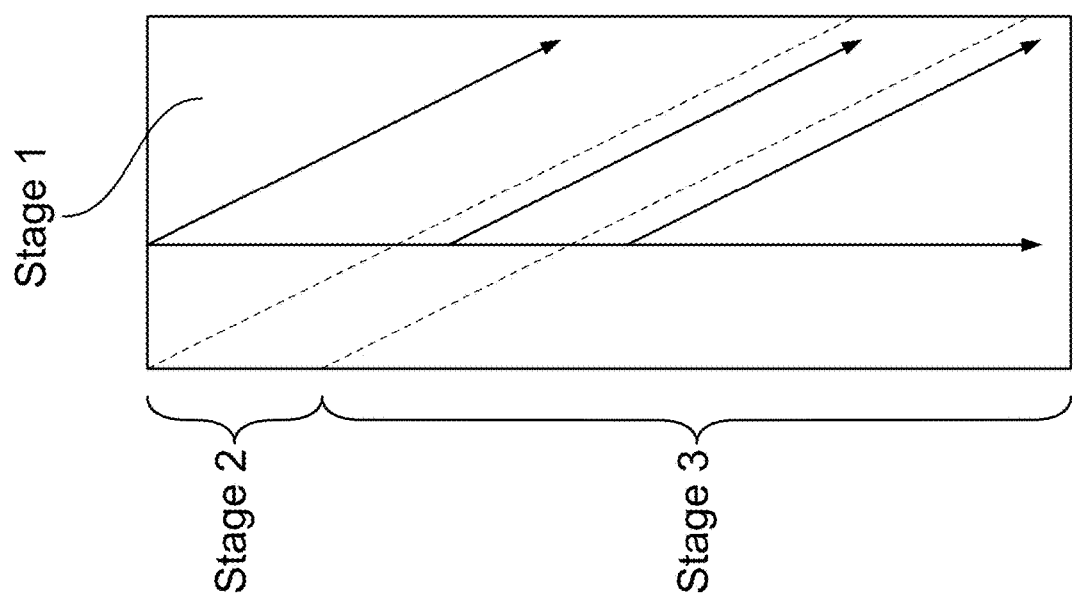
FIG. 31 is a schematic depiction of a multi-stage device with a small footprint.

Devices of the invention also feature a small-footprint. Reducing the footprint of an array can lower cost, and reduce the number of collisions with obstacles to eliminate any potential mechanical damage or other effects to particles. The length of a multiple stage array can be reduced if the boundaries between stages are not perpendicular to the direction of flow. The length reduction becomes significant as the number of stages increases. FIG. 31 shows a small-footprint three-stage array.

Additional Components

In addition to an array of gaps, devices of the invention may include additional elements, e.g., for isolating, collection, manipulation, or detection. Such elements are known in the art. Arrays may also be employed on a device having components for other types of separation, including affinity, magnetic, electrophoretic, centrifugal, and dielectrophoretic separation. Devices of the invention may also be employed with a component for two-dimensional imaging of the output from the device, e.g., an array of wells or a planar surface. Preferably, arrays of gaps as described herein are employed in conjunction with an affinity enrichment.

The invention may also be employed in conjunction with other enrichment devices, either on the same device or in different devices. Other enrichment techniques are described, e.g., in International Publication Nos. 2004/029221 and 2004/113877, U.S. Pat. No. 6,692,952, U.S. Application Publications 2005/0282293 and 2005/0266433, and U.S. Application No. 60/668,415, each of which is incorporated by reference.

Methods of Fabrication

Devices of the invention may be fabricated using techniques well known in the art. The choice of fabrication technique will depend on the material used for the device and the size of the array. Exemplary materials for fabricating the devices of the invention include glass, silicon, steel, nickel, poly(methylmethacrylate) (PMMA), polycarbonate, polystyrene, polyethylene, polyolefins, silicones (e.g., poly (dimethylsiloxane)), and combinations thereof. Other materials are known in the art. For example, deep Reactive Ion Etching (DRIE) is used to fabricate silicon-based devices with small gaps, small obstacles and large aspect ratios (ratio of obstacle height to lateral dimension). Thermoforming (embossing, injection molding) of plastic devices can also be used, e.g., when the smallest lateral feature is 20 microns and the aspect ratio of these features is less than 3 Additional methods include photolithography (e.g., stereolithography or x-ray photolithography), molding, embossing, silicon micromachining, wet or dry chemical etching, milling, diamond cutting, Lithographie Galvanoformung and Abformung (LIGA), and electroplating. For example, for glass, traditional silicon fabrication techniques of photolithography followed by wet (KOH) or dry etching (reactive ion etching with fluorine or other reactive gas) can be employed. Techniques such as laser micromachining can be adopted for plastic materials with high photon absorption efficiency. This technique is suitable for lower throughput fabrication because of the serial nature of the process. For mass-produced plastic devices, thermoplastic injection molding, and compression molding may be suitable. Conventional thermoplastic injection molding used for mass-fabrication of compact discs (which preserves fidelity of features in submicrons) may also be employed to fabricate the devices of the invention. For example, the device features are replicated on a glass master by conventional photolithography. The glass master is electroformed to yield a tough, thermal shock resistant, thermally conductive, hard mold. This mold serves as the master template for injection molding or compression molding the features into a plastic device. Depending on the plastic material used to fabricate the devices and the requirements on optical quality and throughput of the finished product, compression molding or injection molding may be chosen as the method of manufacture. Compression molding (also called hot embossing or relief imprinting) has the advantages of being compatible with high-molecular weight polymers, which are excellent for small structures, but is difficult to use in replicating high aspect ratio structures and has longer cycle times. Injection molding works well for high-aspect ratio structures but is most suitable for low molecular weight polymers.

A device may be fabricated in one or more pieces that are then assembled. Layers of a device may be bonded together by clamps, adhesives, heat, anodic bonding, or reactions between surface groups (e.g., wafer bonding). Alternatively, a device with channels in more than one plane may be fabricated as a single piece, e.g., using stereolithography or other three-dimensional fabrication techniques.

To reduce non-specific adsorption of cells or compounds, e.g., released by lysed cells or found in biological samples, onto the channel walls, one or more channel walls may be chemically modified to be non-adherent or repulsive. The walls may be coated with a thin film coating (e.g., a monolayer) of commercial non-stick reagents, such as those used to form hydrogels. Additional examples chemical species that may be used to modify the channel walls include oligoethylene glycols, fluorinated polymers, organosilanes, thiols, poly-ethylene glycol, hyaluronic acid, bovine serum albumin, poly-vinyl alcohol, mucin, poly-HEMA, methacrylated PEG, and agarose. Charged polymers may also be employed to repel oppositely charged species. The type of chemical species used for repulsion and the method of attachment to the channel walls will depend on the nature of the species being repelled and the nature of the walls and the species being attached. Such surface modification techniques are well known in the art. The walls may be functionalized before or after the device is assembled. The channel walls may also be coated in order to capture materials in the sample, e.g., membrane fragments or proteins.

Methods of Operation

Devices of the invention may be employed in any application where the production of a sample enriched in particles above or below a critical size is desired. A preferred use of the device is in produced samples enriched in cells, e.g., rare cells. Once an enriched sample is produced, it may be collected for analysis or otherwise manipulated, e.g., through further enrichment.

The method of the invention uses a flow that carries cells to be separated through the array of gaps. The flow is aligned at a small angle (flow angle) with respect to a line-of-sight of the array. Cells having a hydrodynamic size larger than a critical size migrate along the line-of-sight in the array, whereas those having a hydrodynamic size smaller than the critical size follow the flow in a different direction. Flow in the device occurs under laminar flow conditions.

Figure 32:
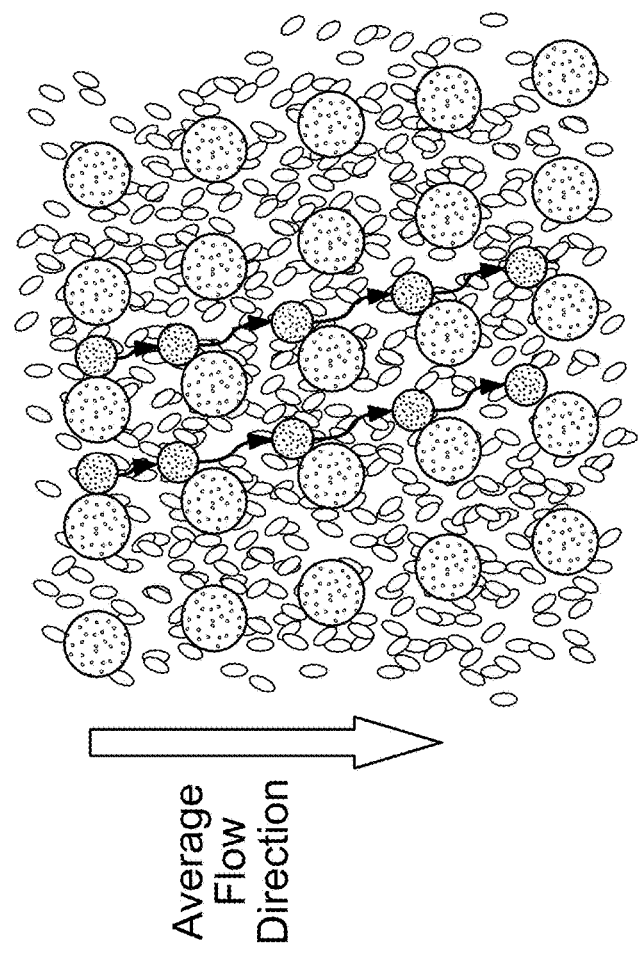
FIG. 32 is a schematic depiction of blood passing through a device.

The method of the invention may be employed with concentrated samples, e.g., where particles are touching, hydrodynamically interacting with each other, or exerting an effect on the flow distribution around another particle. For example, the method can separate white blood cells from red blood cells in whole blood from a human donor. Human blood typically contains ~45% of cells by volume. Cells are in physical contact and/or coupled to each other hydrodynamically when they flow through the array. FIG. 32 shows schematically that cells are densely packed inside an array and could physically interact with each other.

Enrichment

In one embodiment, the methods of the invention are employed to produce a sample enriched in particles of a desired hydrodynamic size. Applications of such enrichment include concentrating particles, e.g., rare cells, and size fractionization, e.g., size filtering (selecting cells in a particular range of sizes). The methods may also be used to enrich components of cells, e.g., nuclei. Nuclei or other cellular components may be produced by manipulation of the sample, e.g., lysis as described herein, or be naturally present in the sample, e.g., via apoptosis or necrosis. Desirably, the methods of the invention retain at least 1%, 10%, 30%, 50%, 75%, 80%, 90%, 95%, 98%, or 99% of the desired particles compared to the initial mixture, while potentially enriching the desired particles by a factor of at least 1, 10, 100, 1000, 10,000, 100,000, or even 1,000,000 relative to one or more non-desired particles. The enrichment may also result in a dilution of the separated particles compared to the original sample, although the concentration of the separated particles relative to other particles in the sample has increased. Preferably, the dilution is at most 90%, e.g., at most 75%, 50%, 33%, 25%, 10%, or 1%.

In a preferred embodiment, the method produces a sample enriched in rare particles, e.g., cells. In general, a rare particle is a particle that is present as less than 10% of a sample. Exemplary rare particles include, depending on the sample, fetal cells, nucleated red blood cells (e.g., fetal or maternal), stem cells (e.g., undifferentiated), cancer cells, immune system cells (host or graft), epithelial cells, connective tissue cells, bacteria, fungi, viruses, parasites, and pathogens (e.g., bacterial or protozoan). Such rare particles may be isolated from samples including bodily fluids, e.g., blood, or environmental sources, e.g., pathogens in water samples. Fetal cells, e.g., nucleated RBCs, may be enriched from maternal peripheral blood, e.g., for the purpose of determining sex and identifying aneuploidies or genetic characteristics, e.g., mutations, in the developing fetus. Cancer cells may also be enriched from peripheral blood for the purpose of diagnosis and monitoring therapeutic progress. Bodily fluids or environmental samples may also be screened for pathogens or parasites, e.g., for coliform bacteria, blood borne illnesses such as sepsis, or bacterial or viral meningitis. Rare cells also include cells from one organism present in another organism, e.g., an in cells from a transplanted organ.

In addition to enrichment of rare particles, the methods of the invention may be employed for preparative applications. An exemplary preparative application includes generation of cell packs from blood. The methods of the invention may be configured to produce fractions enriched in platelets, red blood cells, and white cells. By using multiplexed devices or multistage devices, all three cellular fractions may be produced in parallel or in series from the same sample. In other embodiments, the method may be employed to separate nucleated from enucleated cells, e.g., from cord blood sources.

Using the methods of the invention is advantageous in situations where the particles being enriched are subject to damage or other degradation. As described herein, devices of the invention may be designed to enrich cells with a minimum number of collisions between the cells and obstacles. This minimization reduces mechanical damage to cells and also prevents intracellular activation of cells caused by the collisions. This gentle handling of the cells preserves the limited number of rare cells in a sample, prevents rupture of cells leading to contamination or degradation by intracellular components, and prevents maturation or activation of cells, e.g., stem cells or platelets. In preferred embodiments, cells are enriched such that fewer than 30%, 10%, 5%, 1%, 0.1%, or even 0.01% are activated or mechanically lysed.

Figure 33:
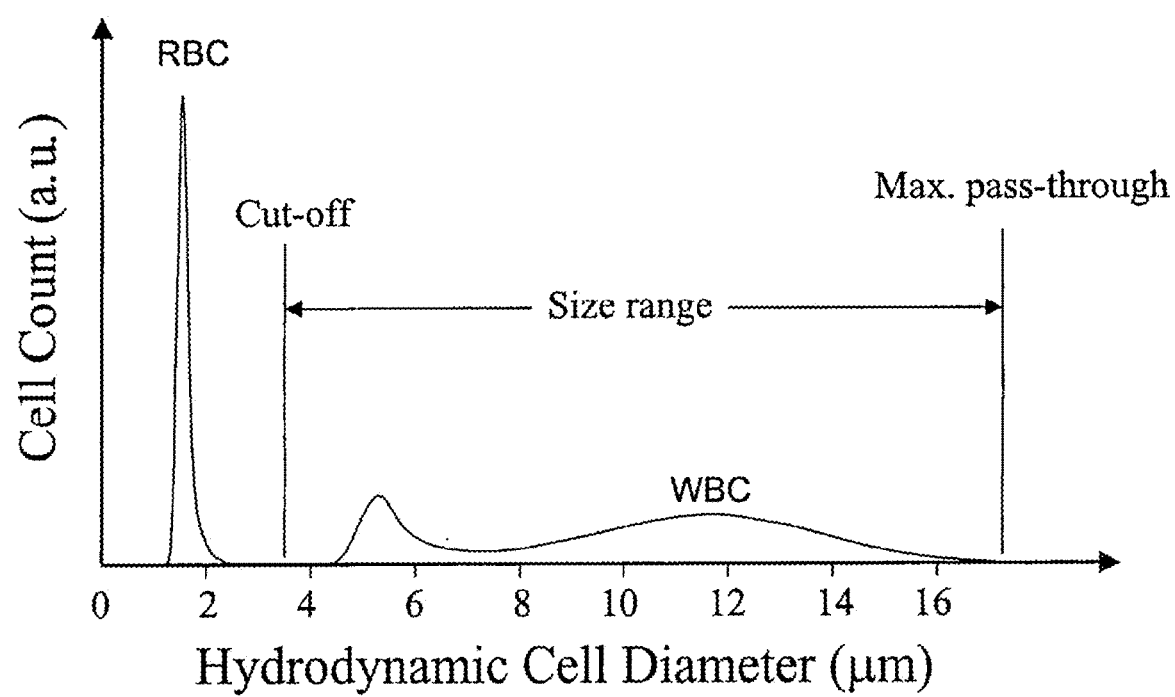
FIG. 33 is a graph illustrating the hydrodynamic size distribution of blood cells.

FIG. 33 shows a typical size distribution of cells in human peripheral blood. The white blood cells range from ~4 µm to ~18 µm, whereas the red blood cells are ~1.5 µm (short axis). An array designed to separate white blood cells from red blood cells typically has a cut-off size (i.e., critical size) of 2 to 4 µm and a maximum pass-through size of greater than 18 µm.

In an alternative embodiment, the device would function as a detector for abnormalities in red blood cells. The deterministic principle of sorting enables a predictive outcome of the percentage of enucleated cells deflected in the device. In a disease state, such as malarial infection or sickle cell anemia, the distortion in shape and flexibility of the red cells would significantly change the percentage of cells deflected. This change can be monitored as a first level sentry to alert to the potential of a diseased physiology to be followed by microscopy examination of shape and size of red cells to assign the disease. The method is also generally applicable monitoring for any change in flexibility of particles in a sample.

In an alternative embodiment, the device would function as a detector for platelet aggregation. The deterministic principle of sorting enables a predictive outcome of the percentage of free platelets deflected in the device. Activated platelets would form aggregates, and the aggregates would be deflected. This change can be monitored as a first level sentry to alert the compromised efficacy of a platelet pack for reinfusion. The method is also generally applicable monitoring for any change in size, e.g., through agglomeration, of particles in a sample.

Alteration

In other embodiments of the methods of this invention, cells of interest are contacted with an altering reagent that may chemically or physically alter the particle or the fluid in the suspension. Such applications include purification, buffer exchange, labeling (e.g., immunohistochemical, magnetic, and histochemical labeling, cell staining, and flow in-situ fluorescence hybridization (FISH)), cell fixation, cell stabilization, cell lysis, and cell activation.

Figure 34B:
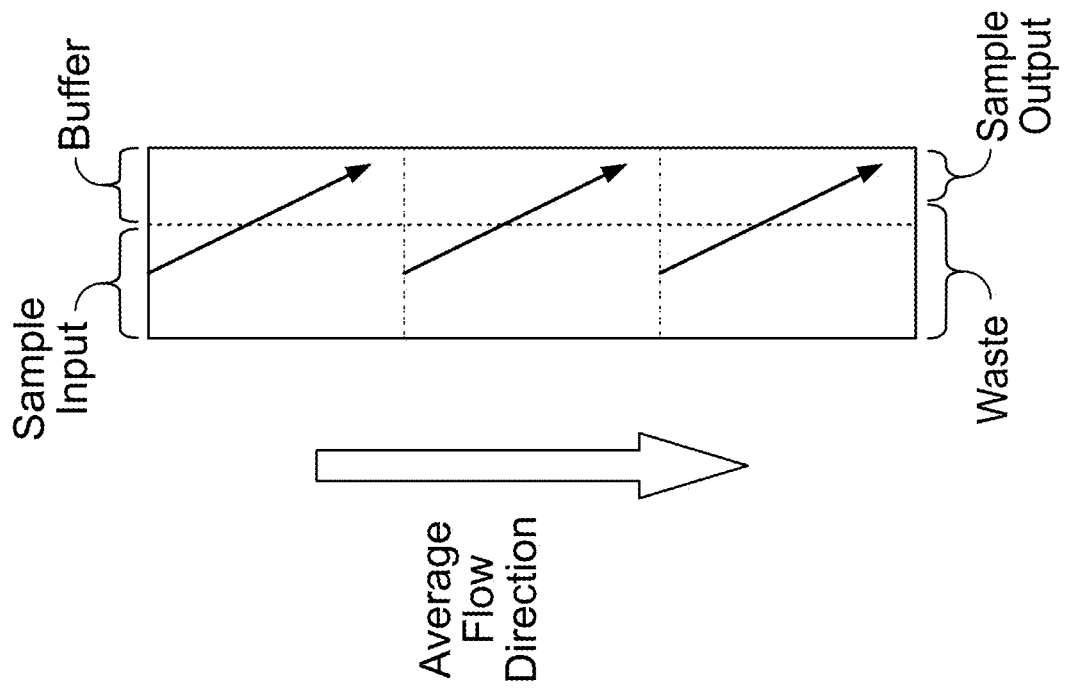
FIGS. 34A-34D are schematic depictions of moving a particle from a sample to a buffer in a single stage (A), three-stage (B), duplex (C), or three-stage duplex (D) device.
Figure 34A:
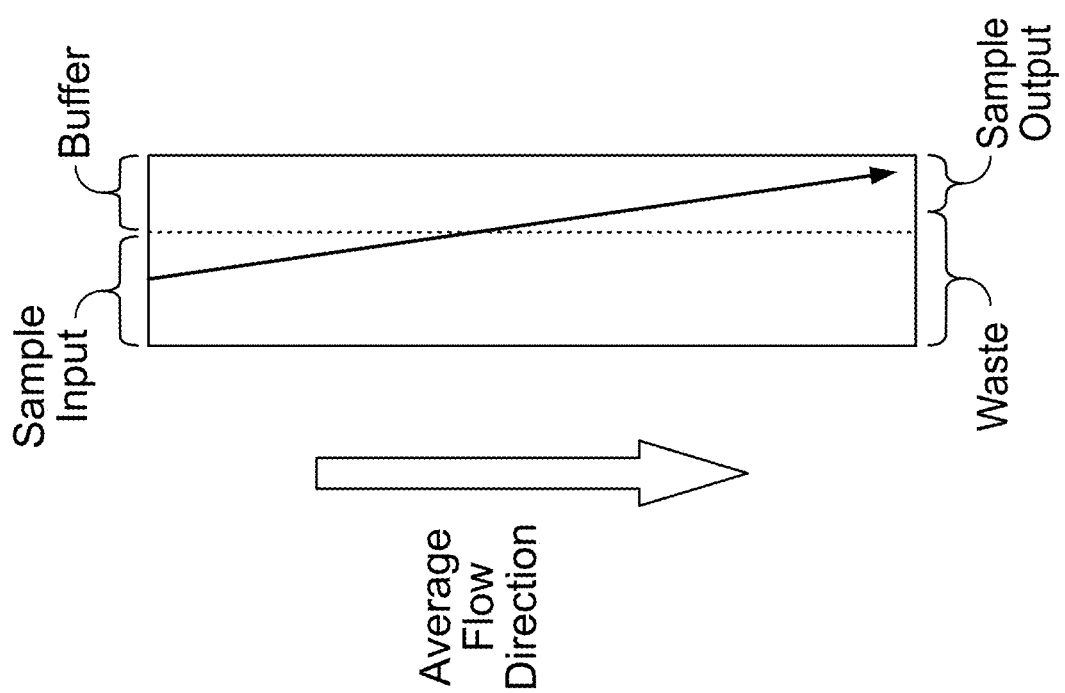
Figure 34D:
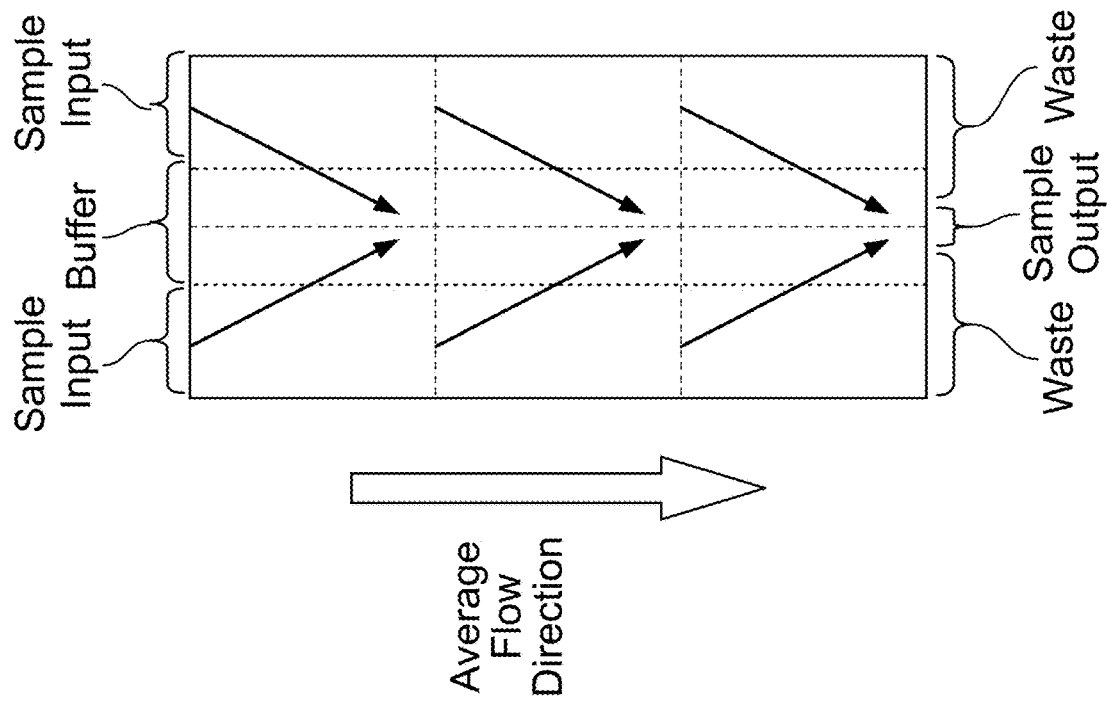
Figure 34C:
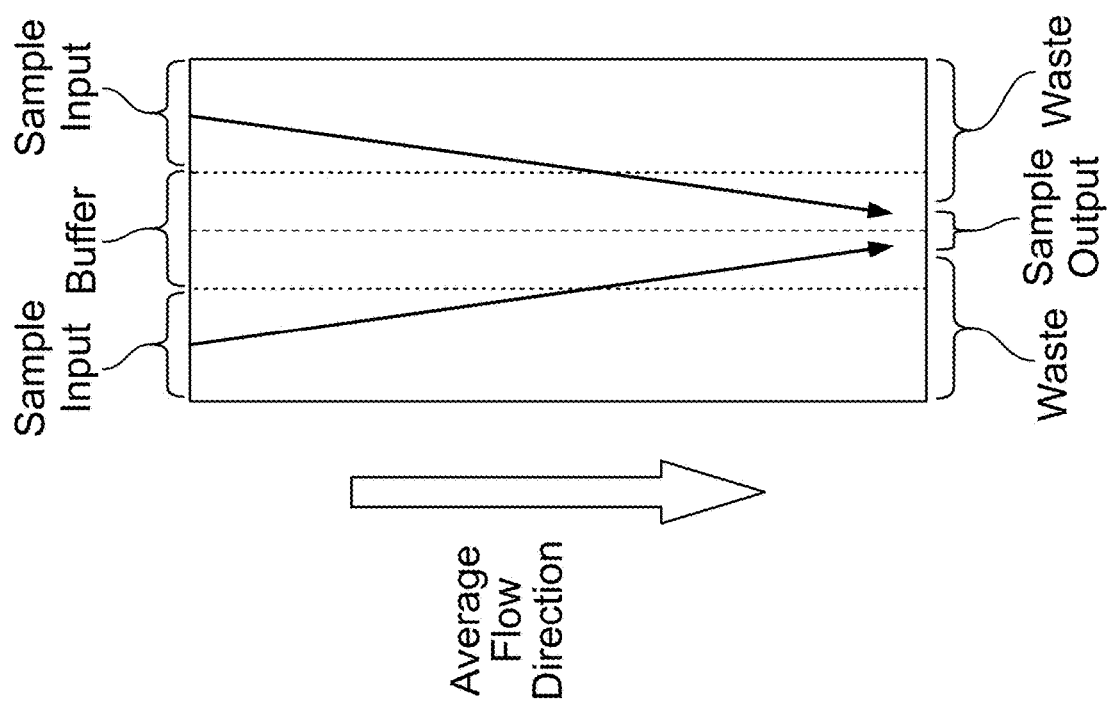

Such methods allow for the transfer of particles from a sample into a different liquid. FIG. 34A shows this effect schematically for a single stage device, FIG. 34B shows this effect for a multistage device, FIG. 34C shows this effect for a duplex array, and FIG. 34D shows this effect for a multistage duplex array. By using such methods, blood cells may be separated from plasma. Such transfers of particles from one liquid to another may be also employed to effect a series of alterations, e.g., Wright staining blood on-chip. Such a series may include reacting a particle with a first reagent and then transferring the particle to a wash buffer, and then to another reagent.

Figure 35A:
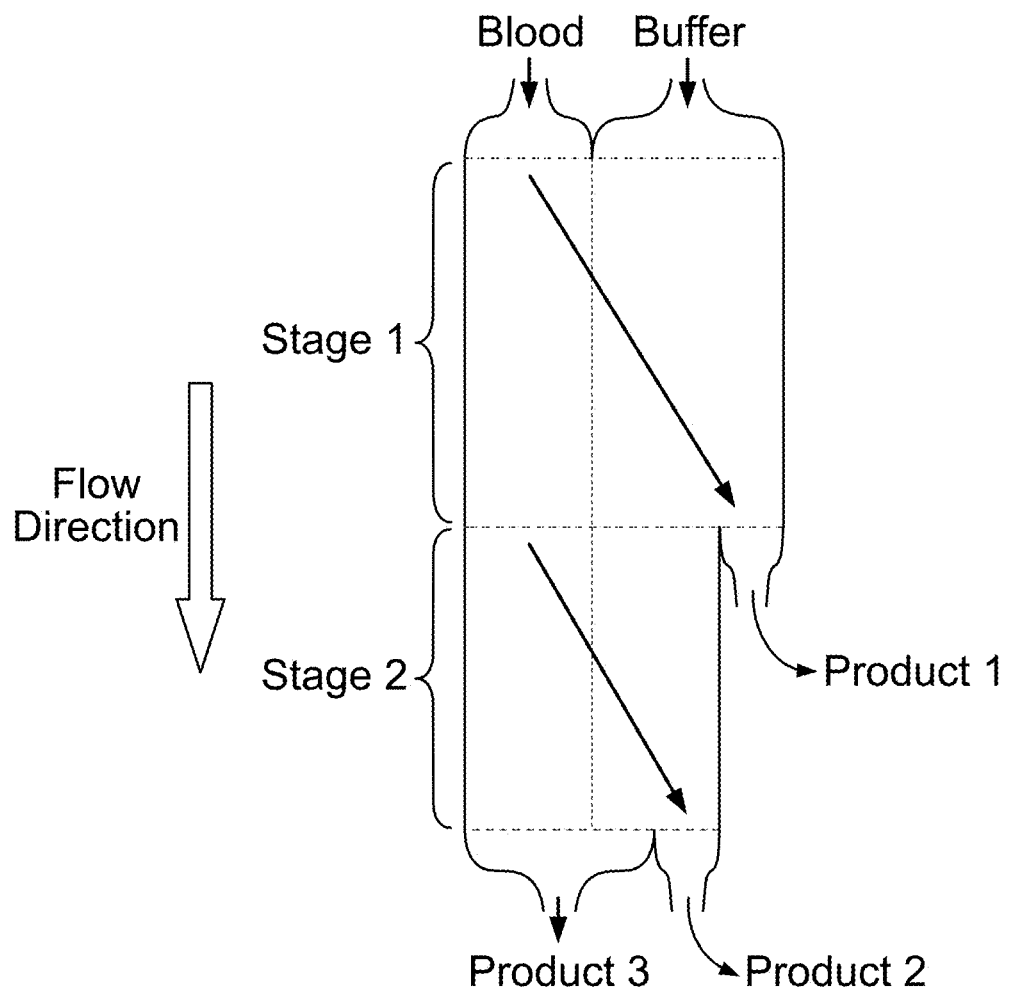
FIG. 35A is a schematic depiction of a two-stage device employed to move a particle from blood to a buffer to produce three products.
Figure 35B:
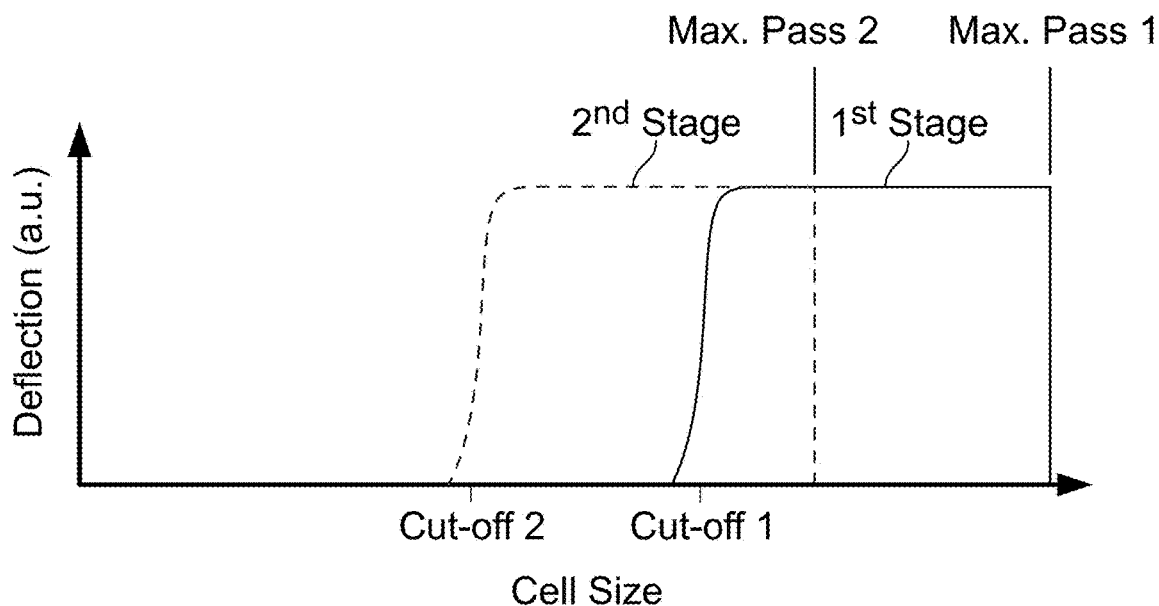
FIG. 35B is a schematic graph of the maximum size and cut off size of the two stages.
Figure 35C:
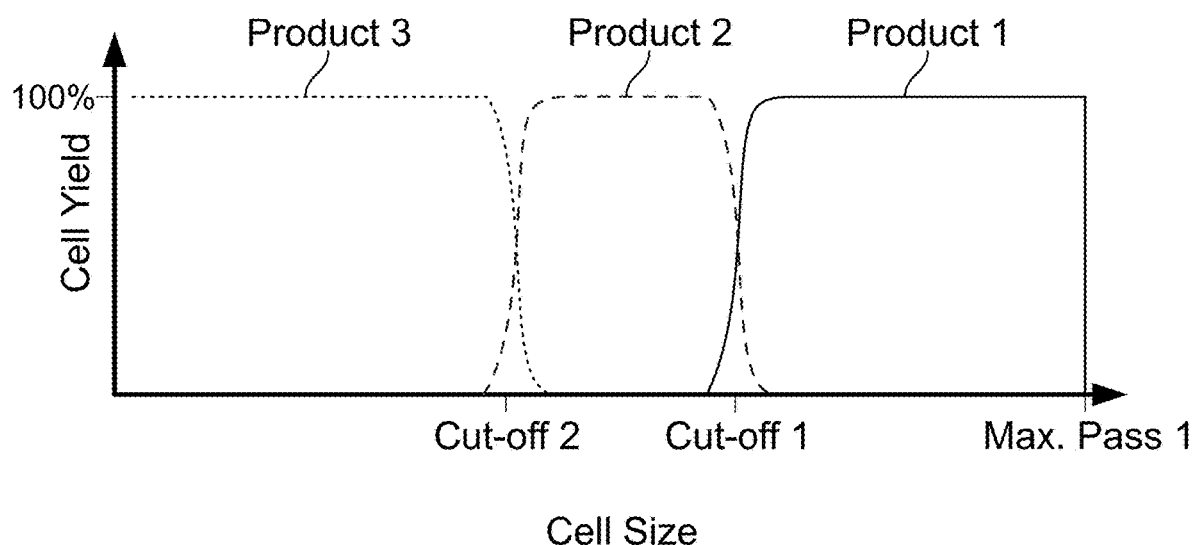
FIG. 35C is a schematic graph of the composition of the three products.

FIGS. 35A, 35B, 35C illustrate a further example of alteration in a two-stage device having two bypass channels. In this example, large blood particles are moved from blood to buffer and collected in stage 1, medium blood particles are moved from blood to buffer in stage 2, and then small blood particles that are not removed from the blood in stages 1 and 2 are collected. FIG. 35B illustrates the size cut-off of the two stages, and FIG. 35C illustrates the size distribution of the three fractions collected.

Figure 37:
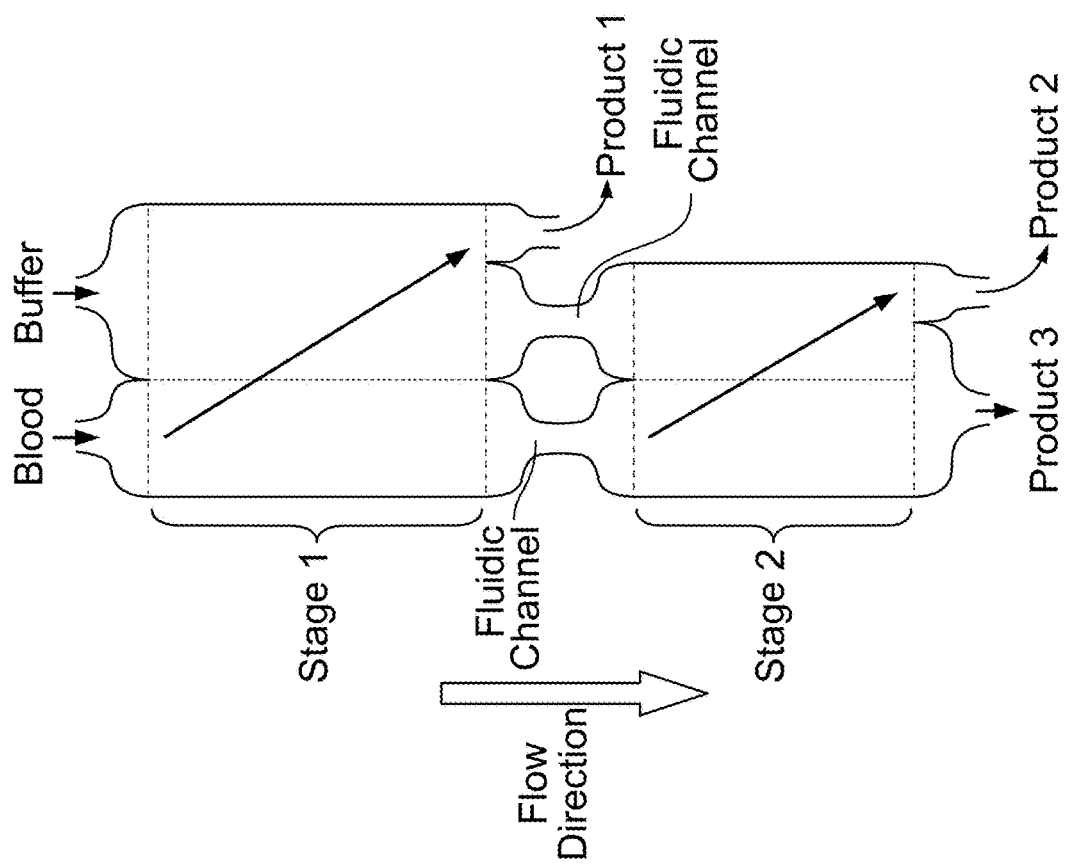
FIG. 37 is a schematic depiction of the use of fluidic channels to connect two stages in a device.
Figure 36:
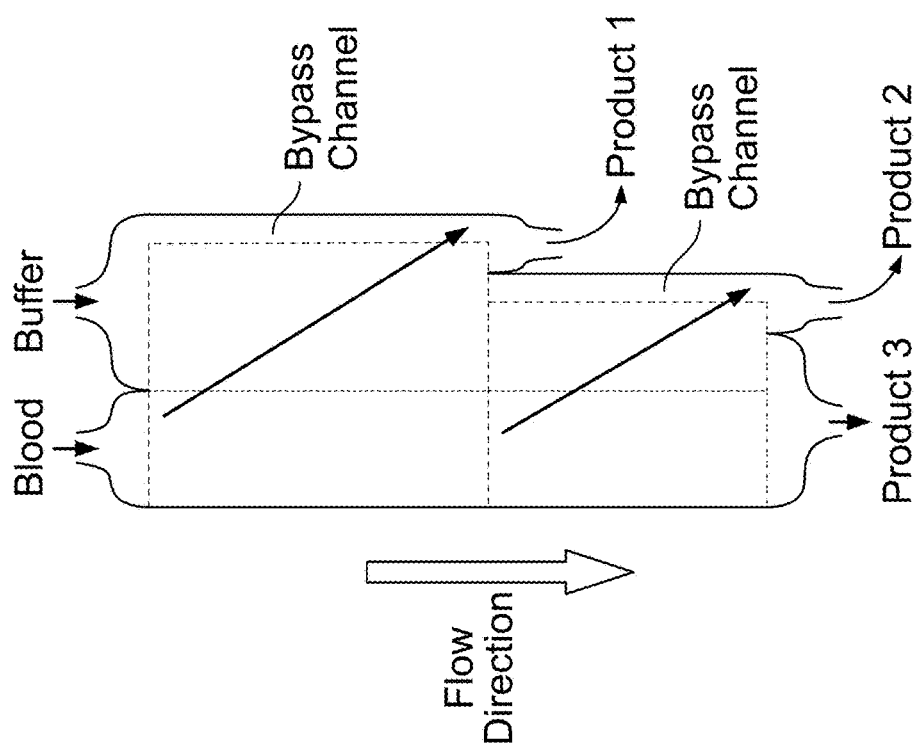
FIG. 36 is a schematic depiction of a two-stage device for alteration, where each stage has a bypass channel.
Figure 38:
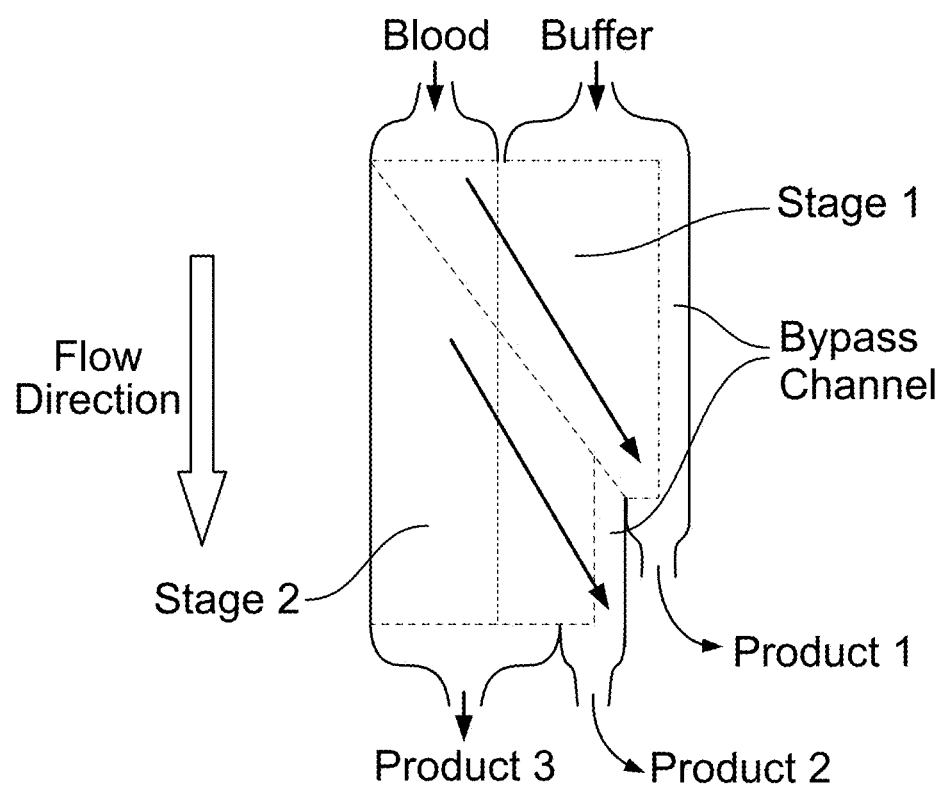
FIG. 38 is a schematic depiction of the use of fluidic channels to connect two stages in a device, wherein the two stages are configured as a small footprint array.
Figure 39A:
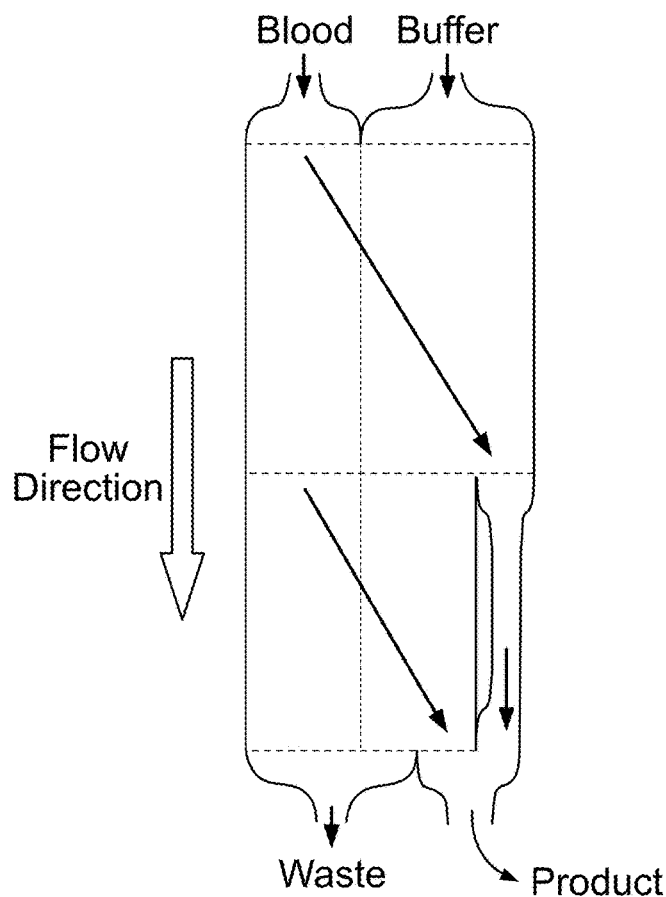
FIG. 39A is a schematic depiction of a two-stage device having a bypass channel that accepts output from both stages.
Figure 39B:
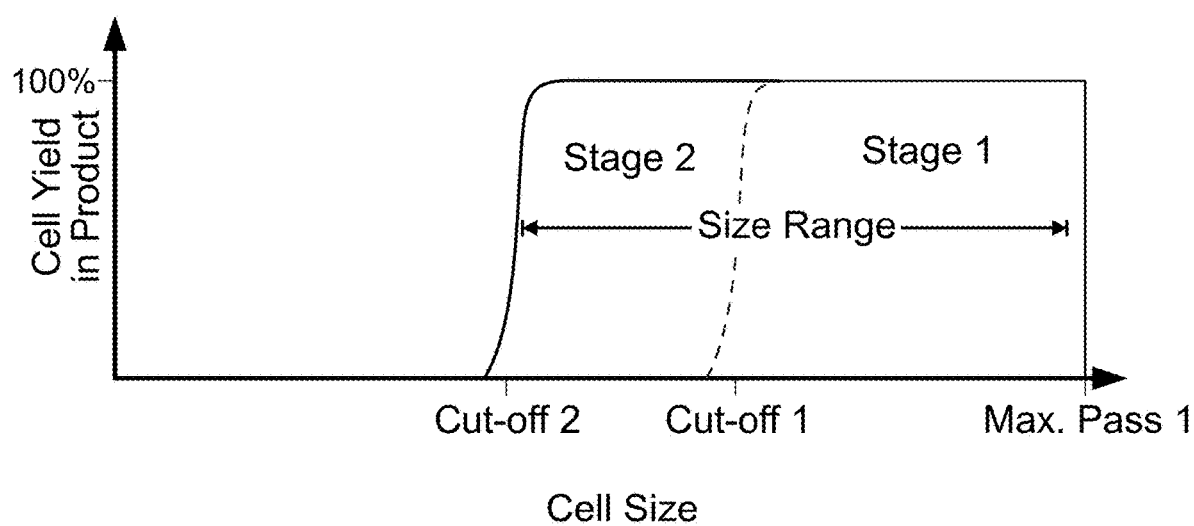
FIG. 39B is a schematic graph of the range of product sizes achievable with this device.
Figure 40:
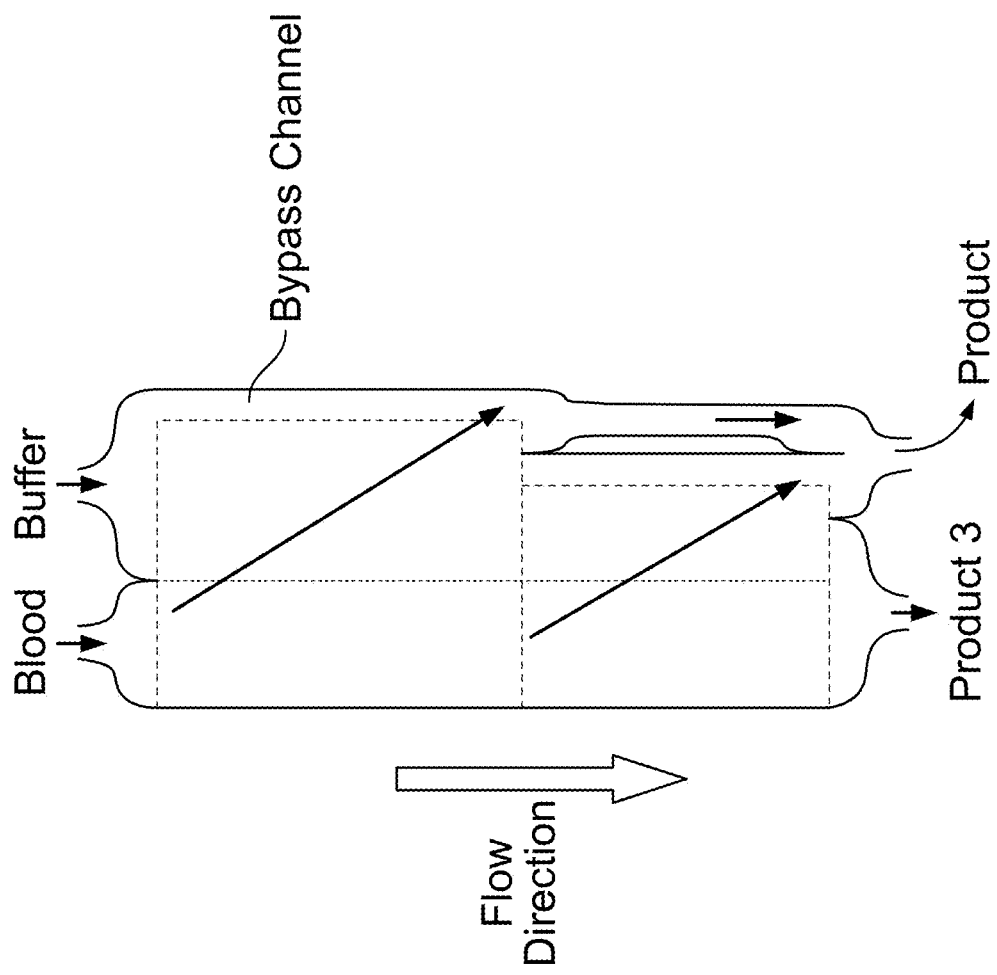
FIG. 40 is a schematic depiction of a two-stage device for alteration having bypass channels that flank each stage and empty into the same outlet.

FIG. 36 illustrates an example of alteration in a two-stage device having bypass channels that are disposed between the lateral edge of the array and the channel wall. FIG. 37 illustrates a device similar to that in FIG. 36, except that the two stages are connected by fluidic channels. FIG. 38 illustrates alteration in a device having two stages with a small footprint. FIGS. 39A-39B illustrates alteration in a device in which the output from the first and second stages is captured in a single channel. FIG. 40 illustrates another device for use in the methods of the invention.

Figure 41:
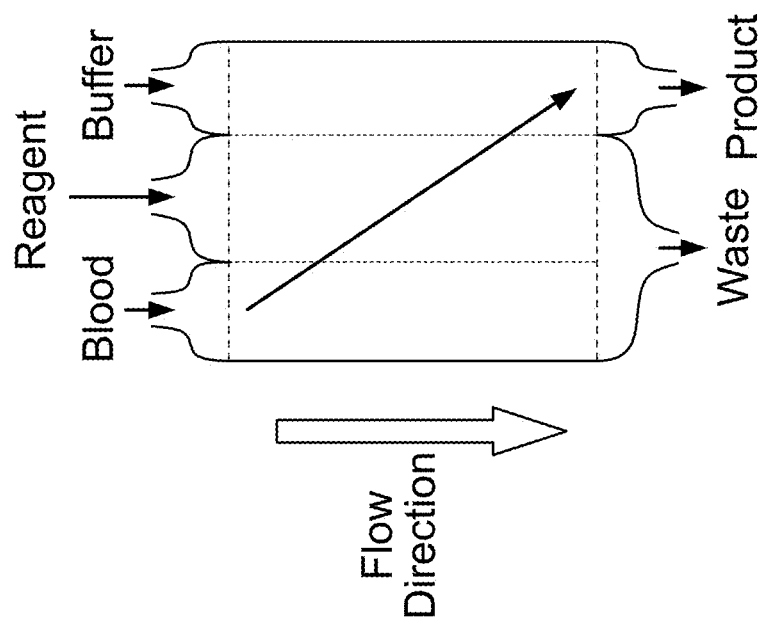
FIG. 41 is a schematic depiction of a device for the sequential movement and alteration of particles.

FIG. 41 illustrates the use of a device to perform multiple, sequential alterations on a particle. In this method, a blood particle is moved from blood into a reagent that reacts with the particle, and the reacted particle is then moved into a buffer, thereby removing the unreacted reagent or reaction byproducts. Additional steps may be added.

In another embodiment, reagents are added to the sample to selectively or nonselectively increase the hydrodynamic size of the particles within the sample. This modified sample is then pumped through an obstacle array. Because the particles are swollen and have an increased hydrodynamic diameter, it will be possible to use obstacle arrays with larger and more easily manufactured gap sizes. In a preferred embodiment, the steps of swelling and size-based enrichment are performed in an integrated fashion on a device. Suitable reagents include any hypotonic solution, e.g., deionized water, 2% sugar solution, or neat non-aqueous solvents. Other reagents include beads, e.g., magnetic or polymer, that bind selectively (e.g., through antibodies or avidin-biotin) or non-selectively.

In an alternate embodiment, reagents are added to the sample to selectively or nonselectively decrease the hydrodynamic size of the particles within the sample. Nonuniform decrease in particles in a sample will increase the difference in hydrodynamic size between particles. For example, nucleated cells are separated from enucleated cells by hypertonically shrinking the cells. The enucleated cells can shrink to a very small particle, while the nucleated cells cannot shrink below the size of the nucleus. Exemplary shrinking reagents include hypertonic solutions.

In another embodiment, affinity functionalized beads are used to increase the volume of particles of interest relative to the other particles present in a sample, thereby allowing for the operation of a obstacle array with a larger and more easily manufactured gap size.

Enrichment and alteration may also be combined, e.g., where desired cells are contacted with a lysing reagent and cellular components, e.g., nuclei, are enriched based on size. In another example, particles may be contacted with particulate labels, e.g., magnetic beads, which bind to the particles. Unbound particulate labels may be removed based on size.

Combination with other Enrichment Techniques

Enrichment and alteration methods employing devices of the invention may be combined with other particulate sample manipulation techniques. In particular, further enrichment or purification of a particle may be desirable. Further enrichment may occur by any technique, including affinity enrichment. Suitable affinity enrichment techniques include contact particles of interest with affinity agents bound to channel walls or an array of obstacles.

Fluids may be driven through a device either actively or passively. Fluids may be pumped using electric field, a centrifugal field, pressure-driven fluid flow, an electro-osmotic flow, and capillary action. In preferred embodiments, the average direction of the field will be parallel to the walls of the channel that contains the array.

Methods of Preferential Lysis

The invention further provides methods for preferentially lysing cells of interest in a sample, e.g., to extract clinical information from a cellular component, e.g., a nucleus, of the cells of interest. In general, the method employs differential lysis between the cells of interest and other cells (e.g., other nucleated cells) in the sample.

Lysis

Cells of interest may be lysed using any suitable method. In one embodiment of the methods of this invention, cells may be lysed by being contacted with a solution that causes preferential lysis. Lysis solutions for these cells may include cell specific IgM molecules and proteins in the complement cascade to initiate complement mediated lysis. Another kind of lysis solution may include viruses that infect a specific cell type and cause lysis as a result of replication (see, e.g., Pawlik et al. Cancer 2002, 95:1171-81). Other lysis solutions include those that disrupt the osmotic balance of cells, e.g., hypotonic or hypertonic (e.g., distilled water), to cause lysis. Other lysis solutions are known in the art. Lysis may also occur by mechanical means, e.g., by passing cells through a sieve or other structure that mechanically disrupts the cells, through the addition of heat, acoustic, or light energy to lyse the cells, or through cell-regulated processes such as apoptosis and necrosis. Cells may also be lysed by subjecting them to one or more cycles of freezing and thawing. Additionally, detergents may be employed to solubilize the cell membrane, lysing the cells to liberate their contents.

In one embodiment, the cells of interest are rare cells, e.g., circulating cancer cells, fetal cells (such as fetal nucleated red blood cells), blood cells (such as nucleated red blood cells, including maternal and/or fetal nucleated red blood cells), immune cells, connective tissue cells, parasites, or pathogens (such as, bacteria, protozoa, and fungi). Most circulating rare cells of interest have compromised membrane integrity as a result of the immune attack from the host RES (Reticulo-Endothelial-System), and accordingly are more susceptible to lysis.

In one embodiment, the cells of interest are lysed as they flow through a microfluidic device, e.g., as described in International Publications WO 2004/029221 and WO 2004/113877 or as described herein. In another embodiment, cells of interest are first bound to obstacles in a microfluidic device, e.g., as described in U.S. Pat. No. 5,837,115, and then lysed. In this embodiment, the cellular components of cells of interest are released from the obstacles, while cellular components of undesired cells remain bound.

Collection of Cellular Components

Desired cellular components may be separated from cell lysate by any suitable method, e.g., based on size, weight, shape, charge, hydrophilicity/hydrophobicity, chemical reactivity or inertness, or affinity. For example, nucleic acids, ions, proteins, and other charged species may be captured by ion exchange resins or separated by electrophoresis. Cellular components may also be separated based on size or weight by size exclusion chromatography, centrifugation, or filtration. Cellular components may also be separated by affinity mechanisms (i.e., a specific binding interaction, such antibody-antigen and nucleic acid complementary interactions), e.g., affinity chromatography, binding to affinity species bound to surfaces, and affinity-based precipitation. In particular, nucleic acids, e.g., genomic DNA, may be separated by hybridization to sequence specific probes, e.g., attached to beads or an array. Cellular components may also be collected on the basis of shape or deformability or non-specific chemical interactions, e.g., chromatography or reverse phase chromatography or precipitation with salts or other reagents, e.g., organic solvents. Cellular components may also be collected based on chemical reactions, e.g., binding of free amines or thiols. Prior to collection, cellular components may also be altered to enable or enhance a particular mode of collection, e.g., via denaturation, enzymatic cleavage (such as via a protease, endonuclease, exonuclease, or restriction endonuclease), or labeling or other chemical reaction.

The level of purity required for collected cellular components will depend on the particular manipulation employed and may be determined by the skilled artisan. In certain embodiments, the cellular component may not need to be isolated from the lysate, e.g., when the cellular component of interest may be analyzed or otherwise manipulated without interference from other cellular components. Affinity based manipulations (e.g., reaction with nucleic acid probes or primers, aptamers, antibodies, or sequence specific intercalating agents, with or without detectable labels) are amenable for use without purification of the cellular components.

In one embodiment, a device, e.g., as described in U.S. Application Publication 2004/0144651 or as described herein, is employed to isolate particulate cellular components of interest, e.g., nuclei, from the lysate based on size. In this embodiment, the particulate cellular components of interest may be separated from other particulate cellular components and intact cells using the device.

Manipulation of Cellular Components

Once released by lysis or otherwise obtained, e.g., via size based separation methods described herein, desired cellular components may be further manipulated, e.g., identified, enumerated, reacted, isolated, or destroyed. In one embodiment, the cellular components contain nucleic acid, e.g., nuclei, mitochondria, and nuclear or cytoplasmic DNA or RNA. In particular, nucleic acids may include RNA, such as mRNA or rRNA, or DNA, such as chromosomal DNA, e.g., that has been cleaved, or DNA that has undergone apoptotic processing. Genetic analysis of the nucleic acid in the cellular component may be performed by any suitable methods, e.g., PCR, FISH, and sequencing. Genetic information may be employed to diagnose disease, status as a genetic disease carrier, or infection with pathogens or parasites. If acquired from fetal cells, genetic information relating to sex, paternity, mutations (e.g., cystic fibrosis), and aneuploidy (e.g., trisomy 21) may be obtained. In some embodiments, analysis of fetal cells or components thereof is used to determine the presence or absence of a genetic abnormality, such as a chromosomal, DNA, or RNA abnormality. Examples of autosomal chromosome abnormalities include, but are not limited to, Angleman syndrome (15q11.2-q13), cri-du-chat syndrome (5p-), DiGeorge syndrome and Velo-cardiofacial syndrome (22q11.2), Miller-Dieker syndrome (17p13.3), Prader-Willi syndrome (15q11.2-q13), retinoblastoma (13q14), Smith-Magenis syndrome (17p11.2), trisomy 13, trisomy 16, trisomy 18, trisomy 21 (Down syndrome), triploidy, Williams syndrome (7q11.23), and Wolf-Hirschhorn (4p-). Examples of sex chromosome abnormalities include, but are not limited to, Kallman syndrome (Xp22.3), steroid sulfate deficiency (STS) (Xp22.3), X-linked ichthiosis (Xp22.3), Klinefelter syndrome (XXY); fragile X syndrome; Turner syndrome; metafemales or trisomy X; and monosomy X. Other less common chromosomal abnormalities that can be analyzed by the systems herein include, but are not limited to, deletions (small missing sections); microdeletions (a minute amount of missing material that may include only a single gene); translocations (a section of a chromosome is attached to another chromosome); and inversions (a section of chromosome is snipped out and reinserted upside down). In some embodiments, analysis of fetal cells or components thereof is used to analyze SNPs and predict a condition of the fetus based on such SNPs. If acquired from cancer cells, genetic information relating to tumorgenic properties may be obtained. If acquired from viral or bacterial cells, genetic information relating to the pathogenicity and classification may be obtained. For non-genetic cellular components, the components may be analyzed to diagnose disease or to monitor health. For example, proteins or metabolites from rare cells, e.g., fetal cells, may be analyzed by any suitable method, including affinity-based assays (e.g., ELISA) or other analytical techniques, e.g., chromatography and mass spectrometry.

General Considerations

Samples may be employed in the methods described herein with or without purification, e.g., stabilization and removal of certain components. Some sample may be diluted or concentrated prior to introduction into the device.

In another embodiment of the methods of this invention, a sample is contacted with a microfluidic device containing a plurality of obstacles, e.g., as described in U.S. Pat. No. 5,837,115 or as described herein. Cells of interest bind to affinity moieties bound to the obstacles in such a device and are thereby enriched relative to undesired cells, e.g., as described in WO 2004/029221.

In another embodiment of the methods of the invention employing a similar device, cells of non-interest bind to affinity moieties bound to the obstacles, while allowing the cells of interest to pass through resulting in an enriched sample with cells of interest, e.g., as described in WO 2004/029221. The sized based method and the affinity-based method may also be combined in a two-step method to further enrich a sample in cells of interest.

In another embodiment of the methods of the invention, a cell sample is pre-filtered by contact with a microfluidic device containing a plurality of obstacles disposed such that particles above a certain size are deflected to travel in a direction not parallel to the average direction of fluid flow, e.g., as described in U.S. Application Publication 2004/0144651 or as described herein.

EXAMPLES

Example 1

A Silicon Device Multiplexing 14 3-stage Array Duplexes

FIGS. 42A-42E show an exemplary device of the invention, characterized as follows.

Dimension: 90 mm×34 mm×1 mm.

Array design: 3 stages, gap size=18, 12, and 8 μm for the first, second and third stage, respectively. Bifurcation ratio=1/10. Duplex; single bypass channel Device design: multiplexing 14 array duplexes; flow resistors for flow stability Device fabrication: The arrays and channels were fabricated in silicon using standard photolithography and deep silicon reactive etching techniques. The etch depth is 150 μm. Through holes for fluid access are made using KOH wet etching. The silicon substrate was sealed on the etched face to form enclosed fluidic channels using a blood compatible pressure sensitive adhesive (9795, 3M, St Paul, Minn.).

Device Packaging: The device was mechanically mated to a plastic manifold with external fluidic reservoirs to deliver blood and buffer to the device and extract the generated fractions.

Device Operation: An external pressure source was used to apply a pressure of 2.4 PSI to the buffer and blood reservoirs to modulate fluidic delivery and extraction from the packaged device.

Figure 42A:
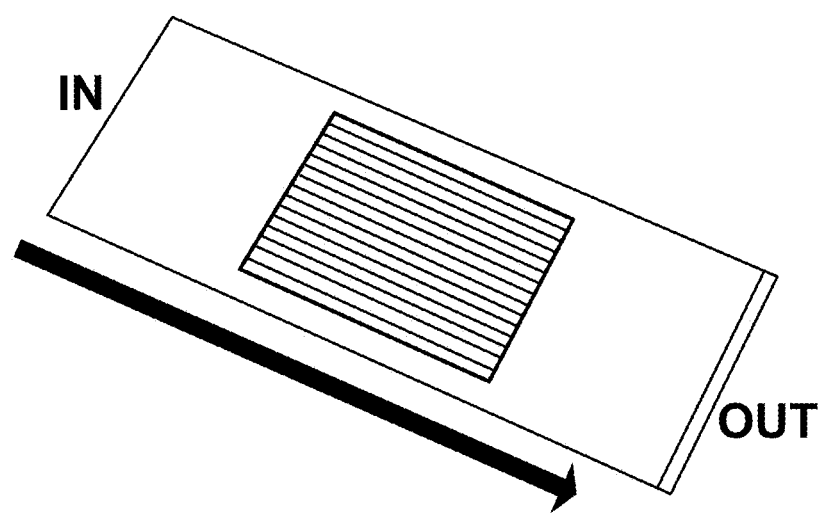
FIG. 42A is a photograph of a device of the invention.
Figure 42B:
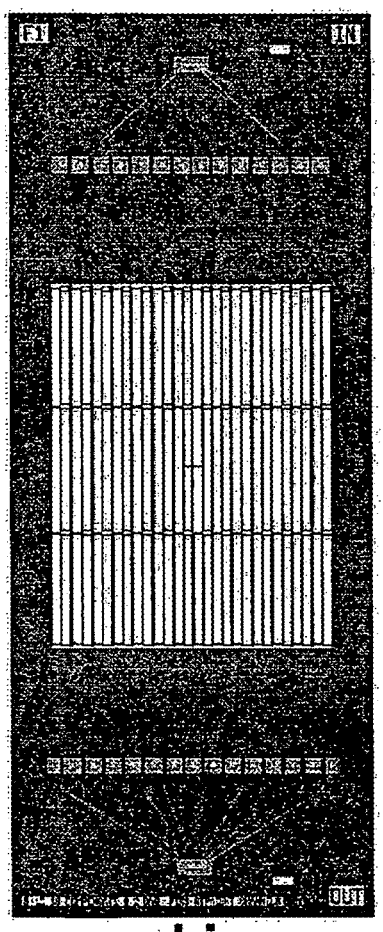
FIGS. 42B-42E are depictions the mask used to fabricate a device of the invention.
Figure 42C:
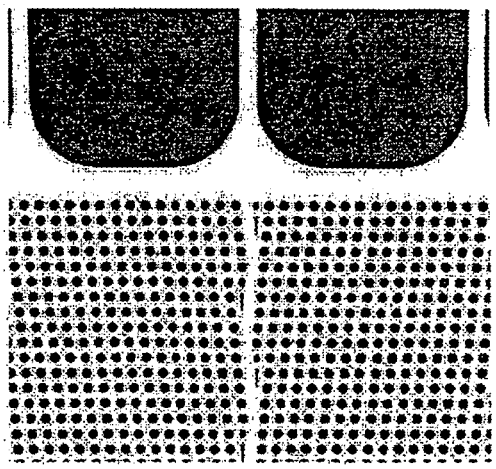
Figure 42D:
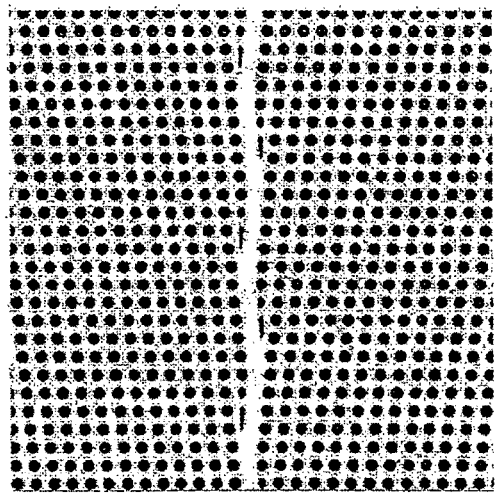
Figure 42E:
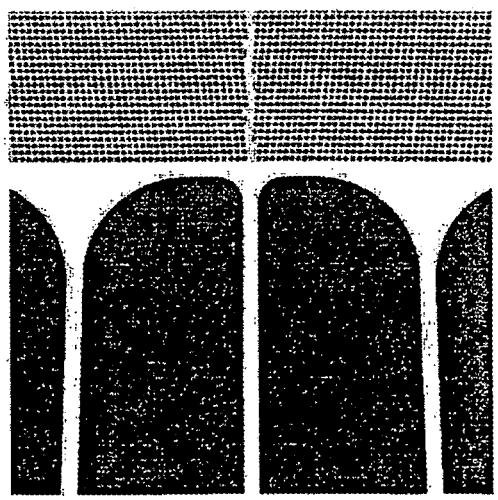
Figure 42F:
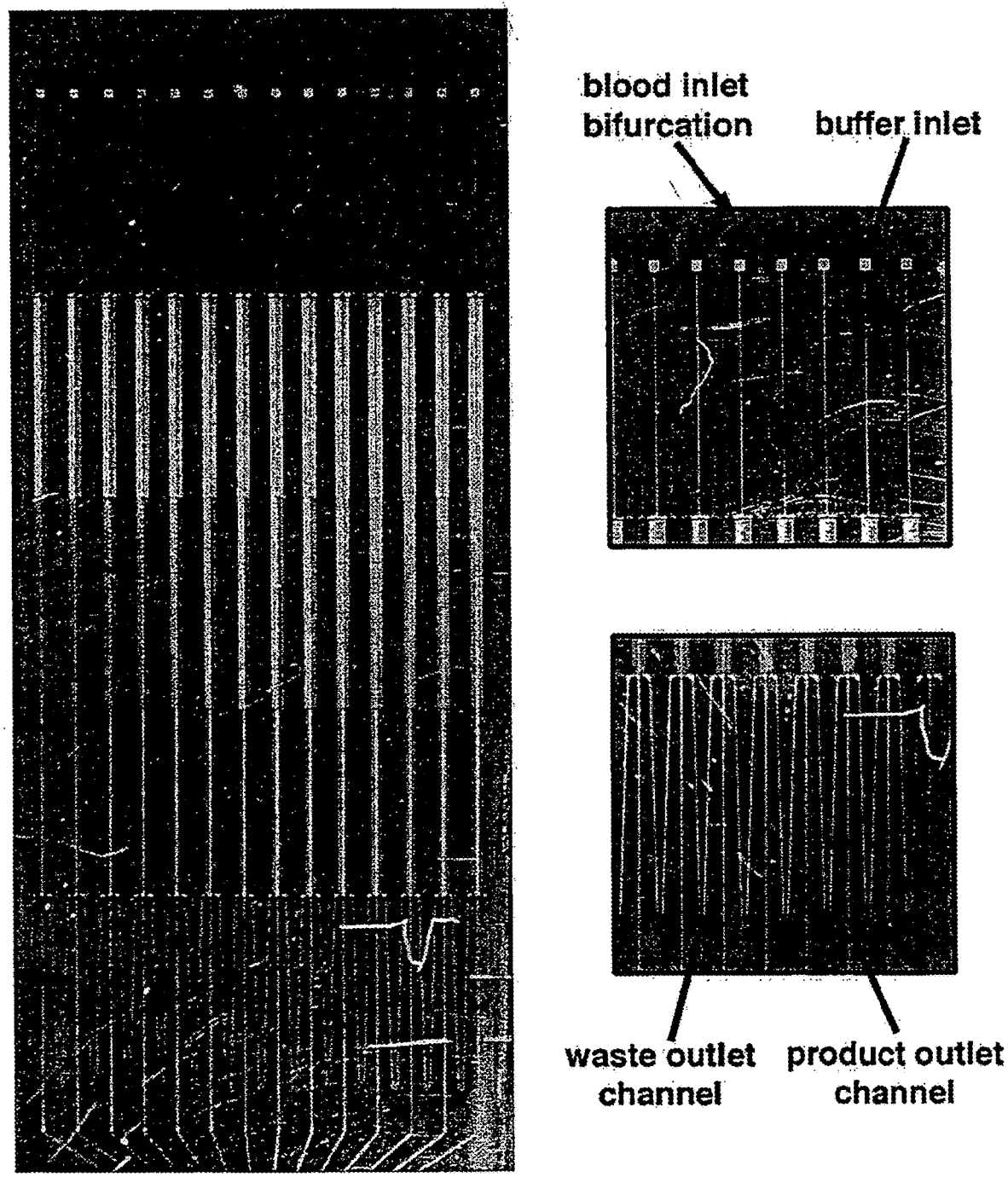
FIG. 42F is a series of photographs of the device containing blood and buffer.
Figure 43A:
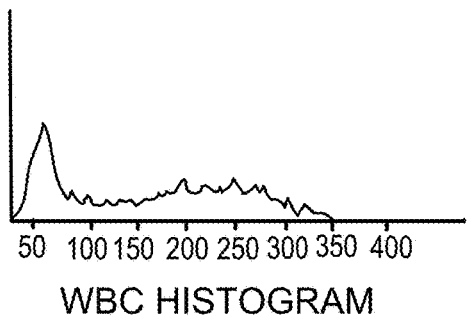
FIGS. 43A-43F are typical histograms generated by the hematology analyzer from a blood sample and the waste (buffer, plasma, red blood cells, and platelets) and product (buffer and nucleated cells) fractions generated by the device of FIG. 42.
Figure 43B:
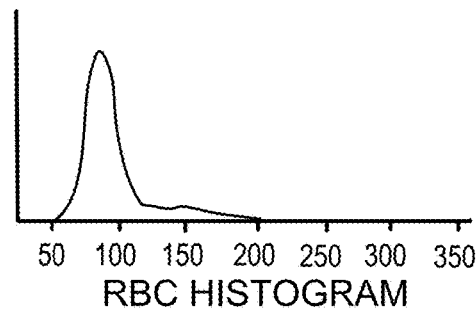
Figure 43C:
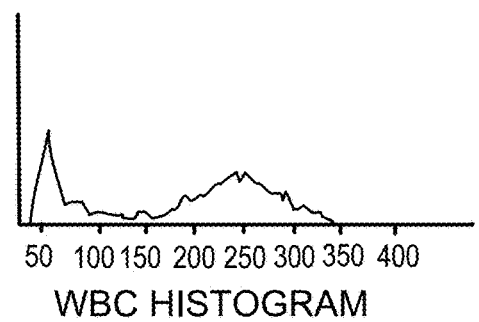
Figure 43D:
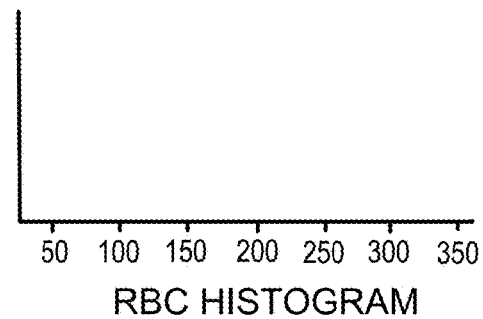
Figure 43E:
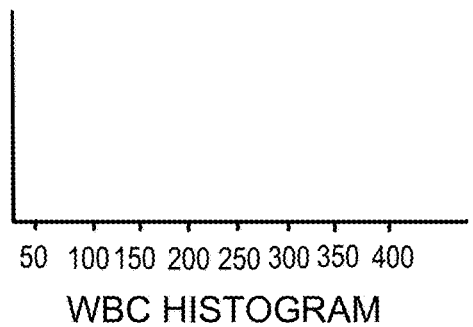
Figure 43F:
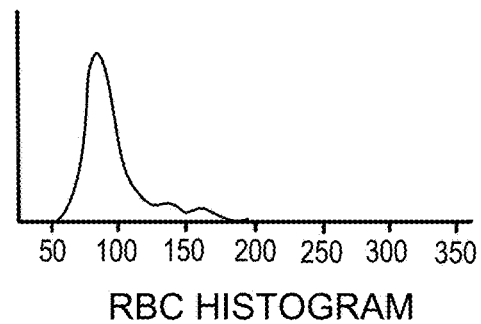

Experimental conditions: human blood from consenting adult donors was collected into K$_2$EDTA vacutainers (366643, Becton Dickinson, Franklin Lakes, N.J.). The undiluted blood was processed using the exemplary device described above (FIG. 42F) at room temperature and within 9 hrs of draw. Nucleated cells from the blood were separated from enucleated cells (red blood cells and platelets), and plasma delivered into a buffer stream of calcium and magnesium-free Dulbecco's Phosphate Buffered Saline (14190-144, Invitrogen, Carlsbad, Calif.) containing 1% Bovine Serum Albumin (BSA) (A8412-100ML, Sigma-Aldrich, St Louis, Mo.).

Measurement techniques: Complete blood counts were determined using a Coulter impedance hematology analyzer (COULTER® Ac.T Diff™, Beckman Coulter, Fullerton, Calif.).

Performance: FIGS. 43A-43F shows typical histograms generated by the hematology analyzer from a blood sample and the waste (buffer, plasma, red blood cells, and platelets) and product (buffer and nucleated cells) fractions generated by the device. The following table shows the performance over 5 different blood samples:

| Sample number | Throughput | Performance Metrics | | |
|---|---|---|---|---|
| | | RBC removal | Platelet removal | WBC loss |
| 1 | 4 mL/hr | 100% | 99% | <1% |
| 2 | 6 mL/hr | 100% | 99% | <1% |
| 3 | 6 mL/hr | 100% | 99% | <1% |
| 4 | 6 mL/hr | 100% | 97% | <1% |
| 5 | 6 mL/hr | 100% | 98% | <1% |

Example 2

A Silicon Device Multiplexing 14 Single-stage Array Duplexes

FIG. 44 shows an exemplary device of the invention, characterized as follows.

Dimension: 90 mm×34 mm×1 mm

Array design: 1 stage, gap size=24 μm. Bifurcation ratio=1/60. Duplex; double bypass channel Device design: multiplexing 14 array duplexes; flow resistors for flow stability Device fabrication: The arrays and channels were fabricated in silicon using standard photolithography and deep silicon reactive etching techniques. The etch depth is 150 μm. Through holes for fluid access are made using KOH wet etching. The silicon substrate was sealed on the etched face to form enclosed fluidic channels using a blood compatible pressure sensitive adhesive (9795, 3M, St Paul, Minn.).

Device Packaging: The device was mechanically mated to a plastic manifold with external fluidic reservoirs to deliver blood and buffer to the device and extract the generated fractions.

Device Operation: An external pressure source was used to apply a pressure of 2.4 PSI to the buffer and blood reservoirs to modulate fluidic delivery and extraction from the packaged device.

Experimental conditions: human blood from consenting adult donors was collected into K$_2$EDTA vacutainers (366643, Becton Dickinson, Franklin Lakes, N.J.). The undiluted blood was processed using the exemplary device described above at room temperature and within 9 hrs of draw. Nucleated cells from the blood were separated from enucleated cells (red blood cells and platelets), and plasma delivered into a buffer stream of calcium and magnesium-free Dulbecco's Phosphate Buffered Saline (14190-144, Invitrogen, Carlsbad, Calif.) containing 1% Bovine Serum Albumin (BSA) (A8412-100ML, Sigma-Aldrich, St Louis, Mo.).

Measurement techniques: Complete blood counts were determined using a Coulter impedance hematology analyzer (COULTER® Ac.T Diff™, Beckman Coulter, Fullerton, Calif.).

Performance: The device operated at 17 mL/hr and achieved >99% red blood cell removal, >95% nucleated cell retention, and >98% platelet removal.

Example 3

Separation of Fetal Cord Blood

FIG. 45 shows a schematic of the device used to separate nucleated cells from fetal cord blood.

Dimension: 100 mm×28 mm×1 mm

Array design: 3 stages, gap size=18, 12, and 8 μm for the first, second and third stage, respectively. Bifurcation ratio=1/10. Duplex; single bypass channel.

Device design: multiplexing 10 array duplexes; flow resistors for flow stability Device fabrication: The arrays and channels were fabricated in silicon using standard photolithography and deep silicon reactive etching techniques. The etch depth is 140 μm. Through holes for fluid access are made using KOH wet etching. The silicon substrate was sealed on the etched face to form enclosed fluidic channels using a blood compatible pressure sensitive adhesive (9795, 3M, St Paul, Minn.).

Device Packaging: The device was mechanically mated to a plastic manifold with external fluidic reservoirs to deliver blood and buffer to the device and extract the generated fractions.

Device Operation: An external pressure source was used to apply a pressure of 2.0 PSI to the buffer and blood reservoirs to modulate fluidic delivery and extraction from the packaged device.

Experimental conditions: Human fetal cord blood was drawn into phosphate buffered saline containing Acid Citrate Dextrose anticoagulants. One milliliter of blood was processed at 3 mL/hr using the device described above at room temperature and within 48 hrs of draw. Nucleated cells from the blood were separated from enucleated cells (red blood cells and platelets), and plasma delivered into a buffer stream of calcium and magnesium-free Dulbecco's Phosphate Buffered Saline (14190-144, Invitrogen, Carlsbad, Calif.) containing 1% Bovine Serum Albumin (BSA) (A8412-100ML, Sigma-Aldrich, St Louis, Mo.) and 2 mM EDTA (15575-020, Invitrogen, Carlsbad, Calif.).

Measurement techniques: Cell smears of the product and waste fractions (FIG. 46A-46B) were prepared and stained with modified Wright-Giemsa (WG16, Sigma Aldrich, St. Louis, Mo.).

Performance: Fetal nucleated red blood cells were observed in the product fraction (FIG. 46A) and absent from the waste fraction (FIG. 46B).

Example 4

Isolation of Fetal Cells from Maternal Blood

The device and process described in detail in Example 1 were used in combination with immunomagnetic affinity enrichment techniques to demonstrate the feasibility of isolating fetal cells from maternal blood.

Experimental conditions: blood from consenting maternal donors carrying male fetuses was collected into $K_2$EDTA vacutainers (366643, Becton Dickinson, Franklin Lakes, N.J.) immediately following elective termination of pregnancy. The undiluted blood was processed using the device described in Example 1 at room temperature and within 9 hrs of draw. Nucleated cells from the blood were separated from enucleated cells (red blood cells and platelets), and plasma delivered into a buffer stream of calcium and magnesium-free Dulbecco's Phosphate Buffered Saline (14190-144, Invitrogen, Carlsbad, Calif.) containing 1% Bovine Serum Albumin (BSA) (A8412-100ML, Sigma-Aldrich, St Louis, Mo.). Subsequently, the nucleated cell fraction was labeled with anti-CD71 microbeads (130-046-201, Miltenyi Biotech Inc., Auburn, Calif.) and enriched using the MiniMACS™ MS column (130-042-201, Miltenyi Biotech Inc., Auburn, Calif.) according to the manufacturer's specifications. Finally, the CD71-positive fraction was spotted onto glass slides.

Measurement techniques: Spotted slides were stained using fluorescence in situ hybridization (FISH) techniques according to the manufacturer's specifications using Vysis probes (Abbott Laboratories, Downer's Grove, Ill.). Samples were stained from the presence of X and Y chromosomes. In one case, a sample prepared from a known Trisomy 21 pregnancy was also stained for chromosome 21.

Figure 48:
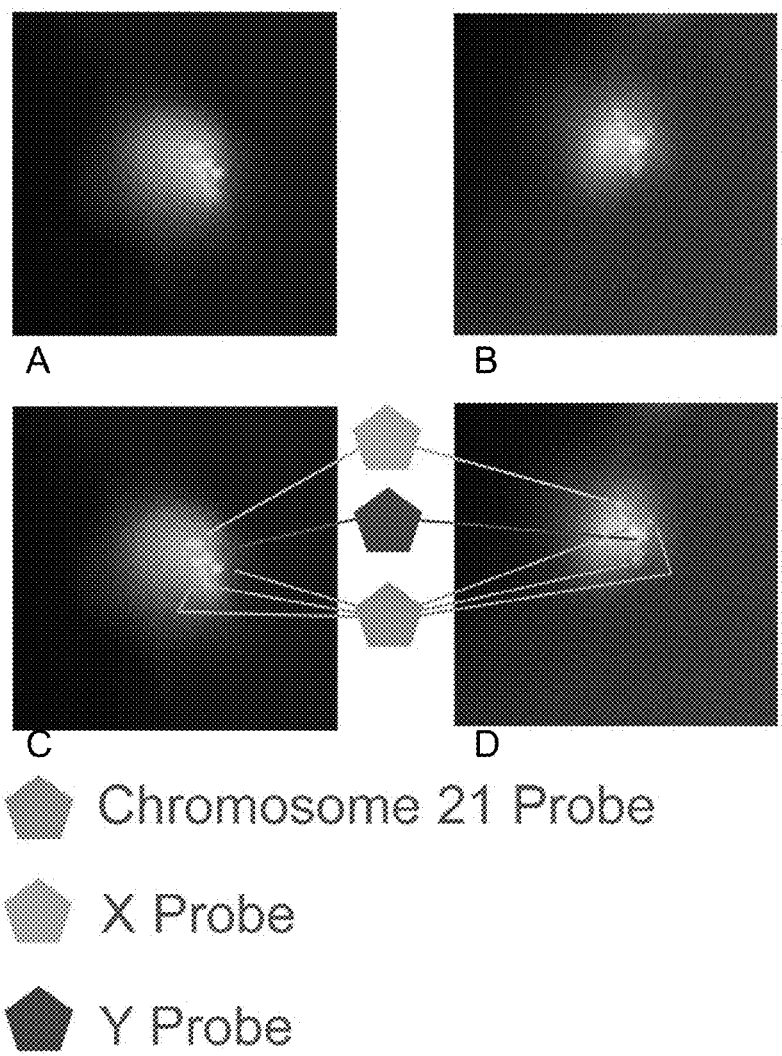
FIG. 48 is a series of micrographs showing the positive identification of sex and trisomy 21.

Performance: Isolation of fetal cells was confirmed by the reliable presence of male cells in the CD71-positive population prepared from the nucleated cell fractions (FIG. 47). In the single abnormal case tested, the trisomy 21 pathology was also identified (FIG. 48).

The following examples show specific embodiments of devices of the invention. The description for each device provides the number of stages in series, the gap size for each stage, ε (Flow Angle), and the number of channels per device (Arrays/Chip). Each device was fabricated out of silicon using DRIE, and each device had a thermal oxide layer.

Example 5

This device includes five stages in a single array.
Array Design: 5 stage, asymmetric array.
Sizes: Stage 1: 8 μm
    Stage 2: 10 μm
    Stage 3: 12 μm
    Stage 4: 14 μm
    Stage 5: 16 μm
Flow Angle: 1/10
Arrays/Chip: 1
Array Design: 5 stage, asymmetric array
Gap Sizes: Stage 1: 8 μm
    Stage 2: 10 μm
    Stage 3: 12 μm
    Stage 4: 14 μm
    Stage 5: 16 μm
Flow Angle: 1/10
Arrays/Chip: 1

Example 6

Figure 49A:
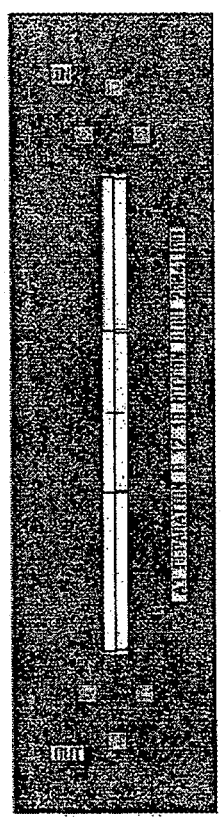
FIGS. 49A-49D are depictions the mask used to fabricate a device of the invention.
Figure 49B:
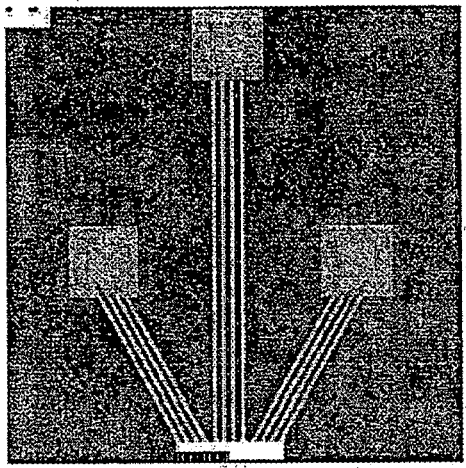
Figure 49C:
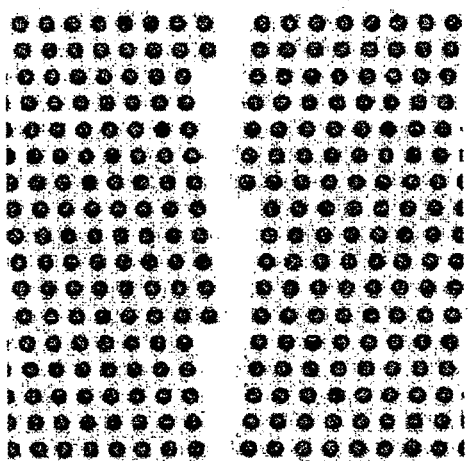
Figure 49D:
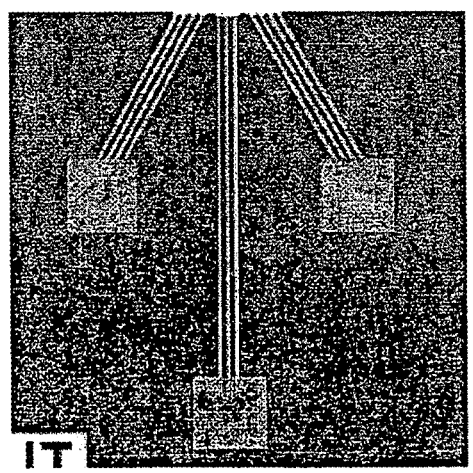
Figure 50A:
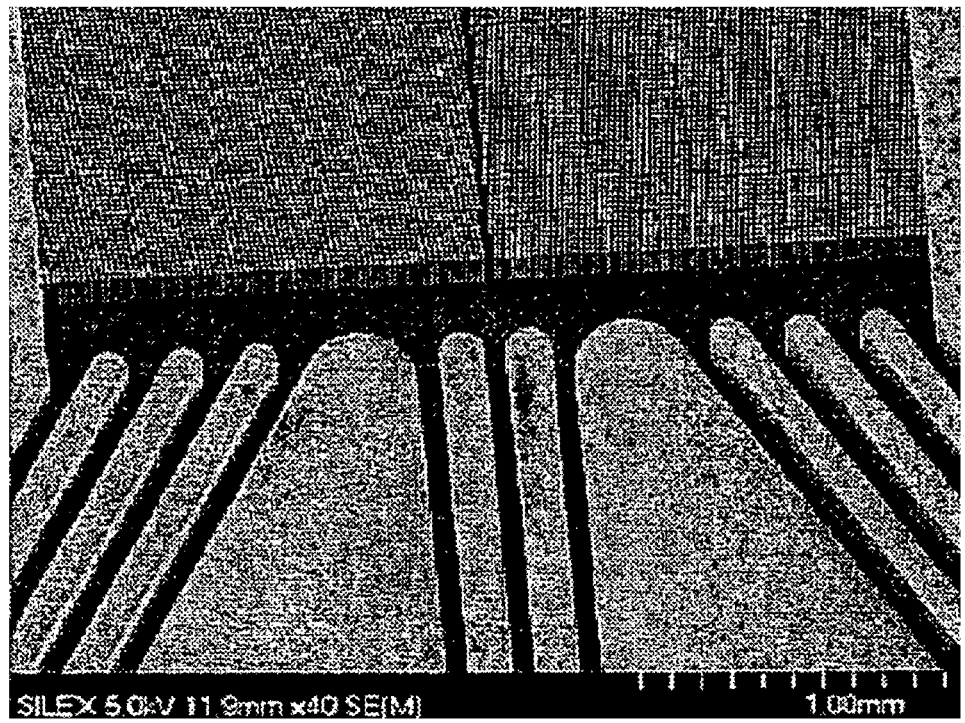
FIGS. 50A-50G are electron micrographs of the device of FIG. 49.
Figure 50B:
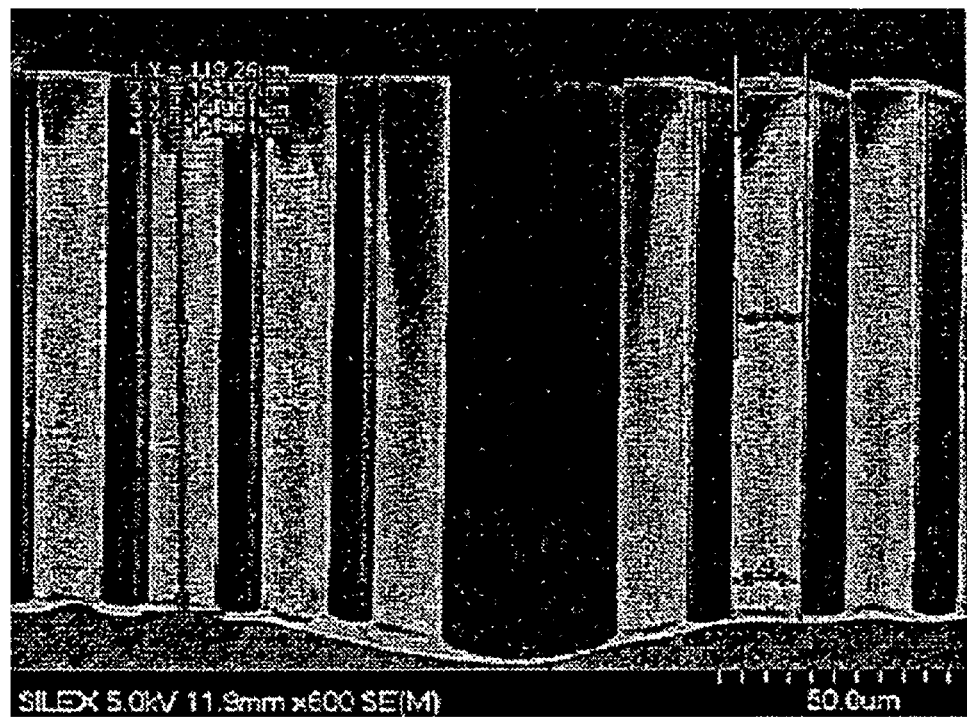
Figure 50C:
Figure 50D:
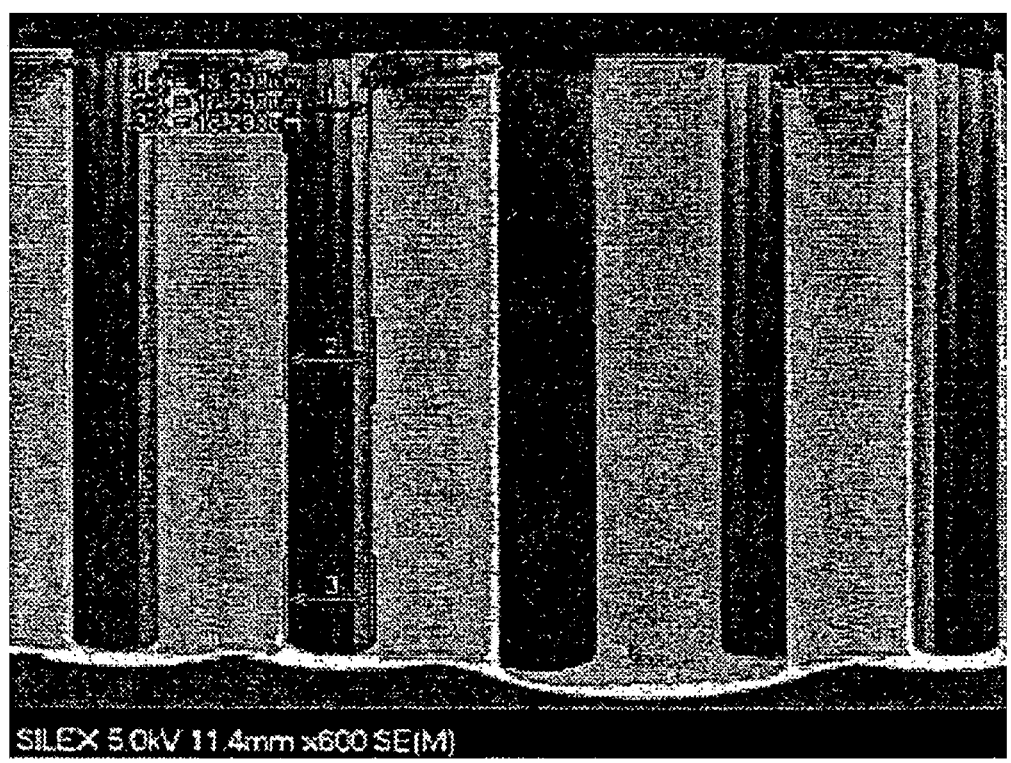
Figure 50E:
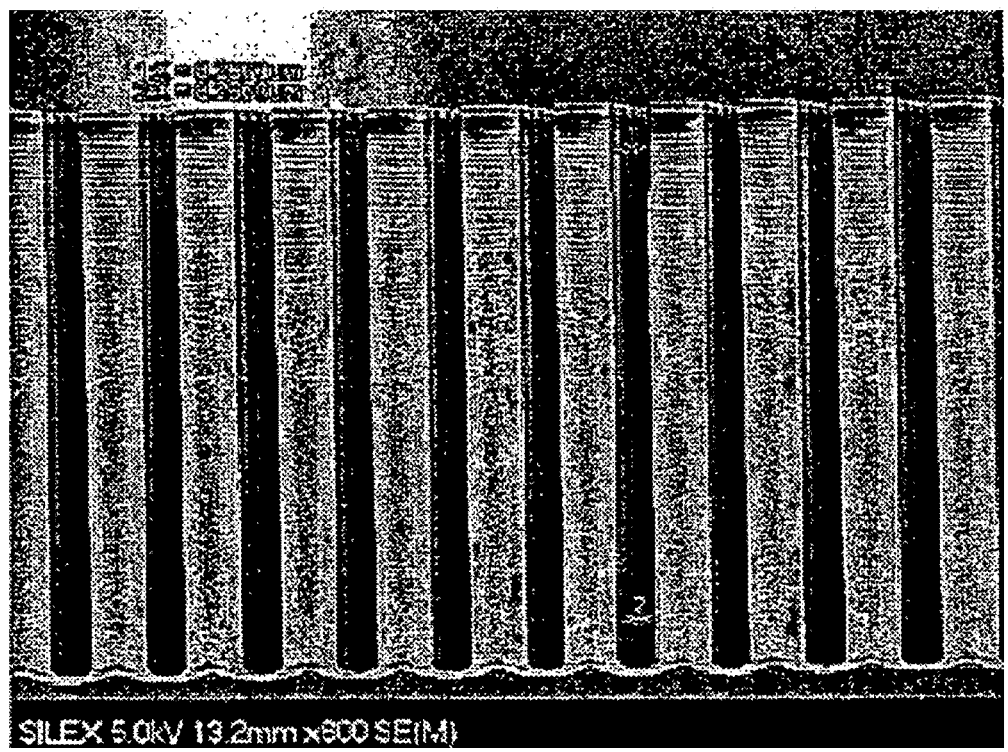
Figure 50F:
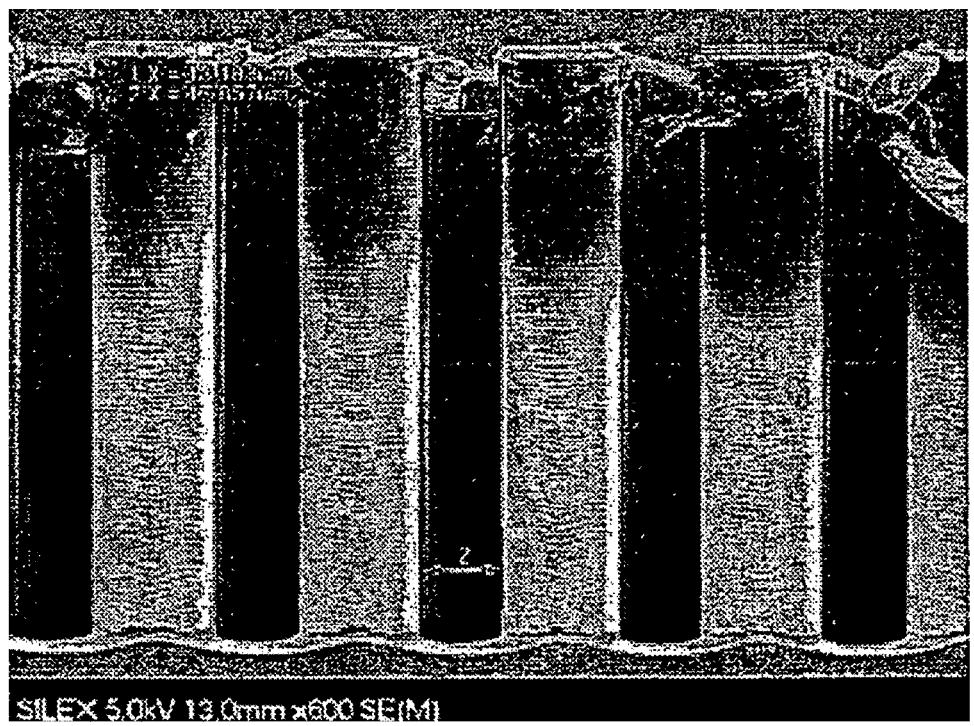
Figure 50G:
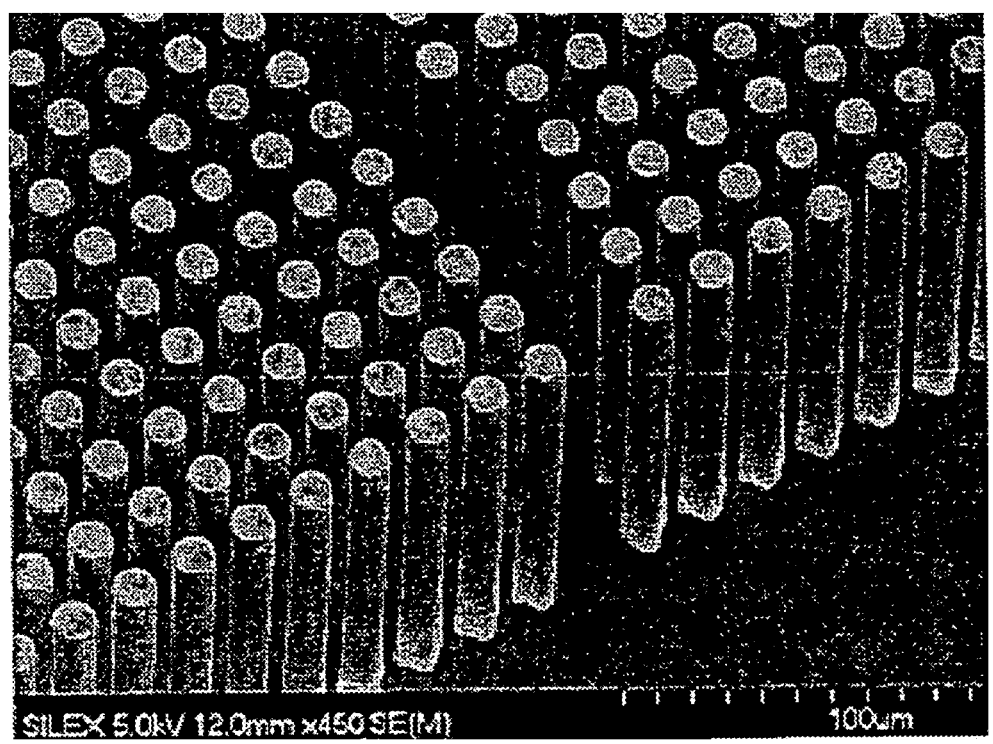

This device includes three stages, where each stage is a duplex having a bypass channel. The height of the device was 125 μm.
Array Design: symmetric 3 stage array with central collection channel
Gap Sizes: Stage 1: 8 μm
    Stage 2: 12 μm
    Stage 3: 18 μm
    Stage 4:
    Stage 5:
Flow Angle: 1/10
Arrays/Chip: 1
Other: central collection channel
Array Design: Symmetric 3 stage array with central collection channel
Gap Sizes: Stage 1: 8 μm
    Stage 2: 12 μm
    Stage 3: 18 μm Stage 4:
Stage 5:
Flow Angle: 1/10
Arrays/Chip: 1
Other: central collection channel FIG. 49A shows the mask employed to fabricate the device. FIGS. 49B-49D are enlargements of the portions of the mask that define the inlet, array, and outlet. FIGS. 50A-50G show SEMs of the actual device.

Example 7

This device includes three stages, where each stage is a duplex having a bypass channel "Fins" were designed to flank the bypass channel to keep fluid from the bypass channel from re-entering the array. The chip also included on-chip flow resistors, i.e., the inlets and outlets possessed greater fluidic resistance than the array. The height of the device was 117 μm.

Figure 51A:
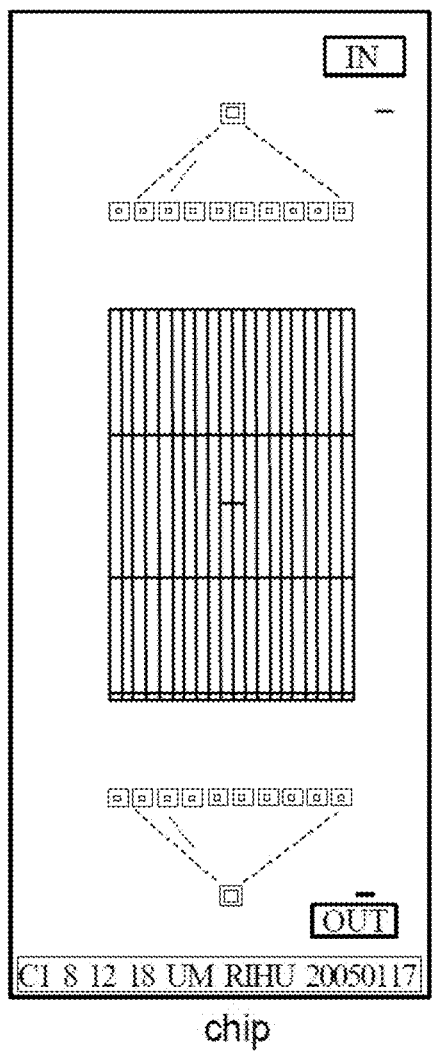
FIGS. 51A-51D are depictions the mask used to fabricate a device of the invention.
Figure 51B:
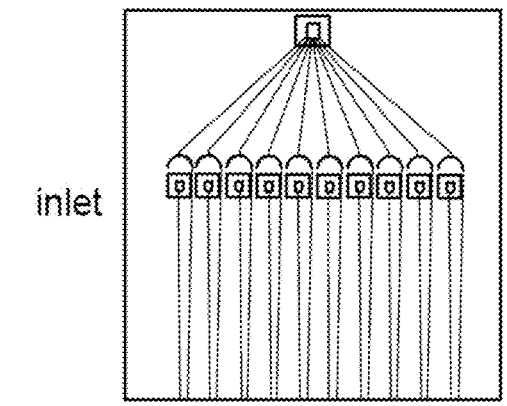
Figure 51C:
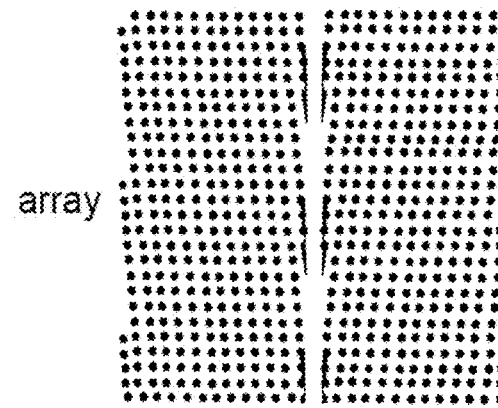
Figure 51D:
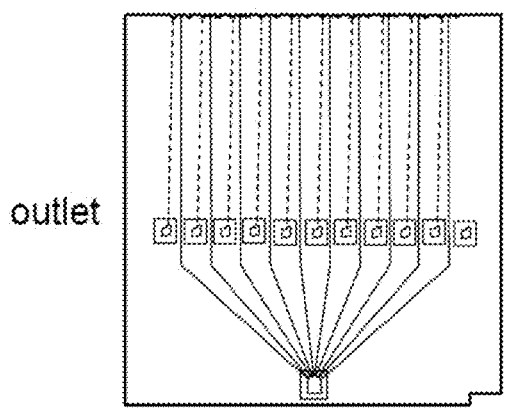
Figure 52A:
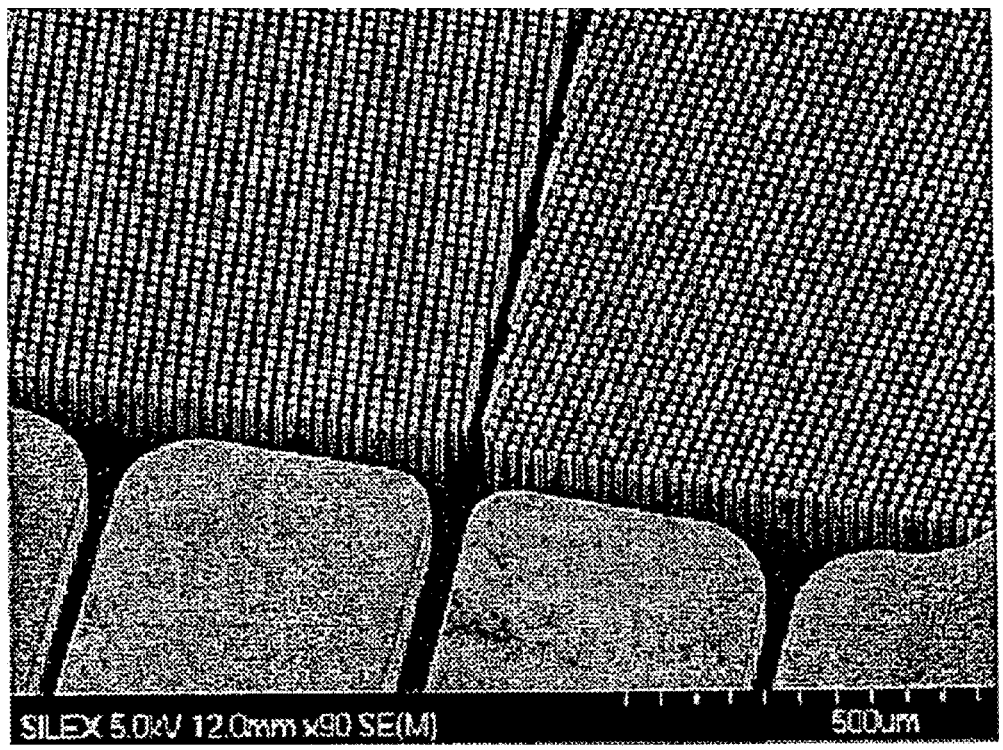
FIGS. 52A-52F are electron micrographs of the device of FIG. 51.
Figure 52B:
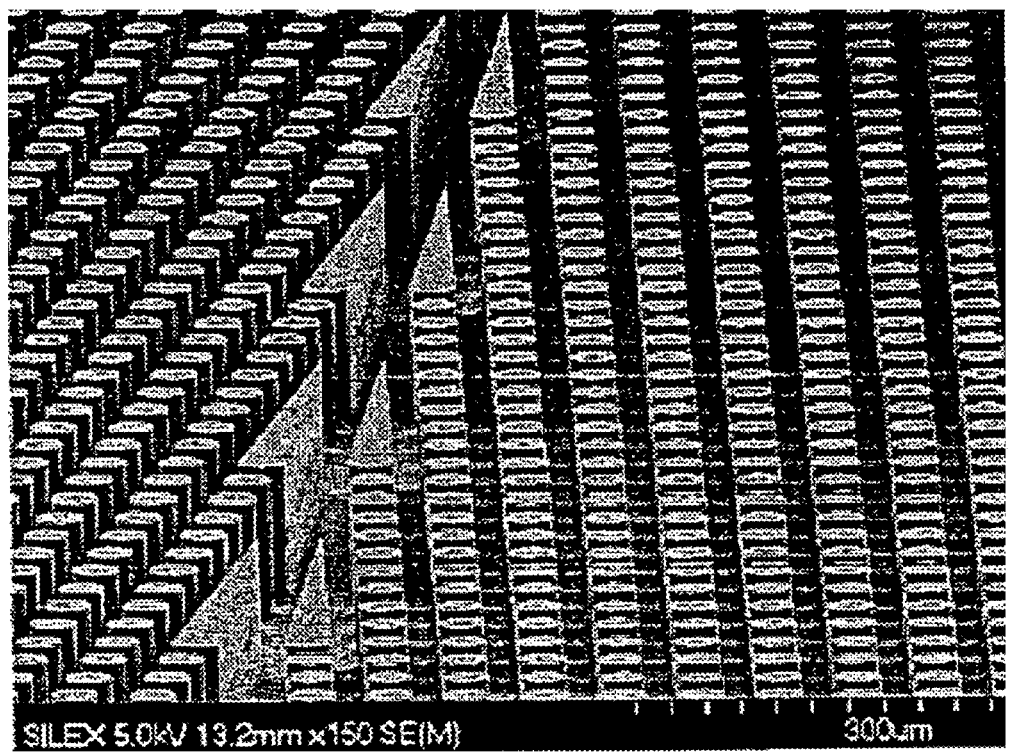
Figure 52C:
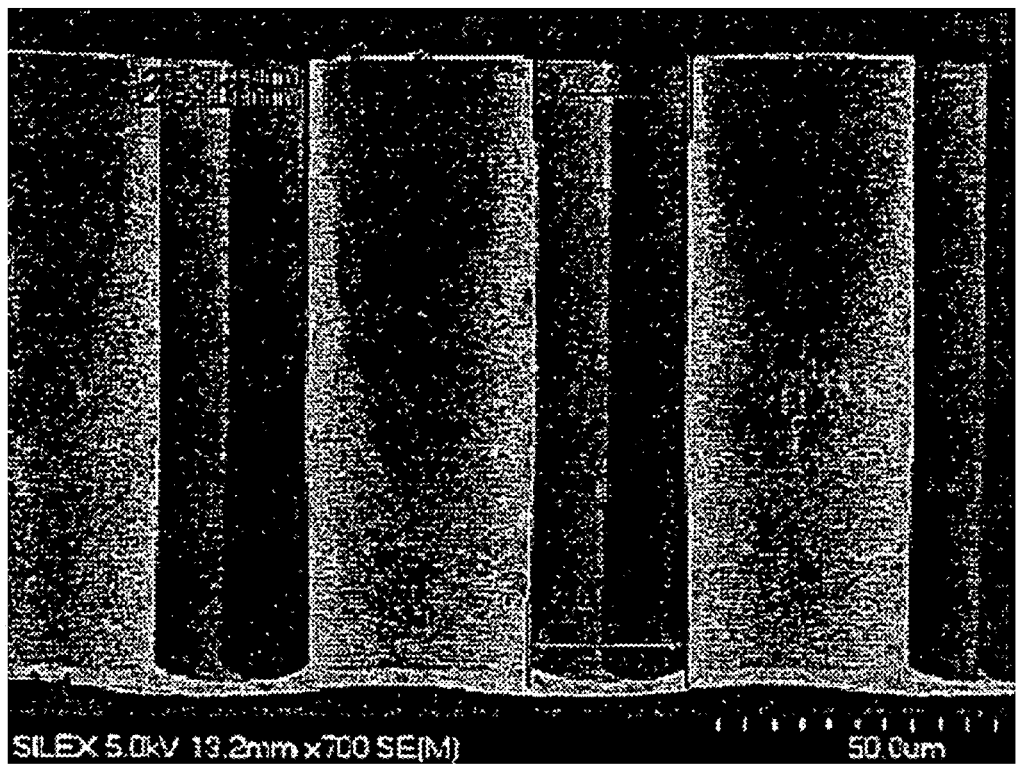
Figure 52D:
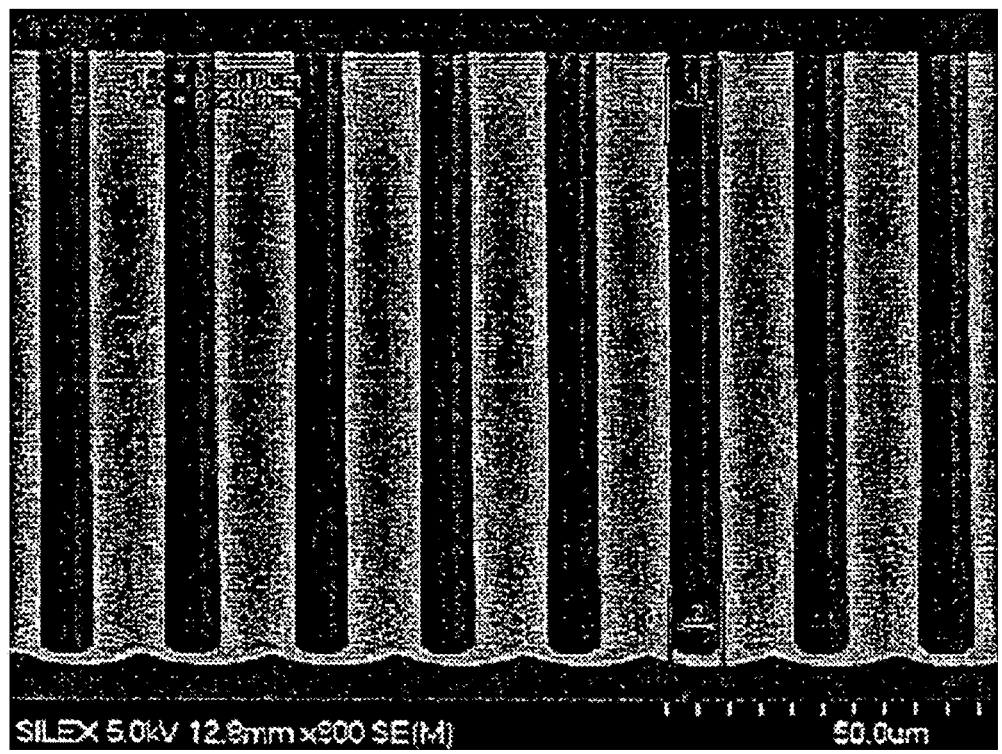
Figure 52E:
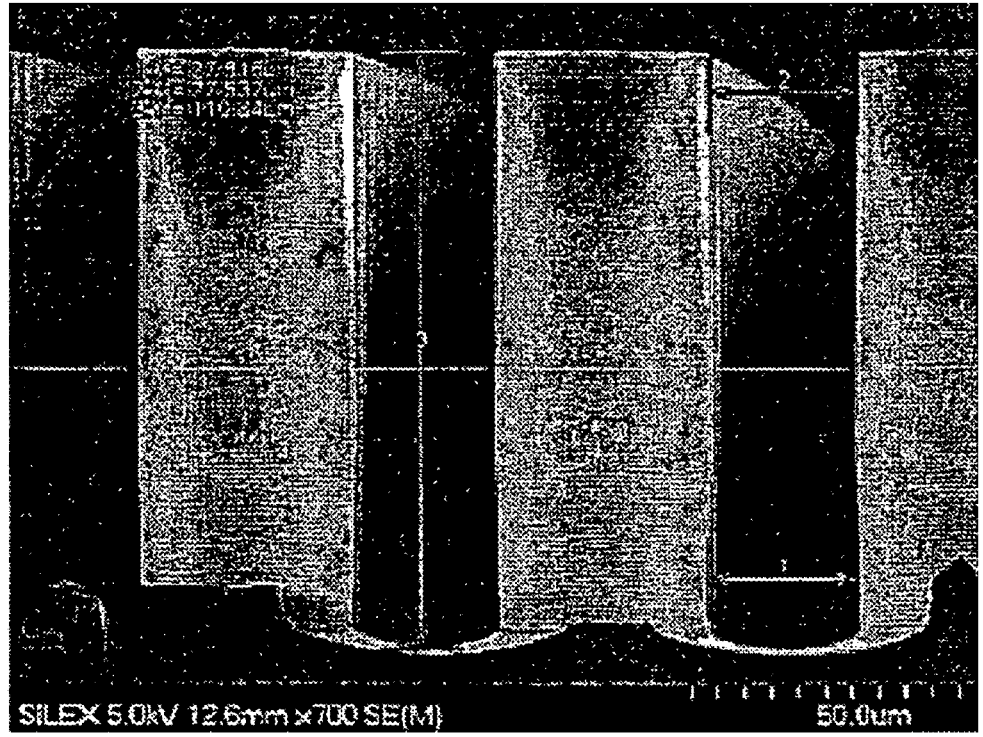
Figure 52F:
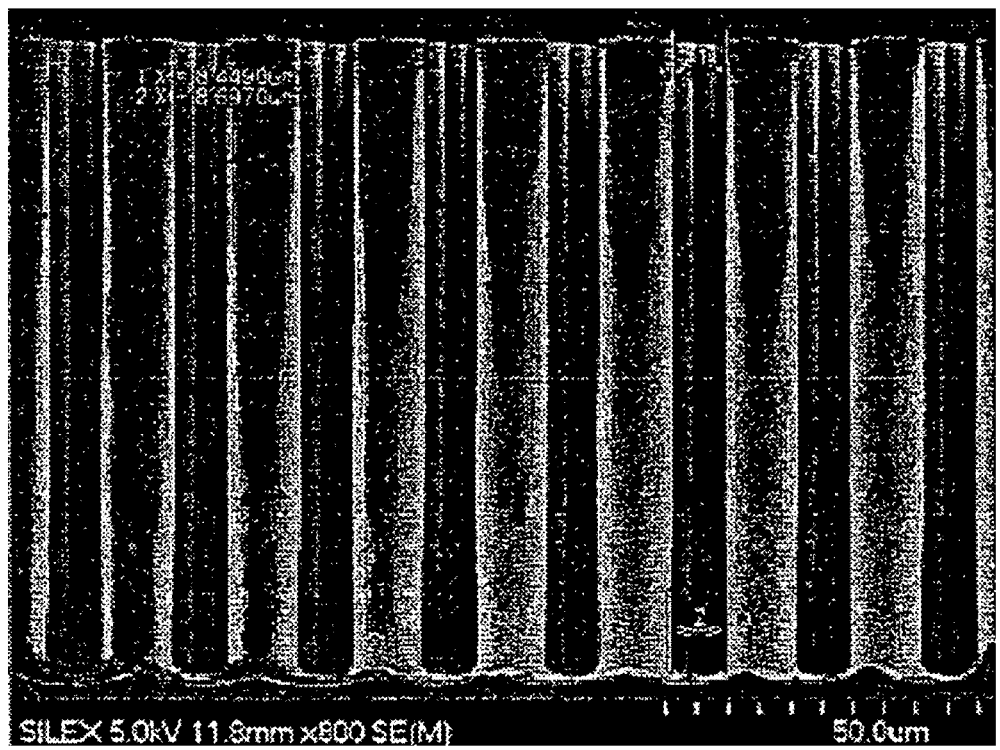
Figure 53A:
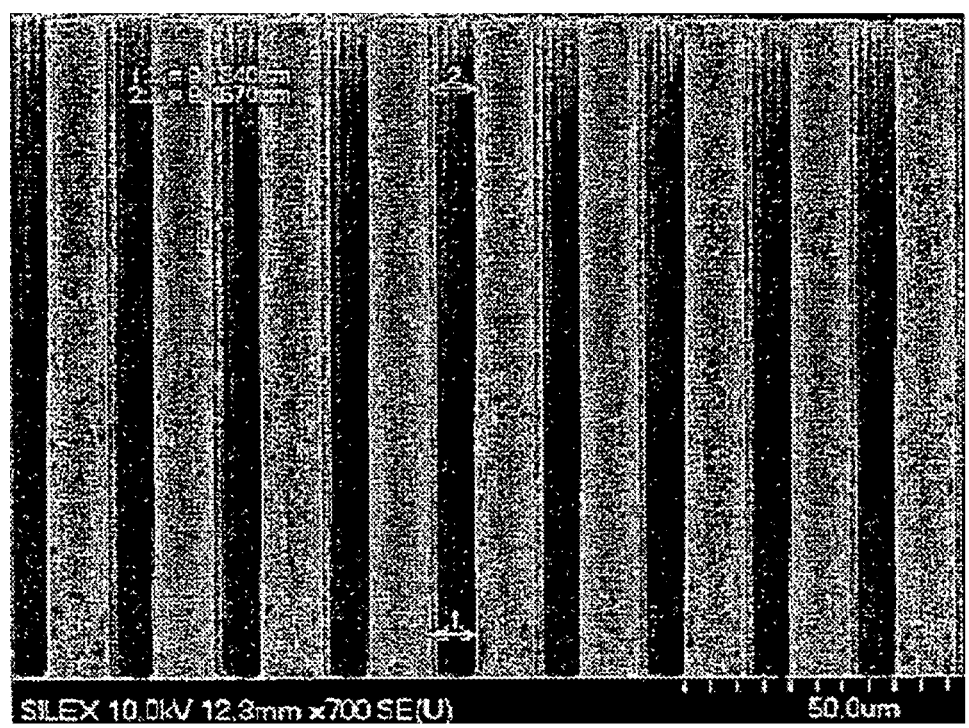
FIGS. 53A-53F are electron micrographs of the device of FIG. 45.
Figure 53B:
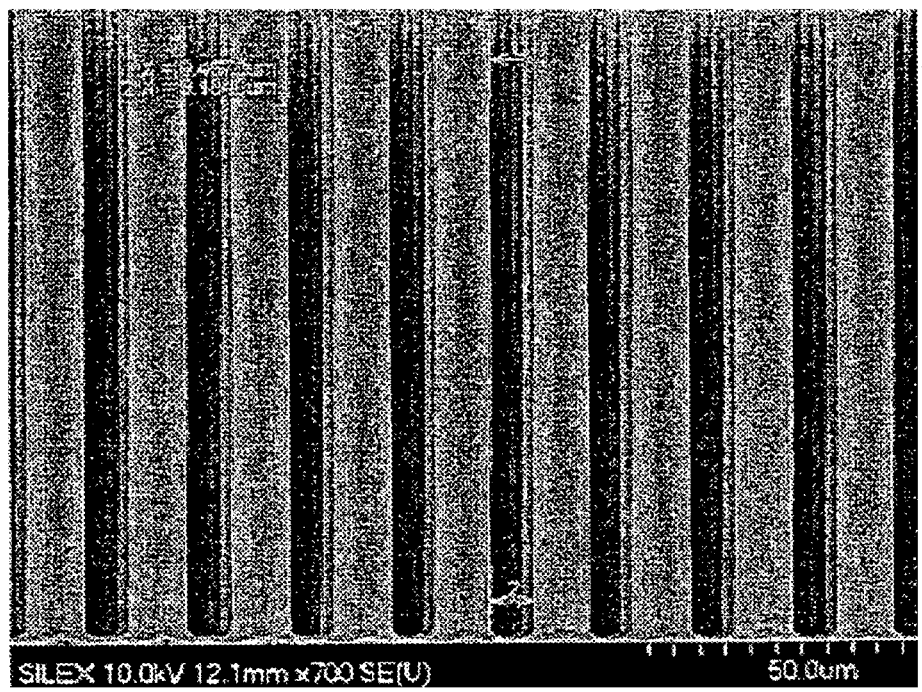
Figure 53C:
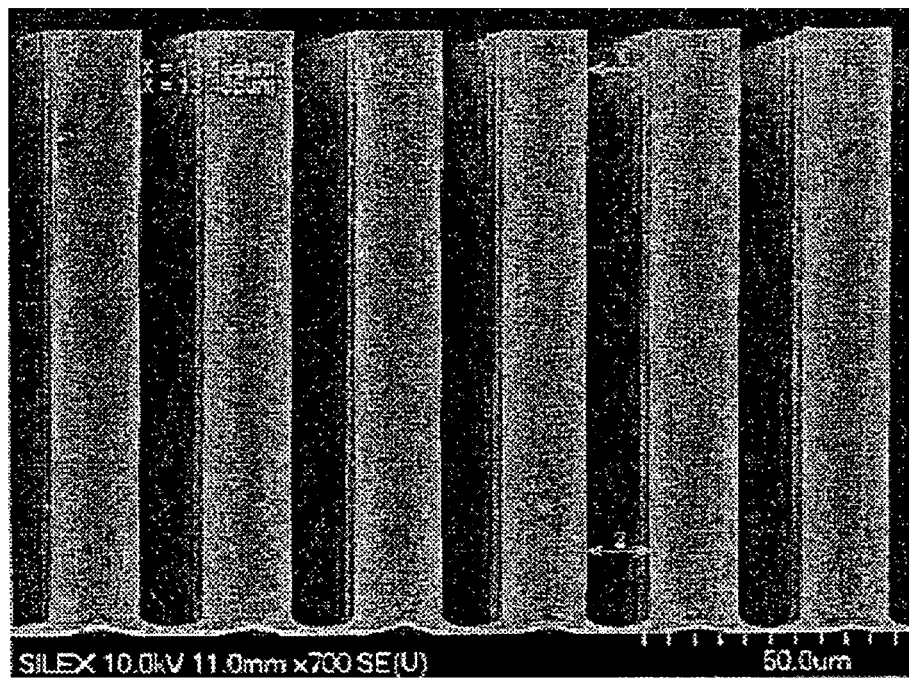
Figure 53D:
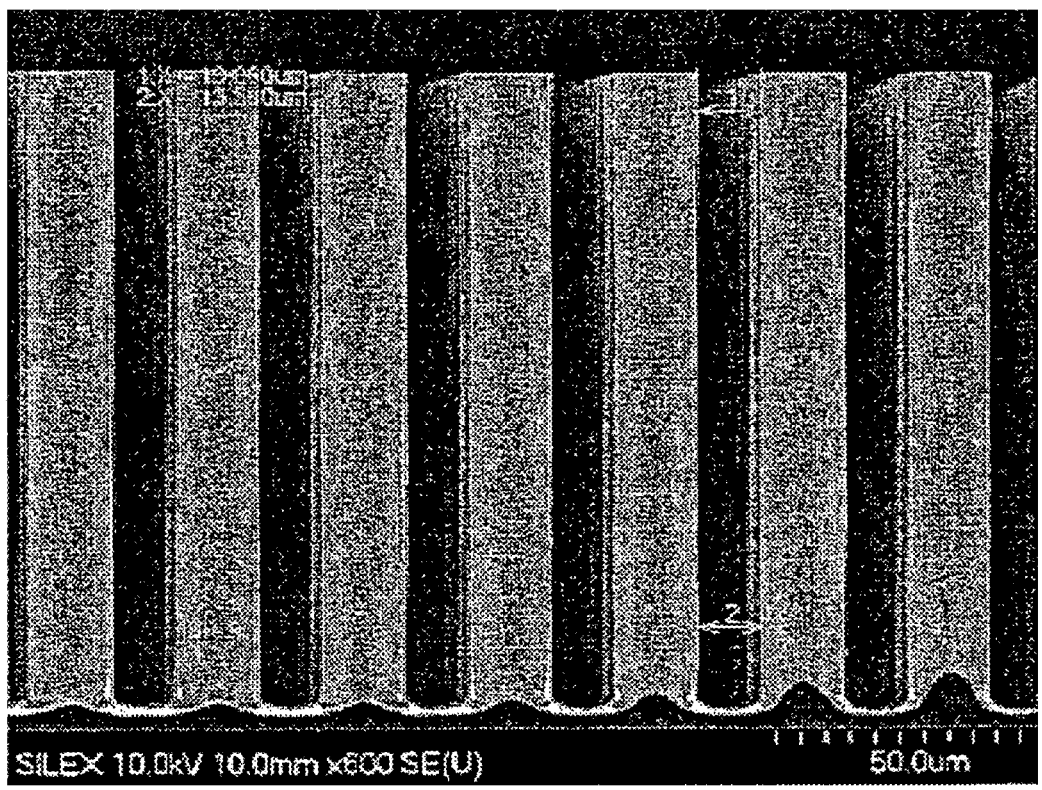
Figure 53E:
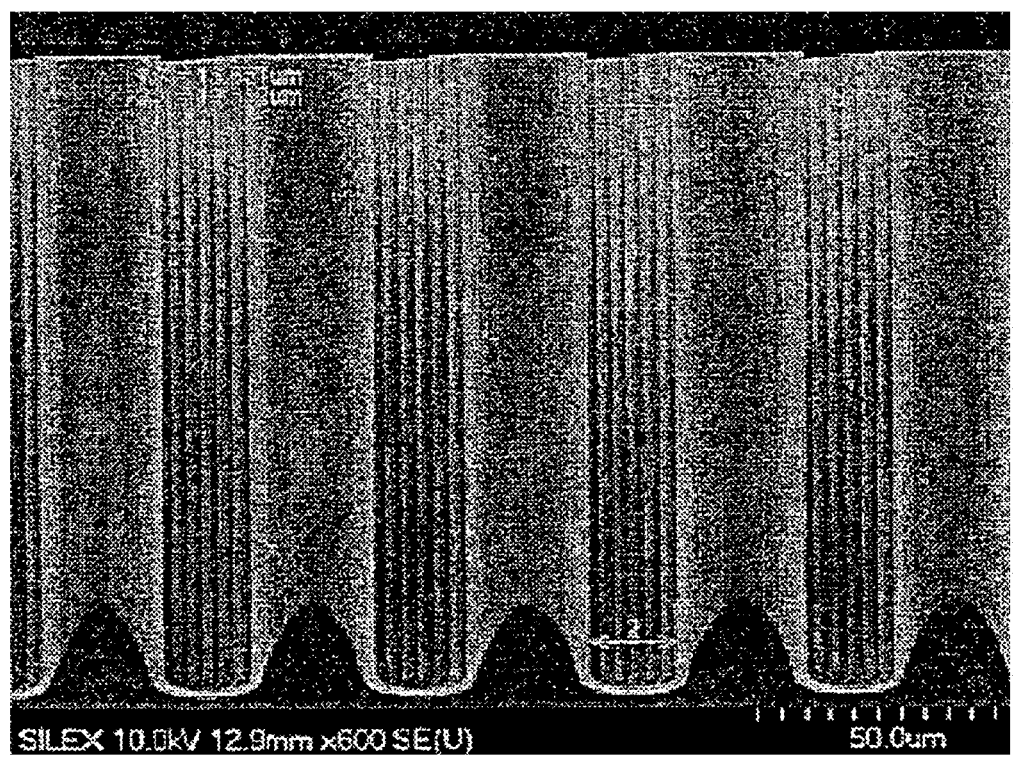
Figure 53F:
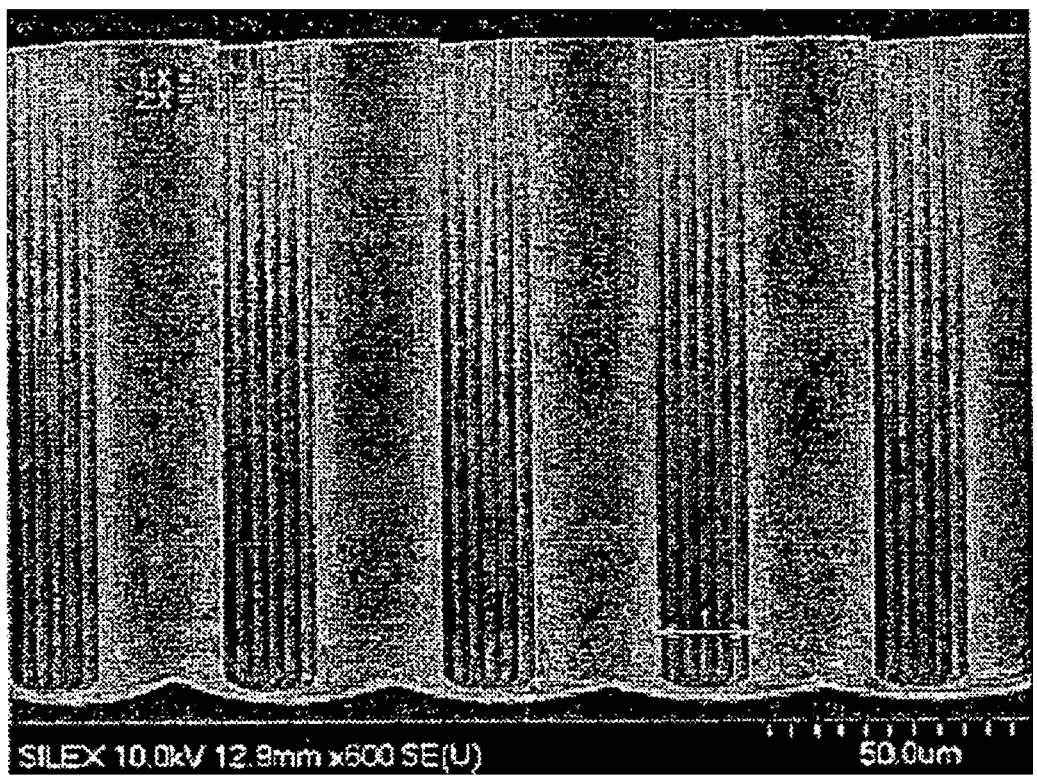

Array Design: 3 stage symmetric array
Gap Sizes: Stage 1: 8 μm
    Stage 2: 12 μm
    Stage 3: 18 μm
    Stage 4:
    Stage 5:
Flaw Angle: 1/10
Arrays/Chip: 10
Other: large fin central collection channel
    on-chip flow resistors
Array Design: 3 stage symmetric array
Gap Sizes: Stage 1: 8 μm
    Stage 2: 12 μm
    Stage 3: 18 μm
    Stage 4:
    Stage 5:
Flow Angle: 1/10
Arrays/Chip: 10
Other: Large fin central collection channel on-chip flow resistors FIG. 51A shows the mask employed to fabricate the device. FIGS. 51B-51D are enlargements of the portions of the mask that define the inlet, array, and outlet. FIGS. 52A-52F show SEMs of the actual device.

Example 8

This device includes three stages, where each stage is a duplex having a bypass channel "Fins" were designed to flank the bypass channel to keep fluid from the bypass channel from re-entering the array. The edge of the fin closest to the array was designed to mimic the shape of the array. The chip also included on-chip flow resistors, i.e., the inlets and outlets possessed greater fluidic resistance than the array. The height of the device was 138 μm.

| Array Design: | 3 stage symmetric array |
| --- | --- |
| Gap Sizes: | Stage 1: 8 μm |
|  | Stage 2: 12 μm |
|  | Stage 3: 18 μm |
|  | Stage 4: |
|  | Stage 5: |

| Flow Angle: | 1/10 |
| --- | --- |
| Arrays/Chip: | 10 |
| Other: | alternate large fin central collection channel on-chip flow resistors |

Figure 45A:
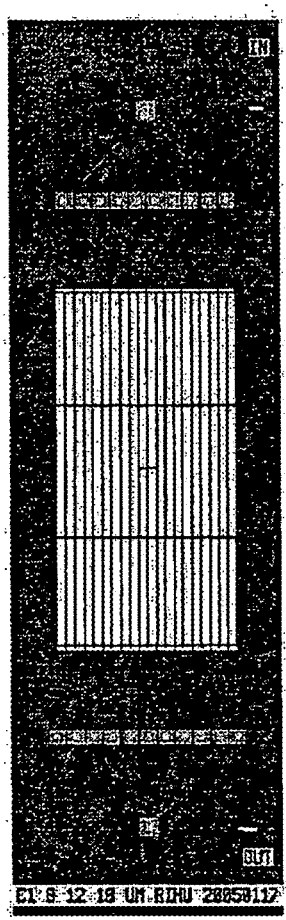
FIGS. 45A-45D are depictions the mask used to fabricate a device of the invention.
Figure 45B:
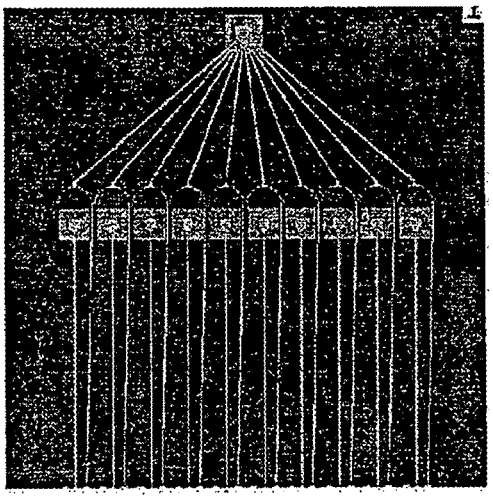
Figure 45C:
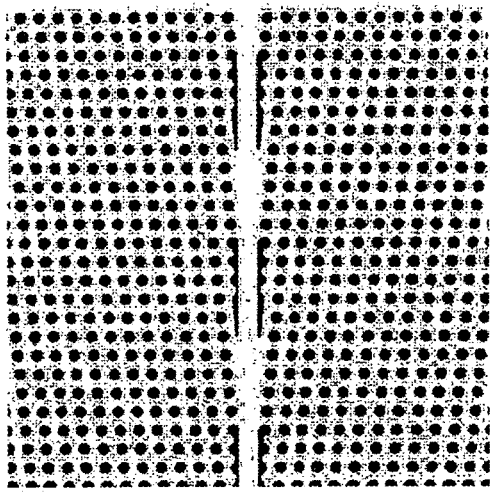
Figure 45D:
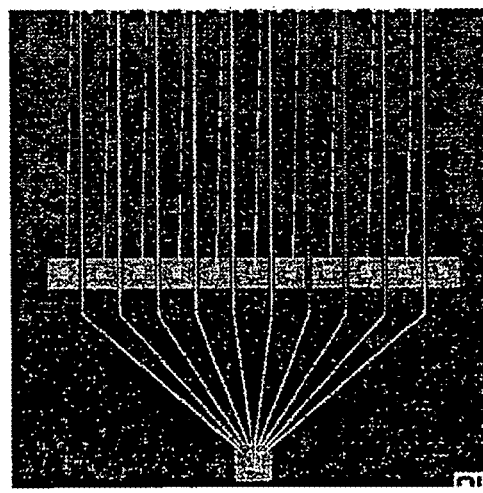

Array Design: 3 stage symmetric array
Gap Sizes: Stage 1: 8 μm
    Stage 2: 12 μm
    Stage 3: 18 μm
    Stage 4:
    Stage 5:
Flow Angle: 1/10
Arrays/Chip: 10
Other: Alternate large fin central collection channel on-chip flow resistors FIG. 45A shows the mask employed to fabricate the device. FIGS. 45B-45D are enlargements of the portions of the mask that define the inlet, array, and outlet. FIGS. 532A-532F show SEMs of the actual device.

Example 9

This device includes three stages, where each stage is a duplex having a bypass channel "Fins" were optimized using Femlab to flank the bypass channel to keep fluid from the bypass channel from re-entering the array. The edge of the fin closest to the array was designed to mimic the shape of the array. The chip also included on-chip flow resistors, i.e., the inlets and outlets possessed greater fluidic resistance than the array. The height of the device was 139 or 142 μm.

Figure 54A:
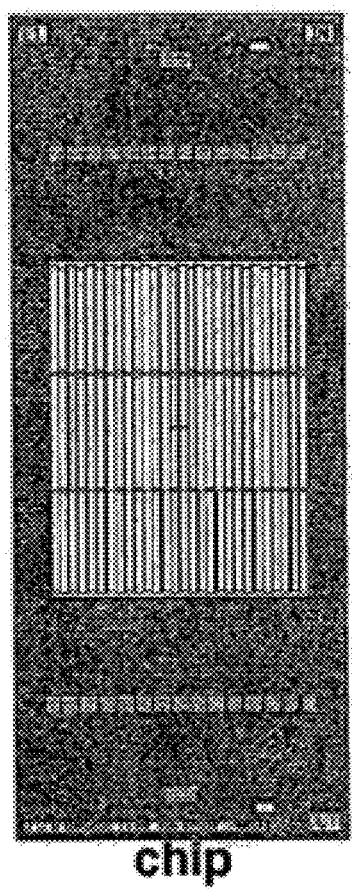
FIGS. 54A-54D are depictions the mask used to fabricate a device of the invention.
Figure 54B:
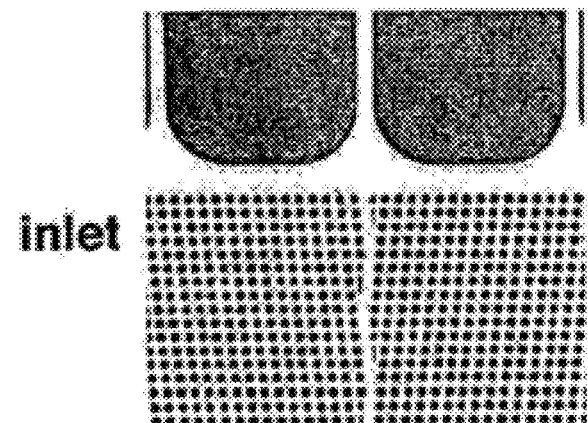
Figure 54C:
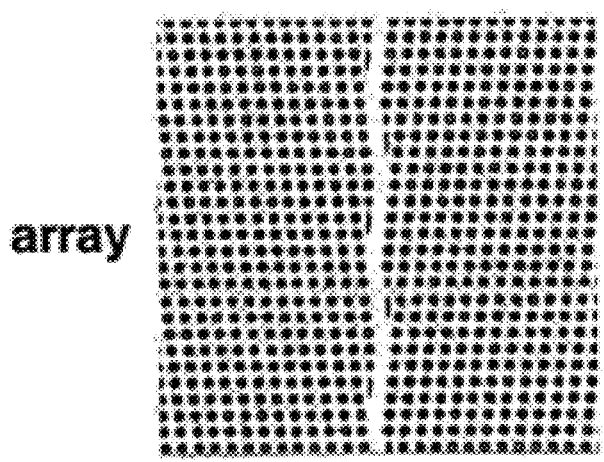
Figure 54D:
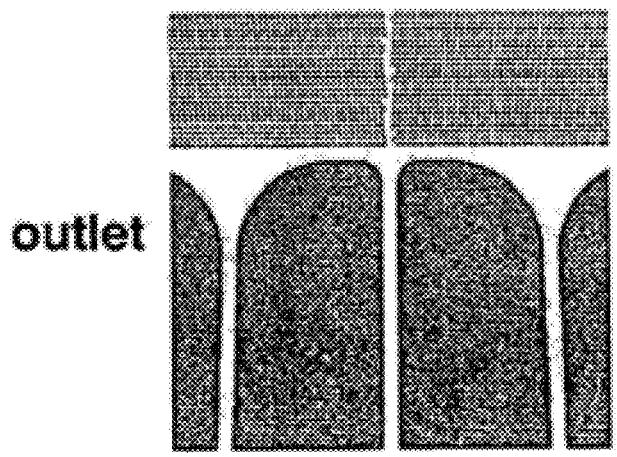
Figure 55A:
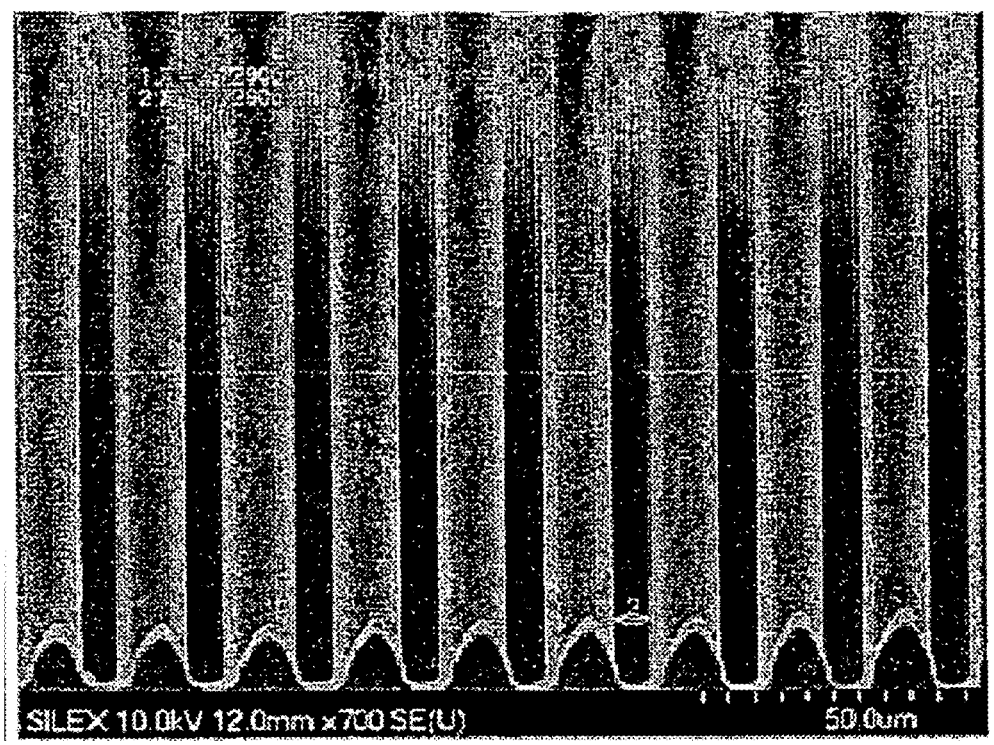
FIGS. 55A-55S are electron micrographs of the device of FIG. 54.
Figure 55B:
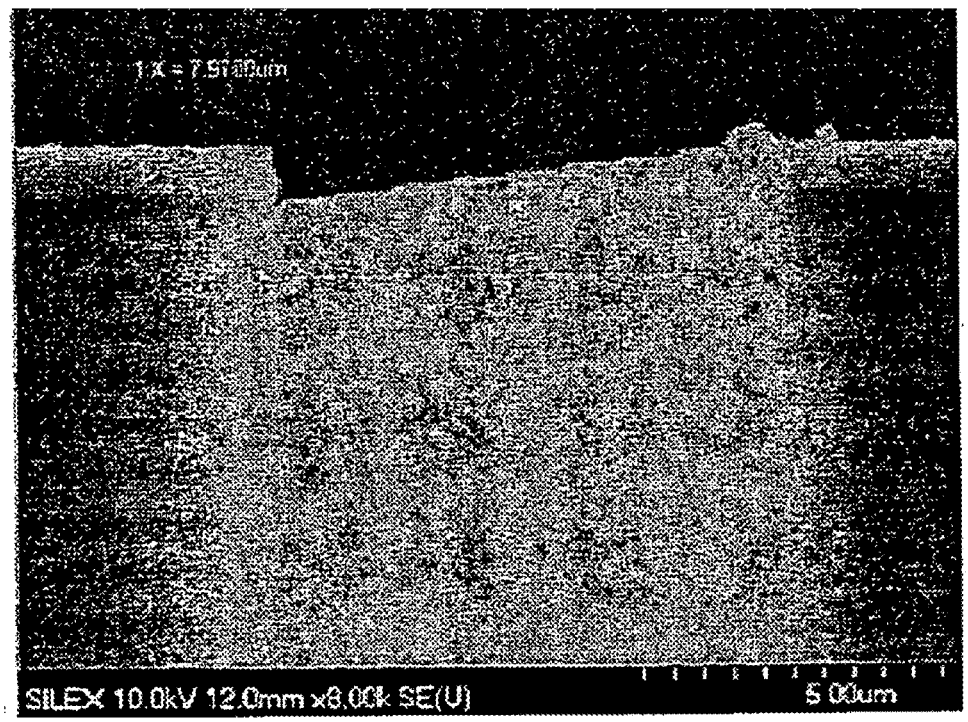
Figure 55C:
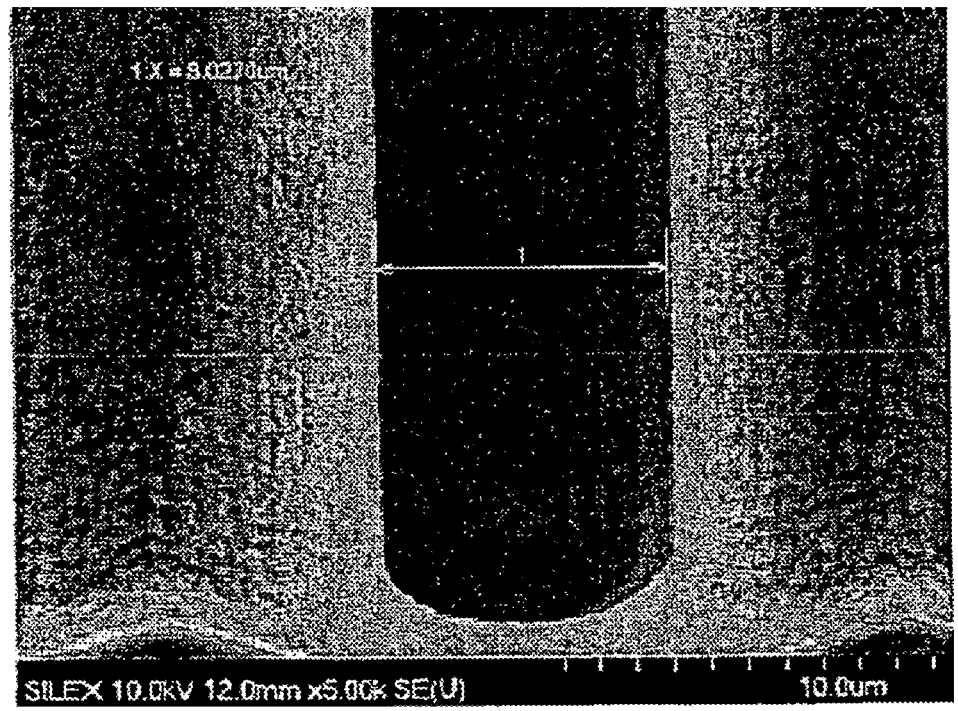
Figure 55D:
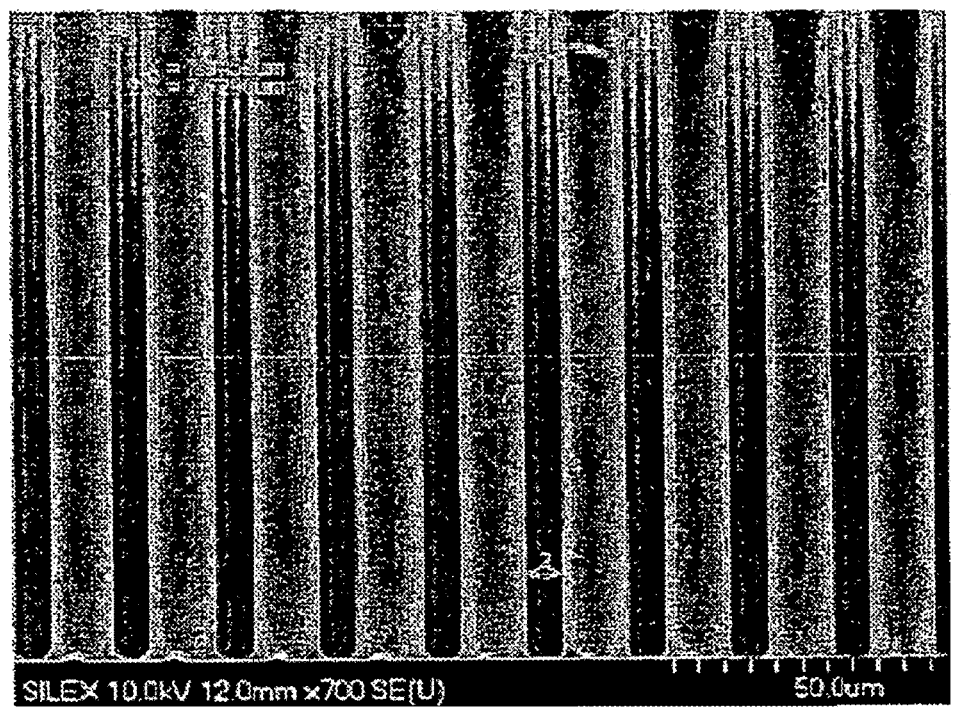
Figure 55E:
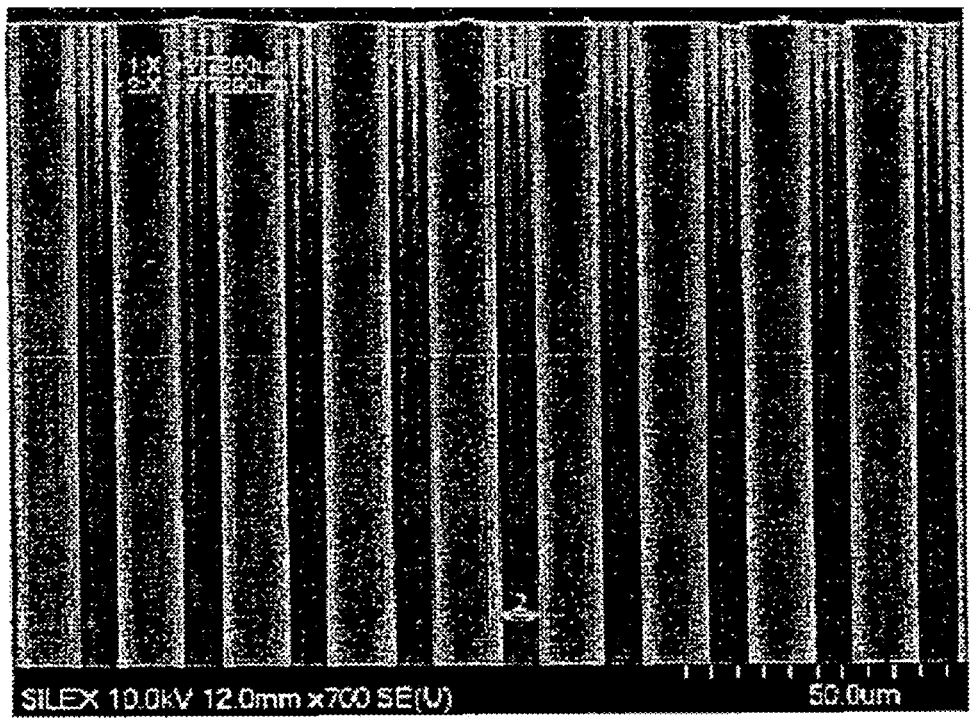
Figure 55F:
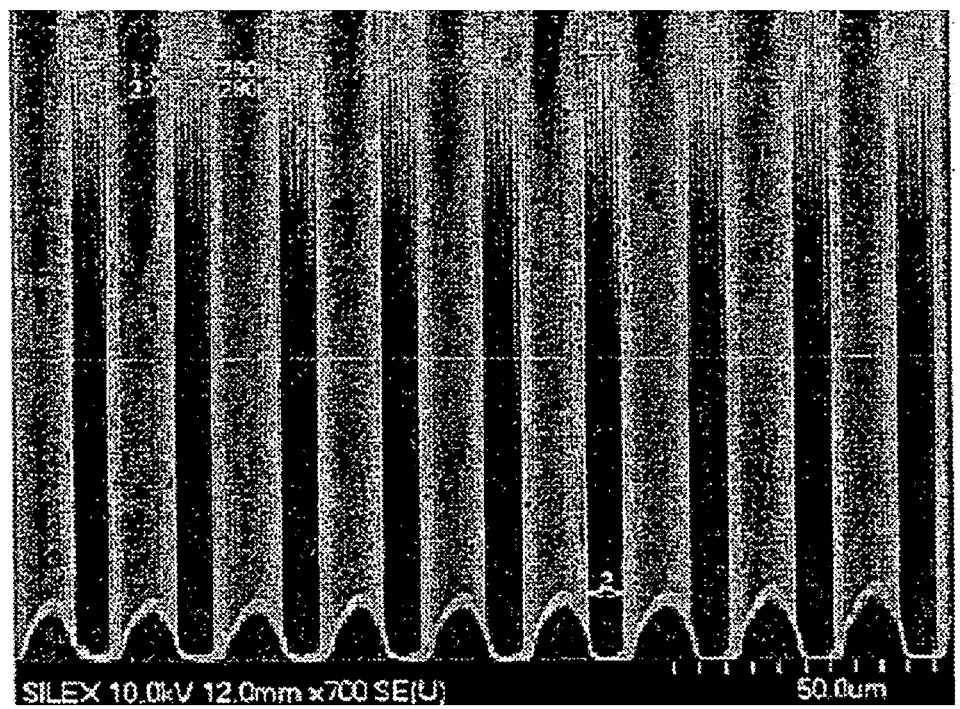
Figure 55G:
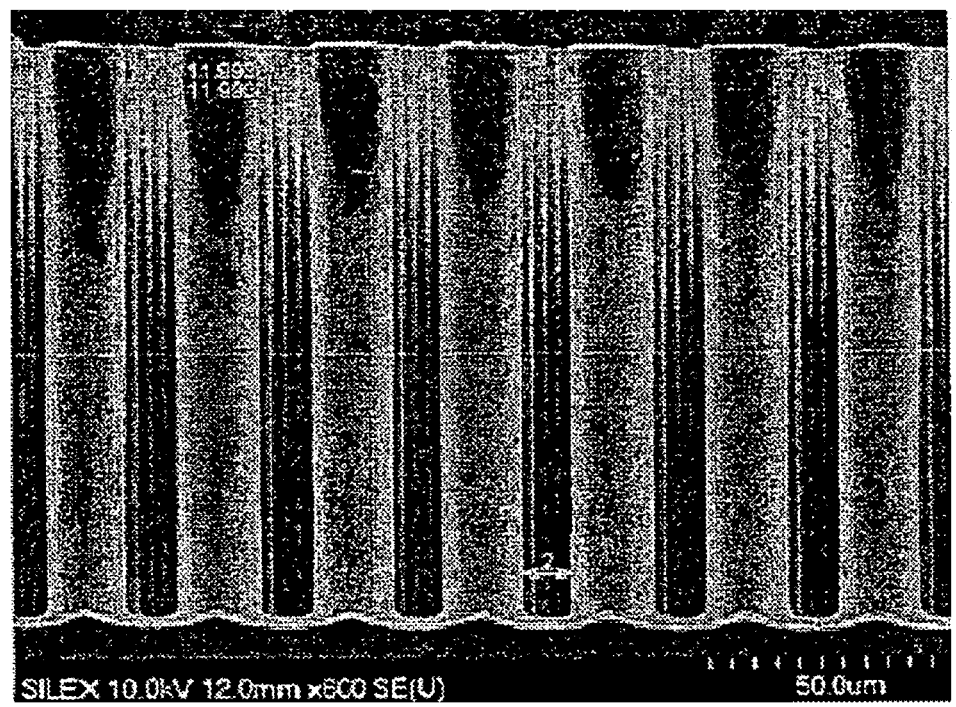
Figure 55H:
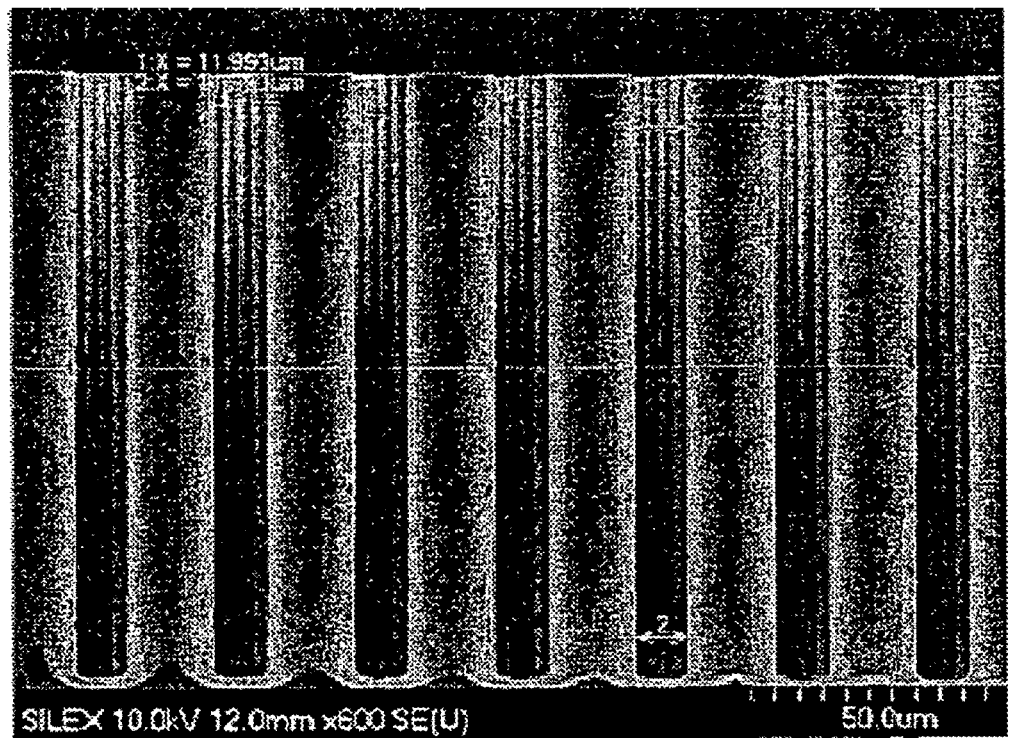
Figure 55I:
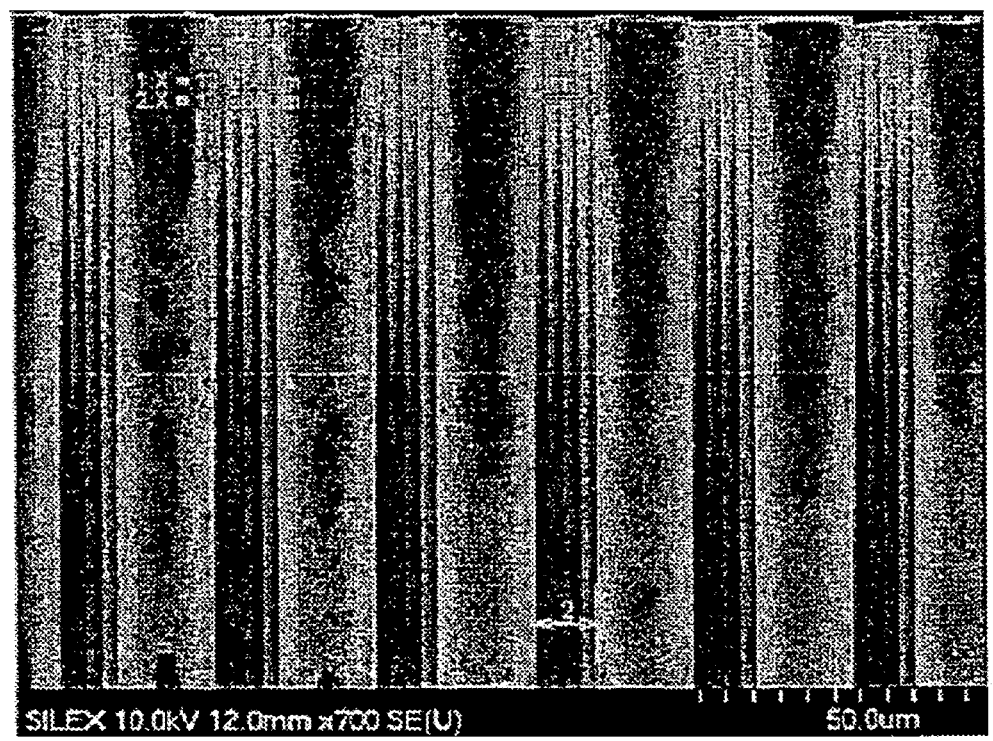
Figure 55J:
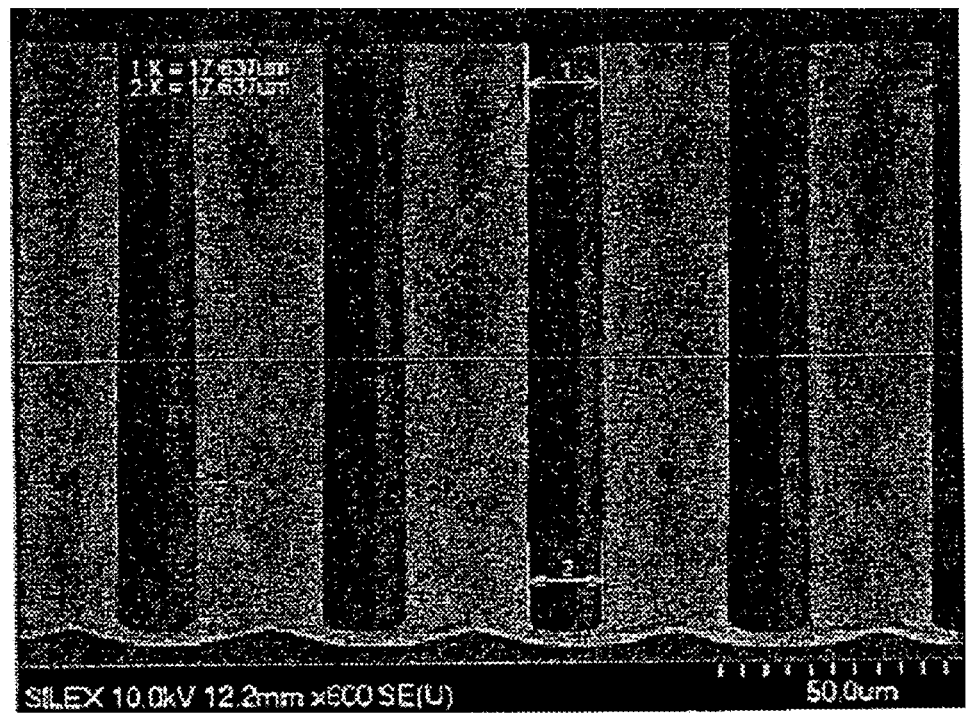
Figure 55K:
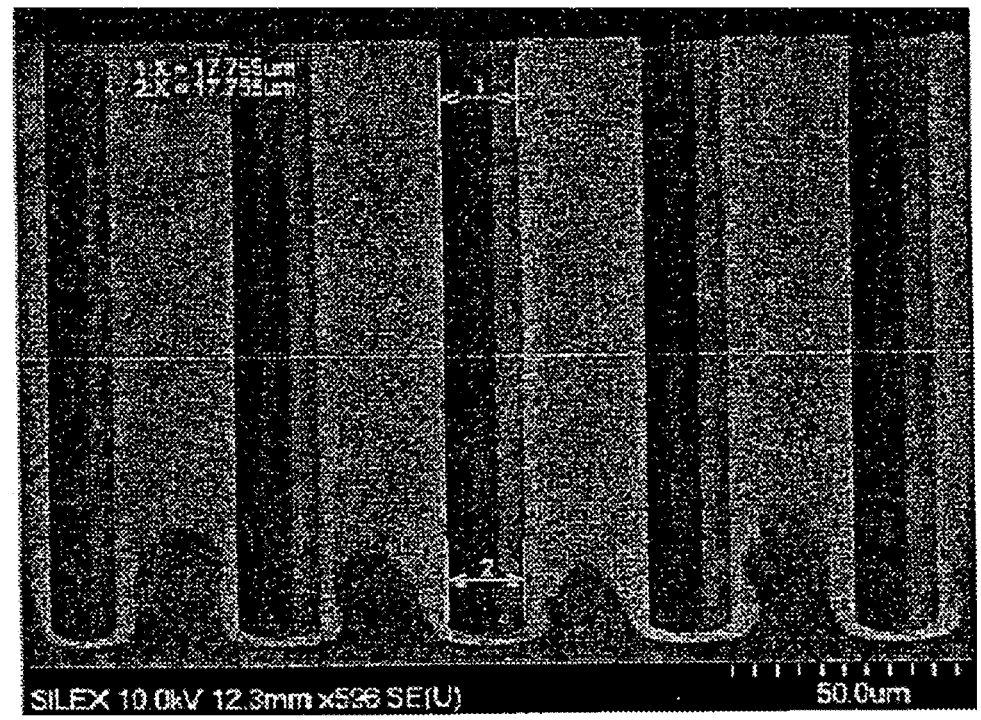
Figure 55L:
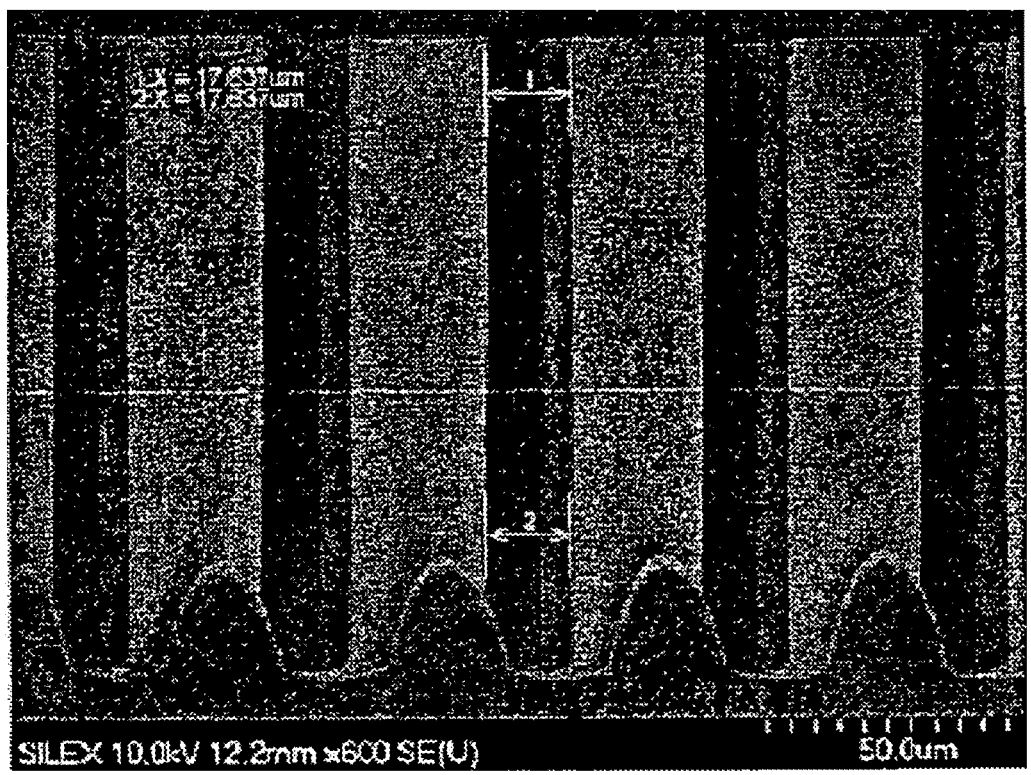
Figure 55M:
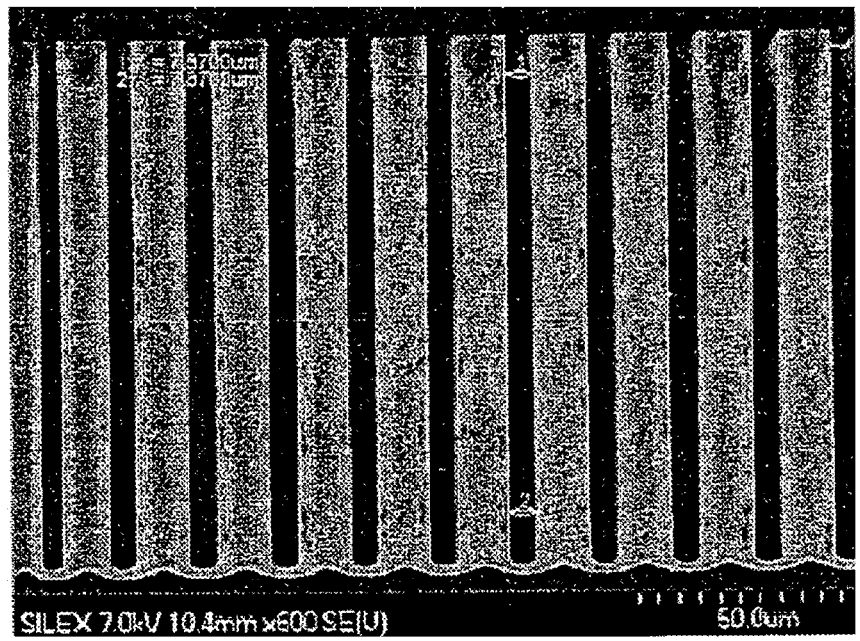
Figure 55N:
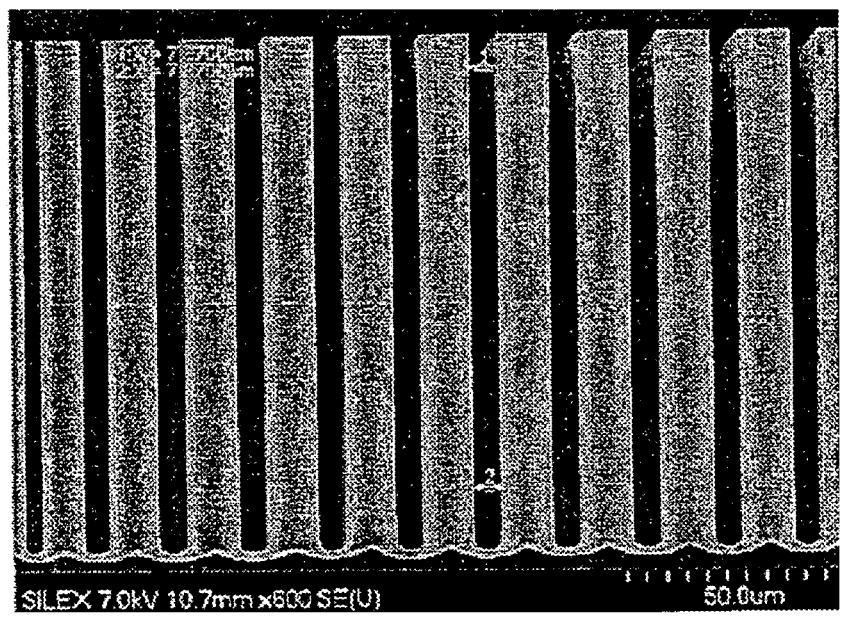
Figure 55O:
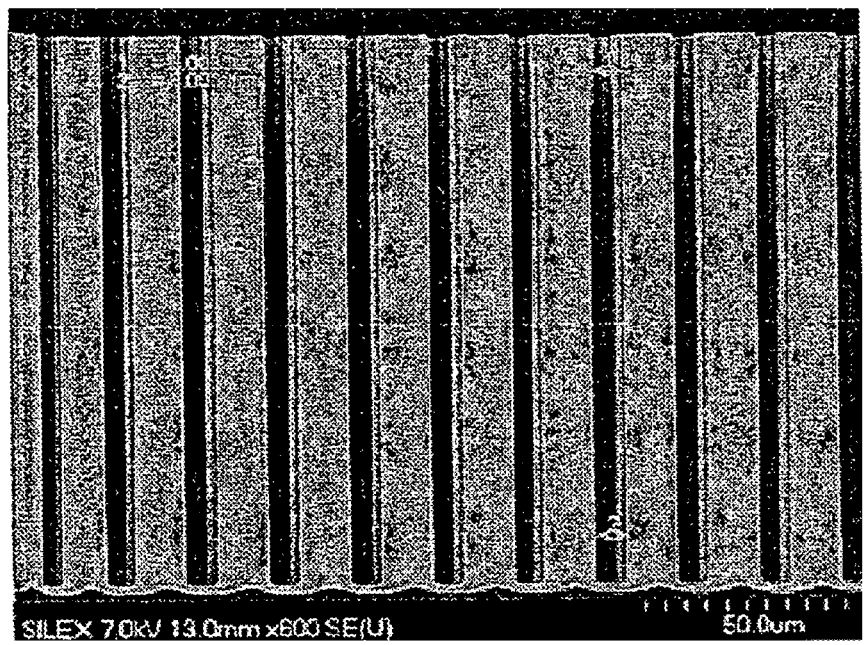
Figure 55P:
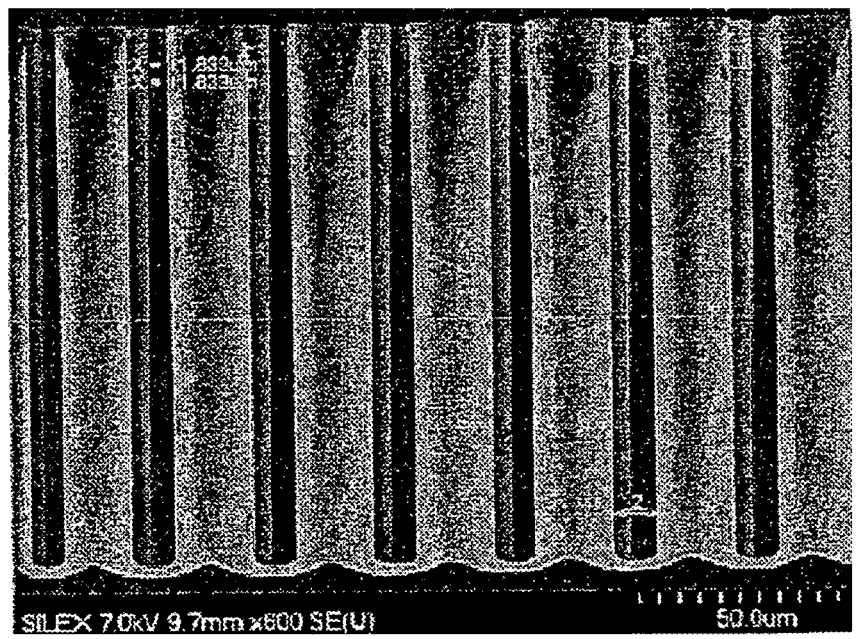
Figure 55Q:
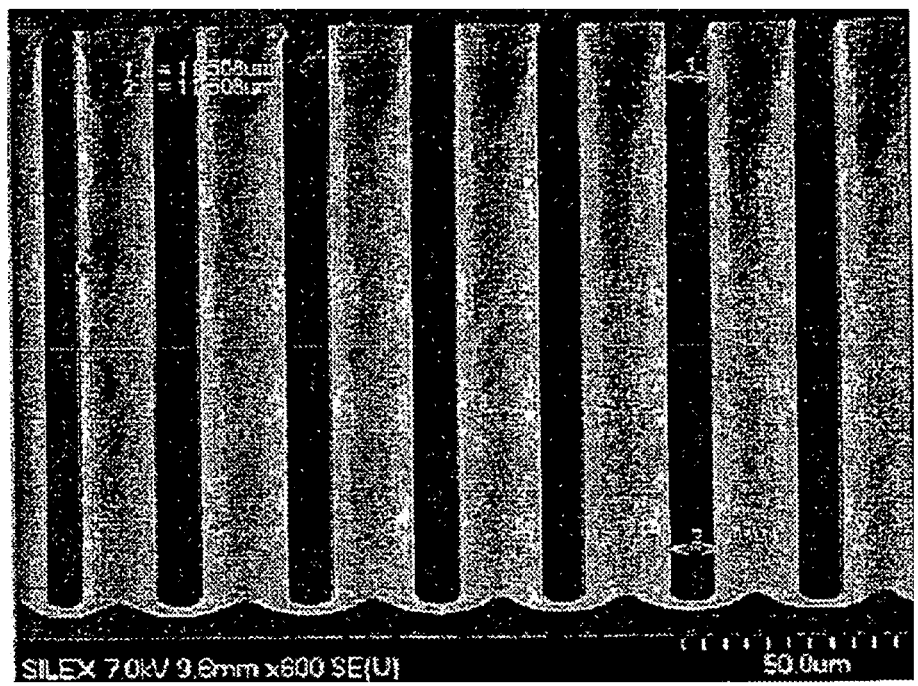
Figure 55R:
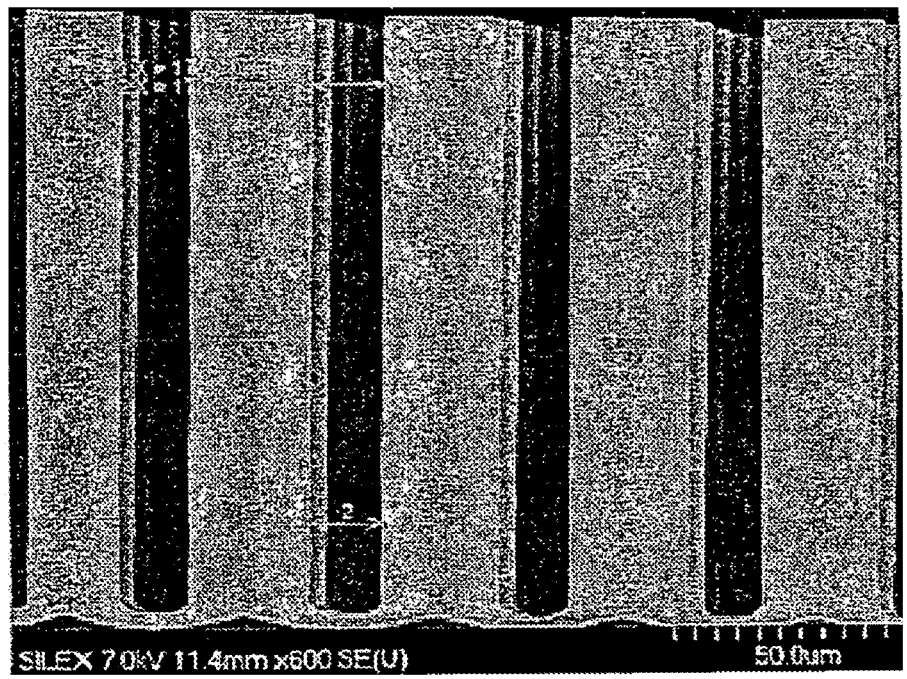
Figure 55S:
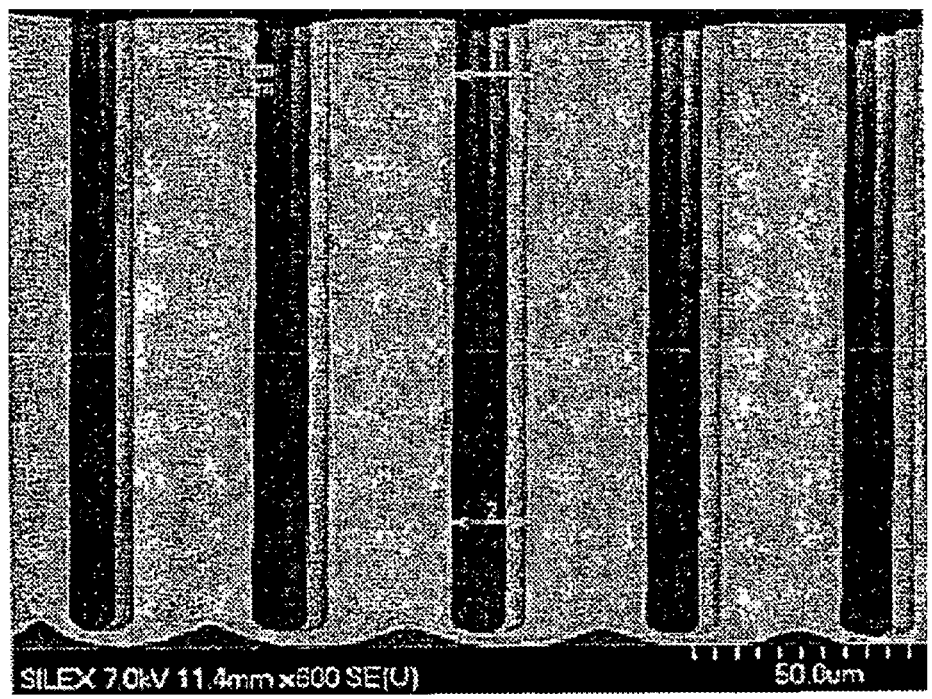

Array Design: 3 stage symmetric array
Gap Sizes: Stage 1: 8 μm
    Stage 2: 12 μm
    Stage 3: 18 μm
    Stage 4:
    Stage 5:
Flow Angle: 1/10
Arrays/Chip: 10
Other: Femlab optimized central collection channel (Femlab 1) on-chip flow resistors
Array Design: 3 stage symmetric array
Gap Sizes: Stage 1: 8 μm
    Stage 2: 12 μm
    Stage 3: 18 μm
    Stage 4:
    Stage 5:
Flow Angle: 1/10
Arrays/Chip: 10
Other: Femlab optimized central collection channel (Femlab 1) on-chip flow resistors FIG. 54A shows the mask employed to fabricate the device. FIGS. 54B-54D are enlargements of the portions of the mask that define the inlet, array, and outlet. FIGS. 55A-55S show SEMs of the actual device.

Example 10

This device includes a single stage, duplex device having a bypass channel disposed to receive output from the ends of both arrays. The obstacles in this device are elliptical. The array boundary was modeled in Femlab. The chip also included on-chip flow resistors, i.e., the inlets and outlets possessed greater fluidic resistance than the array. The height of the device was 152 μm.

Figure 44A:
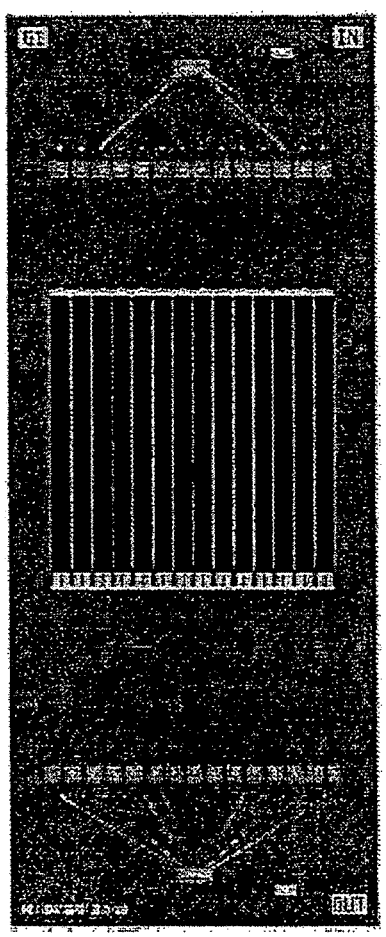
FIGS. 44A-44D are depictions the mask used to fabricate a device of the invention.
Figure 44B:
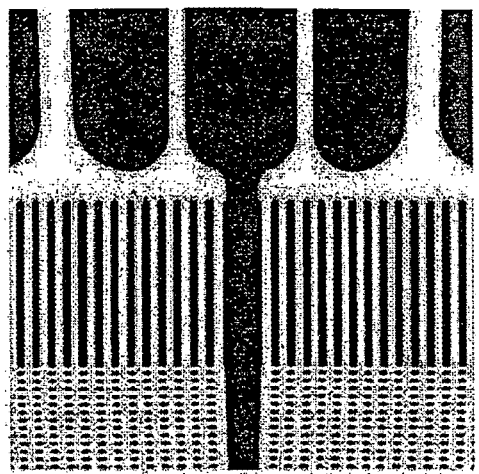
Figure 44C:
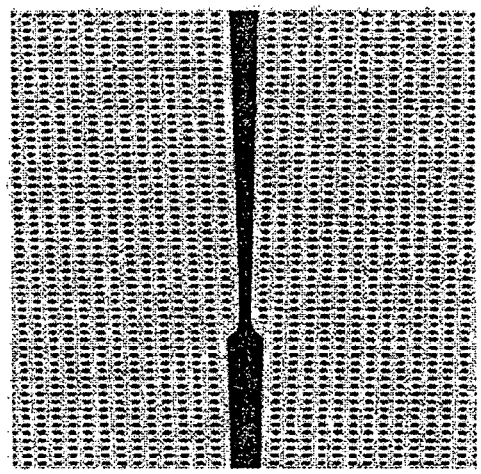
Figure 44D:
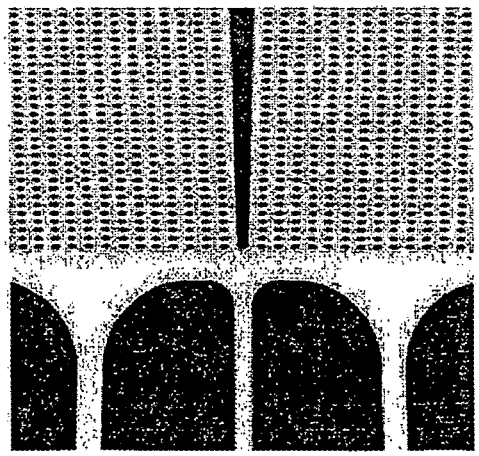
Figure 56A:
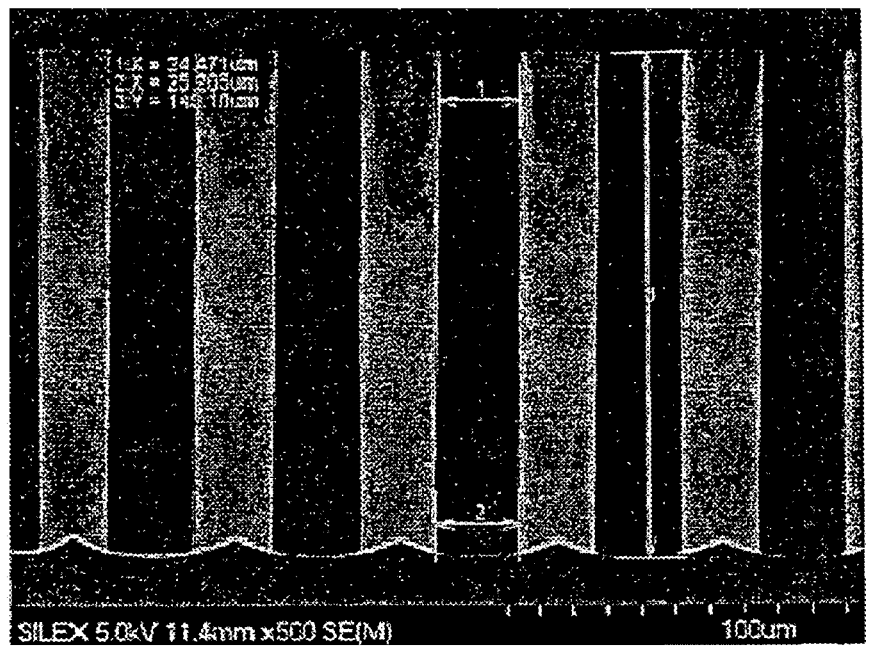
FIGS. 56A-56C are electron micrographs of the device of FIG. 44.
Figure 56B:
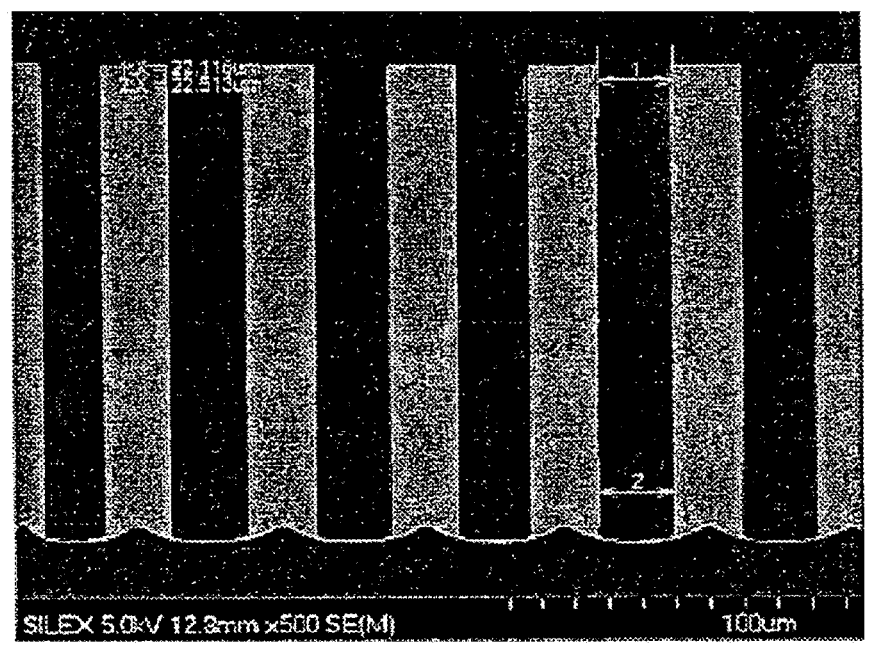
Figure 56C:
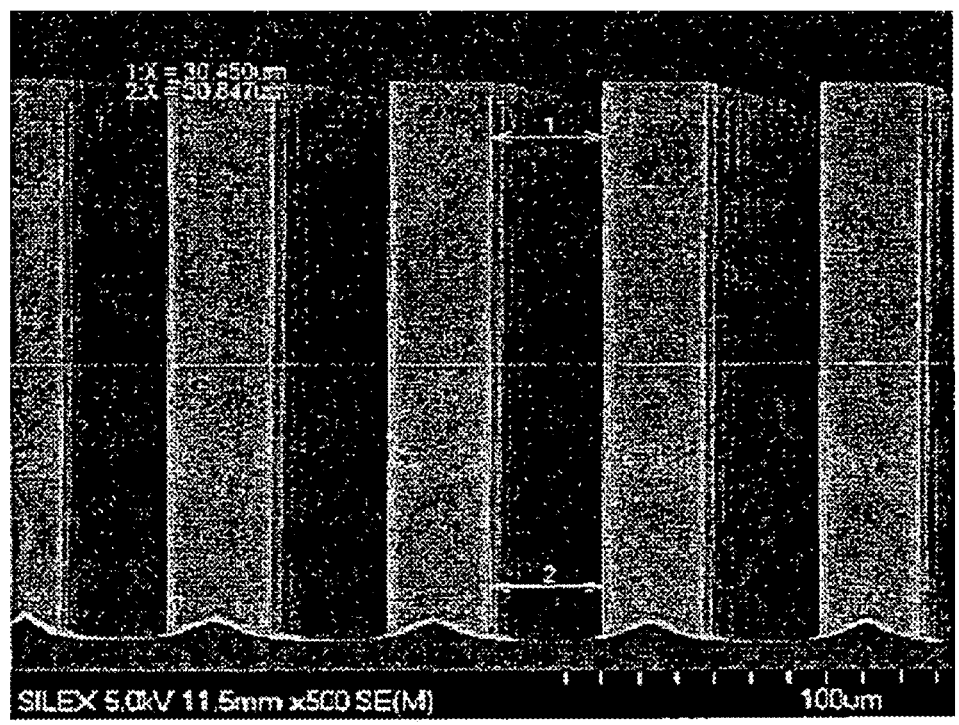

Array Design: single stage symmetric array
Sizes: Stage 1: 0.24 μm
  Stage 2:
  Stage 3:
  Stage 4:
  Stage 5:
Flow Angle: 1/60
Arrays/Chip: 14
Other: central barrier
  ellipsoid posts
  on-chip resistors
  Femlab modeled array boundary
Array Design: Single stage symmetric array
Gap Sizes: Stage 1: 24 μm
  Stage 2:
  Stage 3:
  Stage 4:
  Stage 5:
Flow Angle: 1/60
Arrays/Chip: 14
Other: Central barrier
  Ellipsoid posts
  On-chip resistors
  Femlab modeled array boundary FIG. 44A shows the mask employed to fabricate the device. FIGS. 44B-44D are enlargements of the portions of the mask that define the inlet, array, and outlet. FIGS. 56A-56C show SEMs of the actual device.

Example 11

Though the following examples focus on extraction of a purified population of nuclei of circulating fetal cells from whole maternal blood, the methods described are generic for isolation of cellular components from other cells.

Isolation of Fetal Nuclei

Figure 57:
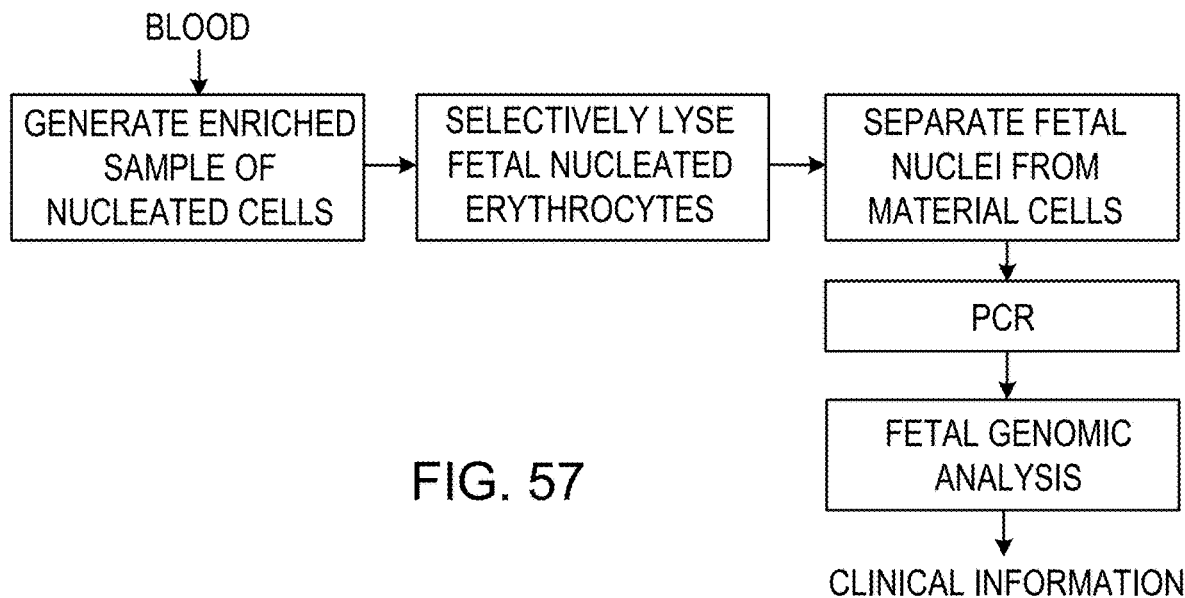
FIG. 57 is a flowchart describing the isolation of fetal red blood cell nuclei.
Figure 58:
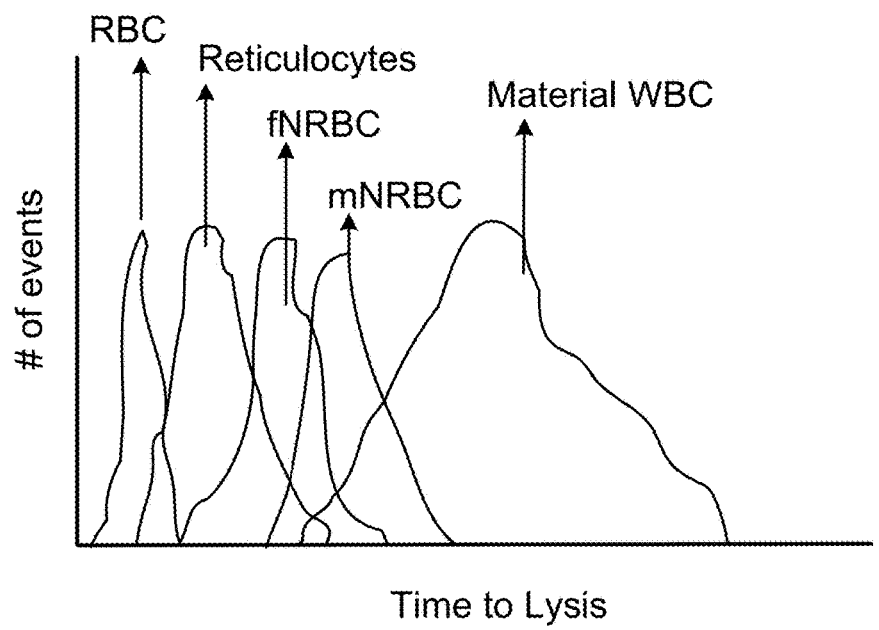
FIG. 58 is a schematic graph of the course of lysis of cells in a maternal blood sample.

FIG. 57 shows a flowchart for a method of isolating fetal nuclei from a maternal blood sample. The method results in the preferential lysis of red blood cells (FIG. 58).

Figure 59:
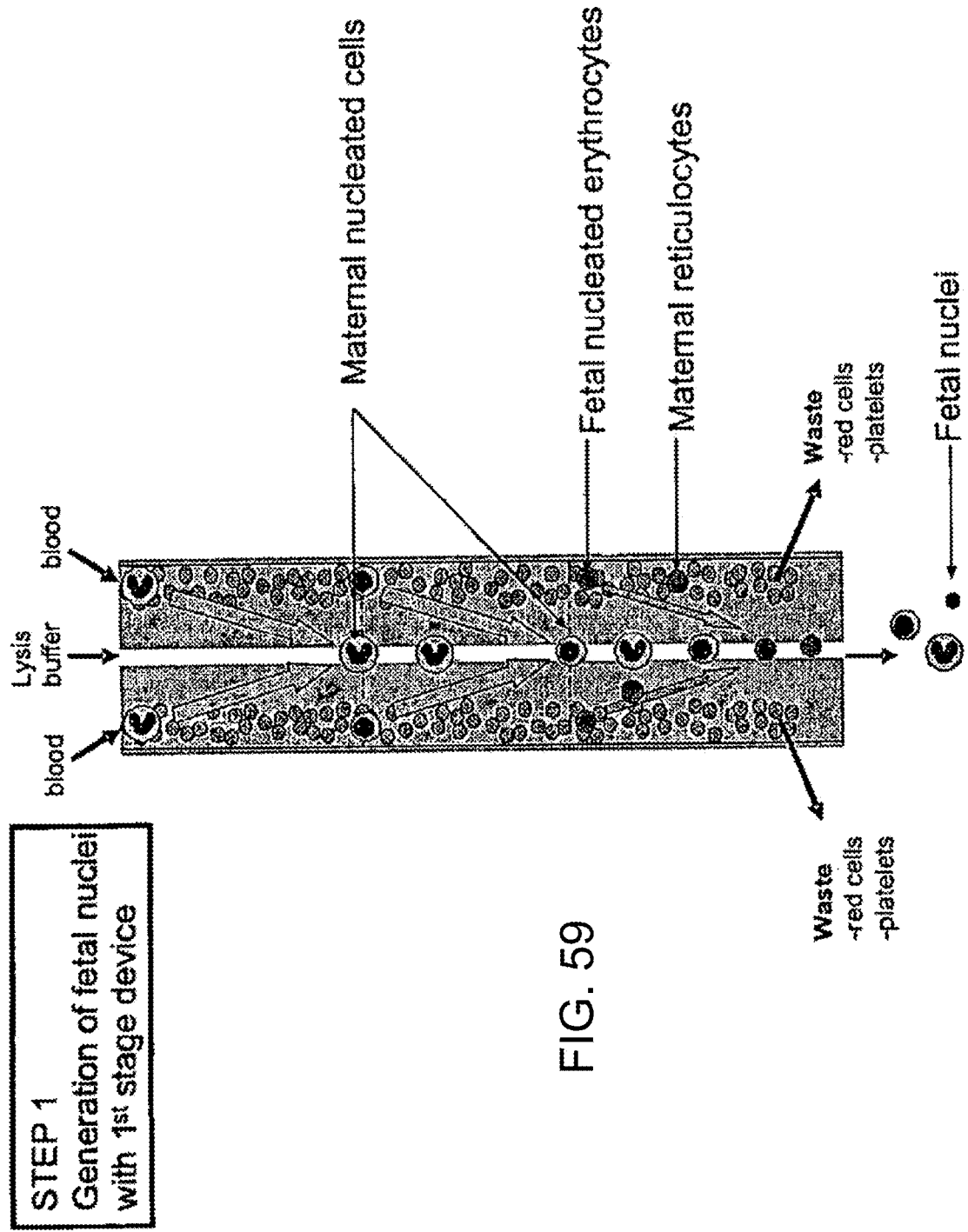
FIG. 59 is a schematic diagram of a microfluidic method to enrich the cells of interest and preferentially lyse the cells of interest in the enriched sample. The sample is first enriched by size-based direction of cells of interest into a preferred channel, and the cells of interest are then selectively lysed by controlling their residence time in a lysis solution.
Figure 60:
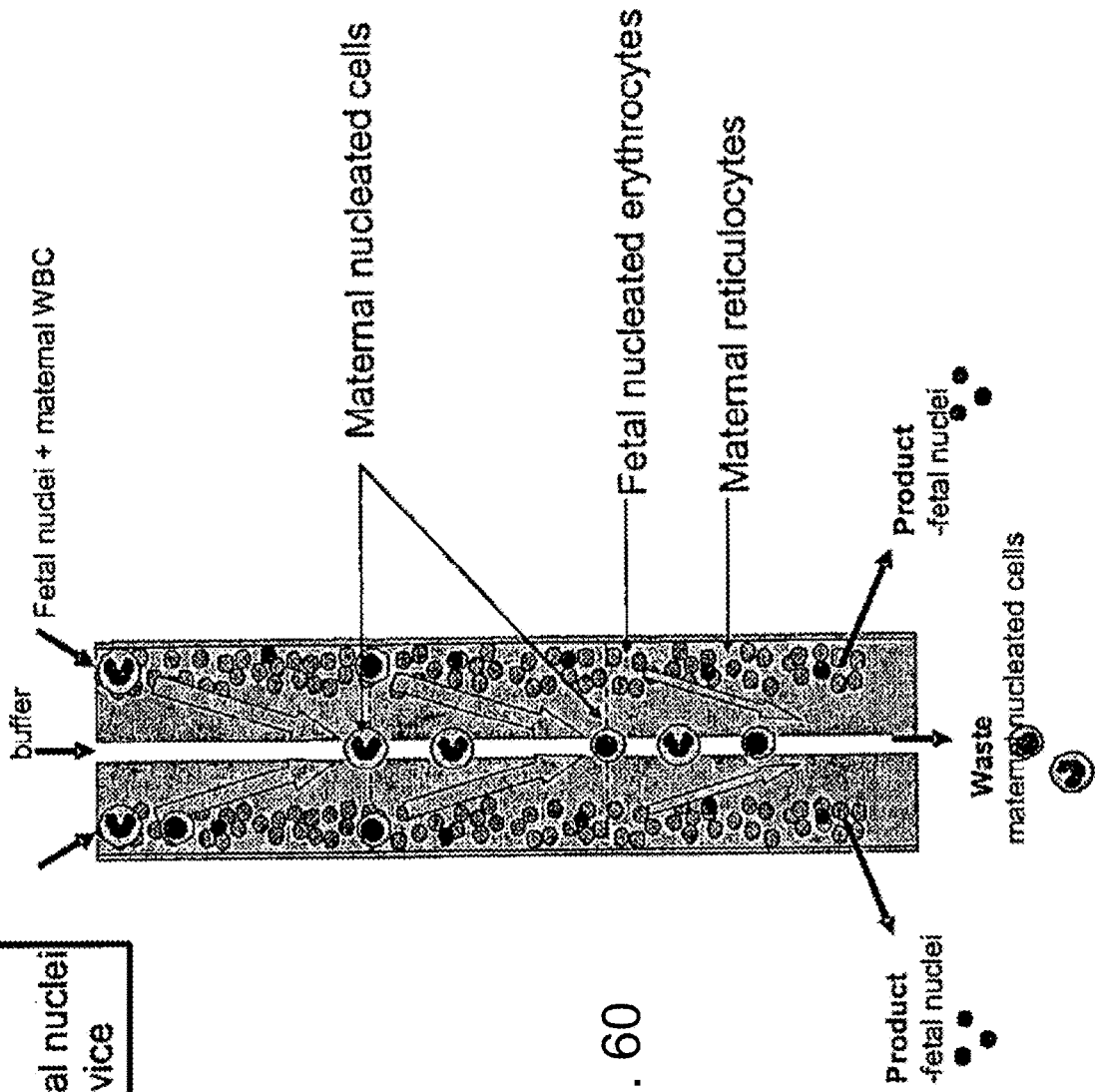
FIG. 60 is a schematic diagram of a microfluidic method of size-based isolation of the nuclei of the lysed cells of interest from non-lysed whole cells of non-interest. The cells of non-interest are directed into the waste, while the nuclei are retained in the desired product streams.
Figure 61:
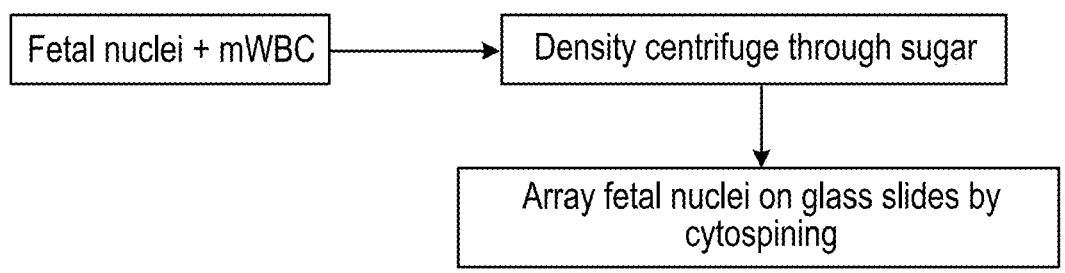
FIG. 61 is a flowchart describing an alternate method for the separation of fetal nuclei from maternal white blood cells.

Several embodiments of a method that isolates from whole blood a purified population of nuclei from circulating cells of interest for genomic analysis are described below:

a) The method includes microfluidic processing, as described herein, of whole blood to 1) generate an enriched sample of nucleated cells by depletion of 1 to 3 log of the number of enucleated red blood cells and platelets, 2) release fetal nuclei by microfluidic processing of the enriched nucleated sample to lyse residual enucleated red cells, enucleated reticulocytes, and nucleated erythrocytes, preferentially over nucleated maternal white blood cells, 3) separate nuclei from maternal nucleated white blood cells by microfluidic processing through a size based device, and 4) analyze fetal genome using commercially available gene analysis tools.

b) The method can be designed to allow Steps 1 and 2 of Embodiment 1 in one pass through a microfluidic device, followed by use of a downstream device, or component of a larger device, for Step 3 (see FIGS. 59 & 60). FIG. 59 shows a schematic diagram of a microfluidic device for producing concomitant enrichment and lysis. The device employs two regions of obstacles that deflect larger cells from the edges of the device, where the sample is introduced, into a central channel containing a lysis solution (e.g., a duplex device as described herein). For maternal blood, the regions of obstacles are disposed such that maternal enucleated red blood cells and platelets remain at the edges of the device, while fetal nucleated red blood cells and other nucleated cells are deflected into a central channel. Once deflected into the central channel, the fetal red blood cells (cells of interest) are lysed. FIG. 60 shows a schematic diagram for a microfluidic device for separating nuclei (cellular component of interest) from unlysed cells. The device is similar to that of FIG. 59, except the obstacles are disposed such that nuclei remain at the edges of the device, while larger particles are deflected to the central channel.

c) A combination method of microfluidic based generation of fetal nuclei in maternal blood sample, followed by bulk processing techniques, such as density gradient centrifugation to separate the fetal nuclei from maternal cells (see FIG. 61).

d) Methods and Proof of Principle

Selective Lysis and Partitioning of Nucleated Erythrocytes. Contaminating red blood cells in donor blood samples spiked with full term cord blood were lysed using two methods, hypotonic and ammonium chloride lysis. Since enucleated red cells undergo lysis in hypotonic solution faster than nucleated cells, controlling the exposure time of the mixed cell population in the hypotonic solution will result in a differential lysis of cell populations based on this time. In this method, the cells are sedimented to form a pellet, and the plasma above the pellet is aspirated. Deionized water is then added, and the pellet is mixed with the water. Fifteen seconds of exposure is sufficient to lyse >95% of the enucleated red blood cells with minimal nucleated red blood cell lysis, 15 to 30 seconds of exposure is sufficient to lyse >70% of the nucleated red blood cells but <15% of other nucleated cells, and >30 seconds will increase the percentage of lysis of other nucleated cells. After the desired exposure time, a 10×HBSS (hypertonic balanced salt) solution is added to return the solution back to isotonic conditions. Exposure to ammonium chloride lysing solutions at standard concentrations (e.g., 0.15 M isotonic solution) will lyse the bulk of red blood cells with minimal effects on nucleated cells. When the osmolality of the lysing solution is decreased to create a hypotonic ammonium chloride solution, the bulk of nucleated red blood cells are lysed along with the mature red blood cells.

Density centrifugation methods were used to obtain an enriched population of lymphocytes. An aliquot of these lymphocytes were exposed to a hypotonic ammonium chloride solution for sufficient time to lyse >95% of the cells. These nuclei were then labeled with Hoechst 33342 (bisbenzimide H 33342), a specific stain for AT rich regions of double stranded DNA, and added back to the original lymphocyte population to create a 90:10 (cell: nuclei) mixture. This mixture was fed into a device that separated cells from nuclei based on size, as depicted in FIG. 60, and the waste and product fractions were collected and the cell: nuclei ratio contained in each fraction were measured.

Density Gradient Centrifugation of Lysed Product. The lysed nuclei of mixed cell suspensions that have been processed through a differential lysis procedure can be enriched by adding a sucrose cushion solution to the lysate. This mixture is then layered on a pure sucrose cushion solution and then centrifuged to form an enriched nuclei pellet. The unlysed cells and debris are aspirated from the supernatant; the nuclei pellet is re-suspended in a buffer solution and then cytospun onto glass slides.

Figures 66, 67:
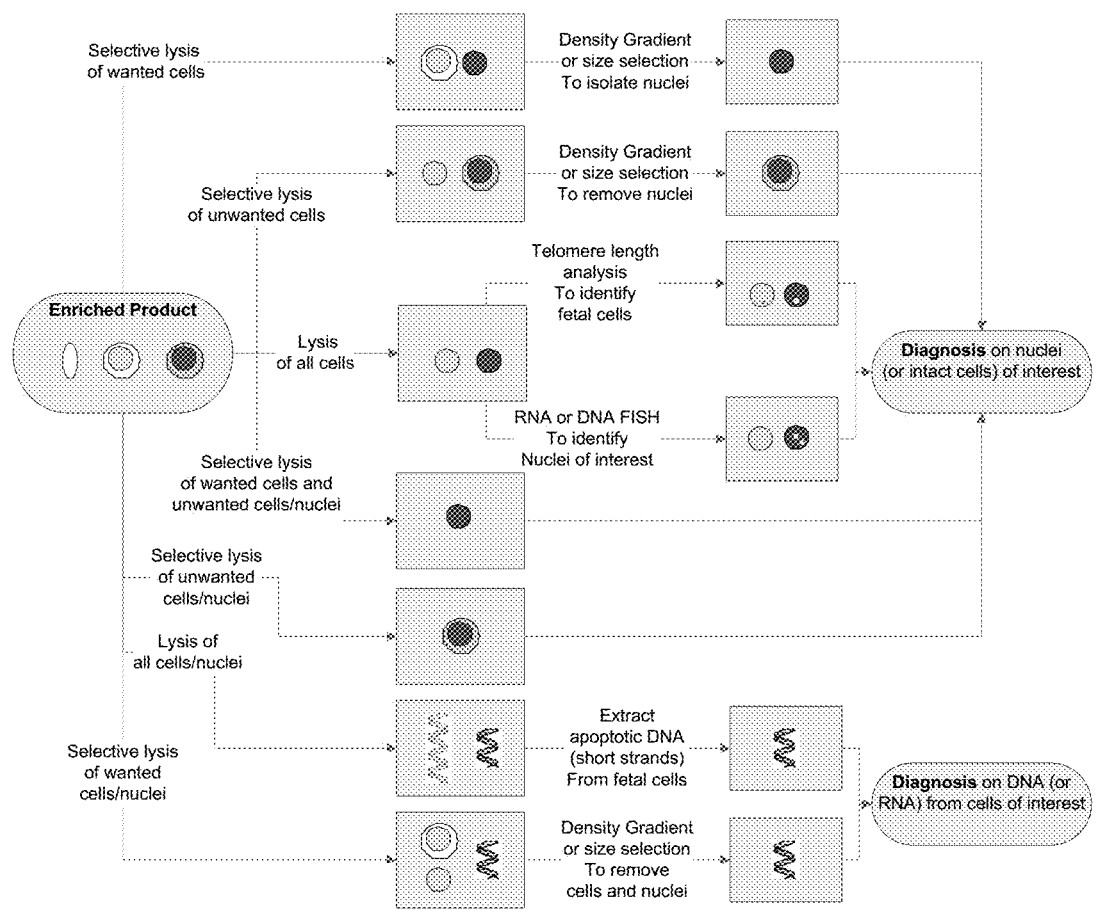
FIG. 66 is a table that illustrates the nuclei recovery after Cytospin using Carney's fix solution total cell lysis procedure as described herein.
FIG. 67 is a flowchart detailing various options for lysis of cells and nuclei.

Acid Alcohol Total Cell Lysis and Nuclear RNA FISH for Targeted Cell Identification. Product obtained from a device that separated cells based on size, as depicted in FIG. 60, was exposed to an acid alcohol solution (methanol:acetic acid 3:1 v/v) for 30 minutes on ice resulting in the lysis of >99% of enucleated cells and >99.0% lysis of nucleated cells. A hypotonic treatment by exposing the cells to salt solution (0.6% NaCl) for 30 minutes to swell the nuclei before acid alcohol lysis can also be included. The released nuclei can be quantitatively deposited onto a glass slide by cytospin and FISHed (FIG. 66). The cells of interest, such as fetal nucleated erythrocytes, can be identified using RNA-FISH with probes for positive selection, such as zeta-, epsilon, gamma-globins, and negative selection such as beta-globin or analyzing the length of telomeres. Other methods for distinguishing between fetal and non-fetal cells are known in the art, e.g., U.S. Pat. No. 5,766,843.

Example 12

Figure 62:
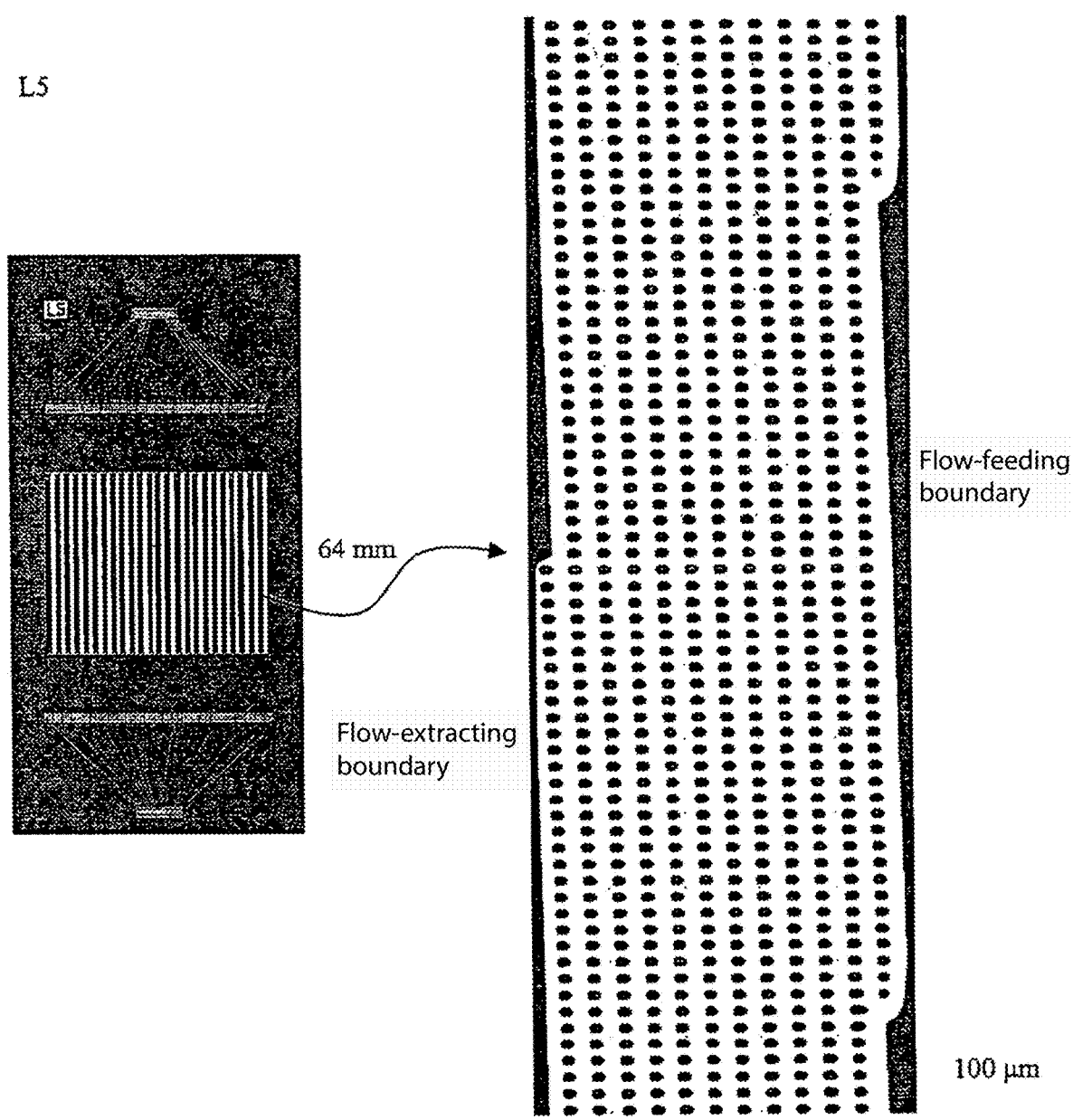
FIG. 62 is a schematic diagram of a device of the invention employing a substantially constant gap width and flow-feeding and flow-extracting boundaries.

FIG. 62 shows a device that is optimized for separation of particles in blood. It is a one-stage device with a fixed gap width of 22 μm, with 48 multiplexed arrays for parallel sample processing. The parameters of the device are as follows:

| | |
|---|---|
| Array Design: | L5 |
| Gap Sizes: | Stage 1: 22 μm |
| Flow Angle: | 1/50 |
| Arrays/Chip: | 48 |
| Nominal Depth | 150 μm |
| Device Footprint | 32 mm × 64 mm |
| Design Features | Multiplexed single arrays |
| | Optimized bypass channels |
| | Flow stabilization |
| | Flow-feeding and Flow-extracting boundaries |

Blood was obtained from pregnant volunteer donors and diluted 1:1 with Dulbecco's phosphate buffered saline (without calcium and magnesium)(iDPBS). Blood and Running Buffer (iDPBS with 1% BSA and 2 mM EDTA) were delivered using an active pressure of 0.8 PSI to the device engaged with a manifold as described in Example 13. Blood was separated into two components nucleated cells in Running Buffer and enucleated cells and plasma proteins in Running Buffer. Both components were analyzed using a standard impedance counter. The component containing nucleated cells was additionally characterized using a propidium iodide staining solution in conjunction with a standard Nageotte counting chamber to determine total nucleated cell loss. Data collected were used to determine blood process volume (mL), blood process rate (mL/hr), RBC/platelet removal, and nucleated cell retention. The following table provides results of cell enrichments employing this device:

| | | | | | |
|---|---|---|---|---|---|
| Volume Processed (mL) | 26.5 | 8 | 15.4 | 17 | 19 |
| Throughput (mL/h) | 10.6 | 10.0 | 11.8 | 9.8 | 9.8 |
| WBC in the waste/input WBC (Nageotte) | 0.013% | 0.012% | 0.005% | 0.014% | 0.030% |
| RBC Removal | 99.993% | 99.992% | 99.997% | 99.995% | 99.999% |
| Platelet Removal | >99.6% | >99.7% | >99.7% | >99.7% | >99.7% |

Example 13

Figure 63A:
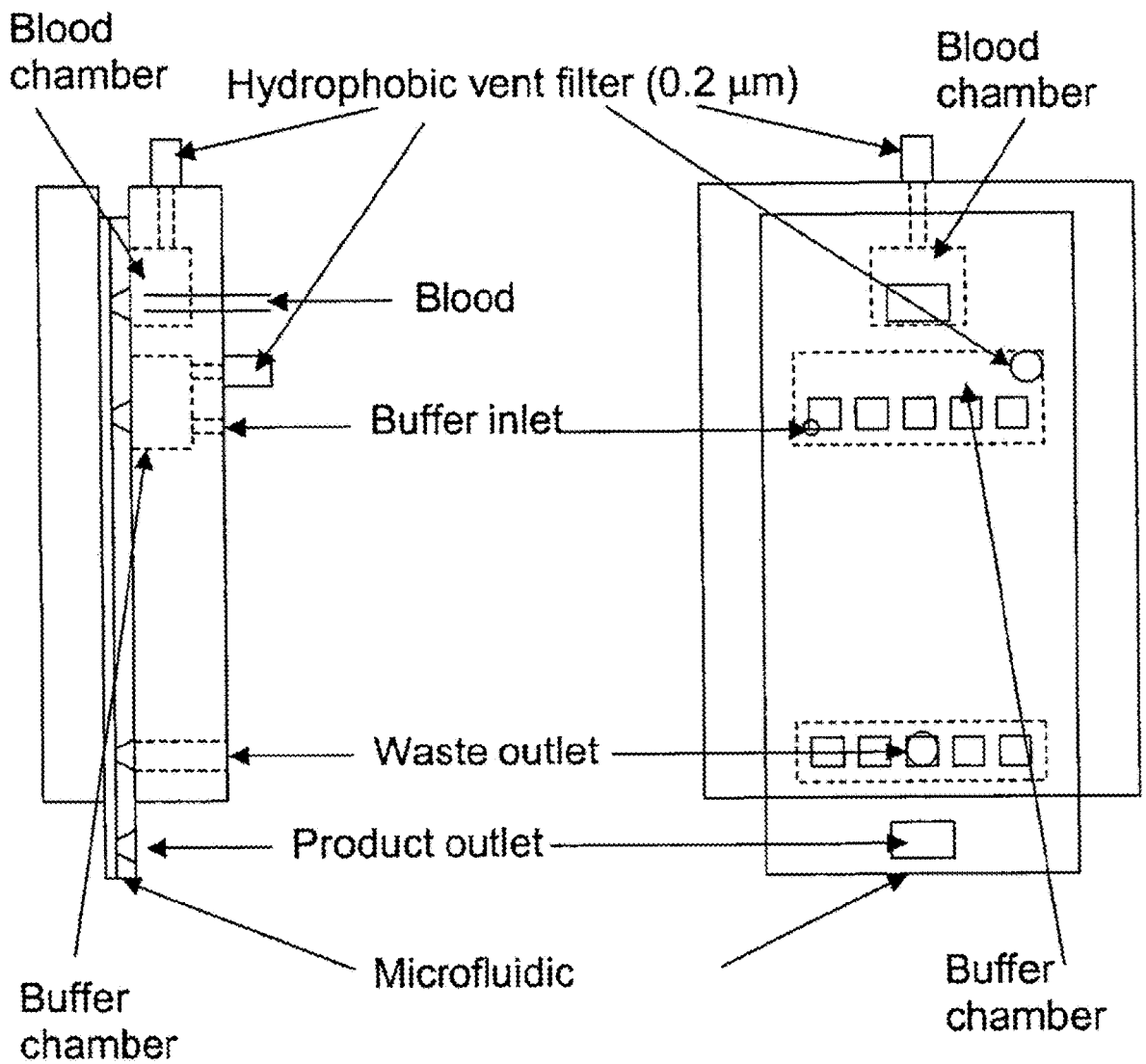
FIG. 63$a$ is a schematic depiction of a manifold of the invention.
Figure 63B:
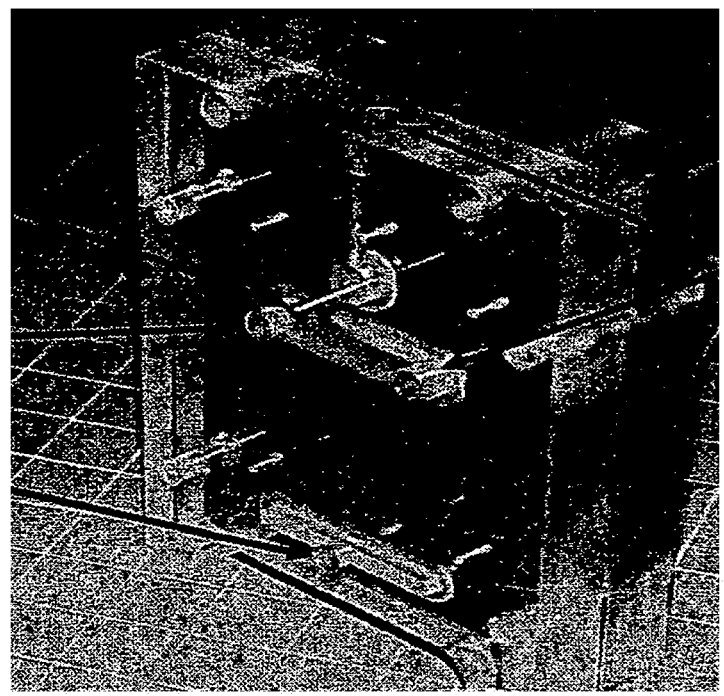

An exemplary manifold into which a microfluidic device of the invention is inserted is shown in FIG. 63. The manifold has two halves between which a microfluidic device of the invention is disposed. One half of the manifold includes separate inlets for blood and buffer, each of which is connected to a corresponding fluid reservoir. The channels in the device are oriented so that they connect to the reservoirs via through holes in the device. Typically, the device is oriented vertically, and the processed blood is collected as it drips out of the product outlet. A region around the product outlet of the microfluidic device may also be marked with a hydrophobic substance, e.g., from a permanent marker, to limit the size of drops formed. The device also includes two hydrophobic vent filters, e.g., 0.2 μm PTFE filters. These filters allow air trapped in the device to be displaced by aqueous solutions, but do not let the liquid pass at low pressures, e.g., <5 psi.

To prime the device, buffer, e.g., Dulbecco's PBS with 1% bovine serum albumin (w/v) and 2 mM EDTA, is degassed for 5-10 min under reduced pressure and while being stirred. The buffer is then pumped into the device via the buffer inlet in the manifold at a pressure of <5 psi. The buffer then fills the buffer chamber by displacing air through the hydrophobic vent filter and then fills the channels in the microfluidic device and the blood chamber. A hydrophobic vent filter connected to the blood chamber allows for the displacement of air in the chamber. Once the blood chamber is filled, buffer is pumped into the blood inlet. In certain embodiments, after 1 minute of priming at 1 psi, the blood inlet is clamped, and the pressure is increased to 3 psi for 3 minutes.

Example 14

A fetal nRBC population enriched by any of the devices described herein is subjected to hypotonic shock by adding a large volume of low ionic strength buffer, e.g., deionized water to lyse enucleated RBCs and nRBCs selectively and release their nuclei. The hypotonic shock is then terminated by adding an equal volume of a high ionic strength buffer. The released nuclei, which may be subsequently harvested through gradient centrifugation such as passage through a solution of iodixanol in water, ρ=1.32 g/mL, are analyzed.

Figure 64:
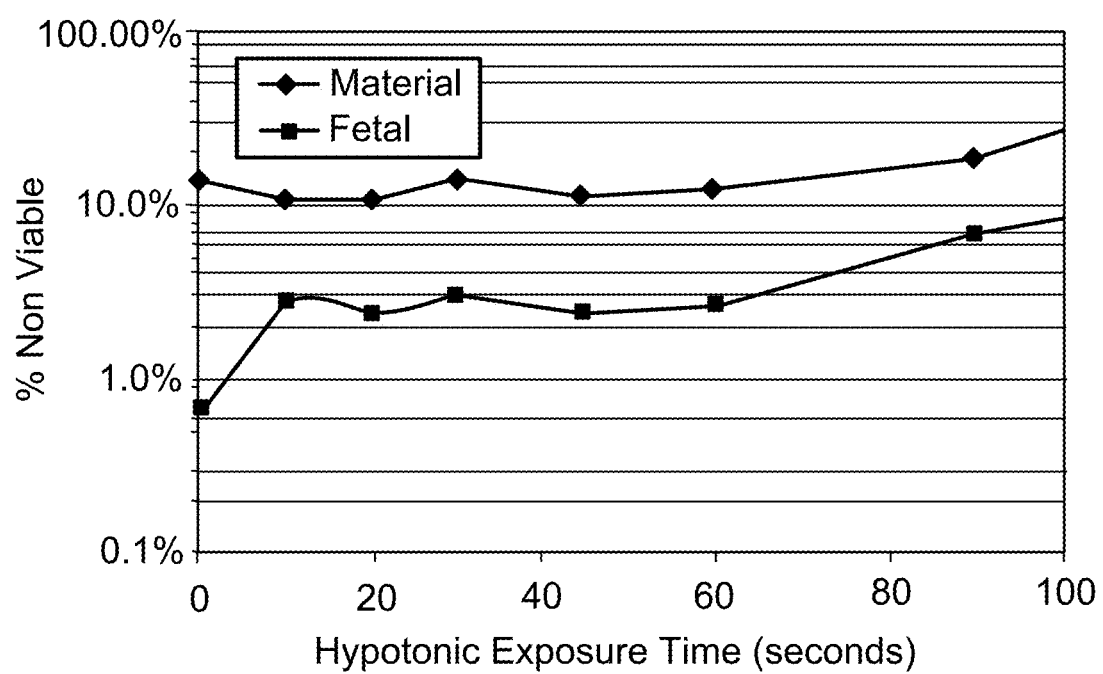
FIG. 64 is a graph of the percentage of viable cells as a function of exposure to a hypotonic lysis solution.

FIG. 64 illustrates the selective lysis of fetal nRBCs vs. maternal nRBCs as a function of the duration of exposure to lysing conditions. This selective lysis procedure also can be used to lyse selectively fetal nRBCs in a population of cells composed of fetal nRBC, maternal nRBC, enucleated fetal and maternal RBCs, and fetal and maternal white blood cells. Using distilled water to induce hypotonic shock for a given time period and then adding an equal volume of 10×salt solution, such as PBS, to halt it, fetal nRBCs and maternal nRBCs were lysed over time during which the number of lysed (non-viable) fetal nRBCs increased by a factor of 10, whereas the number of lysed maternal nRBCs increased by a smaller multiple. At any given time point, the lysed cells were stained with propidium iodide and were concentrated through gradient centrifugation to determine the ratio of lysed fetal nRBCs vs. maternal nRBCs. An optimized time duration can be determined and applied to enrich selectively for fetal nRBCs nuclei.

Example 15

To lyse enucleated RBCs and maternal nucleated RBCs selectively, a sample enriched in fetal nRBCs is treated with a RBC lysis buffer, such as 0.155 M $NH_4Cl$, 0.01 M $KHCO_3$, 2 mM EDTA, 1% BSA with a carbonic anhydrase inhibitor, such as acetazolamide (e.g., at 0.1-100 mM), to induce lysis, followed by termination of the lysis process using a large volume of balanced salt buffer, such as 10×volume of 1×PBS, or balanced salt buffer, such as 1×PBS, with an ion exchange channel inhibitor such as 4,4'-diisothiocyanostilbene-2,2'-disulphonic acid (DIDS). The surviving fetal cells may then be subjected to additional rounds of selection and analysis.

Figure 65:
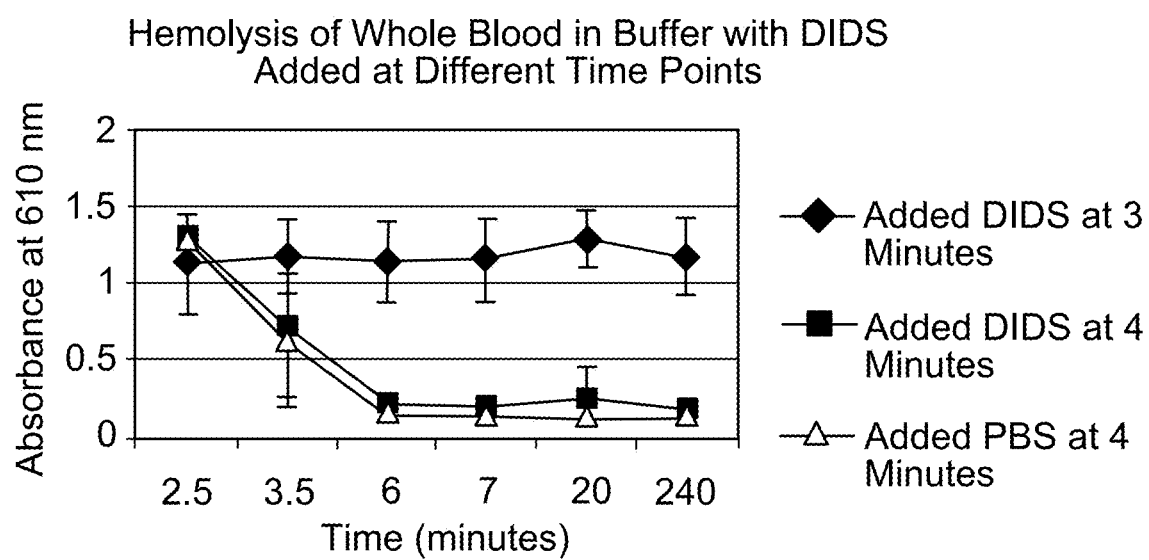
FIG. 65 is a graph of hemolysis of whole blood as a function of time in a lysis buffer.

K562 cells, to simulate white blood cells, were labeled with Hoechst and calcein AM at room temperature for 30 minutes (FIG. 65). These labeled K562 cells were added to blood specimens, followed by the addition of buffer (0.155 M $NH_4Cl$, 0.01 M $KHCO_3$, 2 mM EDTA, 1% BSA, and 10 mM acetazolamide) (the ratio of buffer volume to spiked blood volume is 3:2). The spiked blood specimens were incubated at room temperature for 4 hours with periodic gentle agitation. The fraction of viable cells in each spiked specimen were determined by measuring the green fluorescence at 610 nm at multiple time-points. Cell lysis is observed only after three minutes of treatment (in the absence of DIDS).

Example 16

A sample enriched in fetal nRBC, e.g., by any of the devices or methods discussed herein, may be lysed and analyzed for genetic content. Possible methods of cell lysis and isolation of the desired cells or cell components include:

a) A sample enriched in fetal nRBC may be subjected to total cell lysis to remove cytoplasm and isolate the nuclei. Nuclei may be immobilized through treatment with fixing solution, such as Carnoy's fix, and adhesion to glass slides. The fetal nuclei may be identified by the presence of endogenous fetal targets through immunostaining for nuclear proteins and transcription factors or through differential hybridization, RNA FISH of fetal pre-mRNAs (Gribnau et al. *Mol Cell* 2000. 377-86; Osborne et al. *Nat Gene.* 2004. 1065-71; Wang et al. *Proc. Natl. Acad. Sci.* 1991. 7391-7395; Alfonso-Pizarro et al. *Nucleic Acids Research.* 1984. 8363-8380.) These endogenous fetal targets may include globins such as zeta-, epsilon-, gamma-, delta-, beta-, alpha- and non-globin targets such as I-branching enzyme (Yu et al., *Blood.* 2003 101:2081), N-acetylglucosamine transferase, or IgnT. The oligo nucleotide probes employed by RNA FISH may be either for intron-exon boundaries or other regions, which uniquely identify the desired target or by analyzing the length of telomeres.

b) A sample enriched in fetal nRBC may be lysed selectively using treatments with buffers and ion exchange inhibitors described in example 15 to isolate fetal cells. The surviving fetal cells may be further subjected to selection by the presence or absence of intracellular markers such as globins and I-branching beta 1, 6-N-acetylglucosaminyl-transferase or surface markers such as antigen I. In another embodiment, the enriched fetal nRBCs can be subjected to selective lysis to remove both the enucleated RBCs and maternal nRBCs as described in Example 15, followed by a complement mediated cell lysis using an antibody against CD45, a surface antigen present in all nucleated white blood cells. The resulting intact fetal nRBCs should be free of any other contaminating cells.

c) A sample enriched in fetal nRBC may be lysed through hypotonic shock as described in Example 14 to isolate fetal nuclei. Nuclei may be immobilized through treatment with fixing solution, such as Carnoy's fix, and adhesion to glass slides.

Once isolated, the desired cells or cell components (such as nuclei) may be analyzed for genetic content. FISH may be used to identify defects in chromosomes 13 and 18 or other chromosomal abnormalities such as trisomy 21 or XXY. Chromosomal aneuploidies may also be detected using methods such as comparative genome hybridization. Furthermore, the identified fetal cells may be examined using micro-dissection. Upon extraction, the fetal cells' nucleic acids may be subjected to one or more rounds of PCR or whole genome amplification followed by comparative genome hybridization, or short tandem repeats (STR) analysis, genetic mutation analysis such as single nucleotide point mutations (SNP), deletions, or translocations.

Example 17

The product obtained from a device as depicted in FIG. 60 including 3 ml of erythrocytes in 1×PBS is treated with 50 mM sodium nitrite/0.1 mM acetazolamide for 10 minutes. The cells are then contacted with a lysis buffer of 0.155 M $NH_4Cl$, 0.01 M $KHCO_3$, 2 mM EDTA, 1% BSA and 0.1 mM acetazolamide, and the lysis reaction is stopped by directly dripping into a quenching solution containing BAND 3 ion exchanger channel inhibitors such as 4,4'-diisothiocyanostilbene-2,2'-disulphonic acid (DIDS). The enucleated RBCs and nucleated RBCs are counted after Wright-Giemsa staining, and FISH is used to count the fetal nRBCs. Values are then compared to an unlysed control. One such experimental result is shown below:

|        | Before Lysis | After Lysis | Cell Recovery % |
|--------|--------------|-------------|-----------------|
| eRBCs  | $2.6 \times 10^6$ | $0.03 \times 10^6$ | ~1% |
| nRBCs  | 42           | 26          | 62%             |
| fnRBCs | 6            | 4           | 68%             |

Example 18

Chaotropic Salt or Detergent Mediated Total Lysis and Oligo-Nucleotide Mediated Enrichment of Apoptotic DNA from Fetal Nucleated RBCs The product obtained from a device as depicted in FIG. 60 is lysed in a chaotropic salt solution, such as buffered guanidinium hydrochloride solution (at least 4.0 M), guanidinium thiocyanate (at least 4.0 M) or a buffered detergent solution such as tris buffered solution with SDS. The cell lysate is then incubated at 55° C. for 20 minutes with 10 μl of 50 mg/ml protease K to remove proteins and followed by a 5 minutes at 95° C. to inactive protease. The fetal nRBCs undergo apoptosis when entering maternal blood circulation, and this apoptotic process leads to DNA fragmentation of fetal nRBC DNA. By taking advantage of reduced size of fetal nRBCs DNA and higher efficiency of isolating smaller DNA fragments over intact genomic DNA using oligonucleotide mediated enrichment, the apoptotic fetal nRBCs DNA can be selectively enriched through hybridization to oligonucleotides in solution, attached to beads, or bound to an array or other surface in order to identify the unique molecular markers such as short tandem repeats (STR). After hybridization, the unwanted nucleic acids or other contaminants may be washed away with a high salt buffered solution, such as 150 mM sodium chloride in 10 mM Tris HCL pH 7.5, and the captured targets then released into a buffered solution, such as 10 mM Tris pH 7.8, or distilled water. The apoptotic DNA thus enriched is then analyzed using the methods for analysis of genetic content, e.g., as described in Example 16.

Example 19

FIG. 67 shows a flowchart detailing variations on lysis procedures that may be performed on maternal blood samples. Although illustrated as beginning with Enriched Product, e.g., produced using the devices and methods described herein, the processes may be performed on any maternal blood sample. The chart illustrates that lysis may be employed to lyse (i) wanted cells (e.g., fetal cells) selectively, (ii) wanted cells and their nuclei selectively, (iii) all cells, (iv) all cells and their nuclei, (v) unwanted cells (e.g., maternal RBCs, WBCs, platelets, or a combination thereof), (vi) unwanted cells and their nuclei, and (vii) lysis of all cells and selective lysis of nuclei of unwanted cells. The chart also shows exemplary methods for isolating released nuclei (devices and methods of the invention may also be sued for this purpose) and methods for assaying the results.

Example 20

This is an example of titrating whole cell lysis within a microfluidic environment. A blood sample enriched using size based separation as described herein was divided into 4 equal volumes. Three of the volumes were processed through a microfluidic device capable of transporting the cells into a first pre-defined medium for a defined path length within the device and then into a second pre-defined medium for collection. The volumetric cell suspension flow rate was varied to allow controlled incubation times with the first pre-defined medium along the defined path length before contacting the second pre-defined medium. In this example DI water was used as the first pre-defined medium and 2×PBS was used as the second predefined medium. Flow rates were adjusted to allow incubation times of 10, 20, or 30 seconds in DI water before the cells were mixed with 2><PBS to create an isotonic solution. Total cell numbers of the 3 processed volumes and the remaining unprocessed volume were calculated using a Hemacytometer

| Sample | Starting Cell Count | Final Cell Count | % Remaining |
| --- | --- | --- | --- |
| 1 unprocessed | $6.6 \times 10^6$ | $6.6 \times 10^6$ | 100% |
| 2 10 second exposure | $6.6 \times 10^6$ | $7.2 \times 10^5$ | 10.9% |
| 3 20 second exposure | $6.6 \times 10^6$ | $4.6 \times 10^5$ | 6.9% |
| 4 30 second exposure | $6.6 \times 10^6$ | $3.4 \times 10^5$ | 5.2% |

Other Embodiments

All publications, patents, and patent applications mentioned in the above specification are hereby incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A method of enriching a sample in fetal cells relative to maternal cells, the method comprising:
   (a) introducing a maternal blood sample into a microfluidic device capable of enriching fetal nucleated cells relative to maternal cells based on size, shape, deformability, or affinity to produce an enriched sample;
   (b) lysing all cells in the enriched sample to release nuclei;
   (c) performing telomere length analysis to identify fetal nuclei;
   (d) collecting fetal nuclei; and
   (e) analyzing fetal nuclei.

2. The method of claim 1, wherein step (d) comprises collecting fetal nuclei by selectively lysing nuclei of unwanted cells relative to fetal nuclei.

3. The method of claim 1, wherein the microfluidic device comprises a channel having a structure that deterministically directs fetal nucleated cells in a first direction and at least some maternal cells in a second direction based on deterministic lateral displacement.

4. The method of claim 3, wherein the microfluidic device is a duplex device comprising a channel comprising a first section comprising first and second outer regions, each outer region comprising a structure that deterministically directs particles having a hydrodynamic size above a critical size in a first direction and particles having a hydrodynamic size below the critical size in a second direction, wherein the first and second outer regions are aligned in parallel in the channel.

5. The method of claim 1, wherein step (e) comprises employing RNA Fluorescence In Situ Hybridization (FISH) for positive or negative selection of fetal nuclei.

6. The method of claim 1, wherein step (e) comprises employing sequencing for positive or negative selection of fetal nuclei.

7. The method of claim 1, wherein step (e) comprises analyzing fetal nuclei by micro-dissection.

8. The method of claim 1, wherein step (e) comprises analyzing fetal nuclei by polymerase chain reaction (PCR) or whole genome amplification (WGA).

9. The method of claim 1, wherein step (e) comprises analyzing fetal nuclei by analysis of short tandem repeats (STR).

10. The method of claim 1, wherein step (e) comprises analyzing fetal nuclei by analysis of single nucleotide point mutations (SNP), deletions, or translocations.

11. The method of claim 1, wherein step (e) comprises analyzing fetal nuclei by detecting chromosomal aneuploidies.

12. The method of claim 11, wherein chromosomal aneuploidies are detected using comparative genome hybridization.

13. A method of enriching a sample in fetal cells relative to maternal cells, the method comprising:
   (a) introducing a maternal blood sample into a microfluidic device capable of enriching fetal nucleated cells relative to maternal cells based on size, shape, deformability, or affinity to produce an enriched sample;
   (b) lysing all cells in the enriched sample to release nuclei;
   (c) selectively lysing nuclei of unwanted cells and extracting fetal apoptotic DNA from fetal nuclei; and
   (d) analyzing the extracted fetal apoptotic DNA.

14. The method of claim 13, wherein the microfluidic device comprises a channel having a structure that deterministically directs fetal nucleated cells in a first direction and at least some maternal cells in a second direction based on deterministic lateral displacement.

15. The method of claim 14, wherein the microfluidic device is a duplex device comprising a channel comprising a first section comprising first and second outer regions, each outer region comprising a structure that deterministically directs particles having a hydrodynamic size above a critical size in a first direction and particles having a hydrodynamic size below the critical size in a second direction, wherein the first and second outer regions are aligned in parallel in the channel.

16. The method of claim 13, wherein step (d) comprises analyzing the extracted fetal apoptotic DNA by polymerase chain reaction (PCR) or whole genome amplification (WGA).

17. The method of claim 13, wherein step (d) comprises analyzing the extracted fetal apoptotic DNA by analysis of short tandem repeats (STR).

18. The method of claim 13, wherein step (d) comprises analyzing the extracted fetal apoptotic DNA by analysis of single nucleotide point mutations (SNP), deletions, or translocations.

19. The method of claim 13, wherein step (d) comprises analyzing the extracted fetal apoptotic DNA by detecting chromosomal aneuploidies.

20. The method of claim 19, wherein chromosomal aneuploidies are detected using comparative genome hybridization.

* * * * *

UNITED STATES PATENT AND TRADEMARK OFFICE
CERTIFICATE OF CORRECTION

PATENT NO. : 10,786,817 B2
APPLICATION NO. : 15/965128
DATED : September 29, 2020
INVENTOR(S) : Lotien Richard Huang et al.

It is certified that error appears in the above-identified patent and that said Letters Patent is hereby corrected as shown below:

On the Title Page

Related U.S. Application Data:

Page 2, Column 1, Lines 6-7:
Delete "2006, which is a continuation of application No. 60/704,067, filed on Jul. 29, 2005."
And Insert -- 2006. --

Page 2, Column 1, Lines 8-9:
Delete "Provisional application No. 60/668,415, filed on Apr. 5, 2005."
And Insert -- Provisional application No. 60/704,067, filed on Jul. 29, 2005, and provisional application No. 60/668,415, filed on Apr. 5, 2005. --

Signed and Sealed this
Twenty-second Day of December, 2020

Andrei Iancu
*Director of the United States Patent and Trademark Office*